(12) United States Patent
DeLaporte et al.

(10) Patent No.: US 6,511,801 B1
(45) Date of Patent: Jan. 28, 2003

(54) HIV-1 GROUP O ANTIGENS AND USES THEREOF

(75) Inventors: Eric DeLaporte, Saint Jean de Cuculles (FR); Martine Peeters, Saint Jean de Cuculles (FR); Eric Saman, Bornem (BE); Marleen Vanden Haesevelde, Oudenaarde (BE)

(73) Assignee: Innogenetics, N.V. (BE)

( * ) Notice: Subject to any disclaimer, the term of this patent is extended or adjusted under 35 U.S.C. 154(b) by 0 days.

(21) Appl. No.: 09/462,917

(22) PCT Filed: Jul. 20, 1998

(86) PCT No.: PCT/EP98/04522

§ 371 (c)(1),
(2), (4) Date: Apr. 3, 2000

(87) PCT Pub. No.: WO99/04011

PCT Pub. Date: Jan. 28, 1999

(30) Foreign Application Priority Data

Jul. 18, 1997 (EP) ............................................. 97870110

(51) Int. Cl.$^7$ ................................................ C12Q 1/70
(52) U.S. Cl. .......................... 435/5; 435/7.1; 435/7.92; 435/974; 435/975; 436/536; 530/326; 530/826; 424/208.1
(58) Field of Search .................. 530/350, 324, 530/325, 326, 826, 388.35; 435/5, 7.1, 974, 975, 7.92, 235.1; 424/188.1, 204.1, 208.1; 436/536

(56) References Cited

U.S. PATENT DOCUMENTS 5,798,205 A  8/1998  Hauser et al. .................. 435/5

FOREIGN PATENT DOCUMENTS

| AU | 715731 B | 2/2000 | ............ C12N/15/49 |
| EP | 0 727 483 A2 | 8/1996 | ............ C12N/7/00 |
| WO | WO 95 32293 A | 11/1995 | ............ C12N/15/48 |
| WO | WO 96 12809 A | 5/1996 | ............ C12N/15/49 |
| WO | WO 96 27012 A | 9/1996 | ............ C12N/15/49 |
| WO | WO 96 27013 A | 9/1996 | ............ C12N/15/49 |

OTHER PUBLICATIONS

Vanden Haesevelde, M. et al., Genomic Cloning and Complete Sequence Analysis of a Highly Divergent African Human Immunodeficiency Virus Isolate:, *Journal of Virology* 68:1586–1596 (1993).

Charneau, P. et al., "Isolation and Envelope Sequence of a Highly Divergent HIV–1 Isolate: Definition of a New HIV–1 Group", *Virology* 205:247–253 (1994).

Mauclère, P. et al., "Serological and virological characterization of HIV–1 group O infection in Cameroon", *AIDS*, 11:445–453 (1997).

Gürtler, L. et al., "HIV–1 subtype O: epidemiology, pathogenesis, diagnosis, and perspectives of the evolution of HIV" *Archives of Virology* 11(Suppl.):195–202 (1996).

Bibollet–Ruche, F. et al., "AC Y09780", *EMBL Database*, XP002086957 Heidelberg, Sep. 30, 1997.

Bibollet–Ruche, F. et al., "AC Y09773", *EMBL Database*, XP002086958 Heidelberg, Sep. 30, 1997.

Bibollet–Ruche, F. et al., "AC Y09780", *EMBL Database*, XP002086959 Heidelberg, Sep. 20, 1997.

*Primary Examiner*—Jeffrey Stucker
(74) *Attorney, Agent, or Firm*—Howrey Simon Arnold & White, LLP

(57) ABSTRACT

The claimed invention relates to an HIV-1 group O envelope antigen comprising SEQ ID NO: 100, and the use of said antigen as a reagent in the diagnosis of HIV-1 group O infection, and a kit therefore.

4 Claims, 66 Drawing Sheets

FIG. 1A

```
                  10         20         30         40         50
                  |          |          |          |          |
ID$ANT70    NLLRAIQAQQQLLRLSXWGIRQLRARLLALETLLQNQQLLSLWGCKGKLV
ID$BSD649   NLLRAIQAQQQLLRLSVWGIRQLRARLLALETLIQNQQLLNLWGCRGRQV
ID$MP448P   NLLRAIQAQQHLLRLSVWGIRQLRARLLALETLIQNQQLLNSWGCKGKIV
ID$MP448    NLLRAIQAQQHLLRLSVWGIRQLRARLLALETLIQNQQLLNSWGCKGKIV
ID$772P94   NLLRAIQAQQHLLRLSVWGIRQLRARLQALETLMQNQQLLNLWGCKGKSI
ID$MP95B    NLLRAIQAQQHLLRLSVWGIRQLRARLQALETFIQNQQLLSLWGCKGKLI
ID$MP340P   NLLRAIQAQQELLRLSVWGIRQLRARLLALETLIQNQQLLNLWGCKGRIV
ID$MP450P   NLLRAIQAQQLLRLSVWGIRQLRARLLALETLIQNQQLLNLWGCKGRIV
ID$MP450    NLLRAIQAQQQLLRLSVWGIRQLRARLLALETLIQNQQLLNLWGCKGRIV
ID$189      NLLRAIQAQQQLLRLSVWGIRQLRARLLALETLIQDQQLLNLWGCKGRIV
ID$MP340    NLLKAIQAQQELLRLSVWGIRQLRARLLALETLIXNQXLLNLWGCKGRIX
ID$320      NLLXXIQAXQELLRLSVWGIRQXRXXLXALETLIXNQXLLNLWGCKGRLV
IDMVP5180   NLLRAIQAQQQLLRLSVWGIRQLRARLLALETLIQNQQLLNLWGCKGRLI
ID$BSD422   NLLRAIQAQHQLLKLSVWGIRQLRARLLALETFIQNQQLLNLWGCKGNLI
ID$MP575    NLLRAIQAQQQLLRLSVWGIXQLRARLLAXETLIQNXQLLNLWGCKGXLV
ID$BSD189   NLLRAIQAQQQLLRLSVWGIRQLRARLLALETLIQNQQLLNLWGCKGRLI
ID$MP539    NLLRAIQAQQELLRLSVWGIRQLRARLLALETFIRNQQLLNLWGCKGRLI
ID$BSD242   NLLRAIQAQQHLLRLSVWGIRQLRARLQALETLIQNQQRLNLWGCKGKLI
ID$533      NLLRAIQAQQHLLRLSVWGIRQLRARLQALETLIQNQQRLNLWGCKGKMI
ID$VAU      NLLRAIQAQQHLLRPSVWGIKQLRARELIQNQQRLNLWGCKGKMI
ID$FABAP    NLLKAIQAQQLLRLSVWGIKQLRARIRLIQNQQLLNLWGCKNRLI
ID$FABA     XLLRAIQAQQQLVRLSVWGIRQIRGXLVALETLIQNQXXNLWGCKGRVV
            **  *** ** *  *:* *** *      * *    *     **

Immunodominant domain (ID) (23-51)
                    ------------------------------
                    ISU (23-39)          PID (45-51)
```

FIG. 1B

```
                   60          70          80          90         100
                    ʌʌ  ʌʌʌʌʌʌʌʌʌ---  ʌʌʌ|        ʌʌʌ|  ʌʌ|         |
IDŞANT70     CYTSVKWNRTWIGN--------ESIWDTLTWQEWDRQISNISSTIYEEIQK    3
IDŞBSD649    CYTSVIWNETWIGN--------ETIWEELTWQEWDRQISNISSTIYDEIQK    3
IDŞMP448P    CYTAVKWNKTWTGN--------ESIWDHLTWQQWDQQIDNVSSTIYEEILK    3
IDŞMP448     CYTAVKWNRTWTGN--------ESIWDHLTWQQWDQQIDNVSSTIYEEILK    3
IDŞ772P94    CYTSVKWNNTWGGN--------LSIWDSLTWQQWDQQVANVSSLIYDKIQE    4
IDŞMP95B     CYTSVKWNTSWGGN--------ESIWNNLTWQQWDQQIDNISSIIYDEIQK    3
IDŞMP340P    CYTSVKWNDTW-------RHVTNMSEVWDKLTWQEWDRQIDNISYVIYDEIQR    4
IDŞMP450P    CYTSVKWNNTW-------RNVTNMSEVWDTLTWQEWDRQIDNISYVIYDEIQR    4
IDŞMP450     CYTSVKWNNTW-------RNVTNMSEVWDTLTWQEWDRQIDNISVIYDEIQR    4
IDŞ189       CYTSVKWNNTW-------RHVTNMSEVWDKLTWQEWDRQIDNISYVIYDEIQR    3
IDŞMP340     CYTSVKWNDTW-------RHVTNMSEVWDKLTWQEWDRQIDNISYVIYDEIQR    3
IDŞ320       CYTSVKWNXTW-------KHVTXMSEVWDKLTWQEWDRXIDNISYVIYDXIQR    4
IDŞKGT008    CYTSVKWNKTWI-N-KTDTEIENIWENLTWQEWDQQISNISSTIYEEIQK       4
IDŞBSD422    CYTSVHWNKTWT-N-KTDKDLEDMWDNLTWQQWDQQISNISATIYEEIQK       4
IDŞMP575     CYTSVKWNETWKGD-RTFTDMENIWNNLTWQEWDQQISNISSTIYDEIQK       3
IDŞBSD189    CYTSVXWNRTWTNN----TNLDSIWENLTWQEWDQQINSISSTIYEEIQK       4
IDŞMP539     CYTSVQWNMTWTNN----SNLETIWDNLTWQEWDQQINSISSVIYEEIQR       3
IDMVP5180    CYTSVQWNKTWG-----NLXDNESIWDDXTWQEWDKRVXNVXATIFEEIRR      ND
IDŞBSD242    CYTSVKWNNTSWSGR-----YNDDSIWDNLTWQQWDQHINNVSSIIYDEIQA     3
IDŞ533       CYTSVKWNTSW-GD-----YND-SIWGNXTWQQWDQEISNVSSIIYDKIQE       4
IDŞVAU       CYTSVPWNTSW-GN-----YND-SIWDKYTWQQWDREIDNVSYIIYEKIQE       3
IDŞFABAP     CYTSVKWNKTWGGD-----NESIWDELTWQQWDQQINNVSSFIYEKIQE        3
IDŞFABA      CYTSVKWNNTWTKNITNITDLDEIWDKFTWQQWDQQINHISDVIYEEIPK       3
             XYTSVKWNNTWTKNITNITDLDEIWDKFTWQQWDQQINNISDVLYEEIQK        3
             **.*.*.*          .   . ..**.   *     *      .*
```

110
|

| | | |
|---|---|---|
| IDSANT70 | AQVQQEQNEKKLLELDEW | (SEQ ID NO 30) |
| IDSBSD649 | AQVQQEQNEKKLLELDE- | (SEQ ID NO 14) |
| IDSMP448P | AQVQQEQNEQKLLELDE- | (SEQ ID NO 16) |
| IDSMP448 | AQVQQEQNEXXLLELDE- | (SEQ ID NO 36) |
| IDS772P94 | AQEQQEENERALLELDE- | (SEQ ID NO 38) |
| IDSMP95B | AQEQQEQNEKSLLELDE- | (SEQ ID NO 2) |
| IDSMP340P | AQVQQEQNEKKLLELDE- | (SEQ ID NO 10) |
| IDSMP450P | AQVQQEQNEKKLLELDE- | (SEQ ID NO 12) |
| IDSMP450 | AQVQQEQNEKKLLELDE- | (SEQ ID NO 18) |
| IDS189 | AQVQQGPNEKKLLELDE- | (SEQ ID NO 4) |
| IDSMP340 | AQVQQEQNEKKLLELDE- | (SEQ ID NO 20) |
| IDS320 | AQIQQEHNEKLLELDEW | (SEQ ID NO 24) |
| IDSKGT008 | AQVQQEYNERKLLELDE- | (SEQ ID NO 22) |
| IDSBSD422 | AQVQQEQNEKKLLELSE- | (SEQ ID NO 26) |
| IDSMP575 | AQXQQEYXEKKLLELDX- | (SEQ ID NO 28) |
| IDSBSD189 | AQVQQEQNEKKLLELEE- | (SEQ ID NO 40) |
| IDSMP539 | AQEQQEQNEKALLELDE- | (SEQ ID NO 32) |
| IDMVP5180 | AQDQQEKNVKALLELDEW | (SEQ ID NO 34) |
| IDSBSD242 | AQDQQERNVKALLELDE- | |
| IDS533 | AQDQQEKNVKALLELDE- | |
| IDSVAU | AQEQQEKNEKELLELDEW | (SEQ ID NO 6) |
| IDSFABAP | AQVQQGPNERLLELDEW | (SEQ ID NO 8) |
| IDSFABA | AQVQQEQNERKLLELDE- | |

```
                        10        20        30        40        50
                        |         |         |         |    +    |
V3MVP5180       IMGKNITESAKNIIVTLNTPINMTCIREGIAEVQDIYTGPMRWRSMTLKR
V3$ANT70        MMAKDILEGGKNIIVTLNSTLNMTCERP-QIDIQEMRIGPMAWYSMGIGG
V3189           IMGKNISDNGKNIIVTLNSTLNSTLKMTCERPGNHTVQQMKIGPMSWYSMGLEK
V3FABA          IIGKNISDSGKNIIVTLNPTVNLTCERPGNNSIQQMKIGPLAWYSMGLER
V3MP340         IMGKNISDSAENIIVTLNSTVNITCERPGNQSVQEIKIGPMAWYSIGIGT
V3MP450         IMGKNISNSAVNIIVTLNSTVNITCVRPWNQTVQEIQTGPMAWYSIHLRT
V3MP448         LMAKNISATGQNIIVTLNTTINMTCQRPGNLTIQEIKIGPMSWYSMGIGQ
V3MP539         RMGENNPSDRKKILVTLNSPINITCERPYYQSVQELRIGPMAWYSMTLER
V3$VAU          IMGKNISDSGENILITLNTNITIACERPGNQTIQKIMAGPMAWYSMALSN
                  .  . :   .****.:: *: .  :*  .      **::**:      .

60        70        80        90       100
                        |    +    |         |         |         |
V3MVP5180       SNNTSPRSRVAYCTYNKTVWENALQQTAIRYLNLVNQT--ENVTIIFSRT
V3$ANT70        TAGN---SSRAAYCKYNATDWGKILKQTAERYLELVNNT--GSINMTFNHS
V3189           NNTS---SRRAFCKYNATNWEKTLKQMAERYLELVNNTSNNTVTMIFNTS
V3FABA          NKSS---ISRLAYCRYNTTTWEQALQQTAERYLELVNNT--DNITIMFNRS
V3MP340         TPAN---WSRIAYCQYNITDWEKALKQTAERYLELVNHTRNDTVSITFNSS
V3MP450         PLAN---LSRIAYCKYNAADWEKALKQTAERYLELVNNTSNNNVTIIFNNS
V3MP448         EDHS---KSRNAYCEYNITDWVQALKQTAERYLELVNNT--NTNINMTFENS
V3MP539         DRAGSDI-RAAYCKYNASDWRNTLKGVAERYLELRNE--EGPVNVTFNGS
V3$VAU          TKGDT---RAAYCNYSATDWNKALKNITERYLELV-EYNQTDVTMKFGNH
                 :      . .*.:*..   . :: :****** *    ****       
```

FIG. 2A

```
                110
                 |
V3MVP5180    SGGDAEVSHLHFNC----            (SEQ ID NO 50)
V3$ANT70     SGGDLEVTHLHFNC----            (SEQ ID NO 44)
V3189        SDGDPEV-----------            (SEQ ID NO 42)
V3FABA       TDGDSEVTHMHFN-----            (SEQ ID NO 46)
V3MP340      TGGD-----------L--            (SEQ ID NO 48)
V3MP450      TGGDPETTQLHFNCHGVL            (SEQ ID NO 52)
V3MP448      TGGDPE------------
V3MP539      AGGDPEIRFLHF------
V3$VAU       SGEDAEVTNFFFN-----
                   *
```

| | 70 | 80 | 90 | 100 | 110 | 120 |
|---|---|---|---|---|---|---|
| ANT70 | AGACAACTCCGAGCTCGCCTGCTAGCCTTAGAAAACCTTACTACAGAATCAGCAACTCCTA |
| MVP5180 | AGACAACTCCGAGCTCGCCTGCTAGCCTTAGAAAACCCTTATACAGAATCAGCAACGCCTA |
| VAU | AGACAACTCCGAGCTCGCCTGCTAGCCTTAGAAAACCTTATACAGAATCAGCAACTCCTT |
| VI686 | AGACAACTCCGAGCTCGCCTGCTAGCCTTAGAAAACCTTAATACAGAATCAGCAACTCCTA |
| MP340-PBMC | AGACAACTCCGAGCTCGCCTGCTAGCCTTAGAAAACCTTAATACAGAATCAGCAGCTCCTA |
| MP340 | AGACAAXTCCGAGXTXGCCTGXTAGCCTTAGAAAACCTTAATACAXAATCAGCAXCTCCTA |
| FABA-PBMC | AGACAACTCCGAGCTCGCCTGCTAGCCTTAGAAAACCTTAATACAGAATCAGCAACTCCTA |
| FABA | AAACAAATCCGAGGTXGCCTGGTAGCCTTAGAAAACCTTAATACAGAATCAGCAAXTCCTX |
| MP450-PBMC | AGACAACTCCGAGCTCGCCTGCTAGCCTTAGAAAACCTTAATACAGAATCAGCAGCTCCTA |
| MP450 | AGACAACTCCGAGCTCGCCTGCTAGCCTTAGAAAACCTTAATACAGAATCAGCAGCTCCTA |
| MP448-PBMC | AGACAACTCCGAGCTCGCCTGCTAGCCTTAGAAAACCTTAATACAGAATCAGCAGCTCCTA |
| MP448 | ÅGACAACTCCGAGCTCGCCTGCTAGCCTTAGAAAACCTTAATACAGATCAGCAGCTCCTA |
| 189 | AGACAACTCCGAGCTCGCCTGCTAGCCTTAGAAAACCTTAATACAGAACCAGCAACTCCTA |
| 320 | AGACAACTCCGAGCTCGCCTGCTAGCCTTAGAAAACCTTATACAGAATCAGCAACTCCTA |
| BSD422 | AGACAACTCCGAGCTCGCCTGCTAGCCTTAGAAAACCTTTATACAGAATCAGCAACTCCTA |
| KGT008 | AGACAACTCCGAGCTCGCCTGCTAGCCTTAGAAAACCTTAATACAGAGTCAGCAACTCCTA |
| MP575 | AXACAACTCCGAGCTCGCCTGCTAGCCTTAGAAAACCTTAATACAGAATCXGCAACTCCTG |
| BSD189 | AGACAACTCCGAGCTCGCCTGTTGGCCTTAGAAAACCTTAATACAGAATCAGCAACTCCTA |
| BSD649 | AGACAACTCCGAGCTCGCCTGCTAGCCTTAGAAAACCTTAGAAAACCTTAGAACATXAGAATCAGCAACTCCTA |
| BSD242 | AGACAACTCCGAGCTCGCCTGCTAGCCTTAGAAAACCTTAGAAAACCTTAGAAAACCTTATACAGAATCAGCAACTCCTA |
| 533 | AGACAACTCCGAGCTCGCCTGCTAGCCTTAGAAAACCTTATACAGAATCAGCAACGCCTA |
| 772P94 | AGACAACTCCGAGCTCGCCTGCTAGCCTTAGAAAACCCTTATGCAAATCAGCAACTCCTA |
| MP95B | AGACAACTCCGAGCTCGCCTGCTAGCCTTAGAAAACCTTTATACAGAACCAGCAACTCCTA |
| MP539 | AGACAACTCCGAGCTCGCCTGCTAGCCTTAGAAAACCTTTATACGGAATCAGCAACTCCTA |
| SIVCPZ-GAB | AAACAACTACAAGCCAGATTGCTTGCTGTGTAGAAAGGTACCTGCAGGATCAGCAGATTCTG |
| | * * * * * * * * * * ** * * ** * * * * * ** * ** ** |

FIG. 3B

```
                      130         140         150         160         170         180
                       |           |           |           |           |           |
ANT70        AGCCTATGGGGCTGTAAAGGAAAGCTAGTCTGCTACACATCAGTAAAATGGAATAGAACA
MVP5180      AACCTATGGGGCTGTAAAGGAAAACTAATCTGTTACACATCAGTAAATGGAACACATCA
VAU          AACCTGTGGGGCTGCAAGAATAGACTAATCTGCTACACATCAGTAAGTGGAATAAAACA
VI686        AACCTGTGGGGCTGTAAAGGAAGGCTAATCTGCTACACCTCAGTACACATCAGTAACAAAACA
MP340-PBMC   AACCTATGGGGTTGTAAGGAAGGATAGTCTGCTACACATCAGTAAAATGGAACGATACA
MP340        AACCTATGGGGTTGTAAGGAAGGAAGGATAXTXTGCTACACATCAGTAAAATGGAACXATACA
FABA-PBMC    AACCTATGGGGCTGTAAAGGAAGGCTAGTCTGCTACACATCAGTAAAATGGAACAATACA
FABA         AACCTATGGGGCTGTAAAGGAAGGGTAGTTTGXTACACATCAGTAAAATGGAACAATACA
MP450-PBMC   AACCTATGGGGTTGTAAGGAAGGATAGTCTGCTACACATCAGTAAAATGGAACAATACA
MP450        AACCTATGGGGTTGTAAGGAAGGATAGTCTGCTACACATCAGTAAAATGGAACAATACA
MP448-PBMC   AACCTATGGGGCTGTAAGGAAAAGATAGTCTGTTACACAGCAGTAAAATGGAACAAGACA
MP448        AACTCATGGGGCTGTAAGGAAAAGATAGTCTGTTACACAGCAGTAAAATGGAACAGGACA
189          AACTCATGGGGCTGTAAGGAAAAGATAGTCTGCTACACATCAGTAAAATGGAACAGGACA
320          AACCTATGGGGCTGTAAGGAAGGCTAGTCTGCTACACATCAGTAAAATGGAACGATACA
BSD422       AACCTATGGGGCTGTAAAGGAAGGCTAATCTGCTACACATCAGTAAAATGGAACAAGACA
KGT008       AACCTGTGGGGCTGTAAGGAAGGAAACCTAATCTGCTACACATCAGTAAAATGGAACAAGACA
MP575        AACCTATGGGGCTGTAAGGAAXGCTAGTCTGCTACACATCAGTACTAAGTAXAATGGAACAGGACA
BSD189       AACCTATGGGGCTGTAAGGATGTAAGGAAGGCTAATCTGCTACACATCAGTACACATGGAACATGACA
BSD649       AACCTATGGGGCTGTAGAGGAAGGCAAGTCTGCTACACATCAGTACACATCAGTAATATGGAATGAGACA
BSD242       AACCTATGGGGCTGTAAGGGAAGGAAAGATGATCTGTTACACATCAGTAAAATGGAACACATCA
533          AACCTATGGGGCTGTAAGGAAAGGAAAGATGATCATCAATCAGTAAAATGGAACACATCA
772P94       AACCTATGGGGCTGTAAGGAAGAAAATCAATCTGCTACACATCAGTAAAATGGAACAACACA
MP95B        AGCCTATGGGATGTAAGGAAAGCTAATCTGTTACACATCTGTAAACATCAGTAAAATGGAACACATCA
MP539        AACCTCTGGGGCTGTAAGGAAGGCTAATTGCTATACATCAGTACAATGAACAAAACA
                 *****           *         *     *      *    *    *         *****
```

FIG. 3C

```
                        190              200              210              220              230              240
                         |                |                |                |                |                |
ANT70         TGGATAGGAAAC------------------------------------------GAAAGCATTTGGGACACCTTAACATGG
MVP5180       TGGTCAGGAAGATA-----------------------TAATGATGACAGTATTTGGGACAACCTTACATGG
VAU           TGGGGAGGAG---------------------------ATAATGAATCAATTTGGGATGAGTAACCTAACATGG
VI686         TGGACA---AACAAGTC------------AAATGTTGACTTGGAGAATATTTGGGCAACCTAACATGG
MP340-PBMC    TGGAGACA---------------------TGTCACTAATATGAGTGAAGTTTGGGACAAACTAACCTGG
MP340         TGGAAACA---------------------TGTCACTXATATGAGTGAAGTTTGGGACAAACTAACCTGG
FABA-PBMC     TGGACAAAAAAACATCACAAACATCACAGAGACCTAGACGAGAGATTTGGGACAAATTTACATGG
FABA          TGGACAAAAAAACATCACAAACATCACAGAGACCTAGACGAGAGATTTGGGACAAATTTACATGG
MP450-PBMC    TGGAGAAA---------------------TGTCACTAATATGAGTGAAGTTTGGGACACACTAACCTGG
MP450         TGGAGAAA---------------------TGTCACTAATATGAGTGAAGTTTGGGACACACTAACCTGG
MP448-PBMC    TGGACAGGAAAT-----------------------------GAAAGTATTTGGGACCACCTCACATGG
MP448         TGGACAGGAAAT-----------------------------GAAAGTATTTGGGACCACCTCACATGG
189           TGGAGACA---------------------TGTCACTAATATGAGTGAAGTTTGGGACAAATTAACCTGG
320           TGGATAAATAAAA-----C----------TGACACTGAGATATAGGAGAATATTTGGGAAAATCTGACATGG
BSD422        TGGAAAGGAGATAGGAC------------TTTTACTGACATGGAAATATATTTGGGAACAACCTAACATGG
KGT008        TGGACA---AATAAGAC------------AGATAAGGATTTGGAGGATATGTGGGACAACCTAACATGG
MP575         TGGACA---AACAA---------------TACTAATTTAGATTCAATTTGGGAAAATCTAACATGG
BSD189        TGGACA---AACAA---------------TTCTAATCTGGAAACAATTTGGGACAACCTAACATGG
BSD649        TGGATAGGAAAC------------------------------GAAACCATTTGGGAAGAACTAACATGG
BSD242        TGG-----GGAGA----------------CTATAATGACAGTATTTGGGCAACTAAGTAACACATGG
533           TGG-----GGAAA----------------CTATAATGACAGTATTTGGGATAAGTATACATGG
772P94        TGGGGAGGAA-------------------------ATCTC--TCAATTTGGGACAGCTTAACATGG
MP95B         TGGGGAGGA--------------------------------AATGAGTATTTGGGAACAATCTAACATGG
MP539         TGGGGT----------------------AATTTGAXXGATAATGAGTCAATTTGGGATGACATXACATGG
              ***                                                  *   ***    *** ***
```

FIG. 3D

| | 250 | 260 | 270 | 280 | 290 | 300 |
|---|---|---|---|---|---|---|

```
ANT70       CAGGAATGGGATCGGCAGAGATAAGCAACATAAGCTCCACCATATATGAGGAAATACAAAAG
MVP5180     CAGCAATGGGACCAACAACATAAACATAGTAAGCTCCATTATATATGATGAAATACAAGCA
VAU         CAGCAGTGGGATCAACAGATAAACAACGTAAGCTCCTTCATATATGAAAAAATACAAGAG
VI686       CAGGAATGGGATCAGCAGATAACATAAGTAGCACCATATATGTTATATATGAAATACAAAAG
MP340-PBMC  CAGGAATGGGATCGGCAGATAGACAACATAAGCTATGTTATATATGATGAAATACAAAGA
MP340       CAGGAATGGGATCGGCAGATAGACAACATAAGCTATGTTATATATGATGAAATACAAAGA
FABA-PBMC   CACCAATGGGATCAACAGATAGACAACATAAGTGATGTCATATATGAAGAAATACCAAAG
FABA        CAGCAATGGGATCAACAGATAAACCACATAAGCAACATAAGTGATGTCCTATATGAAGAAATACAAAAG
MP450-PBMC  CAGGAATGGGATCGGCAGATAGACAACATAAGCTATGTTATATATGATGAAATACAAAGA
MP450       CAGGAATGGGATCGGCAGATAGACAACATAAGCTATGTTATATATGATGAAATACAAAGA
VI686       CAGCAATGGGATCAGCAGATAGACAACATAAGCTAAGCTCCACCATATATGAGGAAATACTAAAA
MP448-PBMC  CAGCAATGGGATCAGCAGATAGACAACATGTAAGCTCCACCATATATGAGGAAATACTAAAA
MP448       CAGCAATGGGATCAGCAGATAGACAACATAAGCTAAGCTCCACCATATATGAGGAAATACTAAAA
189         CAGGAATGGGATCGGCAGCAAATAAGCAACATAAGCTCCACCATATATGAGGAAATACAAAAG
320         CAGGAATGGGATCAGCAGCAAATAAGCAACATAAGCTCCACCATATATGAGGAAATACAAAAG
BSD422      CAGGAATGGGATCAGCAGCAGCAGATAAGCAACATAAGCTCCACCATATGACGAAATACAAAAG
KGT008      CAGCAATGGGATCAGCAGCAGCAGATAAGTAACATAAGCGCCACCATATATGAGGAAATACAAAAG
MP575       CAGGAATGGGATCAGCAGCAGCAGATAAGCAACATAAGCTCCACCATATATGAGGAAATACAAAAG
BSD189      CAGGAATGGGATCAGCAGCAGCAGATAAGCAACATAAGCTCTGTCATATATGAGGAAATACAAGG
BSD649      CAGCAATGGGATCGGCAGCAGCAGATAAGCAACATAAGCTCCACCATATATGATGAAATACAAAAG
BSD242      CAACAATGGGATCGGCAGGAAATAAGCAACATAAGCTAAGCTCCATTATTATATGACAAAATACAAGAA
533         CAACAATGGGACCGAGAGAAATAAGCAACATAATGTAAGCTAAGCTCCATTATATATGAAAAAAATACAAGAA
772P94      CAGCAGTGGGATCAACAGCCAATGTAAGCTACATAAGTCTTTGATATATGACAAAATACAAAAG
MP95B       CAGCAGTGGGATCAACAGATAGACAACATAAGTTCCATCATATATGATGAAATACAAAAG
MP539       CAGGAGTGGGATAAGCGGGTAGAXAATGTAAGXGCCACCATATTGAAGAAATACGAAGG
                *  *****        *                *               *        *       *
```

| Label | Sequence | SEQ ID NO |
|---|---|---|
| ANT70 | GCACAAGTACAGCAGGAACAAGAAAAATGAGAAAAAGTTGCTGGAGTTAGATGAAT | 1 |
| MVP5180 | GCACAAGACCAACAGGAGAAAAGAATGTAAAAGCATTGTTGGAGCTAGATGAAT | 3 |
| VAU | GCACAAGAACAACAGGAGAAGAAATGAGAGAAAAGTTGCTGGAGTTAGATGAAT | 5 |
| VI686 | GCACAAGTACAGCAGCAAGAACAAAATGAGCAAAAGTTGCTGGAGTTAGATGAAT | 7 |
| MP340-PBMC | GCACAAGTACAGCAGCAAGAACAAAATGAGAAGAAGAAGTTGCTGGAGTTAGATGAAT | 9 |
| MP340 | GCACAAGTACAGCAGCAAGAACAAAATGAGAAGAAGAAGTTGCTGGAGTTAGATGAAT | 11 |
| FABA-PBMC | GCACAAGTACAGCAGGACCAGGACCAAATGAGAGGAGAAGTTGCTGGAGTTAGATGAAT | 13 |
| FABA | GCACAAGTACAGCAGGAACAAAATGAGAAATGAGAGAAGAAGTTGCTGGAGTTAGATGAAT | 15 |
| MP450-PBMC | GCACAAGTACAGCAGCAAGAACAAAATGAGAGAGAAGAAGTTGCTGGAGTTAGATGAAT | 17 |
| MP450 | GCACAAGTACAGCAGCAAGAACAGAATGAGCAAAAGTTGCTGGAGTTAGATGAAT | 19 |
| MP448-PBMC | GCACAAGTACAGCAGCAAGAACAGAATGAGXAAAAXTTGCTGGAGTTAGATGAAT | 21 |
| MP448 | GCACAAGTACAGCAGGAACAGGACCAAATGAGAAGAAGAAGTTGCTGGAGTTAGATGAAT | 23 |
| 189 | GCACAAATACAACAGGAACATAATGCAAAATGAGAAAAAAGTTGCTGGAGCTAGATGAAT | 25 |
| 320 | GCACAAGTACAACAGGAGAAGAAATGAGAGAAAAGTTACTAGAGTTAAGTGAAT | 27 |
| BSD422 | GCACAAGTACAACAGGAGAATACAAATGAATGAGAAAAAGTTGTTGGAGTTAGATGAAT | 29 |
| KGT008 | GCACAAXTACAGCAGGAGAATACXATGAGAAAAAGTTGCTAGAGTTAGATXAAT | 31 |
| MP575 | GCACAAGTACAGCAGCAAGAACAAAACGAGAAAAAGTTGCTGGAGTTAGATGAAT | 33 |
| BSD189 | GCACAAGTACAGCAGCAAGAACAAAATGAGAAAAAAGTTGCTGGAGTTAGAGGAAT | 35 |
| BSD649 | GCACAAGTACAGCAGCAAGAACAAAATGAGAAATGCTGCTGGAGTTAGATGAAT | 37 |
| BSD242 | GCACAAGTACAGCAGGAACAGGAGAGGAGAAGTGTAAAAGCATTGTTGGAGCTAGATGAAT | 39 |
| 533 | GCACAAGGACCAACAGGAGAGGAGAAATGAGAAAATGAAAATGTAAAAGGGCCTTGCTGGAGTTAGATGAAT |  |
| 772P94 | GCACAAGAACAACAGGAGAATGTAAAATGAGAAAAATGCATTGTTGGAGCTAGATGAAT |  |
| MP95B | GCACAAGAGCAACAGGAACAAAATGAGAAAAGTTGCTTGGAGCTTGATGAAT |  |
| MP539 | GCACAAGAACAACAGGAACAAAATGAGAAGGCTTTGCTAGAATTAGATGAAT |  |

```
           10         20         30         40         50         60
            |          |          |          |          |          |
MVP5180    A------ATTATGGGAAAAAATATTACAGAGAATATCAGCAAGAATAATCATAGTAACCCTAAAC
ANT70C2V3  A------ATGATGGCAAAAGATATTTTGGAAGGTGGAAAAATATCATAGTGACCCTAAAC
VI686C2V3  -------ATAATGGGAAAAAATATTTCGGACAGTGGAAAATATCATAGTAACCCTAAAT
189C2V3    -TAAGAATAATGGGAAAAAATATTTCAGACAATAGTGGACAGTGGAAAATATCATAGTAACCCTAAAT
FABAC2V3   -------ATTATAGGAAAAAAACATTTCGGACAGTGGAAAATATCATAGTGACCCTAAAT
MP340C2V3  -TAAGA-TTATGGGAAAAAATATCTCGGACAGTGGAAAATATCATAGTGACCCTAAAT
MP448V3    ATAAGACTGATGCCAAAAAATATTTCGGCTACTGGCCAAAATATCATAGTGACCCTAAAT
MP450C2V3  ATAAGAATTATGGGAAAAAATATCTCGAACAGTCAGTAAATATCATAGTGACCCTGAAT
MP539C2V3  --AAGAAGGATGGGGGAAAACAATCCTTCAGATCGGAAGAAGATCCTAGTGACCCTAAAT
           **  **     ***  **    *     *    *    *   ******* ***** *****

70         80         90         100        110        120
            |          |          |          |          |          |
MVP5180    ACTCCTATAAACATGACCTGCATAAGAGAGAAGGAATTGCAGAGGTACAAGATATATATACA
ANT70C2V3  TCTACCCTAAACATGACCTGTGTGAGAGACCACAAA--TAGACA--TACAAGAGATGAGAATA
VI686C2V3  TCTTCTATAAGTATGACCTGTGTGAGAGACCAGGGAATCATACAGTACAAGAGATGAAGATA
189C2V3    TCTACTCTAAAAATGACTTGTGTGAGAGACCAGGGAATCATACAGTACAACAGATGAAGATA
FABAC2V3   CCTACTGTAAACATGACCTGTTGTGAGAGACCAGGGAATAATTCAATACAACAGATGAAAATA
MP340C2V3  TCTACTGTAAACATAACCTGTGTGAGAGACCAGGGAATCAGTCAGTACAATACAAGAGATAAAAATA
MP448V3    ACTACTATAAACATAACCTGCGCCAGAGACCAGGAAATCTAACAATACAGGAGAAATAAAGATA
MP450C2V3  TCTGTAAACATAACCTGTGTGAGAGACCATGGAATGCAGAGATCAGAAGATACAACA
MP539C2V3  TCCCCTATAAACATAACCTGCGCGAGAGACCATCAGTCAGTACAAGAGTTAAGGATA
           *   *              *             *              *    *

```
                       130       140       150       160       170       180
                        |         |         |         |         |         |
MVP5180      GGTCCAATGAGATGGCGCAGTATGACACTTAAAAGAAGTAACAATACATCACCAAGATCA
ANT70C2V3    GGTCCAATGGCCTGGTACAGCATGG-GAATAGGGGG---AACAGCAGGAAACAGC--TCA
VI686C2V3    GGTCCAATGGCCTGGTATAGCATGG-GCCTAGAGGAA--AACAAAA--CCAA-C---TCA
189C2V3      GGTCCAATGTCCTGGTATAGCATGG-GCTTAGAGAAA--AACAATA--CCAG-C---TCA
FABAC2V3     GGTCCACTGGCCTGGTACAGCATGG-GCCTAGAGGA---AACAAAAGCTCAATC---TCT
MP340C2V3    GGTCCAATGGCCTGGTACAGCATTG-GCATAG-GGAC--AACACCCGCAAACTGG--TCA
MP448V3      GGTCCAATGTCCTGGTACAGCATGG-GCATAGGGCAG--GAAGACCACTC-TAAG--TCA
MP450C2V3    GGTCCAATGGCCTGGTATAGCATTC-ACTTGA-GGAC--ACCACTCGCAAACTTG--TCA
MP539C2V3    GGTCCAATGGCTTGGTACAGCATGACAT-TAGAACGAGAGACAGGGCAGG-CAGTGACAT-A
             ******  **   ***  ** ** *  *   *                            *

190       200       210       220       230       240
                        |         |         |         |         |         |
MVP5180      AGGGTAGCTTATTGTACATATAATAAGACTGTATGGAAAATGCCCTACAACAAACAGCT
ANT70C2V3    AGGGCAGCTTATTGCAAGTATAATGCCACTGATTGGGAAATATTAAAACAAACAGCT
VI686C2V3    AGGAGAGCTTATTGCAGGTATAATGCCACTGACTGATTGGGAAAAAGCCTTAAAACAAATGACT
189C2V3      AGAAGAGCTTTTTGCAGGTATAATGCCACTAATTGGGAAAAACCTTAAAACAAATGGCT
FABAC2V3     AGATTAGCTTATTGCAGGTATAATACCACTACGTGATTGGGAACAAGCCTTACAACAAACAGCT
MP340C2V3    AGGATAGCTTATTGCCAGTATAATATCACTGATTCACTGATTGGGAAAAAGCCTTAAAACAAACAGCT
MP448V3      AGAAACGCTTATTGTGAGTATAATAATGCCGCTGATTGGTACAGGCCTTAAAACAGACAGCT
MP450C2V3    AGGCAGCTTATTGCAAGTATAATGCCTGATTGGTGGAAAAAGCCTTAAAACAAACAGCT
MP539C2V3    AGGGCAGCTTATTGCAAGTATAATGCCTCTGACTGGAGAAATACATTAAAGGAGTAGCT
             **  ***   *                 *                            **
```

```
              250         260         270         280         290         300
               |           |           |           |           |           |
MVP5180     ATAAGGTATTTAAATCTTGTAAACCAAACAGAGAAT----------GTTACCATATATTCAGC
ANT70C2V3   GAAAGGTATTTAGAACTAGTAAACAATACAGGTAGTA----------TTAACATGACATTCAAT
VI686C2V3   GAAAGGTATTTAGAACTCGTAAACAATACAGTAGTAAACAGTAACAATCAGTAATGATATTCAAT
189C2V3     GAAAGGTATTTAGAACTCGTAAACAATACAGTAGTAAACAATAACAGTGACAATGATATTCAAT
FABAC2V3    GAAAGGTATCTAGAACTTGTGAACAATACACGGACAATA------TTACAATAATGTTCAAT
MP340C2V3   GAAAGGTACTTAGAACTTGTAAACCATACAAGAAATGATACTGTTAGCATAACATTCAAT
MP448V3     GAAAGGTATTTAGAATTAGTAAACAATACAAATACTAATA----TAAACATGACATTCGAG
MP450C2V3   GAAAGGTACTTAGAACTTGTAAATAACAAGTAATAATGTTACCATATATTCAAT
MP539C2V3   GAGAGATATTTAGAACTTAGAAAT-------GAGGAA--GGCCCGGTGAACGTGACCTTCAAT
              *   *  ****** *      *  *                          *   ***

310         320         330         340         350         360
               |           |           |           |           |           |
MVP5180     AGAACTAGTGGTGGAGATGCAGA-------------------------------------
ANT70C2V3   CACAGCAGCGGTGGAGATGGAGAGATCTAGA-----------------------------
VI686C2V3   CAAAGCAATGATGGAGATGGAGATCCAGAGGTAACCCATTGCATTTAAC-----------
189C2V3     ACAAGCAGTGATGGAGATGGAGATCCAGAGGTA--CC-----------------------
FABAC2V3    CGCAGCACTGATGGAGATTCAGAGGTAACCCATATGCATTTAAC---------------
MP340C2V3   AGCAGCAGCTGGTGGAGATGGAGATCCAGAGGT---------------------------
MP448V3     AACAGCACTGGTGGAGGAGATCCAGAGGT-------------------------------
MP450C2V3   AACAGCACTGGTGGAGATCCAGAGACAACCCAGTTACATTTAACTGTGTCATTTT-----
MP539C2V3   GGAAGTGCGGGGTGGAGATCCAGAGATACGCTTTCTGCATTTT-----------------
              *  ******  ******** ***
```

FIG. 4C

| | |
|---|---|
| MVP5180 | -- |
| ANT70C2V3 | -- |
| VI686C2V3 | -- |
| 189C2V3 | -- (SEQ ID NO 49) |
| FABAC2V3 | -- (SEQ ID NO 43) |
| MP340C2V3 | -- (SEQ ID NO 41) |
| MP448V3 | -- (SEQ ID NO 47) |
| MP450C2V3 | TA (SEQ ID NO 45) |
| MP539C2V3 | -- (SEQ ID NO 51) |

A. NUCLEIC ACID SEQUENCES

SEQ ID NO 1 (MP 340-PBMC, gp41)

AACCTGCTAA GAGCAATACA GGCCCAGCAA GAATTGCTGA GGCTATCTGT ATGGGGTATC
AGACAACTCC GAGCTCGCCT GCTAGCCTTA GAAACCTTAA TACAGAATCA GCAGCTCCTA
AACCTATGGG GTTGTAAGGG AAGGATAGTC TGCTACACAT CAGTAAAAATG GAACGATACA
TGGAGACATG TCACTAATAT GAGTGAAGTT TGGGACAAAC TAACCTGGCA GGAATGGGAT
CGGCAGATAG ACAACATAAG CTATGTTATA TATGATGAAA TACAAAGAGC ACAAGTACAG
CAAGAACAAA ATGAGAAGAA GTTGCTGGAG TTAGATGAAT

SEQ ID NO 3 (MP 340, gp41)

AACCTGCTAA SANCAATACA GGCCCCAKCAA GAATTGCTGA GGCTATCTGT ATGGGGTATC
AGACAAMTCC GAGSTYGCCT GSTAGCCTTA GAAACCTTAA TACASAATCA GCASCTCCTA
AACCTATGGG GTTGTAAAGG AAGGATASTN TGCTACACAT CAGTAAAAATG GAACNATACA
TGGAAACATG TCACTNATAT GAGTGAAGTT TGGGACAAAC TAACCTGGCA GGAATGGGAT
CGGCNGATAG ACAACATAAG CTATGTTATA TATGATGNNA TACAAAGAGC ACAAGTACAG
CAAGAACAAA ATGAGAAGAA GTTGCTGGAG TTAGATGAAT

FIG. 6B

SEQ ID NO 5 (FABA-PBMC, gp41)

AACCTGCTAA AAGCAATACA GGCCCAGCAG CAATTGCTGA GGTTATCTGT ATGGGGTATC
AAACAACTCC GAGCTCGCCT GCTAGCCTTA GAAACCTTAA TACAGAATCA GCAACTCCTA
AACCTATGGG GCTGTAAAGG AAGGCTAGTC TGCTACACAT CAGTAAAATG GAACAATACA
TGGACAAAAA ACATCACAAA CATCACAGAC CTAGACGAGA TTTGGGACAA ATTTACATGG
CACCAATGGG ATCAACAGAT AAACCACATA AGTGATGTCA TATATGAAGA AATACCAAAG
GCACAAGTAC AGCAGGGACC AAATGAGAGG AAGTTGCTGG AGTTAGATGA AT

SEQ ID NO 7 (FABA, gp41)

NACCTGTTAA GAGCAATACA GGCCCAGCAG CAATTGGTGA GGTTATCTGT ATGGGGTATC
AGACAAAATCC GAGGTNGCCT GCTAGCCTTA GAAACCTTAA TACAGAATCA GCAANTCCTN
AACCTATGGG GCTGTAAAGG AAGGGTAGTT TGNTACACAT CAGTAAAATG GAACAATACA
TGGACAAAAA ACATCACAAA CATCACAGAC CTAGACGAGA TTTGGGACAA ATTTACATGG
CAGCAATGGG ATCAACAGAT AAACAACATA AGTGATGTCC TATATGAAGA AATACAAAAG
GCACAAGTAC AGCAGGAACA AAATGAGAGG AAGTTGCTGG AGTTAGATGA AT

SEQ ID NO 9 (MP 450-PBMC, gp41)

AACCTGCTAA GAGCAATACA GGCCCAGCAG CAATTGCTGA GGCTATCTGT ATGGGGTATC
AGACAACTCC GAGCTCGCC GTTGTAAAGGG AAGGATAGTC TGCTACACAT CAGTAAAATG GCAGCTCCTA
AACCTATGGG GTTGTAAAGG AAGGATAGTC TGCTACACAT CAGTAAAATG GAACAATACA
TGGAGAAATG TCACTAATAT GAGTGAAGTT TGGGACACAC TAACCTGGCA GGAATGGGAT
CGGCAGATAG ACAACATAAG CTATGTTATA TATGATGAAA TACAAAGAGC ACAAGTACAG
CAGGAACAAA ATGAGAAGAA GTTGCTGGAG TTAGATGAAT

SEQ ID NO 11 (MP 450, gp 41)

AACCTGCTAA GAGCAATACA GGCCCAGCAG CAATTGCTGA GGCTATCTGT ATGGGGTATC
AGACAACTCC GAGCTCGCCT GCTAGCCTTA GAAACCTTAA TACAGAATCA GCAGCTCCTA
AACCTATGGG GTTGTAAGGG AAGGATAGTC TGCTACACAT CAGTAAAAATG GAACAATACA
TGGAGAAATG TCACTAATAT GAGTGAAGTT TGGGACACAC TAACCTGGCA GGAATGGGAT
CGGCAGATAG ACAACATAAG CTATGTTATA TATGATGAAA TACAAAGAGC ACAAGTACAG
CAGGAACAAA ATGAGAAGAA GTTGCTGGAG TTAGATGAAT

SEQ ID NO 13 (MP 448-PBMC, gp 41)

AACCTGCTAA GAGCAATACA GGCCCAGCAG CACTTGCTGA GGCTATCTGT ATGGGGTATC
AGACAACTCC GAGCTCGCCT GCTAGCCTTA GAAACCTTAA TACAGAATCA GCAACTCCTA
AACTCATGGG GCTGTAAGGG AAAGATAGTC TGTTACACAG CAGTAAAAATG GAACAAGACA
TGGACAGGAA ATGAAAGTAT TTGGGACCAC CTCACATGGC AGCAATGGGA TCAGCAGATA
GACAATGTAA GCTCCACCAT ATATGAGGAA ATACTAAAAG CACAAGTACA GCAGGAACAG
AATGAGCAAA AGTTGCTGGA GTTAGATGAA T

SEQ ID NO 15 (MP 448, gp 41)

AACCTGCTAA GAGCAATACA GGCCCAGCAG CACTTGCTGA GGCTATCTGT ATGGGGTATC
AGACAACTCC GAGCTCGCCT GCTAGCCTTA GAAACCTTAA TACAGAATCA GCAACTCCTA
AACTCATGGG GCTGTAAGGG AAAGATAGTC TGTTACACAG CAGTAAAAATG GAACAGGACA
TGGACAGGAA ATGAAAGTAT TTGGGACCAC CTCACATGGC AGCAATGGGA TCAGCAGATA
GACAATGTAA GCTCCACCAT ATATGAGGAA ATACTAAAAG CACAAGTACA GCAGGAACAG
AATGAGMAAA ARTTGCTGGA GTTAGATGAA T

SEQ ID NO 17 (189, gp 41)

AACCTGCTAA AAGCAATACA GGCCCAGCAG GAATTGCTGA GGCTATCTGT ATGGGGTATC
AGACAACTCC GAGCTCGCCT GCTAGCCTTA GAAACCTTAA TACAGGATCA GCAGCTCCTA
AACCTATGGG GTTGTAAGGG AAGGATAGTC TGCTACACAT CAGTAAAATG GAACGATACA
TGGAGACATG TCACTAATAT GAGTGAAGTT TGGGACAAAT TAACCTGGCA GGAATGGGAT
CGGCAGATAG ACAACATAAG CTATGTTATA TATGATGAAA TACAAAGAGC ACAAGTACAG
CAAGGACCAA ATGAGAAGAA GTTGCTGGAG TTAGATGAAT

SEQ ID NO 19 (320, gp 41)

AACCTGCTAA GAGCAATACA GGCCCAGCAG CAATTGCTGA GGCTATCTGT ATGGGGTATC
AGACAACTCC GAGCTCGCCT GCTAGCCTTA GAAACCTTAA TACAGAACCA GCAACTCCTA
AACCTATGGG GCTGTAAGGG AAGGCTAGTC TGCTACACAT CAGTAAAATG GAACAAGACA
TGGATAAATA AAACTGACAC TGAGATAGAG AATATTTGGG AAAATCTGAC ATGGCAGGAA
TGGGATCAGC AAATAAGCAA CATAAGCTCC ACCATATATG AGGAAATACA AAAGGCACAA
ATACAACAGG AACATAATGA GAAAAAGTTG CTGGAGCTAG ATGAATGG

SEQ ID NO 21 (BSD 422, gp 41)

AACCTGCTAA GAGCAATACA GGCTCAGCAT CAACTGCTGA AGCTATCTGT ATGGGGTATC
AGACAACTCC GAGCTCGCCT GCTAGCCTTA GAAACCTTTA TACAGAATCA GCAACTCCTA
AACCTATGGG GCTGTAAGGG AAACCTAATC TGCTACACAT CAGTAAAATG GAACGAAACA
TGGAAAGGAG ATAGGACTTT TACTGACATG GAAAATATTT GGAACAACCT AACATGGCAG
GAATGGGATC AGCAGATAAG CAACATAAAG ATGACGAAAT AACAAAAGCA
CAAGTACAGC AGGAACAAAA TGAGAAAAAG TTACTAGAGT TAAGTGAAT

FIG. 6E

SEQ ID NO 23 (KGT 008-PBMC, gp 41)

AACCTGCTAA GAGCAATACA GGCCCAGCAG CAATTGCTGA GGCTATCTGT ATGGGGTATC
AGACAACTCC GAGCTCGCCT GCTAGCCTTA GAAACCTTAA TACAGAGTCA GCAACTCCTA
AACCTGTGGG GCTGTAAGGG AAGGCTAATC TGCTACACCT CAGTGCATTG GAATAAGACA
TGGACAAATA AGACAGATAA GGATTTGGAG GATATGTGGG ACAACCTAAC ATGGCAGCAA
TGGGATCAGC AGATAAGTAA CATAAGCGCC ACCATATATG AGGAAATACA AAAGGCACAA
GTACAACAAG AATACAATGA GAGAAAGTTG TTGGAGTTAG ATGAAT

SEQ ID NO 25 (MP 575, gp 41)

AACCTGCTAA GAGCAATACA GGCCCAGCAG CAATTGCTGA GGCTATCTGT ATGGGGTATC
ANACAACTCC GAGCTCGCCT GCTAGCATYA GAAACCTTAA TACAGAATCA GCAACTCCTG
AACCTATGGG GCTGTAAGGG AAKGCTAGTC TGCTACACAT CAGTAMAATG GAACAGGACA
TGGACAAACA ATACTAATTT AGATTCAATT TGGGAAAATC TAACATGGCA GGAATGGGAT
CAGCAGATAA GCAACATAAG CTCCACCATA TATGAAGAAA TACAAAAGGC ACAARTACAG
CAGGAATACR ATGAGAAAAA GTTGCTAGAG TTAGATKAAT

SEQ ID NO 27 (BSD 189, gp 41)

AACCTGCTAA GAGCAATACA GGCCCAGCAG CAATTGCTGA GGCTATCTGT ATGGGGTATC
AGACAACTCC GAGCTCGCCT GTTGGCCTTA GAAACCTTAA TACAGAATCA GCAACTCCTA
AACCTATGGG GATGTAAGGG AAGGCTAAGC TGCTACACAT CAGTACAATG GAACATGACA
TGGACAAACA ATTCTAATCT GGAAACAATT TGGGACAACC TAACATGGCA GGAATGGGAT
CAGCAGATAA ACAGCATAAG CTCTGTCATA TATGAAGAAA TACAAAAGGC ACAAGTACAG
CAGGAAACAA ACGAGAAAAA GTTGCTGGAG TTAGAGGAAT

SEQ ID NO 29 (BSD 649, gp 41)

AACCTGCTGA GAGCAATACA GGCCCAGCAG CAATTGCTGA GGCTATCTGT ATGGGGTATC
AGACAACTCC GAGCTCGCCT GCTAGCCTTA GAAACCTTAA TACAGAATCA GCAACTCCTA
AACCTATGGG GCTGTAGAGG AAGGCAAGTC TGCTACACAT CAGTAATATG GAATGAGACA
TGGATAGGAA ACGAAACCAT TTGGGAAGAA CTAAACATGGC AGGAATGGGA TCGGCAGATA
AGCAACATAA GCTCCACCAT ATATGATGAA ATACAAAAGG CACAAGTACA GCAGAACAA
AATGAGAAAA AATTGCTGGA GTTAGATGAA T

SEQ ID NO 31 (BSD 242, gp 41)

AACCTGCTGA GAGCGATACA GGCCCAGCAA CACTTGCTGA GGTTATCTGT ATGGGGTATT
AGACAACTCC GAGCTCGCCT GCAAGCCTTA GAAACCCTTA TACAGAATCA GCAACGCCTA
AACCTATGGG GCTGTAAGGG AAAGATGATC TGTTACACAT CAGTAAAATG GAACACATCA
TGGGAGACT ATAATGACAG TATTTGGGGC AACTANACAT GGCAACAATG GGACCAAGAA
ATAAGCAATG TAAGCTCCAT TATATATGAC AAAATACAAG AAGCACAGGA CCAACAGGAG
AGGAATGTAA AAGCATTGTT GGAGCTGGAT GAAT

SEQ ID NO 33 (533, gp 41)

AACCTGCTGA GAGCGATACA GGCCCAGCAA CACTTGCTGA GGTTATCTGT ATGGGGTATC
AGACAACTCC GAGCTCGCCT GCAAGCCTTA GAAACCCTTA TACAGAATCA GCAACGCCTA
AACCTATGGG GCTGTAAGGG AAAGATGATC TGTTACACAT CAGTACCATG GAACACATCA
TGGGAAACT ATAATGACAG TATTTGGGAT AAGTATACAT GGCAACAATG GGACCGAGAA
ATAGACAATG TAAGCTACAT TATATATGAA AAAATACAAG AAGCACAAGA CCAACAGGAG
AAGAATGTAA AAGCATTGTT GGAGCTAGAT GAAT

SEQ ID NO 35 (772 P94, gp 41)

AACCTGCTGA GAGCAATACA GGCCCAGCAA CATCTGCTGA GGTTATCTGT ATGGGTATT
AGACAACTCC GAGCTCGCCT GCAAGCCTTA GAAACCCTTA TGCAAAATCA GCAACTCCTA
AACCTATGGG GCTGTAAAGG AAAATCAATC TGCTACACAT CAGTACAAATG GAACAACACA
TGGGGAGGAA ATCTCTCAAT TTGGGACAGC TTAACATGGC AGCAATGGGA TCAACAGGTA
GCCAATGTAA GCTCTTTGAT ATATGACAAA ATACAAGAAG CACAAGAACA ACAGGAGGAA
AATGAAAGGG CCTTGCTGGA GTTAGATGAA T

SEQ ID NO 37 (MP 95B, gp 41)

AACCTGTTGA GAGCGATACA GGCCCAGCAA CACCTGCTGA GGTTATCTGT ATGGGTATA
AGACAACTCC GAGCTCGCCT GCAAGCCTTA GAAACCTTTA TACAGAACCA GCAACTCCTA
AGCCTATGGG GATGTAAGGG AAAGCTAATA TGTTACACAT CTGTAAAATG GAACACATCA
TGGGGAGGAA ATGAGAGTAT TTGGAACAAT CTAACATGGC AGCAGTGGGA TCAACAGATA
GACAACATAA GTTCCATCAT ATATGATGAA ATACAAAAGG CACAAGAGCA ACAGGAACAA
AATGAGAAAA GCTTGCTGGA GTTAGATGAA T

SEQ ID NO 39 (MP 539, gp 41)

AACCTGCTAA GAGCAATACA GGCCCAGCAA GAGCTGCTGA GGCTATCTGT ATGGGTATC
AGACAACTCC GAGCTCGCCT GCTAGCCTTA GAAACCTTTA TACGGAATCA GCAACTCCTA
AACCTCTGGG GCTGTAAGGG AAGGCTAATT TGCTATACAT CAGTACAATG GAACAAAACA
TGGGGTAATT TGAMWGATAA TGAGTCAATT TGGGATGACA TRACATGGCA GGAGTGGGAT
AAGCGGGTAG AKAATGTAAG YGCCACCATA TTTGAAGAAA TACGAAGGGC ACAAGAACAA
CAGGAACAAA ATGAGAAGGC TTTGCTAGAA TTAGATGAAT

SEQ ID NO 41 (MP 340-PBMC, V3)

TAAGATTATG GGAAAAAATA TCTCGGACAG TGCAGAAAAT ATCATAGTGA CCCTAAATTC
TACTGTAAAC ATAACCTGTG AGAGACCAGG GAATCAGTCA GTACAAGAGA TAAAAATAGG
TCCAATGGCC TGGTACAGCA TTGGCATAGG GACAACACCC GCAAACTGGT CAAGGATAGC
TTATTGCCAG TATAATATCA CTGATTGGGA AAAAGCCTTA AACAAACAG CTGAAAGTA
CTTAGAACTT GTAAACCATA CAAGAAATGA TACTGTTAGC ATAACATTCA ATAGCAGCAC
TGGTGGAGAT CTAGA

SEQ ID NO 43 (FABA-PBMC, V3)

ATTATAGGAA AAAACATTTC GGACACAGTGGG AAAAATATCA TAGTGACCCT AAATCCTACT
GTAAACCTGA CTTGTGAGAG ACCAGGAAAT AATTCAATAC AACAGATGAA AATAGGTCCA
CTGGCCTGGT ACAGCATGGG CCTAGAGAGA AACAAAGCT CAATCTCTAG ATTAGCTTAT
TGCAGGTATA ATACCACTAC GTGGGAACAA GCCTTACAAC AAACAGCTGA AAGGTATCTA
GAACTTGTGA ACAACACGGA CAATATTACA ATAATGTTCA ATCGCAGCAC TGATGGAGAT
TCAGAGGTAA CCCATATGCA TTTTAAC

SEQ ID NO 45 (MP 450-PBMC, V3)

ATAAGAATTA TGGGAAAAAA TATCTCGAAC AGTGCAGTAA ATATCATAGT GACCCTGAAT
TCTACTGTAA ACATAACCTG TGTGAGACCA TGGAATCAGA CAGTACAAGA GATACAAACA
GGTCCAATGG CCTGGTATAG CATTCACTTG AGGACACCAC TCGCAAACTT GTCAAGGATA
GCTTATTGCA AGTATAATGC CGCTGATTGG GAAAAAGCCT TAAAACAAAC AGCTGAAAGG
TACTTAGAAC TTGTAAATAA TACAAGTAAT AATAATGTTA CCATAATATT CAATAACAGC
ACTGGGTGGAG ATCCAGAGAC AACCCAGTTA CATTTTAACT GTCATGGAGT TCTTTA

SEQ ID NO 47 (MP 448-PBMC, V3)

ATAAGACTGA TGGCAAAAAA TATTTCGGCT ACTGGCCAAA ATATCATAGT GACCCTAAAT
ACTACTATAA ACATGACCTG CCAGAGACCA GGAAATCTAA CAATACAGGA AATAAAGATA
GGTCCAATGT CCTGGTACAG CATGGGCATA GGGCAGGAAG ACCACTCTAA GTCAAGAAAC
GCTTATTGTG AGTATAATAT CACTGATTGG GTACAGGCCT TAAAACAGAC AGCTGAAAGG
TATTTAGAAT TAGTAAACAA TACAAATACT AATATAAACA TGACATTCGA GAACAGTACT
GGAGGAGATC CAGAGGT

SEQ ID NO 49 (189, V3)

TAAGAATAAT GGGAAAAAAT ATTTCAGACA ATGGGAAAAA TATCATAGTA ACCCTAAATT
CTACTCTAAA AATGACCTGT GAGAGACCAG GGAATCATAC AGTACAACAG ATGAAGATAG
GTCCAATGTC CTGGTATAGC AGAGACTTAG AGAAAACAA TACCAGCTCA AGAAGAGCTT
TTTGCAAGTA TAATGCCACT AATTGGGAAA AAACCTTAAA ACAAATGGCT GAAAGTTATT
TAGAACTCGT AAACAATACA AGTAATAACA CAGTGACAAT GATATTCAAT ACAAGCAGTG
ATGGAGATCC AGAGGTACC

SEQ ID NO 51 (MP 539, V3)

AAGAAGGATG GGGGAAAAACA ATCCTTCAGA TCGGAAGAAG ATCCTAGTGA CCCTAAATTC
CCCTATAAAC ATAACCTGCG AGAGACCATA CTATCAGTCA GTACAAGAGT TAAGGATAGG
TCCAATGGCT TGGTACAGCA TGGGACCATTAGA ACCAGACAGG GCAGGCAGTG ACATAAGGGC
AGCTTATTGC AAGTATAATG CCTCTGACTG GAGAAATACA TTAAAAGGAG TAGCTGAGAG
ATATTTAGAA CTTAGAAATG AGGAAGGCCC GGTGAACGTG ACCTTCAATG GAAGTGCGGG
TGGAGATCCA GAGATACGCT TTCTGCATTT T

B. AMINO ACID SEQUENCES

SEQ ID NO 2 (MP 340-PBMC, gp41)

NLLRAIQAQQ ELLRLSVWGI RQLRARLLAL ETLIQNQQLL NLWGCKGRIV CYTSVKWNDT
WRHVTNMSEV WDKLTWQEWD RQIDNISYVI YDEIQRAQVQ QEQNEKKLLE LDE

SEQ ID NO 4 (MP 340, gp 41)

NLLXXIQAXQ ELLRLSVWGI RQXRXXLXAL ETLIXNQXLL NLWGCKGRIX CYTSVKWNXT
WKHVTXMSEV WDKLTWQEWD RXIDNISYVI YDXIQRAQVQ QEQNEKKLLE LDE

SEQ ID NO 6 (FABA-PBMC, gp 41)

NLLKAIQAQQ QLLRLSVWGI KQLRARLLAL ETLIQNQQLL NLWGCKGRLV CYTSVKWNNT
WTKNITNITD LDEIWDKFTW HQWDQQINHI SDVIYEEIPK AQVQQGPNER KLLELDE

SEQ ID NO 8 (FABA, gp 41)

XLLRAIQAQQ QLVRLSVWGI RQIRGXLVAL ETLIQNQQXX NLWGCKGRVV XYTSVKWNNT
WTKNITNITD LDEIWDKFTW QQWDQQINNI SDVLYEEIQK AQVQQEQNER KLLELDE

SEQ ID NO 10 (MP 450-PBMC, gp 41)

NLLRAIQAQQ QLLRLSVWGI RQLRARLLAL ETLIQNQQLL NLWGCKGRIV CYTSVKWNNT
WRNVTNMSEV WDTLTWQEWD RQIDNISYVI YDEIQRAQVQ QEQNEKKLLE LDE

SEQ ID NO 12 (MP 450, gp 41)

NLLRAIQAQQ QLLRLSVWGI RQLRARLLAL ETLIQNQQLL NLWGCKGRIV CYTSVKWNNT
WRNVTNMSEV WDTLTWQEWD RQIDNISYVI YDEIQRAQVQ QEQNEKKLLE LDE

SEQ ID NO 14 (MP 448-PBMC, gp 41)

NLLRAIQAQQ HLLRLSVWGI RQLRARLLAL ETLIQNQQLL NSWGCKGKIV CYTAVKWNRT
WTGNESIWDH LTWQQWDQQI DNVSSTIYEE ILKAQVQQEQ NEQKLLELDE

SEQ ID NO 16 (MP 448, gp 41)

NLLRAIQAQQ HLLRLSVWGI RQLRARLLAL ETLIQNQQLL NSWGCKGKIV CYTAVKWNRT
WTGNESIWDH LTWQQWDQQI DNVSSTIYEE ILKAQVQQEQ NEXXLLELDE

SEQ ID NO 18 (189, gp 41)

NLLKAIQAQQ ELLRLSVWGI RQLRARLLAL ETLIQDQQLL NLWGCKGRIV CYTSVKWNDT
WRHVTNMSEV WDKLTWQEWD RQIDNISYVI YDEIQRAQVQ QGPNEKKLLE LDE

SEQ ID NO 20 (320, gp 41)

NLLRAIQAQQ QLLRLSVWGI RQLRARLLAL ETLIQNQQLL NLWGCKGRLV CYTSVKWNKT
WINKTDTEIE NIWENLTWQE WDQQISNISS TIYEEIQKAQ IQQEHNEKKL LELDEW

SEQ ID NO 22 (BSD 422, gp 41)

NLLRAIQAQH QLLKLSVWGI RQLRARLLAL ETFIQNQQLL NLWGCKGNLI CYTSVKWNET
WKGDRTFTDM ENIWNNLTWQ EWDQQISNIS STIYDEIQKA QVQQEQNEKK LLELSE

SEQ ID NO 24 (KGT 008-PBMC, gp 41)

NLLRAIQAQQ QLLRLSVWGI RQLRARLLAL ETLIQSQQLL NLWGCKGRLI CYTSVHWNKT
WTNKTDKDLE DMWDNLTWQQ WDQQISNISA TIYEEIQKAQ VQQEYNERKL LELDE

SEQ ID NO 26 (MP 575, gp 41)

NLLRAIQAQQ QLLRLSVWGI XQLRARLLAX ETLIQNXQLL NLWGCKGXLV CYTSVXWNRT
WTNNTNLDSI WENLTWQEWD QQISNISSTI YEEIQKAQXQ QEYXEKKLLE LDX

SEQ ID NO 28 (BSD 189, gp 41)

NLLRAIQAQQ QLLRLSVWGI RQLRARLLAL ETLIQNQQLL NLWGCKGRLI CYTSVQWNMT
WTNNSNLETI WDNLTWQEWD QQINSISSVI YEEIQRAQVQ QEQNEKKLLE LEE

SEQ ID NO 30 (BSD 649, gp 41)
NLLRAIQAQQ QLLRLSVWGI RQLRARLLAL ETLIQNQQLL NLWGCRGRQV CYTSVIWNET
WIGNETIWEE LTWQEWDRQI SNISSTIYDE IQKAQVQQEQ NEKKLLELDE

SEQ ID NO 32 (BSD 242, gp 41)
NLLRAIQAQQ HLLRLSVWGI RQLRARLQAL ETLIQNQQRL NLWGCKGKMI CYTSVKWNTS
WGDYNDSIWG NXTWQQWDQE ISNVSSIIYD KIQEAQDQQE RNVKALLELD E

SEQ ID NO 34 (533, gp 41)
NLLRAIQAQQ HLLRLSVWGI RQLRARLQAL ETLIQNQQRL NLWGCKGKMI CYTSVPWNTS
WGNYNDSIWD KYTWQQWDRE IDNVSYIIYE KIQEAQDQQE KNVKALLELD E

SEQ ID NO 36 (722 P94, gp 41)
NLLRAIQAQQ HLLRLSVWGI RQLRARLQAL ETLMQNQQLL NLWGCKGKSI CYTSVKWNNT
WGGNLSIWDS LTWQQWDQQV ANVSSLIYDK IQEAQEQQEE NERALLELDE

SEQ ID NO 38 (MP 95B, gp 41)
NLLRAIQAQQ HLLRLSVWGI RQLRARLQAL ETFIQNQQLL SLWGCKGKLI CYTSVKWNTS
WGGNESIWNN LTWQQWDQQI DNISSIIYDE IQKAQEQQEQ NEKSLLELDE

FIG. 6N

SEQ ID NO 40 (MP 539-PBMC, gp 41)

NLLRAIQAQQ ELLRLSVWGI RQLRARLLAL ETFIRNQQLL NLWGCKGRLI CYTSVQWNKT
WGNLXDNESI WDDXTWQEWD KRVXNVXATI FEEIRRAQEQ QEQNEKALLE LDE

SEQ ID NO 42 (MP 340-PBMC, V3)

IMGKNISDSA ENIIVTLNST VNITCERPGN QSVQEIKIGP MAWYSIGIGT TPANWSRIAY
CQYNITDWEK ALKQTAERYL ELVNHTRNDT VSITFNSSTG GDL

SEQ ID NO 44 (FABA-PBMC, V3)

IIGKNISDSG KNIIVTLNPT VNLTCERPGN NSIQQMKIGP LAWYSMGLER NKSSISRLAY
CRYNTTTWEQ ALQQTAERYL ELVNNTDNIT IMFNRSTDGD SEVTHMHFN

SEQ ID NO 46 (MP 450-PBMC, V3)

IMGKNISNSA VNIIVTLNST VNITCVRPWN QTVQEIQTGP MAWYSIHLRT PLANLSRIAY
CKYNAADWEK ALKQTAERYL ELVNNTSNNN VTIIFNNSTG GDPETTQLHF NCHGVL

SEQ ID NO 48 (MP 448-PBMC, V3)

LMAKNISATG QNIIVTLNTT INMTCQRPGN LTIQEIKIGP MSWYSMGIGQ EDHSKSRNAY
CEYNITDWVQ ALKQTAERYL ELVNNTNTNI NMTFENSTGG DPE

FIG. 6N

SEQ ID NO 50 (189, V3)

IMGKNISDNG KNIIVTLNST LKMTCERPGN HTVQQMKIGP MSWYSMGLEK NNTSSRRAFC
KYNATNWEKT LKQMAERYLE LVNNTSNNTV TMIFNTSSDG DPEV

SEQ ID NO 52 (MP 539, V3)

RMGENNPSDR KKILVTLNSP INITCERPYY QSVQELRIGP MAWYSMTLER DRAGSDIRAA
YCKYNASDWR NTLKGVAERY LELRNEEGPV NVTFNGSAGG DPEIRFLHF

FIG. 60

| | |
|---|---|
| HIV-1 M CONSENSUS | L Q A R V L A V E R Y L K D Q Q L |
| |                           R |
| SIVcpz GAB | L Q A R L L A V E R Y L Q D Q Q L |
| SIVcpz ANT | L Q A R M L A V E K Y L R D Q Q I |
| HIV-1 O CONSENSUS | L R A R L L A L E T L I Q N Q Q L |
| |                    Q |

FIG. 7A

```
          10        20        30        40        50        60
          |         |         |         |         |         |
TTCACAATTTTAAAAGAAAAGGGGGATTGGGGGTACAGTGCAGGGGGAAAGAATAATAG

PheThrIleLeuLysGluLysGlyLeuGlyLysGlyThrValGlnGlyLysGlu------  Pol
SerGlnPhe---LysLysArgGlyAspTrpGlyValGlnCysArgGlyLysAsnArg
HisAsnPheLysArgLysGlyLysGlyValIleGlyGlyTyrSerAlaGlyGluArgIleIleAsp 70        80        90        100       110       120
          |         |         |         |         |         |
ACATAATAGCATCAGATATACAAACTAAAGAACTACAAAACAAATTACAAAATTCAAA

Thr-----HisGlnIleTyrLysLeuLysAsnTyrLysAsnLysLeuGlnLysPheLys   Pol
HisAsnSerIleArgTyrThrAsn---ArgThrLysThrLysAsnTyrLysAsnSerLys
IleIleAlaSerAspIleSerAspIleGlnThrLysGluLeuGlnLysIleThrLysIleGlnAsn 130       140       150       160       170       180
          |         |         |         |         |         |
ATTTTCGGGTTTATTACAGGACAGAGATCCAATTTGGAAAGGACCAGCAAAACTAC

IlePheGlyPheIleThrAlaGluIleGlnPheGlyLysAspGlnAsnTyr           Pol
PheSerGlyLeuLeuGlnLysGlnLeuAsnLeuGlnSerLysThrThr
PheArgValTyrTyrArgGlySerArgAspProIleTrpLysProAlaLysLeuLeu 190       200       210       220       230       240
          |         |         |         |         |         |
TCTGGAAAGGTGAAGGGCAGTAGTAATACAGGACAATGTGATATAAAGGTAGTACCAA

SerGlyLysValLysGlyGln------TyrArgThrIleValIle---Arg---TyrGln  Pol
LeuGluArg---ArgGlySerSerAsnThrGlyGln------TyrLysGlySerThrLys
TrpLysGlyValAlaValValIleGlnAspAsnSerAspIleLysAspIleLysValProArg
```

FIG. 8A-1

```
         250           260           270           280           290           300
          |             |             |             |             |             |
GAAGAAAAGCAAAAATCATTAAGGATTATGGAAAACAGATGGCAGGTGATGATTGTGTGG

GluGluLysGlnLysSerLeuArgIleMETGluAsnArgTrpGlnValMETIleValTrp         Vif
LysLysSerLysAsnHis---GlyLeuTrpLysThrAspGlyArg------LeuCysGly
ArgLysAlaLysIleIleLysAspTyrGlyLysGlnMETAlaGlyAspCysValAla            Pol 310           320           330           340           350           360
          |             |             |             |             |             |
CAAGTAGACAGAATGAGGATTAGAACATGGAACAGTCTAGTAAAGCATCATATGTATATT

GlnValAspArgMETArgIleArgThrTrpAsnSerLeuValLysHisHisMETTyrIle         Vif
Lys---ThrGlu---GlyLeuHisGluThrVal------SerIleIleCysIlePhe
SerArgGlnAsnGluAsp---AsnMETGluGlnSerSerLysAlaSerTyrValTyrPhe         Pol 370           380           390           400           410           420
          |             |             |             |             |             |
TCTAAGAAAGCTACAGATTGGGTTTATAAACATCACTATGATAGTAGACATCCAAAAGTA

SerLysLysAlaThrAspTrpValTyrLysHisHisTyrAspSerArgHisProLysVal         Vif
LeuArgGlyLeuGlnIleLeuGlyPheIleAsnIleThrMETIleValAspIleGlnLys---
---GluSerTyrArgLeuGlyLeu---ThrSerLeu------ThrLysSerLys 430           440           450           460           470           480
          |             |             |             |             |             |
AGCTCAGAAGTACACATTCCACTAGGGGATGCTAAATTGGTAATAAGAACATATTGGGGT

SerSerGluValHisIleProLeuGlyAspAlaLysLeuValIleArgThrTyrTrpGly         Vif
AlaGlnLysTyrThrPheHis---GlyMETLeuAsnTrp------GluHisIleGlyVal
LeuArgSerThrHisSerThrArgGlyCys---IleGlyAsnLysAsnIleLeuGlySer
```

FIG. 8A-2

```
        490           500          510         520          530          540
         |             |            |           |            |            |
CTACATACAGGAGAAAGAGACTGGGCATTGGGTCATGGGGTCTCCATAGAATGGAAACAG
LeuHisThrGlyGluArgAspTrpHisLeuGlyHisGlyValSerIleGluTrpLysGln                Vif
 TyrIleGlnGluLysGluIleThrGlyIleTrpValMETGlySerPro---AsnGlyAsnArg
  ThrTyrArgArgLysArgLeuAlaPheGlySerTrpGlyLeuHisArgMETGluThrGlu 550           560          570         580          590          600
         |             |            |           |            |            |
AGAAGATATAGCACACAAATAGATCCTGACCTAGCAGACCAGATGATTCACCTGCATTAT
ArgArgTyrSerThrGlnIleAspProAspLeuAlaAspGlnMETIleHisLeuHisTyr                Vif
 GluAspIleAlaHisLys---IleLeuThr---GlnThrAsn---PheThrCysIleIle
  LysIle---HisThrAsnArgSer---ProSerArgProThrAspSerProAlaLeuPhe 610           620          630         640          650          660
         |             |            |           |            |            |
TTTAACTGTTTTTCAGAATCTGCCATAAGAAAAGCCATACTAGGACAAGTAGTTAGACCT
PheAsnCysPheSerGluSerAlaIleArgLysAlaIleLeuGlyGlnValValArgPro                Vif
 LeuThrValPheGlnAsnLeuPro---GluLysProTyr---AspLys---LeuAspLeu
  ---LeuPhePheArgIleCysHisLysLysSerHisThrArgThrSerSer---Thr---

670           680          690         700          710          720
         |             |            |           |            |            |
AGGTGTGATTATCCAGCAGGACATAGTAAGGTAGGATCTCTACAATATTTGGCACTGAAA
ArgCysAspTyrProAlaGlyHisSerLysValGlySerLeuGlnTyrLeuAlaLeuLys                Vif
 GlyValIleGlnGlnAspIleValArg---AspLeuTyrAsnIleTrpHis---Lys
  Val---LeuSerArgThr------GlyArgIleSerThrIlePheGlyThrGluSer
```

```
                730        740        750        760        770        780
                 |          |          |          |          |          |
        GCATTAGTAACACCAACAAGGACAAAGCCACCTTTGCCTAGTGTTAAGAAATTAACAGAA
        AlaLeuValThrProThrArgThrLysProThrLysProProLeuProSerValLysLeuThrGlu        Vif
        His------HisGlnGlnGlyGlnSerHisLeuCysLeuValLeuArgAsn---GlnLys
        IleSerAsnThrAsnLysAspLysAlaThrPheAla---Cys---GluIleAsnArgArg 790        800        810        820        830        840
                 |          |          |          |          |          |
        GACAGATGGAACAAGCCCCAGAAGACCAGGGGGCACAGAGGGAGCGGTCCAATGTATGGA
        AspArgTrpAsnLysProGlnLysThrArgGlyHisArgGlySerGlyProMETTyrGly        Vif
        ThrGlyThrSerProArgArgProGlyGlyThrGluGlyAlaValGlnCysMETAsp
        GlnMETGluGlnAlaProGluAspGlnGlyAlaGlnArgGluArgSerAsnValTrpThr        Vpr 850        860        870        880        890        900
                 |          |          |          |          |          |
        CATTAGAGATCTATTAGAGGAGCTTAAACATGAAGCTGTTAGACATTTCCTAGGCCTTGGC
        His---IleTyr---ArgSerLeuAsnMETLysLeuLeuAspIlePheLeuGlyLeuGly        Vif
        IleArgSerIleArgGlyAla---Thr---SerCys---ThrPheSer---AlaLeuAla
        LeuAspLeuLeuLysHisGluAlaValArgHisPheProArgProTrpLeu        Vpr 910        920        930        940        950        960
                 |          |          |          |          |          |
        TCCAGGGATTAGGACAATATATCTATGAAACATATGGGGATACCTGGGAAGGAGTTGAAG
        SerArgAsp---AspAsnIleSerMETLysHisMETGlyIleProGlyLysGluLeuLys
        ProGlyIleArgThrIleTyrLeu---AsnIleTrpGlyTyrLeuGlyArgSer---Ser
        GlnGlyLeuGlyGlnTyrIleTyrGluThr⎯⎯⎯⎯⎯⎯⎯⎯⎯⎯⎯⎯⎯⎯GlyValGluAla        Vpr
```

```
         970         980         990         1000        1010        1020
          |           |           |           |           |           |
CTATAATAAGAATTTGCAACAACTACTGTTTGCCCATTTTAGAATTGGATGCCAACATA
Leu------GluPheCysAsnAsnTyrCysLeuProIleLeuGluLeuAspAlaAsnIle
    TyrAsnLysAsnPheAlaThrThrValCysProPhe---AsnTrpMETProThr---          Vpr
         IleIleArgIleLeuGlnLeuLeuPheAlaHisPheArgIleGlyCysGlnHisSer 1030        1040        1050        1060        1070        1080
          |           |           |           |           |           |
GTAGGATAGGAATTAACCCATCTAACCCAAGAGGAAAAGGAAGAGAAAATGGATCCAGTA
ValGly---GluLeuThrHisLeuThrGlnGluGluGluLysGluGluMETAspProVal          Tat
    ---AspArgAsn---ProIle---ProLysArgLysLysLysLysTrpIleGln---          Vpr
         ArgIleGlyIleAsnProSerAsnProArgGlyLysGlyArgArgAsnGlySerSerArg 1090        1100        1110        1120        1130        1140
          |           |           |           |           |           |
GATCCTGAGATACCCCCTGGCATCACCCTGGAAGTCAGCCCCAGACCCCTTGTAATAAC
AspProGluIleProProGlyIleThrLeuGluValSerProArgProLeuValIleThr          Tat
    IleLeuArgTyrProLeuGluGlyIleThrLeuGluValSerProArgProLeuValIleThr
         Ser---AspThrProLeuAlaSerProTrpLysSerAlaProAspProLeu------Leu  Vpr 1150        1160        1170        1180        1190        1200
          |           |           |           |           |           |
TGCTCTTGCAAAAAATGCTGCTACCATTGCTATGTGTTTCACAAGAAAGGGTTTGGAA
CysSerCysLysLysCysCysTyrHisCysTyrValCysPheThrArgLysGlyLeuGlu          Tat
    AlaLeuAlaLysAsnAlaAlaThrIleAlaMETCysValSerGlnGluArgValTrpLys
         LeuLeuGlnLeuLysMETLeuLeuProLeuLeuCysValPheHisLysLysGlyPheGlyAsn

FIG. 8A-5
```

```
             1210       1220       1230       1240       1250       1260
               |          |          |          |          |          |
ATCTCCTATGGCAGGAAGAAGCGACGAAGATCAGCCGCTGAAACGCGTCATCCAGATAAT
IleSerTyrGlyArgLysLysArgArgSerAlaAlaGluThrArgHisProAspAsn             Tat
SerProMETAlaGlyArgSerAspGluAspGlnProLeuLysArgValIleGlnIleIle          Rev
LeuLeuTrpGlnGluAlaThrLysIleSerArg---AsnAlaSerSerArg---Ser 1270       1280       1290       1300       1310       1320
               |          |          |          |          |          |
CAAGATATTGTACCAGAGCAGTAAGTAGCTAATGCAGCTTAGGGACCAGCTAACATTA
GlnAspIleValProGluGln---ValThrLeuMETGlnLeuArgAspGlnLeuThrLeu          Tat/Vpu
LysIleLeuTyrGlnSerSerLys---Arg---CysSerLeuGlyThrSer---His---          Rev
ArgTyrCysThrArgAlaValSerAsnAlaAla---GlyProAlaAsnIleAsn 1330       1340       1350       1360       1370       1380
               |          |          |          |          |          |
ATAATTATTAGTGCTTTGTTTGTTGCTTGTAAATGTAGTTCTATGGACATTTATTCTTAGACAA
IleIleIleSerAlaLeuLeuLeuValAsnValValLeuTrpThrPheIleLeuArgGln          Vpu
---LeuLeuValLeuCysCysLeu---MET---PheTyrGlyHisLeuPheLeuAspAsn
AsnTyr---CysPheValAlaCysLysCysSerSerMETAspIleTyrSer---ThrIle 1390       1400       1410       1420       1430       1440
               |          |          |          |          |          |
TATTTAAAGCAAAAGAAAACAAGATAGAAGGGAAGAAATACTTGAAAGGTTAAGAAGA
TyrLeuLysGlnLysLysAsnLysIleGluGlyLysLysTyrLeuLysGly---GluGlu          Vpu
Ile---SerLysArgAsnLysIleGluGlyGluGluAsnThrArgAsnThr---LysValLysAsn
PheLysAlaLysGluThrArg---LysValLysArgAsnThr---LysValLysLysAsn
```

```
      1690       1700       1710       1720       1730       1740
       |          |          |          |          |          |
TCCCACAGACCCCACTCCACATGAATATCCTTTACACAATGTGACAGATAACTTTAATAT                    Env

SerHisArgProHisSerThr---IleSerPheThrGlnCysAspArg---Leu---Tyr
ProThrAspProThrProHisGluTyrProLeuHisAsnValThrAspAsnPheAsnIle
ProGlnThrProLeuHisMETAsnIleLeuTyrThrMET---GlnIleThrLeuIleTyr 1750       1760       1770       1780       1790       1800
       |          |          |          |          |          |
ATGGAAAAATTACATGGTAGAACAAATGCAGGATGACATTATTAGCTTATGGGAACAGAG                    Env

METGluLysLeuHisGlyArgThrAsnAlaGly---HisTyr---LeuMETGlyThrGlu
TrpLysAsnTyrMETValGluGlnMETGlnAspAspIleIleSerLeuTrpGluGlnSer
GlyLysIleThrTrp---AsnLysCysArgMETThrLeuLeuAlaTyrGlyAsnArgVal 1810       1820       1830       1840       1850       1860
       |          |          |          |          |          |
TTTAAACCTTGTGTTCAAATGACTTTCCTGTGTACAAATGAATTGTACAAGTGTAAG                       Env

PheLysThrLeuCysSerAsnAspPheProValCysThrAsnGluLeuTyrLysCysLys
LeuLysProCysValGlnMETThrPheLeuCysValGlnMETAsnCysThrSerValSer
---AsnLeuValPheLys---LeuSerCysValTyrLys---IleValGlnVal---Val 1870       1880       1890       1900       1910       1920
       |          |          |          |          |          |
TAATAGTAGTGTAAGTAATAGTAGTGTAAGTAATAGTAGTGTAAGTAATAGTAGTGTAAG                    Env

------CysLys------CysLys------CysLys------CysLys
AsnSerValSerAsnSerSerValSerAsnSerSerValSerAsnSerSerValSer
IleValVal---ValIleValVal---ValIleValVal---ValIleValVal---Val
```

FIG. 8A-8

```
      1930        1940        1950        1960        1970        1980
       |           |           |           |           |           |
TGATAGTACTATACCCAAGAAGAAAAATAACAGCAGTCAGAGGACCTTCTGAAACAGTG                    Env
-----TyrTyrThrGlnGluGluLys---GlnGlnLeuArgGlyProSerGluThrVal
AspSerThrIleProLysLysLysAsnAsnSerSerSerGluAspLeuLeuLysGlnCys
    IleValLeuTyrProArgArgLysIleThrAlaAlaGlnArgThrPhe---AsnSerVal 1990        2000        2010        2020        2030        2040
       |           |           |           |           |           |
TGATTTTAATGCAACCACAGTTCTCAAAGACAAAAAGGAGAAAAAACAGACTCTATTTTA
---Phe---CysAsnHisSerSerGlnArgGlnLysGlyGluLysThrAspSerIleLeu
AspPheAsnAlaThrThrValLeuLysLysAspLysLysLysLysArgLysAsnArgLeuTyrLeuPheTyr
    IleLeuMETGlnProGlnPheSerLysThrLysArgArgLysAsnArgLeuTyrPheMET 2050        2060        2070        2080        2090        2100
       |           |           |           |           |           |
TGTATCAGATTTGATGAAACTGACAAATGTCACAAATGTATACATTAATTAA                           Env
CysIleArgPheAspGluThrAspLysCysHisLys---HisAsnValTyrIleAsn---
ValSerAspLeuMETLysLeuThrAsnValThrAsnAspThrMETTyrThrLeuIleAsn
    TyrGlnIle-----Asn---GlnMETSerGlnMETThrGlnCysIleHis---LeuIle 2110        2120        2130        2140        2150        2160
       |           |           |           |           |           |
TTGTAACTCCACAACCATTAAGCAAGCCTGTCCAAAGGTAACTTTTGAGCCAATTCCAAT                   Env
Leu---LeuHisAsnHis---AlaSerLeuSerLysGlyAsnPhe---AlaAsnSerAsn
CysAsnSerThrThrIleLysGlnAlaCysProLysValThrPheGluProIleProIle
    ValThrProGlnPheSerLysProValGlnArg---LeuLeuSerGlnPheGlnTyr
```

FIG. 8A-9

```
        2170        2180        2190        2200        2210        2220
         |           |           |           |           |           |
ACACTATTGTGCTCCAGGGGGTATGCCATCTTTAAGTGTAACAACAGAGTTTAATGG
ThrLeuCysSerSerGlyValCysHisLeu---Val---GlnHisArgVal-----Trp     Env
HisTyrCysAlaProAlaGlyTyrAlaIlePheLysCysAsnAsnThrGluPheAsnGly
ThrIleValLeuGlnArgGlyMETProSerLeuSerValThrThrGlnSerLeuMETGlu 2230        2240        2250        2260        2270        2280
         |           |           |           |           |           |
AACGGGCCCATGCAACAACATTACAGTAGTTACTTGTACACATGGTATCCAGGCCAACAGT          Env
AsnGlyProMETGlnHisTyrSerSerTyrLeuTyrThrTrpTyrGlnAlaAsnSer
ThrGlyProCysAsnAsnIleThrValValThrCysThrHisMETValSerGlyGlnGln---
ArgAlaHisAlaThrLeuGln---LeuLeuValHisMETValSerGlyGlnGln----

2290        2300        2310        2320        2330        2340
         |           |           |           |           |           |
GAGTACGCAACTAATATTAAACGGGACACTCTCTGAAGGAAAAATAAGAATTATGGAAG          Env
GluTyrAlaThrAsnIleLysArgAspThrLeu---ArgLysAsnLysAsnTyrGlyLys
SerThrGlnLeuIleLeuAsnGlyThrLeuSerGluGluLysIleArgIleMETGlyArg
ValArgAsn---Tyr---ThrGlyHisSerLeuLysGluLys---GluLeuTrpGluGlu 2350        2360        2370        2380        2390        2400
         |           |           |           |           |           |
AAATATCACGGACAGTGGAAAAATATTAGTTACCCTAAATTATACTATAAACATAAC                 Env
LysTyrHisGlyGlnTrpLysLysTyrTyrSerTyrProLysLeuTyrTyrLysHisAsn
AsnIleThrAspSerGlyLysValLysAsnIleIleValThrLeuAsnTyrThrIleAsnIleThr
IleSerArgThrValGluLysIleLeu---LeuPro---IleIleLeu---Thr---Leu
```

FIG. 8A-10

```
                    2410        2420        2430        2440        2450        2460
                      |           |           |           |           |           |
                    TTGTGAGAGAACATGGAATCAGTCAGTACAAGAGATACCTATAGTTCCAATGGCCTGGTA                    Env
                    Leu---GluAsnMETGluSerValSerThrArgAspThrTyrArgSerAsnGlyLeuVal
                    CysGluArgThrTrpAsnGlnSerValGlnGluIleGluIleGlyProMETAlaTrpTyr
                     ValArgGluHisGlyIleSerGlnTyrLysArgTyrLeu---ValGlnTrpProGlyThr 2470        2480        2490        2500        2510        2520
                      |           |           |           |           |           |
                    CAGCATGAGCGTAGAGAAAGACAAAAACACAACTGGCTCGAGGTCAGCAGATTGCCAGTA                    Env
                    GlnHisGluArgArgGluArgGlnLysHisAsnTrpLeuGluValSerArgLeuProVal
                    SerMETSerValGluLysAspLysAsnThrGlyLeuArgSerArgSerAlaAspCysGlnTyr
                     Ala---Ala---ArgLysThrThrGlnLeuAlaArgGlyGlnIleAlaSerIle 2530        2540        2550        2560        2570        2580
                      |           |           |           |           |           |
                    TAACACCCTCTGAATGGACAAGAGCCTTAGAACACAAACAGCTGAAAGGTATTTAGAACTGAT                 Env
                    ---HisLeu---METAspLysSerLeuArgThrAsnSer---LysValPheArgThrAsp
                    AsnThrSerGluTrpThrArgAlaLeuGluGlnThrAlaGluArgTyrLeuGluLeuMET
                    ThrProLeuAsnGlyGlnGluPro---AsnLysGlnLeuLysGlyIle---Asn------

2590        2600        2610        2620        2630        2640
                      |           |           |           |           |           |
                    GAACAATACAGGTAATACTGATAATACTACAGTGATATTCAATCATAGCACTGGTGGAGA                    Env
                    GluGlnTyrArg---Tyr------TyrTyrSerAspIleGlnSer---HisTrpTrpArg
                    AsnAsnThrGlyAsnThrAspAsnThrThrValIlePheAsnHisSerThrGlyGlyAsp
                    ThrIleGlnValIleLeuIleIleLeuGln---TyrSerIleIleAlaLeuValGluIle
```

```
      2650        2660        2670        2680        2690        2700
        |           |           |           |           |           |
TCCAGAGGTATCCTTCCTACATTTTAATTGTCATGGAGAGTTCTTCTATTGTAACACATC
SerArgGlyIleLeuProThrPhe---LeuSerTrpArgValLeuLeuLeu---HisIle
ProGluValSerPheLeuHisPheAsnCysHisGlyPheTyrCysAsnThrSer          Env
GlnArgTyrProSerTyrIleLeuIleValMETGluSerSerIleValThrHisLeu 2710        2720        2730        2740        2750        2760
        |           |           |           |           |           |
TGGGATGTTTAATTATACCTTTTCATGTAAAGGAACTAACTGTACCCAAGTTGGTTCCCA
TrpAspVal---LeuTyrLeuPheMET---ArgAsn---LeuTyrProSerTrpPhePro
GlyMETPheAsnTyrThrPheSerCysLysGlyThrAsnCysThrGlnValGlySerGln   Env
GlyCysLeuIleIleProPheHisValLysGluLeuThrValProLysLeuValProLys 2770        2780        2790        2800        2810        2820
        |           |           |           |           |           |
AAATGAATATAATAATCATACAACCAAGATACCTTGCAGGATAAAACAGGTGGTAAGGTC
Lys---Ile------SerTyrAsnGlnAspThrLeuGlnAlaArgSerProLysLysVal
AsnGluTyrAsnAsnHisThrThrLysIleProCysArgIleLysGlnValValArgSer  Env
METAsnIleIleIleIleGlnProArgTyrLeuAlaGly---AsnArgTrp---GlyHis 2830        2840        2850        2860        2870        2880
        |           |           |           |           |           |
ATGGATAAGGGGAGGGTCGGGACTCTATGCACCTCCCAGGCAAGGTCCCCTAAAATGTAG
METAspLysGlyArgValGlyThrLeuCysThrSerGlnAlaArgSerProLysMET---
TrpIleArgGlyGlySerGlyLeuTyrAlaProProArgGlnGlyProLeuLysCysSer  Env
Gly---GlyGluGlyArgAspSerMETHisLeuProGlyLysValPro---AsnValAla
```

FIG. 8A-13

```
           2890      2900      2910      2920      2930      2940
             |         |         |         |         |         |
         CTCAAACATAACTGGAATGATTCTACAATTGGATAAGCCATGGAACAGAAGTGGGCACAA
         LeuLysHisAsnTrpAsnAspSerThrIleGly---AlaMETGluGlnLysTrpAlaGln             Env
         SerAsnIleThrGlyMETIleLeuGlnLeuAspLysProTrpAsnArgSerGlyHisAsn
         GlnThr---LeuGlu---PheTyrAsnTrpIleSerHisGlyThrGluValGlyThrThr 2950      2960      2970      2980      2990      3000
             |         |         |         |         |         |
         CAATGACACCACATTTAGACCAATAGGAGGAGAAATGAAAGATATATGGAGAACTGAATT
         Gln---HisHisIle---ThrAsnArgArgArgAsnGluArgTyrMETGluAsn---Ile             Env
         AsnAspThrThrPheArgProIleGlyGlyGluMETLysAspIleTrpArgThrGluLeu
         METThrProHisLeuAspGln---GluGluLys---LysIleTyrGlyGluLeuAsnCys 3010      3020      3030      3040      3050      3060
             |         |         |         |         |         |
         GTTCAAATACAAAGTAGTAAAGGTAAAACCTTTTAGTGTGGCACCTACAAAAATTGCAAG
         ValGlnIleGlnSerSerLysGlyLysThrPhe---CysGlyThrTyrLysAsnCysLys             Env
         PheLysTyrLysValValLysValLysProPheSerValAlaProThrLysIleAlaArg
         SerAsnThrLys------Arg---AsnLeuLeuLysProPheSerValHisLeuGlnLysGlnGly 3070      3080      3090      3100      3110      3120
             |         |         |         |         |         |
         GCCAGTCATAGGCACGGGCACTCAAAGAAAAGAGAGCAGTAGGATTGGGAATGCTATT
         AlaSerHisArgHisGlyHisSerLysArgLysGluSerSerArgIleGlyAsnAlaIle             Env
         ProValIleGlyThrGlyThrGlnArgGluLysArgAlaValGlyLeuGlyMETLeuPhe
         GlnSer---AlaArgAlaLeuLysGluLysArgGluGln---AspTrpGluCysTyrSer
```

```
            3130       3140       3150       3160       3170       3180
             |          |          |          |          |          |
         CTTAGGGGTTCTAAGTGCAGCAGGTAGCACTATGGGCGCAGCGGGCAACAACGCTGGCGGT
         LeuArgGlySerLysCysSerArg---HisTyrGlyArgSerGlyAsnAsnAlaGlyGly     Env
         LeuGlyValLeuSerAlaAlaGlyLeuSerThrMETGlyAlaAlaAlaThrThrLeuAlaVal
         ---GlyPhe---ValGlnGlnValAlaLeuTrpAlaGlnArgGlnArgTrpArgTyr 3190       3200       3210       3220       3230       3240
             |          |          |          |          |          |
         ACAGACCCACACTTTGATGAAGGGTATAGTGCAACAGCAGGACAACCTGCTAAGAGCAAT
         ThrAspProHisPheAspGluGlyTyrSerAlaThrAlaGlyGlnProAlaLysSerAsn      Env
         GlnThrHisThrLeuMETLysGlyIleValGlyIleValGlnGlnGlnAspAsnLeuLeuArgAlaIle
         ArgProThrLeu-----ArgVal---CysAsnSerArgThrThrCys---GluGlnTyr 3250       3260       3270       3280       3290       3300
             |          |          |          |          |          |
         ACAGGCCCAGCAGCAATTGCTGAGGCTATCTGTATGGGTATCAGACAACTCCGAGCTCG
         ThrGlyProAlaAlaIleAlaGluAlaAlaIleCysMETGlyTyrGlnThrThrProSerSer    Env
         GlnAlaGlnGlnAsnLeuLeuArgLeuSerValTrpGlyValTyrGlnLeuArgGlnLeuArgAlaArg
         ArgProSerSerAsnCys---GlyTyrLeuTyrGlyValSerAspAsnSerGluLeuAla 3310       3320       3330       3340       3350       3360
             |          |          |          |          |          |
         CCTGCTAGCATTAGAAACCTTAATACAGAATCAGCAACTCCTGAACCTATGGGCTGTAA
         ProAlaSerIleArgAsnLeuAsnThrGluSerAlaThrProGluProMETGlyLeu---      Env
         LeuLeuAlaLeuGluThrLeuIleGlnAsnGlnGlnLeuLeuAsnLeuTrpGlyCysLys
         Cys---His---LysPro---TyrArgIleSerAsnSer---ThrTyrGlyAlaValArg
```

FIG. 8A-14

```
            3370        3380        3390        3400        3410        3420
             |           |           |           |           |           |
         GGGAAGGCTAGTCTGCTACACATCAGTACAATGGAACAGGACATGGACACAAACAATACTAA

GlyLysAlaSerLeuLeuHisIleSerThrMETGluGlnAspMETAspLysGlnTyr---
         GlyArgLeuValCysTyrThrSerValGlnTyrAsnArgThrTrpAsnArgThrAsnAsnThrAsn        Env
         GluGly---SerAlaThrHisGlnTyrAsnGlyThrGlyHisGlyThrGlnThrIleLeuIle 3430        3440        3450        3460        3470        3480
             |           |           |           |           |           |
         TTTAGATTCAATTTGGGAAAAATCTAACATGGCAGGAATGGGATCAGCAGATAAGCAACAT

PheArgPheAsnLeuGlyLysSerAsnMETAlaGlyMETGlySerAlaAspLysGlnHis
         LeuAspSerIleTrpGluAsnLeuThrTrpGlnGluTrpAspGlnIleIleSerAsnIle             Env
         ---IleGlnPheGlyLysIle---HisGlyArgAsnGlyIleIleSerArg---AlaThr---

3490        3500        3510        3520        3530        3540
             |           |           |           |           |           |
         AAGCTCCACCATATATGAGGAAATACAAAAGGCACAAATACAGCAGGAATACAATGAGAA

LysLeuHisHisIle---GlyAsnThrLysGlyThrAsnThrAlaGlyIleGln---Glu
         SerSerThrIleTyrGluGluIleGlnLysAlaGlnIleGlnGlnGluTyrAsnGluLys            Env
         AlaProProTyrMETArgLysTyrLysArgHisLysTyrSerArgAsnThrMETArgLys 3550        3560        3570        3580        3590        3600
             |           |           |           |           |           |
         AAAGTTGCTAGAGTTAGAATGAATGGGCCTTCTATTTGGAATTGGCTTGACATAACTAAATG

LysValAlaArgValArg---METGlyPheTyrLeuGluLeuAla---HisAsn---MET
         LysLeuLeuGluLeuAspGluTrpAlaSerIleTrpAsnTrpLeuAspIleThrLysCys          Env
         SerCys---Ser---METAsnGlyLeuLeuPheGlyIleGlyLeuThr---LeuAsnys,
```

```
         10         20         30         40         50         60
          |          |          |          |          |          |
ATTAAAGTAGTACCAAGAAGAAAGGCAAAAATAATCAGACATTATGGAAAAACAGATGGCA
IleLysValValProArgArgLysAlaLysIleIleArgHisTyrGlyLysGlnMETAla      Pol
LeuLys---TyrGlnGluGlyArgGlnLys---SerAspIleMETGluAsnArgTrpGln      Vif
---SerSerThrLysLysLysGlyLysAsnAsnGlnThrLeuTrpLysThrAspGlyArg 70         80         90        100        110        120
          |          |          |          |          |          |
GGTGTGCTGATATGGCAAGTGGACAGAAGTGGACAGAAAGTGAAAGCGTGGAACAGCCTGGTGAA
GlyAlaAspSerMETAlaSerGlyGlnThrGluSerGluSerValGluGlnProGlyGlu      Pol
ValLeuIleValTrpGlnValAspArgSerGlyGlnLysValLysAlaTrpAsnSerLeuVal   Vif
Cys-------TyrGlyLysTrpThrAspArgLys-------LysArgGlyThrAlaTrp---Asn 130        140        150        160        170        180
          |          |          |          |          |          |
ATACCATAAGTACAGAGGTCTAGGAAGGCCAAGGACTGGTGTTACAGAGACACCATTTGAATC
IlePro---ValGlnVal---GluGlyGlnGlyLeuValLeuGlnThrProPhe---Ile    Pol
TyrHisLysTyrArgSerArgLysAlaLysAspTrpCysTyrArgHisHisPheGluSer    Vif
ThrIleSerThrGlyLeuGluGlyArgProArgThrGlyValThrAspThrIleLeuAsnLeu 190        200        210        220        230        240
          |          |          |          |          |          |
TAGAAATCCAAGAGTCAGTTCAAGTTCACATATTCCAGTAGGATGGCTTGGGTAATAGT
---LysSerLysSerGlnPheLysCysThrTyrSerSerArgGlyAspGlyLeuGlyAsnSer
ArgAsnProArgValSerSerSerValHisIleProValGlyMETAlaTrpValIleVal    Vif
GluIleGlnGluSerValGlnValTyrIlePheGln---GlyTrpLeuGly---
```

FIG. 8B-2

```
          250        260        270        280        290        300
           |          |          |          |          |          |
         GACCACATATTGGGGATTGATGCCAGGGGAGAGAGAGGAACAGTTGGGACATGGGGTTAG

AspHisIleLeuGlyIleAspAlaArgGlyGluArgGlyThrValGlyThrTrpGly---    Vif
         ThrThrTyrTrpGlyLeuMETProGlyGluArgGluArgGluLeuGlnLeuHisGlyValSer
         ProHisIleGlyAsp---CysGlnGlyArgGluArgAsnSerTrpAspMETGlyLeuVal 310        320        330        340        350        360
           |          |          |          |          |          |
         TATAGAATGGCAGTACAAAAAGTATACAAAAGTGACCCTGAAACAGCAGACAGGAT

TyrArgMETAlaValGlnLysValTyrAsnThrAsp---Pro---AsnSerArgGlnAsp    Vif
         IleGluTrpGlnTyrLysLysTyrThrThrGlnIleAspProGluAspIleAspAlaAspArgMET
         ---AsnGlySerThrLysIleGlnHisArgLeuThrLeuLysGlnThrGly---

370        380        390        400        410        420
           |          |          |          |          |          |
         GATACATCTGTATTATTTTACCTGTTTTACAGATTCAGCAGTCAGGAAAGCCATCTTAGG

AspThrSerValLeuPheTyrLeuPheTyrArgPheSerSerGlnGluSerHisLeuArg    Vif
         IleHisLeuTyrTyrPheThrCysPheThrAspSerAlaValArgLysAlaIleLeuGly
         TyrIleCysIleIleLeuProValLeuGlnIleGlnSerGlyLysProSer---Gly 430        440        450        460        470        480
           |          |          |          |          |          |
         GCAGAGAATACTGACCAAGTGTGAATACCCTGCAGGACATAGTCAGGTAGGACATTGCA

AlaGluAsnThrAspGlnVal---IleProCysArgThr---SerGlyArgAspIleAla    Vif
         GlnArgIleLeuThrLysCysGluTyrProAlaGlyHisSerGlnValGlyHisSerGlnLeuGln
         ArgGluTyr---ProSerValAsnThrLeuGlnAspIleValArg---GlyHisCysAsn
```

```
                490            500            510            520            530            540
                 |              |              |              |              |              |
       ACTACTAGCTCTAAGAGTAGTAGTAAAAAGCAAAAAGAAATAAGCCTCCCCTACCCAGTGT
       ThrThrSerLeuLysSerSerSerLysLysLys---AlaSerProThrGlnCys
       LeuLeuAlaLeuArgValValLysAlaValValLysAlaAlaValArgAsnLysProProLeuProSerVal    Vif
       Tyr---Leu---Glu-------LysGlnLysGluIleSerLeuProTyrProValSer 550            560            570            580            590            600
                 |              |              |              |              |              |
       CCAGAAATTAACAGAAGAGATGGAGCGAGCACCTGAGGATCAGGGCCAGCTAGAGAG
       ProGluIleAsnArgArg---METGluArgAlaProGluAspGlnGlyProAlaArgGlu                 Vpr
       GlnLysLeuThrGluAspArgTrpSerGluHisLeuArgIleArgGlyGlnLeuGluSer                 Vif
       ArgAsn---GlnLysIleAspGlyAlaSerThr---GlySerGlyAlaSer---ArgAla 610            620            630            640            650            660
                 |              |              |              |              |              |
       CCTTTCAATGAATGGGCACTAGAGATCCTAGAAGAGCTAAAAAGCAGAGGCAGTAAGACAT
       ProPheAsnGluTrpAlaLeuGluIleLeuGluGluLeuLysSer---LysGlnArgGln---AspIle        Vpr
       LeuSerMETAsnGlyHis---ArgSer---LysSer---LysGlnArgGln---AspIle                 Vif
       PheGln---METGlyThrArgAspProArgArgAlaLysSerArgGlySerArgGlySerArgLysThrPhe 670            680            690            700            710            720
                 |              |              |              |              |              |
       TTCCCTAGGCAGTGGCTACAGGCCTTGGGACAGTACATTTATGAGACTTATGGGACACT
       PheProArgGlnTrpLeuGlnAlaLeuGlyGlnTyrIleTyrGluThrTyrGlyAspThr                 Vpr
       SerLeuGlySerGlyTyrArgProTrpAspSerThrPheMETArgLeuMETGlyThrLeu
       Pro---AlaValAlaThrGlyLeuGlyThrValHisLeu---AspLeuTrpGlyHisLeu
```

FIG. 8B-3

```
                                730       740       750       760       770       780
                                 |         |         |         |         |         |
                               TGGGTAGGAGTTATGGCAATTACAAGAATCTTACAACAAATACTATTGCCCATTTTAGA

TrpValGlyValMETAlaIleThrArgIleLeuGlnGlnIleLeuPheAlaHisPheArg        Vpr
                               Gly---GluLeuTrpGlnLeuGlnGluSerTyrAsnLysTyrLeuTyrLeuProIleLeuGlu
                               GlyArgSerTyrGlyAsnTyrLysAsnThrThrAsnLeuThrIleCysProPhe---Asn 790       800       810       820       830       840
                                 |         |         |         |         |         |
                               ATTGGATGTCAACATAGTAGAATAGGAATTAACCCAACTAATACAAGAGGAAGAGGAAGA

IleGlyCysGlnHisSerArgIleGlyIleAsnProThrAsnThrArgGlyArgGlyArg     Vpr
                               LeuAspValAsnIleValGlu---GluLeuThrGlnLeuIleGlnGluGluGluGluGlu
                               TrpMETSerThr------AsnArgAsn---ProAsn---TyrLysArgArgLysLys 850       860       870       880       890       900
                                 |         |         |         |         |         |
                               AGAAATGGATCCAGTAGATCCTGAGATGCCCCCTTGGCATCACCCTGGGAGTCAGCCCCA

ArgAsnGlySerSerArgSer---AspAlaProLeuAlaSerProTrpGluSerAlaPro        Vpr
                               GluMETAspProValAspProGluMETProProTrpHisHisProGlySerGlnProGln     Tat
                               LysTrpIleGln---IleLeuArgCysProLeuGlyIleThrLeuGlyValSerProArg 910       920       930       940       950       960
                                 |         |         |         |         |         |
                               GATCCCTTGTAACAATTGCTATTGCAAAAGATGCTGCTATTCATTGCCTTGTTTGTTTCAC

AspProLeu---GlnLeuLeuGlnLysMETLeuLeuSerLeuProCysLeuPheHis
                               IleProCysAsnAsnCysTyrCysLysArgCysCysTyrHisCysLeuValCysPheThr     Tat
                               SerLeuValThrIleAlaIleAlaAlaLysAspAlaAlaIleIleAlaLeuPheValSerGln
```

```
       970          980          990         1000         1010         1020
        |            |            |            |            |            |
AAGAAAGGGTTTGGGGATCTCCTATGGCAGGAAGAAGCGGGACAACGAAGAGCTGCTGC
LysLysGlyPheGlyAspLeuLeuTrpGlnGluGluAlaAlaThrThrLysSerCysCys        Tat
ArgLysGlyLeuGlyValLeuSerTyrGlyArgLysArgArgGlnArgArgAlaAlaAla        Rev
 GluArgValTrpGlySerProMETAlaGlyArgSerGlyAspAsnGluGluLeuLeuArg 1030         1040         1050         1060         1070         1080
        |            |            |            |            |            |
GAGCCATCCGGATAATAAAGATCTTGTACCAGAGCAGTAAGTAACGCTAATGCATCATAG
GluProSerGly------ArgSerCysThrArgAlaValSerAlaAsnAlaSer---          Tat/Vpu
SerHisProAspAsnLysAspLeuValProGluGln---ValThrLeuMETHisArg          Rev
 AlaIleArgIleIleLysIleLeuTyrGlnSerSerLys---Arg---CysIleIleGly 1090         1100         1110         1120         1130         1140
        |            |            |            |            |            |
GGACCTGCTAGTATTAATAATTAGTGTGTTGCTCTTTGCTGCTTATAAAATGTAATTATATGGAT
GlyProAlaSerIleAsnAsnTyr---CysPheAlaAlaTyrLysCysAsnTyrMETAsp        Vpu
AspLeuLeuValLeuIleIleIleSerAlaLeuLeuLeuIleAsnValIleIleTrpMET
 ThrCys---Tyr------LeuLeuValLeuCysCysLeu---MET---LeuTyrGlyCys 1150         1160         1170         1180         1190         1200
        |            |            |            |            |            |
GTTTATTCTTAGACAATATTTAGAACAGAAGAAACAGGACAGAAGGAAAGAGAGACATACT
ValTyrSer---ThrIlePheArgThrGluGlnLysGlyGlnLysGlyLysArgHisThr        Vpu
PheIleLeuArgGlnTyrLeuGluGlnLysLysGlnAspArgArgGlnArgAspIleLeu
 LeuPheLeuAspAsnIle---AsnArgArgAsnArgThrGluGlyLysGluThrTyrLeu
```

```
            1210       1220       1230       1240       1250       1260
              |          |          |          |          |          |
         TGAAAGGTTAAGAAGAATAGCAGAAATTAAAGATGATAGTGACTATGAAAGCAATGAAGA

---LysValLysLysAsnSerArgAsn---Arg--------Leu---LysGln---Arg           Vpu
         GluArgLeuArgArgIleAlaGluIleLysAspSerAspTyrGluSerAsnGluGlu             Env
             LysGly---GluGlu---GlnLysLeuLysMETIleValThrMETAlaMETLysArg 1270       1280       1290       1300       1310       1320
              |          |          |          |          |          |
         GGAGGAACAGGAAGTTAGAGATCTTATACATAGTCATGGCTTTGATAATCCCATGTTTGA

GlyGlyThrGlySer---ArgSerTyrThr---SerTrpLeu-------SerHisVal---         Vpu
         GluGluGlnGluValArgAspLeuIleLeuIleHisSerHisGlyPheAspAsnProMETPheGlu    Env
             ArgAsnArgLysLeuGluLeuIleLeuTyrIleValMETAlaLeuIleLeuProCysLeuSer

1330
              |
         GCTCTGATCAGAAGTATGC

AlaLeuIleArgSerMET                                                   Vpu
         Leu---SerGluValCys                                                   Env
             SerAspGlnLysTyr
```

FIG. 8B-6

```
                10                    20                    30                    40                    50                    60
                 |                     |                     |                     |                     |                     |
ATTAAAGTAGTACCAAGAAGAAAGGCAAAAATAATCAGAGATTATGGAAAACAAATGGCA

IleLysValValProArgArgLysAlaLysIleIleArgAspTyrGlyLysGlnMETAla                                              Pol
LeuLys---TyrGlnGluArgLys---SerGluIleMETGluAsnLysTrpGln                                                    Vif
---SerSerThrLysLysLysGlyLysLysAsnAsnGlnArgLeuTrpLysThrAsnGlyArg 70                    80                    90                   100                   110                   120
                 |                     |                     |                     |                     |                     |
GGTACTGATAGTATGGCAAGTAGACAGATAGAAACAGAAAGTGAAACAGCTTGGTGAA

GlyThrAspSerMETAlaSerArgGlnThrGluSerGluAsnValGluGluGlnLeuGlyGlu                                          Pol
ValLeuIleValTrpGlnValAspArgGlnLysValLysThrTrpAsnSerLeuValLys                                             Vif
Tyr------TyrGlyLys---ThrAspArgLys---LysArgGlyThrAlaTrp---Asn 130                   140                   150                   160                   170                   180
                 |                     |                     |                     |                     |                     |
ATACCATAAGTACAGGTCTAGAAGGCCAAGGACTGGTACTACAGACATCATTATGAAATC

IlePro---ValGlnVal---GluGlyGlnGlyLeuValLeuValLeuGlnThrSerLeu---Ile                                       Pol
TyrHisLysTyrArgSerArgLysAlaLysAspTrpTyrTyrArgHisHisTyrGluSer                                             Vif
ThrIleSerThrGlyLeuGlyArgProArgThrGlyThrThrAspIleIleMETAsnLeu 190                   200                   210                   220                   230                   240
                 |                     |                     |                     |                     |                     |
TAGAAATCCAAGAATCCAGTTCAGGTGTATATATTCCAGTGGGCCGGCTTGTATAGTAGT

---LysSerLysAsnGlnPheArgCysIleTyrSerSerArgAlaGlyLeuTyrSerSer
ArgAsnProArgIleSerSerGlyValTyrIleProValGlyProAlaCysIleValVal                                             Vif
GluIleGlnGluSerValGlnValTyrIlePheGln---GlyArgLeuVal
```

FIG. 8C-1

```
              250         260         270         280         290         300
               |           |           |           |           |           |
          GAACACATATTGGGGATTGATGCCAGGAGAAAGAGATGAACATCTGGGACATGGGGTTAG
          GluHisIleLeuGlyIleAspAlaArgArgLysArg---ThrSerGlyThrTrpGly---        Vif
          AsnThrTyrTrpGlyLeuMETProGlyLeuArgAspGluHisLeuGlyHisGlyValSer
          ThrHisIleGlyAsp---CysGlnGluLysGluMETAsnIleTrpAspMETGlyLeuVal 310         320         330         340         350         360
               |           |           |           |           |           |
          TATAGAATGGCAGTACACAAGAAGTATACAACACAGATTGACCCTGAAACAGCAGACAGGAT
          TyrArgMETAlaValGlnGluValTyrAsnThrAsp---Pro---AsnSerArgGlnAsp        Vif
          IleGluTrpGlnTyrLysTyrThrThrGlnIleAspProGluThrAlaAspArgMET
          ---AsnGlySerThrArgSerIleGlnHisArgLeuThrLeuLysGlnThrGly---

370         380         390         400         410         420
               |           |           |           |           |           |
          GATACATCTATACTATTTTACCTGTTTTACAGAATCAGGAAAGCCATCCTAGG
          AspThrSerIleLeuPheTyrLeuPheTyrArgIleSerAsnGlnGluSerHisProArg        Vif
          IleHisLeuTyrTyrPheThrCysPheThrGluSerAlaIleArgLysAlaIleLeuGly
          TyrIleTyrThrIleLeuProValLeuGlnAsnGlnSerGlyLysProSer---Gly 430         440         450         460         470         480
               |           |           |           |           |           |
          GCAGAGAGTACTGACCAAGTGTGAATACCCTGCAGGACATAGCCAGGTAGGACACTACA
          AlaGluSerThrAspGlnVal---IleProCysArgThr---ProGlyArgAspThrThr        Vif
          GlnArgValLeuThrLysCysGluTyrProAlaGlyHisSerGlnValGlyThrLeuGln
          ArgGluTyr---ProSerValAsnThrLeuGlnAspIleAlaArg---GlyHisTyrAsn
```

```
                490              500              510              520              530              540
                 |                |                |                |                |                |
       ACTACTAGCTCTAAGAGTTGTAGTAAAGAGAGAAAACATAGGCCTCCCCTACCCAGTGT
       ThrThrSerLysSerCysSerLysArgGluLysThr---AlaSerProThrGlnCys                                         Vif
       LeuLeuAlaLeuArgValValLysGluArgLysHisArgProProLeuProSerVal
       Tyr---Leu---GluLeu-----LysArgGluAsnIleGlyLeuProTyrProValSer 550              560              570              580              590              600
                 |                |                |                |                |                |
       CCAGAAATTAACAGAAGATAGATGGAACAAGCACCTGAGGATCAGGACCAGCTAGAGAG
       ProGluIleAsnArgArg---METGluGlnAlaProGluAspGlnGlyProAlaArgGlu                                      Vpr
       GlnLysLeuThrGluAspArgTrpAsnLysHisLeuArgIleArgAspGlnLeuGluSer                                      Vif
       ArgAsn---GlnLysIleAspGlyThrSerThr---GlySerGlyThrSer---ArgAla 610              620              630              640              650              660
                 |                |                |                |                |                |
       CCATTCAATGAATGGACACTAGAGCTCCTAGAGAGCTAAAAGCAGAAGCAGTAAGACAT
       ProPheAsnGluTrpThrLeuGluLeuLeuGluLeuLysAlaGluAlaValArgHis                                         Vpr
       HisSerMETAsnGlyHis---SerSer---LysSer---LysGlnLysGln---AspIle                                     Vif
       IleGln---METAspThrArgAlaProArgAlaArgArgAlaLysSerArgSerLysThrPhe 670              680              690              700              710              720
                 |                |                |                |                |                |
       TTTCCTAGGCCTTGGCTACAGGCCTTGGGACAATACATTTATGATACTTATGGGACACT
       PheProArgProTrpLeuGlnAlaLeuGlyGlnTyrArgIleTyrAspThrTyrGlyAspThr                                   Vpr
       PheLeuGlyLeuGlyTyrArgProTrpAspAsnThrPheMETIleLeuMETGlyThrLeu
       Ser---AlaLeuAlaThrGlyLeuGlyThrIleHisLeu---TyrLeuTrpGlyHisLeu
```

```
                    730        740        750        760        770        780
                     |          |          |          |          |          |
         TGGGTAGGAGTTATGGCAATTATAAGACTCTTACAATTAATGATATATTGCCCATTTTAGA
                                                                                    Vpr
         TrpValGlyValMETAlaIleIleArgLeuLeuGlnLeuMETIlePheAlaHisPheArg
         Gly---GluLeuTrpGlnLeu---AspSerTyrAsn-----TyrLeuProIleLeuGlu
         GlyArgSerTyrGlyAsnTyrLysThrLeuThrIleAsnAspIleCysProPhe---Asn 790        800        810        820        830        840
                     |          |          |          |          |          |
         ATTGGATGCCAACATAGTAGAATAGGAATTAACCCATCTAACACAAGAGGAAGAGGAAGA
                                                                                    Vpr
         IleGlyCysGlnHisSerArgIleGlyIleAsnProSerAsnThrArgGlyArgGlyArg
         LeuAspAlaAsnIleValGlu---GluLeuThrHisLeuThrGlnGlyGluGluGluGlu
         TrpMETProThr---AsnArgAsn---ProIle---HisLysArgLysArgLysLys 850        860        870        880        890        900
                     |          |          |          |          |          |
         AGAAATGGATCCAGTAGAGACCCTGAGATGCCCCCCTTGGCATCACCCTGGAAGTCAGCCCCA
                                                                                    Vpr
                                                                                    Tat
         ArgAsnGlySerSerArgPro---AspAlaProLeuAlaSerProTrpLysSerAlaPro
         GluMETAspProValAspProGluMETProProTrpHisHisProGlySerGlnProGln
         LysTrpIleGln---ThrLeuArgCysProLeuGlyIleThrLeuGluValSerProArg 910        920        930        940        950        960
                     |          |          |          |          |          |
         GAATCCTTGTAATAAATGCTATTGCAAAAATGCTGCTATCATTGCTATGTTTGTTTCAC
                                                                                    Tat
         GluSerLeu-----METLeuLeuGlnLysMETIleLeuLeuSerLeuLeuCysLeuPheHis
         AsnProCysAsnLysCysTyrCysLysLysCysTyrHisCysTyrValCysPheThr
         IleLeuValIleAsnAlaIleAlaIleAlaLysAsnAlaAlaIleIleAlaMETPheValSerGln
```

```
         970        980        990       1000       1010       1020
          |          |          |          |          |          |
AAGCAAGGGTTTGGGAATCTCCTATGGCAGGAAGAAGCGACGACGACCAGCAGCTGCTGC
LysGlnGlyPheGlyAsnLeuLeuTrpGlnGluGlyAlaThrThrSerSerCysCys           Tat
SerLysGlyLeuGlyIleSerTyrGlyArgLysLysArgArgLysArgSerCysCys           Rev
AlaArgValTrpGluSerProMETAlaGlyArgSerAspAspAspSerProAlaAlaAla
                        AlaArgValTrpGluSerProMETAlaGlyArgSerAspAspAspGlnGlnLeuLeuGln 1030       1040       1050       1060       1070       1080
          |          |          |          |          |          |
AAGCCGCCCGGATAATAAAGATCTTGTACCAGAGCAGTAAGTAACGCTAATGCAGCAAAA
LysProProGly---ArgSerCysThrArgAlaValSerAsnAlaAsnAlaAlaAlaLys        Tat/Vpu
SerArgProAspAsnLysAspLeuValProGluGln---ValThrLeuMETGlnLeuLys        Rev
AlaAlaArgIleIleLysIleLeuTyrGlnSerSerLys---Arg---CysSerLysArg 1090       1100       1110       1120       1130       1140
          |          |          |          |          |          |
GGACCTGCTATTATTAGTAATAATTAGAAATAATAATTCTATGGAT
GlyProAlaIleIleSerAsnTyr---CysPheAlaAlaTyrLysTyrAsnSerMETAsp        Vpu
AspLeuLeuLeuLeuVaIIleIleSerAlaLeuLeuLeuIleAsnIleIleLeuTrpMET
ThrCysTyrTyrTyr------LeuLeuValLeuCysCysLeu---Ile---PheTyrGlyCys 1150       1160       1170       1180       1190       1200
          |          |          |          |          |          |
GTTTAATCTTAGAAAATATTTAGAACAAAAGAAAACAAGAAGGAAAGAGAAATACT
Val---Ser---LysIlePheArgThrLysGluThrArgGlnLysGlyLysArgAsnThr        Vpu
PheAsnLeuArgLysTyrLeuGluGlnLysGlnAspArgArgGluArgGluLysLeuLeu
LeuIleLeuGluAsnIle---AsnLysArgAsnLysThrGluGlyLysGluLysTyrLeu
```

FIG. 8C-6

```
         1210      1220      1230      1240      1250      1260
           |         |         |         |         |         |
TGAAAGGATAAGAAGAATAAGAGAAATTAGAGAGATGATAGTGACTATGAAAGCAATGAAGA

---LysAspLysLysAsnLysArgAsn---Arg------Leu---LysGln---Arg
GluArgIleArgArgIleArgGluIleArgAspSerAspTyrGluSerAsnGluGlu        Vpu
LysGly---GluGlu---GluLysLeuGluMETIleValThrMETLysAlaMETLysArg 1270      1280      1290      1300      1310      1320
           |         |         |         |         |         |
GGAAGAACAAGAAGTTAGGGGTCATCTTGTGCATATGTTTGGCTTTGCTAATCCCGTGTT

GlyArgThrArgSer---GlySerSerCysAlaTyrValTrpLeuCys---SerArgVal
GluGluGlnGluValArgGlyValHisMETPheGlyPheAlaAsnProValPhe          Vpu
LysAsnLysLysLeuGlyValIleLeuCysIleLeuAlaLeuLeuIleProCysLeu       Env 1330      1340
           |         |
TGAGATCTAATGACCTATATGC

---AspLeuMETThrTyrMET
GluIle------ProIleCys                                           Vpu
ArgSerAsnAspLeuTyr                                              Env
```

```
                    10         20         30         40         50         60
                    |          |          |          |          |          |
         ATCAAGGTAGTAGTACCAAGAAGAAAAGCAAAAATCACTCAGGGATTATGGAAAAACAGATGGCA

IleLysValValProArgArgLysAlaLysIleLeuArgAspTyrGlyLysGlnMETAla        Pol
         SerArg---TyrGlnGluGluLysGluLysTyrSerGlyIleMETGluAsnArgTrpGln         Vif
         GlnGlySerThrLysLysLysSerLysAsnThrGlnGlyLeuTrpLysThrAspGlyArg 70         80         90        100        110        120
                    |          |          |          |          |          |
         GGTGCTGATAGTATGGCAAGTGGACAGAGAAAGTGAAAGCATGAATAGCCTGGTAAA

GlyAlaAspSerMETAlaSerGlyGlnThrGluSerGluSerMETGlu---ProGlyLys         Pol
         ValLeuIleValTrpGlnValAspArgGlnLysValLysAlaTrpAsnSerLeuValLys         Vif
         Cys------TyrGlyLysTrpThrAspArgLys---LysHisGlyIleAlaTrp---Asn 130        140        150        160        170        180
                    |          |          |          |          |          |
         ATACCATAAGTACAGGTCTAGAAAGACCCAGAACTGGGATTATAGACATCATTATGAAAAT

IlePro---ValGlnVal---LysAspProGluLeuGlyLeu---ThrSerLeu---Asn
         TyrHisLysTyrArgSerArgLysThrGlnAsnTrpAspTyrArgHisHisTyrGluIle         Vif
         ThrIleSerThrGlyLeuGluArgProArgThrGlyIleIleAspIleIleMETLysSer 190        200        210        220        230        240
                    |          |          |          |          |          |
         CAGAAATCCAAGAATCAGCTCAGGTGTATATATTCCAGTAGTGAAGCTAAGATAGTAGT

GlnLysSerLysAsnGlnLeuArgCysIleTyrSerSerArg---Ser---AspSerSer
         ArgAsnProArgIleSerArgGlyValTyrIleProValGlyGluAlaLysIleValVal         Vif
         GluIleGlnGluSerAlaGlnValTyrIleProheGln---ValLysLeuArg------
```

```
                    250        260        270        280        290        300
                     |          |          |          |          |          |
             GACTACATATTGGGGATTAATGCCAGGGGAAAGAGATGAGCATTTGGGACATGGAGTCAG
             AspTyrIleLeuGlyIleAsnAlaArgGlyLysArg---AlaPheGlyThrTrpSerGln                   Vif
             ThrThrTyrTrpGlyLeuMETProGlyGluArgAspGluHisLeuGlyHisGlyValSer
              LeuHisIleGlyAsp---CysGlnGlyLysGluMETSerIleTrpAspMETGluSerVal 310        320        330        340        350        360
                     |          |          |          |          |          |
             TATAGAATGGCAATACAAAATTATAGTACACAGATTGACCCTGAAACAGCAGATAAAAT
             TyrArgMETAlaIleGlnLysLeu---TyrThrAsp---Pro---AsnSerArg---Asn                   Vif
             IleGluTrpGlnTyrLysAsnThrTyrSerThrGlnIleAspProGluThrAlaAspLysIle
              ---AsnGlyAsnThrLysIleIleValHisArgLeuThrLeuLysGlnIleIleLys---

370        380        390        400        410        420
                     |          |          |          |          |          |
             AATACATCTGCATTATTTCACCTGTGTTTTACAGAGTCAGCAATCAGGAGAGCCATTTTAGG
             AsnThrSerAlaLeuPheHisLeuPheTyrArgValSerAsnGlnGluSerHisPheArg                   Vif
             IleHisLeuHisTyrPheThrCysPheThrGluSerAlaIleArgArgAlaIleLeuGly
              TyrIleCysIleIleSerProValLeuGlnSerGlnSerGlyGluGlyProPhe---Gly 430        440        450        460        470        480
                     |          |          |          |          |          |
             GCAGAGAGTGCTGACCAGGTGTGAATACCCTGCAGGACATAGTCAGGTAGGGACACTGCA
             AlaGluSerAlaAspGlnVal---IleProCysArgThr---SerGlyArgAspThrAla                   Vif
             GlnArgValLeuThrArgCysGluTyrProAlaGlyHisSerGlnValGlyThrLeuGln
              ArgGluCys---ProGlyValAsnThrLeuGlnThrLeuGlnValArg---GlyHisCysAsn
```

FIG. 8D-3

```
           490        500        510        520        530        540
            |          |          |          |          |          |
       ACTCCTAGCATTAAGAGAGCAGTAGTAAAAGACAAAAGAAGTAAACCCTCCCCTACCCAGTGT
       ThrProSerIleLysSerSerLysArgGlnLysLys---ThrSerProThrGlnCys        Vif
       LeuLeuAlaLeuArgAlaAlaValAlaValLysAspLysArgSerLysProProLeuProSerVal
       Ser---His---GluGln-----LysThrLysGluValAlaAsnLeuProTyrProValSer 550        560        570        580        590        600
            |          |          |          |          |          |
       CCAGAAGTTAACAGGAGACAGATGGAACAGGCACCTGAGAATCAGGGACCAGCAAGAGAG
       ProGluValAsnArgArgGlnMETGluGlnAlaProGluAsnGlnGlyProAlaArgGlu        Vpr
       GlnLysLeuThrGlyAspArgTrpAsnArgHisLeuArgIleArgAspGlnGlnSer            Vif
       ArgSer---GlnGluThrAspGlyThrGlyThr---GluSerGlyThrSerLysArgAla 610        620        630        640        650        660
            |          |          |          |          |          |
       CCATTCAATGAATGGGCATTAGAGACCCTGGAAGAAATAAAAGCAGAAGAAGCAGTAAGACAC
       ProPheAsnGluTrpAlaLeuGluThrLeuGluGluIleLysAlaGluAlaValAlaArgHis      Vpr
       HisSerMETAsnGlyHis---ArgProTrpLysLys---LysGlnLysGln---AspThr        Vif
       IleGln---METGlyIleArgAspProArgAsnLysSerArgSerArgSerLysThrLeu 670        680        690        700        710        720
            |          |          |          |          |          |
       TTTCCTAGGCCTTGGCTACACAAAGCTTAGGACAATACATCTATGAGACTTATGGAGACACC
       PheProArgProTrpLeuGlnSerLeuGlyGlnTyrIleTyrGluThrTyrGlyAspThr        Vpr
       PheLeuGlyLeuGlyTyrLysAla---AspAsnThrSerMETArgLeuMETGluThrPro
       Ser---AlaLeuAlaThrLysLeuArgThrIleHisLeu---AspLeuTrpArgHisLeu
```

FIG. 8D-4

```
         730         740         750         760         770         780
          |           |           |           |           |           |
TGGGAAGGAGTTATGGCAATCATAAGAATCTTACAACAGTTGATATTTGCCCATTTTAGA
TrpGluGlyValMETAlaIleIleArgIleLeuGlnGlnLeuIlePheAlaHisPheArg              Vpr
GlyLysGluLeuTrpGlnSer---GluSerTyrAsnSer---TyrLeuProIleLeuGlu
GlyArgSerTyrGlyAsnHisLysAsnLeuThrThrValAspIleCysProPhe---Asn 790         800         810         820         830         840
          |           |           |           |           |           |
ATTGGATGCCAACATAGTAGAATAGGAATTACCCCATCTAACGCAAGAGGAAGAGGAAGA
IleGlyCysGlnHisSerArgIleGlyIleThrProSerAsnAlaArgGlyArgGlyArg              Vpr
LeuAspAlaAsnIleValGlu---GluLeuProHisLeuThrGlnGluGluGluGluGlu
TrpMETProThr------AsnArgAsnTyrProIle---ArgLysArgLysArgLysLys 850         860         870         880         890         900
          |           |           |           |           |           |
AGAAATGGATCCAGTAGATCCTGAGGTGCCCCCCCTGGCATCACCCTGGAAGTCAGCCCCC
ArgAsnGlySerSerArgSer---GlyAlaProLeuAlaSerProTrpLysSerAlaPro              Vpr
GluMETAspProValAspProGluValProProTrpHisProGlySerGlnProPro                 Tat
LysTrpIleGln---IleLeuArgCysProProGlyIleThrLeuGluValSerProGln 910         920         930         940         950         960
          |           |           |           |           |           |
AACCCCTTGCAACGCTTGCTATTGCAAAAGATGCTGTTATCATTGCTATCTTTGTTTCAC
AsnProLeuGlnArgLeuLeuLeuGlnLysMETLeuLeuSerLeuLeuPheHis
ThrProCysAsnAlaCysTyrCysLysCysTyrCysArgCysLysCysTyrLeuCysPheThr           Tat
ProLeuAlaThrLeuAlaLeuAlaLysAspAlaValIleIleAlaIlePheValSerGln
```

```
          970         980         990        1000        1010        1020
           |           |           |           |           |           |
AAAGAAGGGTTTGGGAATCTCCCATGGCAGGAAGAAGCGACGACGACCAGCAGCTGCTGC
LysGluGlyPheGlyAsnLeuProTrpGlnGluGluAlaThrThrSerSerCysCys
LysLysLysLeuGlyLysIleSerHisGlyLysIleGlyLysArgArgProAlaAlaAla   Tat
ArgArgValTrpGluSerProMETAlaGlyLysLysArgSerAspAspGlnGlnLeuLeuGln   Rev 1030        1040        1050        1060        1070        1080
           |           |           |           |           |           |
AAGCTCTTCGAATAATAAAGATCTTGTACCAGAGCAGTAAGTAAAGCTAATGCATCATAA
LysLeuPheGlu------ArgSerCysThrArgAlaValSerLysAlaAsnAlaSer---     Tat/Vpu
SerSerSerAsnAsnLysAspLeuValProGluGln---ValLysLeuMETHisHisLys     Rev
AlaLeuArgIleIleLysIleLeuTyrGlnSerLys---Ser---CysIleIleArg 1090        1100        1110        1120        1130        1140
           |           |           |           |           |           |
GGACTTGCTAATCTTAATAGTTGCTAGTATTTGCTTTTTACAAATATAGTGATATGGAC
GlyLeuAlaAsnLeuAsnSerCys---TyrPheAlaPheTyrLysTyrSerAspMETAsp
AspLeuLeuIleLeuIleValAlaSerIleLeuLeuPheThrAsnIleValIleTrpThr    Vpu
ThrCys---Ser------LeuLeuValPheCysPheLeuGlnIle------TyrGlyHis 1150        1160        1170        1180        1190        1200
           |           |           |           |           |           |
ATTTATTCTTAAGAAATATTTAGAGCAGAAGAAGAACAAGATAGAAGGGAAAGAGAACTACT
IleTyrSer---GluIlePheArgAlaGluGluGlyThrArg------LysGlyLysArgThrThr
PheIleLeuLysLysTyrLeuGluGlnLysGluGlnAspArgArgGluArgGluLeuLeu     Vpu
LeuPheLeuArgAsnIle---SerArgArgAsnLysIleGluGlyLysGluAsnTyr---
```

FIG. 8D-5

```
          1210      1220      1230      1240      1250      1260
           |         |         |         |         |         |
         GAAAAGAATAAAAAGAATAAGAGAAGTCAGGGATGATAGTGATTATGAAAAGCAATGGAGA

GluLysAsnLysLysAsnLysArgSerGlnGly------Leu---LysGlnTrpArg       Vpu
         LysArgIleLysArgIleArgGluValArgAspSerAspTyrGluSerAsnGlyAsp       Env
          LysGlu---GluLysSerGlyMETIleValIleMETLysAlaMETGluMET 1270      1280      1290      1300      1310      1320
           |         |         |         |         |         |
         TGGAGGACAAGAAGTTATACACATCTTGTGCATACTCATGGTTTTGTTAACCCCATGTTTGA

TrpArgThrArgSerTyrThrSerCysAlaTyrSerTrpPheCys---ProHisVal---     Vpu
         GlyGlyGlnValIleHisLeuValHisThrHisGlyPheValAsnProMETPheGlu        Env
         GluAspLysLysLeuTyrIleLeuCysIleLeuMETValLeuLeuThrProCysLeuSer

1330
           |
         GCTCTGACAAGCTATATCG

AlaLeuThrSerTyrIle                                               Vpu
         Leu---GlnAlaIleSer
         SerAspLysLeuTyr                                                  Env
```

FIG. 8D-6

HIV-1 GROUP O ANTIGENS AND USES THEREOF

The current invention relates to new HIV-1 group O antigens, nucleic acids encoding them, and the use of said antigens and/or nucleic acids as reagents in the diagnosis and prophylaxes of AIDS. It also relates to new HIV-1 group O strains comprising these antigens.

The human immunodeficiency virus (HIV) is the responsible agent for the acquired immunodeficiency syndrome (AIDS) in humans. AIDS is usually associated with two distinct types of HIV: HIV-1 and HIV-2, initially described by Gallo et al. (1984) and Barré-Sinoussi et al. (1983) on the one hand, and Clavel et al. (1986) on the other hand. Although both types, HIV-1 and HIV-2, cause a dysfunction of the immune system and induce similar clinical symptoms in infected persons, they are genetically distinct (Clavel et al. 1986) Epidemiological studies have shown that the prevalence of HIV-2 infection is confined mainly to West Africa, whereas HIV-1 infection is a world wide problem. Numerous HIV-1 isolates have been obtained and sequenced from diverse geographical locations. At present, at least ten distinct subgroups or clades (A to J) of HIV-1 have been described, equidistantly related in phylogenetic analysis of the env-and/or gag-gene (Kostrikis et al. 1995; Louwagie et al. 1993; Myers et al 1995).

More recently, HIV-1 group O (for "Outlier") strains have been described as divergent viruses, belonging to an independent cluster (Charneau et al. 1994; Gürtler et al. 1994; Myers et al 1995; Sharp et al. 1994; Vanden Haesevelde et al. 1996), when compared to the vast majority of worldwide HIV-1 strains classified as group M (for "Major"). Although these two groups of viruses share the same genomic structure, the elevated level of divergence between them supports the hypothesis of independent origins.

Most of the currently described group O strains have been characterized from Cameroonian patients or from patients who have travelled in Cameroon (De Leys et al. 1990; Gürtler et al. 1994; Loussert-Ajaka et al. 1995; Vanden Haesevelde et al. 1996). Group O infection is not restricted to Cameroon and its neighbouring countries, but it has also been documented in West, East, and Southern Africa (Peeters et al. 1996; Peeters et al. submitted). In addition, cases of group O infection have been described in several European countries (France, Spain, Germany, Norway) and in the USA (Centres for Disease control and Prevention 1996; Charneau et al. 1994; Hampl et al 1995; Soriano et al. 1996).

Several hypotheses have been developed to explain the paradoxical observation that HIV-1 has been present in African countries for many decades (probably about a century) and that it has only become apparent over the past 15 years. The answer should probably take in account numerous parameters such as demographic, sociologic, ethologic, ethnologic, and virologic parameters. In a mathematical model, May and Anderson (1990) suggest that initial chains of infection were found in isolated populations at low rates with some 'sparks' thrown in the neighbouring villages, and the exponential epidemic has started when there was a sufficient number of fire-boxes. To date, no differences were observed between HIV-1 group M and O pathogenic potential even though a limited number of patients infected by these latter strains have been reported. However some of them have already died or reached stage IV in the CDC classification (Charneau et al. 1994; Gürtler et al. 1994; Loussert-Ajaka et al. 1995). It is possible that group O epidemics, compared to group M, could be rampant at this time. In the next years, it will therefore be extremely important to monitor the prevalence of these viruses, in Africa but also in the developed countries, to detect them as early as possible and to prevent a new HIV epidemic.

HIV-1 group O strains present a public health challenge since they are documented to give incomplete and atypical HIV-1 Western blot profiles (Charneau et al. 1994; Gürtler et al. 1994). Some commercially available ELISA or rapid tests were unable to detect HIV-antibodies in HIV-1 group O infected patients (Loussert-Ajaka et al 1994; Simon et al. 1994). The distribution of group O infections may be much more wide spread than currently thought, because of a lack of adequate detection techniques. Moreover, whereas HIV-1 group M strains have been extensively studied and characterized as to their genetic variability, there is at present no clear view on the genetic diversity of strains belonging to HIV-1 group O.

At present, sequence information on the complete genome is only available for the prototype isolates of HIV-1 group O, namely ANT70 (Vanden Haesevelde et al. 1994), MVP-5180 (Gürtler et al. 1994), and VAU (Charneau et al. 1994). Some additional HIV-1 group O strains have been sequenced in the gag and env regions (for example WO 96/27013, WO 96/12809, EP 0727483).

HIV-viruses show a high degree of genetic variability. In the case of HIV-1 viruses it is more or less accepted that at least one nucleotide change occurs during one replication cycle. Certain regions of the genome, for example those encoding structurally or enzymatically important proteins, may be rather conserved, but other regions, especially the env-region, may be subject of very high genetic variability.

The envelope proteins of HIV are the viral proteins most accessible to immune attack, and much attention has been directed towards elucidating their structure and function. The env gene encoding the envelope proteins consists of hypervariable sequences (V-regions) alternated by more constant regions (C-regions) (Starcich et al, 1986; Willey et al, 1986). The envelope protein is first synthesized as a heavily glycosylated precursor protein (gp160), which is later cleaved by a non-viral protease to generate a transmembrane protein, also referred to as gp41, and an outer surface protein often referred to as gp120. One particular region of the gp120 glycoprotein derived from the HIV-1 virus type has been studied extensively, namely the third hypervariable domain (V3) also known as the principal neutralizing determinant (PND) (Javaherian et al., 1989). The V3 domain of HIV-1 contains a loop structure of 35 amino acids (V3-loop) which is formed by a cysteine-cysteine disulfide bridge (Leonard et al. 1990). The gp41 protein contains an immunodominant domain (ID) as found in all retroviruses. For HIV-viruses, this domain has been divided in two distinct regions, corresponding to an immunosuppressive peptide (ISU) of about 17 aa, and a cysteine loop being the principal immunodominant domain (PU)). The delineation of these respective regions in the gp41 protein is demonstrated in FIG. 1.

The genetic variability of HIV-viruses considerably complicates both diagnosis and prevention of HIV-infection. Sera from patients infected with unknown types of HIV-virus, may contain antibodies which are not detected by the current assay methods, which are based on (poly)peptide sequences of known viral strains. The detection of virus or viral antigen in certain samples, like organs for transplantation, or blood transfusion samples, may be missed due to the presence of hitherto unknown variant types. Variation may occur in those genomic regions which are considered to be important in future vaccines. Finally, it is not known at present if different genoric types may influence the course of the AIDS disease, i.e. its virulence and/or susceptibility for therapeutics.

Therefore, there is a constant need for characterization and sequencing of new HIV-strains, and especially of new HIV-1 group O strains, which until now have only scarcely been characterized. Information on the genetic variability of this "Outlier" group may enable a more rational approach for optimization of diagnostic tests and for development of vaccines. Especially the variability of certain regions in the genome, known to be important target regions for the immune response, or for certain therapeutic drugs, is of utmost importance. New sequencing data may require the revision of existing diagnostic assays, and/or the development of new assays. Depending on the situation, it may be important to obtain a general detection of all HIV-infected samples, with a low number of false positives and false negatives, or to be able to differentiate different types of HIV-infection (such as HIV-1 group M, HIV-1 group O, HIV-2).

It is the aim of the current invention to provide new nucleic acid and peptide sequences originating from HIV-1 group O strains.

It is more specifically the aim of the current invention to provide nucleic acid and peptide sequences corresponding to the env-region of new HIV-1 group O strains, more particularly corresponding to the gp160 env-precursor protein region, and most particularly to the C2V3 region and the gp41 region.

It is also an aim of the present invention to provide for new viral strains belonging to HIV-1 group O.

It is moreover an aim of the present invention to provide for antigens derived from said new HIV-1 group O strains.

It is also an aim of the current invention to provide for nucleic acids derived from said new HIV-1 group O strains.

It is also an aim of the present invention to provide antibodies reacting specifically with the antigens from the new HIV-1 group O strains.

It is moreover an aim of the present invention to provide for probes hybridizing specifically with the nucleic acids of the new HIV-1 group O strains.

It is moreover an aim of the present invention to use said antigens and/or antibodies and/or probes in a test for detecting the presence of HIV-infection and/or to differentiate different types of HIV-infection.

It is thus also an aim of the present invention to provide for assays enabling the detection and/or differentiation of HIV-infections.

It is finally also an aim of the present invention to provide for vaccine compositions providing protection against AIDS.

The following definitions serve to illustrate the terms and expressions used in the different embodiments of the present invention as set out below:

The term "polynucleic acid" corresponds to either double-stranded or single-stranded cDNA or genomic DNA or RNA, containing at least 10, 20, 30, 40 or 50 contiguous nucleotides. Single stranded polynucleic acid sequences are always represented in the current invention from the 5' end to the 3' end.

Polynucleic acids according to the invention may be prepared by any method known in the art for preparing polynucleic acids (e.g. the phosphodiester method for synthesizing oligonucleotides as described by Agarwal et al. (1972), the phosphotriester method of Hsiung et al. (1979), or the automated diethylphosphoroamidite method of Baeucage et al. (1981)). Alternatively, the polynucleic acids of the invention may be isolated fragments of naturally occurring or cloned DNA, cDNA or RNA.

The term "oligonucleotide" refers to a single stranded nucleic acid comprising two or more nucleotides, and less than 100 nucleotides. The exact size of an oligonucleotide depends on the ultimate function or use of said oligonucleotide. For use as a probe or primer the oligonucleotides are preferably about 5–50 nucleotides long, more preferably 10–30 nucleotides long.

The oligonucleotides according to the present invention can be formed by cloning of recombinant plasmids containing inserts including the corresponding nucleotide sequences, if need be by cleaving the latter out from the cloned plasmids upon using the adequate nucleases and recovering them, e.g. by fractionation according to molecular weight. The probes according to the present invention can also be synthesized chemically, e.g. by automatic synthesis on commercial instruments sold by a variety of manufacturers.

The nucleotides as used in the present invention may be ribonucleotides, deoxyribonucleotides and modified nucleotides such as inosine or nucleotides containing modified groups which do not essentially alter their hybridisation characteristics. Moreover, it is obvious to the man skilled in the art that any of the below-specified probes can be used as such, or in their complementary form, or in their RNA form (wherein T is replaced by U).

The oligonucleotides used as primers or probes may also comprise or consist of nucleotide analogues such as phosphorothioates (Matsukcura et al., 1987), alkylphosphorothioiates (Miller et al., 1979) or peptide nucleic acids (Nielsen et al., 1991; Nielsen et al., 1993) or may contain intercalating agents (Asseline et al., 1984).

As most other variations or modifications introduced into the original DNA sequences of the invention, these variations will necessitate adaptions with respect to the conditions under which the oligonucleotide should be used to obtain the required specificity and sensitivity. However the eventual results of the hybridisation or amplification will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules, immobilization to solid phase etc.

The term "probe" refers to single stranded sequence-specific oligonucleotides which have a sequence which is sufficiently complementary to hybridize to the target sequence to be detected.

Preferably said probes are 90%, 95% or more homologous to the exact complement of the target sequence to be detected. These target sequences may be genornic DNA, genomic RNA or messenger RNA, or amplified versions thereof.

The term "hybridizes to" refers to preferably stringent hybridization conditions, allowing hybridisation between sequences showing at least 90%, 95% or more homology with each other.

The term "primer" refers to a single stranded DNA oligonucleotide sequence capable of acting as a point of initiation for synthesis of a primer extension product which is complementary to the nucleic acid strand to be copied. The length and the sequence of the primer must be such that they allow to prime the synthesis of the extension products. Preferably the primer is about 5–50 nucleotides long. Specific length and sequence will depend on the complexity of the required DNA or RNA targets, as well as on the conditions of primer use such as temperature and ionic strength. The fact that amplification primers do not have to match exactly with the corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988; Wu & Wallace, 1989, Barany, 1991), nucleic acid sequence-based amplification (NASBA; Guatelli et al., 1990, Compton, 1991), transcription-based amplification system (TAS; Kwoh et al., 1989), strand displacement amplification (SDA; Duck, 1990; Walker et al., 1992) or amplification by means of Qβ replicase (Lizardi et al., 1988; Lomeli et al., 1989) or any other suitable method to amplify nucleic acid molecules.

The term "complementary" nucleic acids as used in the current invention means that the nucleic acid sequences can form a perfect base paired double helix with each other.

The terms "polypeptide" and "peptide" are used interchangeably throughout the specification and designate a linear series of amino acids connected one to the other by peptide bonds between the alpha-amino and carboxy groups of adjacent amino acids. Polypeptides can be of a variety of lengths, either in their natural (uncharged) forms or in a charged form (=salt form), and either free of modifications such as glycosylation, side chain oxidation, or phosphorylation or containing these modifications. Preferably the peptides of the invention are less than 100 amino acids in length, more preferably less than 50, and even less than 30 amino acids long. It is well understood in the art that amino acid sequences contain acidic and basic groups, and that the particular ionization state exhibited by the peptide is dependent on the pH of the surrounding medium when the protein is in solution, or that of the medium from which it was obtained if the protein is in solid form. Also included in the definition are proteins modified by additional substituents attached to the amino acids side chains, such as glycosyl units, lipids, or inorganic ions such as phosphates, as well as modifications relating to chemical conversions of the chains, such as oxidation of sulfhydryl groups. Thus, "polypeptide" or its equivalent terms is intended to include the appropriate amino acid sequence referenced, subject to those of the foregoing modifications which do not destroy its functionality.

The polypeptides of the invention, and particularly the fragments, can be prepared by classical chemical synthesis.

The synthesis can be carried out in homogeneous solution or in solid phase.

For instance, the synthesis technique in homogeneous solution which can be used is the one described by Houbenweyl in the book entitled "Methode der organischen chemie" (Method of organic chemistry) edited by E. Wunsh, vol. 15-I et II. THIEME, Stuttgart 1974.

The polypeptides of the invention can also be prepared in solid phase according to the methods described by Atherton and Shepard in their book entitled "Solid phase peptide synthesis" (IRL Press, Oxford, 1989).

The polypeptides according to this invention can also be prepared by means of recombinant DNA techniques as described by Maniatis et al., Molecular Cloning: A Laboratory Manual, New York, Cold Spring Harbor Laboratory, 1982). In that case the polypeptides are obtained as expression products of the nucleic acids encoding said polypeptides. The expression occurs in a suitable host cell (eukaryotic or prokaryotic) which has been transformed with a vector in which the nucleic acid encoding the polypeptide has been inserted (called "insert"). The nucleic acid insert may have been obtained through classical genomic cloning techniques (screening of genomic libraries, shotgun cloning etc . . . ), or by amplification of the relevant part in the viral genome, using suitable primer pairs and, for example, the polymerase chain reaction, or by DNA synthesis.

The word "antigen" refers to a molecule which provokes an immune response (also called "immunogen"), or which can be recognized by the immune system (also called "antigen sensu strictu"). The immune response or the immune recognition reaction can be of the cellular or humoral type. The antigens of the current invention are all polypeptides or peptides, and therefore, the words "antigen" and "(poly)peptide" may be used interchangeably throughout the current invention.

The term "antigenic determinant" or "epitope" refers to that portion of an antigenic molecule that is specifically bound by an antibody combining site. Epitopes may be determined by any of the techniques known in the art or may be predicted by a variety of computer prediction models known from the art.

The terms "homologous" and "homology" are used in the current invention as synonyms for "identical" and "identity"; this means that amino acid sequences which are e.g. said to be 55% homologous, show 55% identical amino acids in the same position upon alignment of the sequences. The same definition holds for homologous nucleic acid sequences, i.e. nucleic acid sequences which are e.g. said to be 55% homologous, show 55% identical base pairs in the same position upon alignment of the sequences.

The aims of the present invention have been met by the following embodiments.

The present invention provides for an antigen, derived from the gp160-env precursor protein of a new HIV-1 group O strain, and characterized by an amino acid sequence comprising at least one of the following sequences:

VQQMKI (SEQ ID NO 53),
KIGPMSWYSMG (SEQ ID NO 54),
GLEKN (SEQ ID NO 55),
IQQMKI (SEQ ID NO 56),
KIGPLAWYSMG (SEQ ID NO 57),
MGLERN (SEQ ID NO 58),
QSVQEIKI (SEQ ID NO 59),
KIGPMAWYSIG (SEQ ID NO 60),
IGIGTT (SEQ ID NO 61),
VQEIQT (SEQ ID NO 62),
QTGPMAWYSIH (SEQ ID NO 63),
IHLRTP (SEQ ID NO 64),
IQEIKI (SEQ ID NO 65),
KIGPMSWYSMG (SEQ ID NO 66),
MGIGQE (SEQ ID NO 67),
SVQELRI (SEQ ID NO 68),
RIGPMAWYSMT (SEQ ID NO 69),
MTLERD (SEQ ID NO 70),
SVQEIPI (SEQ ID NO 136),
and/or at least one amino acid sequence chosen from the following group of sequences
RNQQLLNLWGCKGRLIC (SEQ ID NO 71),
CKGRLICYTSVQWNM (SEQ ID NO 72),
LWGCKGRIVC (SEQ ID NO 73),
SLWGCKGKLIC (SEQ ID NO 74),
CKGKSIC (SEQ ID NO 75), CKGKIVC (SEQ ID NO 76),
CRGRQVC (SEQ ID NO 77),
CKGRLICYTSVH (SEQ ID NO 79),
CKGNLIC (SEQ ID NO 80),
CKGKMIC (SEQ ID NO 81),
CKGRVVC (SEQ ID NO 82),
or a fragment of said antigen, said fragment consisting of at least 8, preferably 9, 10, 11, 12, 13, 14, 15, 16, 17, 18, 19, 20, 21, 22, 23, 24, 25, 50 up to the maximum number of contiguous amino acids of the amino acid sequence of said antigen, and being characterized by the fact that it specifically reacts with antibodies raised against said antigen.

The term "derived from" signifies that the antigen contains a fragment of the gp160 env precursor protein.

The expression "specifically reacts with" means that the antigen fragment is specifically recognized by antibodies raised against the antigen from which it is derived. Specificity of reaction may be preferably demonstrated using monoclonal antibodies raised against the antigen of the invention. Specificity of polyclonal antibodies may be obtained after absorption of said antibodies with the corresponding antigens of other HIV-1 group O strains, in order to eliminate non-specific antibodies (=cross reactive antibodies) present in the polyclonal mixture. The expression "specifically react with" also means that sera taken from patients infected with the HIV-1 group O strain from which the antigen of the invention originates, show a preferential reaction with the antigen or antigen fragment of the invention, as compared to the reactivity with a corresponding antigen or antigen fragment of other HIV-1 group O strains (=control), under comparable reaction conditions. This preferential reaction may be measured quantitatively (e.g. ELISA absorption values) and should result in reactivity values which are at least 20%, 30%, 40% and preferably 50% higher than the reactivity with the control antigen. In practice, this means that the selected fragments of the above-mentioned antigens will always show at least one amino acid difference when compared in an alignment with the sequence of corresponding antigens of other HIV-1 group O isolates, such as ANT70, MVP5180, VAU or others.

The above-mentioned amino acid sequences SEQ ID NO 53 to 70 and 136 originate from the central region in the V3 loop of the gp160-env precursor protein of new HIV-1 group O strains, while the amino acid sequences represented by SEQ ID NO 71–77 and 79–82 originate from the gp41-principal immunodominant domain (PID) of the gp160-env precursor protein of the same HIV-1 group O strains.

The current invention also provides for antigens consisting of any of the amino acid sequences represented by SEQ ID NO 53–70, 136, 71–77, 79–82, or consisting of an amino acid sequence according to any of SEQ ID NO 53–70, 136, 71–77, 79–82, whereby said sequence is extended at its N-terminal and/or C-terminal end with at least 1, 2, 3, 4, 5, 6, 7, 8, 9, 10, up to 15 amino acids.

The invention further provides for an antigen as described above, characterized by an amino acid sequence comprising at least one of the following amino acid sequences:
CERPGNNSIQQMKIGPLAWYSM-GLERNKSSISRLAYC (SEQ ID NO 83),
CERPGNNSIQQMKIGPMAWYSM-GLERNKSSISRLAYC (SEQ ID NO 84),
CERPGNQSVQEIKIGPMAWYSIGIGT-TPANWSRIAYC (SEQ ID NO 85),
CERPGNQSVQEIKIGPMAWYSIGIGTTP-TYNWSRIAYC (SEQ ID NO 86),
CVRPWNQTVQEIQTGPMAWYSIHLRT-PLANLSRIAYC (SEQ ID NO 87),
CQRPGNLTIQEIKIGPMSWYSM-GIGQEDHSKSRNAYC (SEQ ID NO 88),
CERPYYQSVQELRIGPMAWYSMTLER-DRAGSDIRAAYC (SEQ ID NO 89),
CERPGNHTVQQMKIGPMSWYSMGLE-KNNTSSRRAFC (SEQ ID NO 90),
CERTWNQSVQEIPIGPMAWYSMS-VELDLNTTGSRSADC (SEQ ID NO 135),
and/or at least one amino acid sequence chosen from the following group of sequences:
DQQLLNLWGCKGRIVCYTSVKWN (SEQ ID NO 91),
NQQLLNLWGCKGRLVCYTSVKWNK (SEQ ID NO 92),
NQQLLNLWGCKGRLVCYTSVKWNN (SEQ ID NO 138),
NQQRLNLWGCKGKMICYTSVPWN (SEQ ID NO 93),
NQQLLNLWGCKGKSICYTSVKWN (SEQ ID NO 94),
NQQLLNLWGCKGRLICYTSVQWN (SEQ ID NO 95),
NQQRLNLWGCKGKMICYTSVKWN (SEQ ID NO 96),
NQQLLNLWGCKGNLICYTSVKWN (SEQ ID NO 97),
NQQLLNLWGCRGRQVCYTSVIWN (SEQ ID NO 98),
SQQLLNLWGCKGRLICYTSVHWN (SEQ ID NO 99),
NQQLLNLWGCKGRIVCYTSVKWN (SEQ ID NO 100),
NQQLLNSWGCKGKIVCYTAVKWN (SEQ ID NO 101),
NQQLLSLWGCKGKLICYTSVKWN (SEQ ID NO 102),
NQQLLNLWGCKGRLVCYTSVQWN (SEQ ID NO 137),
or a fragment of said antigen, said fragment consisting of at least 8, preferably 9, 10, 11, 12, 13, 14, 15, 16, 17, 18, 19, 20, 21, 22, 23, 24, 25, 50 up to the maximum number of contiguous amino acids of the amino acid sequence of said antigen, and being characterized by the fact that it specifically reacts with antibodies raised against said antigen.

The above-mentioned amino acid sequences SEQ ID NO 83 to 90 and 135 represent the V3 loop region of the gp160-env precursor protein of new HIV-1 group O strains, while the amino acid sequences SEQ ID NO 91 to 102, 137 and 138 originate from the gp41-immunodominant domain (ID) of the gp160-env precursor protein of the same HIV-1 group O strains.

The current invention also provides for antigens consisting of any of the amino acid sequences represented by SEQ ID NO 83–102, 135, 137 and 138 or consisting of an amino acid sequence according to any of SEQ ID NO 83–102, 135, 137 and 138, whereby said sequence is extended at its N-terminal and/or C-terminal end with at least 1, 2, 3, 4, 5, 6, 7, 8, 9, 10, up to 15 amino acids.

The invention further provides for antigens as above-defined, characterized by an amino acid sequence comprising at least one of the amino acid sequences represented by SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 20, SEQ ID NO 22, SEQ ID NO 24, SEQ ID NO 26, SEQ ID NO 28, SEQ ID NO 30, SEQ ID NO 32, SEQ ID NO 34, SEQ ID NO 36, SEQ ID NO 38, SEQ ID NO 40 as shown in the alignment on FIG. 1, and/or at least one of the amino acid sequences represented by SEQ ID NO 42, SEQ ID NO 44, SEQ ID NO 46, SEQ ID NO 48, SEQ ID NO 50, or SEQ ID NO 52 as shown in the alignment on FIG. 2, and/or the amino acid sequence represented by SEQ ID NO 134, or a fragment of said antigen, said fragment consisting of at least 8, preferably 9, 10, 11, 12, 13, 14, 15, 16, 17, 18, 19, 20, 21, 22, 23, 24, 25, 50 up to the maximum number of contiguous amino acids of any of the sequences represented by SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 20, SEQ ID NO 22, SEQ ID NO 24, SEQ ID NO 26, SEQ ID NO 28, SEQ ID NO 30, SEQ ID NO 32, SEQ ID NO 34, SEQ ID NO 36, SEQ ID NO 38, SEQ ID NO 40, SEQ ID NO 42, SEQ ID NO 44, SEQ ID NO 46, SEQ ID NO 48, SEQ ID NO 50, SEQ ID NO 52, or SEQ ID NO 134, with said antigen fragment characterized by the fact that it specifically reacts with antibodies raised against the antigen from which it is derived.

Furthermore, the invention provides for an antigen as above-defined, characterized by an amino acid sequence consisting of at least one of the following sequences: SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 20, SEQ ID NO 22, SEQ ID NO 24, SEQ ID NO 26, SEQ ID NO 28, SEQ ID NO 30, SEQ ID NO 32, SEQ ID NO 34, SEQ ID NO 36, SEQ ID NO 38, SEQ ID NO 40, SEQ ID NO 42, SEQ ID NO 44, SEQ ID NO 46, SEQ ID NO 48, SEQ ID NO 50, SEQ ID NO 52, or the amino acid sequence represented by SEQ ID NO 134 or a fragment of said antigen, said fragment consisting of at least 8, preferably 9, 10, 11, 12, 13, 14, 15, 16, 17, 18, 19, 20, 21, 22, 23, 24, 25, 50 up to the maximum number of contiguous amino acids of any of the sequences represented by SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 20, SEQ ID NO 22, SEQ ID NO 24, SEQ ID NO 26, SEQ ID NO 28, SEQ ID NO 30, SEQ ID NO 32, SEQ ID NO 34, SEQ ID NO 36, SEQ ID NO 38, SEQ ID NO 40, SEQ ID NO 42, SEQ ID NO 44, SEQ ID NO 46, SEQ ID NO 48, SEQ ID NO 50, SEQ ID NO 52, or SEQ ID NO 134, with said antigen fragment characterized by the fact that it specifically reacts with antibodies raised against the antigen from which it is derived.

It is to be noted that all the above-mentioned amino acid sequences originate from HIV-1 group O strains, which have until now never been described. More particularly, as is shown further in the examples section, the new amino acid sequences originate from the following strains:

The amino acid sequences represented by SEQ ID NO 2, 4, 42, 73, 59, 60, 61, 73, 85, 86, 100 originate from the gp160 env precursor antigen isolated from a HIV-1 group O strain termed MP340, or a quasi-species thereof.

The amino acid sequences represented by SEQ ID NO 6, 8, 44, 56, 57, 58, 82, 83, 84, 138 originate from the gp160 env precursor antigen isolated from a HIV-1 group O strain termed FABA, or alternatively termed MP331, or a quasi-species thereof.

The amino acid sequences represented by SEQ ID NO 10, 12, 46, 62, 63, 64, 73, 87, 100 originate from the gp160 env precursor antigen isolated from a HIV-1 group O strain termed MP450, or a quasi-species thereof.

The amino acid sequences represented by SEQ ID NO 14, 16, 48, 65, 66, 67, 76, 88, 101 originate from the gp160 env precursor antigen isolated from a HIV-1 group O strain termed MP448, or a quasi species thereof.

The amino acid sequences represented by SEQ ID NO 18, 50, 53, 54, 55, 73, 90, 91 originate from the gp160 env precursor antigen isolated from a HIV-1 group O strain termed 189, or a quasi-species thereof.

The amino acid sequences represented by SEQ ID NO 40, 52, 68, 69, 70, 71, 89, 95 originate from the gp160 env precursor antigen isolated from a HIV-1 group O strain termed MP539, or a quasi-species thereof.

The amino acid sequences represented by SEQ ID NO 20 and 92 originate from the gp160 env precursor antigen isolated from a HIV-1 group O strain termed 320, or a quasi-species thereof.

The amino acid sequences represented by SEQ ID NO 22, 80 and 97 originate from the gp160 env precursor antigen isolated from a HIV-1 group O strain termed BSD422, or a quasi-species thereof.

The amino acid sequences represented by SEQ ID NO 24, 79 and 99 originate from the gp160 env precursor antigen isolated from a HIV-1 group O strain termed KGT008, or a quasi-species thereof.

The amino acid sequence represented by SEQ ID NO 26 originates from the gp160 env precursor antigen isolated from a HIV-1 group O strain termed MP575, or a quasi-species thereof.

The amino acid sequences represented by SEQ ID NO 28, 72 and 95 originate from the gp160 env precursor antigen isolated from a HIV-1 group O strain termed BSD189, or a quasi-species thereof.

The amino acid sequences represented by SEQ ID NO 30, 77 and 98 originate from the gp160 env precursor antigen isolated from a HIV-1 group O strain termed BSD649, or a quasi-species thereof.

The amino acid sequences represented by SEQ ID NO 32, 81 and 96 originate from the gp160 env precursor antigen isolated from a HIV-1 group O strain termed BSD242, or a quasi-species thereof.

The amino acid sequences represented by SEQ ID NO 34, 81 and 93 originate from the gp160 env precursor antigen isolated from a HIV-1 group O strain termed 533, or a quasi-species thereof.

The amino acid sequences represented by SEQ ID NO 36, 75 and 94 originate from the gp160 env precursor antigen isolated from a HIV-1 group O strain termed 772P94, or a quasi-species thereof.

The amino acid sequences represented by SEQ ID NO 38, 74 and 102 originate from the gp160 env precursor antigen isolated from a HIV-1 group O strain termed MP95B, or a quasi-species thereof.

The amino acid sequences represented by SEQ ID NO 134, 135, 136, and 137 originate from the gp160 env precursor antigen isolated from a HIV-1 group O strain termed MP645, or a quasi-species thereof.

It is noted that the amino acid sequence represented by SEQ ID NO 73 is characteristic for the gp41 immunodominant region of at least the following new HIV-1 group O strains: MP340, MP450, and 189.

The current invention therefore specifically relates to env-derived antigens comprising the characteristic sequence represented by SEQ ID NO 73, as well as virus strains containing these antigens.

It is also noted that the amino acid sequence represented by SEQ ID NO 81 is characteristic for the gp41 immunodominant region of at least the following new HIV-1 group O strains: BSD242 and 533.

The current invention therefore specifically relates to env-derived antigens comprising the characteristic sequence represented by SEQ ID NO 81, as well as virus strains containing these antigens.

It is also noted that the amino acid sequence represented by SEQ ID NO 95 is characteristic for the gp41 immunodominant region of at least the following new HIV-1 group O strains: MP539 and BSD189.

The current invention therefore specifically relates to env-derived antigens comprising the characteristic sequence represented by SEQ ID NO 95, as well as virus strains containing these antigens.

The term "quasi-species" refers in general to the group of related but genetically and possibly biologically different viruses (also called "variants") that an infected individual harbors. The term "related" means that the "variants" all arise from a single infectious agent, in this case from a single HIV-1 group O strain. It has been calculated that an HIV-infected patient carries about $10^6$ to $10^8$ genetically distinct HIV-variants, which are generated by the high error rate of reverse transcriptase and the high turnover rate in vivo. In the context of the current description the term "quasi-species" refers also to a strain isolated from the quasi-species "group" as above-defined.

The term "genetically different" means that the nucleic acid sequence of the genome of one strain shows at least one nucleotide difference with the corresponding sequence of another strain belonging to the same quasi-species.

The term "biologically different" means that some strains of a quasi-species may have different biological characteristics compared to the biological characteristics of other strains from the same quasi-species. These biological characteristics may encompass for example the HIV-1 cell tropism, viral virulence, the capacity to induce syncytia, etc.

Nucleic acid sequences originating from quasi-species differ from each other but always show a high percentage of homology, most often a homology of 90%, 95% or higher. The same holds for the sequence of polypeptides originating from quasi-species. Homology percentages on the protein level usually exceed 95%, 96%, 97%, 98%, or even 99%. These percentages of homology count for the comparison of sequence stretches which are at least 100 nucleotides (about 33 amino acids), and preferably 200, 300 or more nucleotides long (66, 100 or more amino acids). It has to be understood that, when very short sequence stretches are compared (e.g. stretches of about 30 nucleotides, or 10 amino acids) the homology ranges may be much lower, if these short sequence stretches contain the mutual differences.

Examples of sequences originating from "quasi-species" are provided further in the examples section, where gp41- and C2V3-nucleotide and amino acid sequences of certain strains belonging to the same "quasi-species" are compared to each other. For example, for strains MP340, FABA, MP450 and MP448 gp41-nucleic acid sequences have been determined on different samples, originating from the same patient, i.e. on serum samples and on peripheral blood monocyte (PBMC) samples. Table 2 shows that, in these specific examples, homology percentages vary from 95% to 100% between gp41-nucleic acid sequences determined on serum samples as compared to PBMC-samples.

It is to be understood that the amino acid and nucleic acid sequences of the current invention also encompass those sequences which are not explicitly recited, but which have been determined on "quasi-species" of the respective viral strains. As indicated above, these "variant" sequences show a homology range of at least 90%, preferably 95% with the sequences which are specifically recited in the current application.

The above-mentioned antigens are polypeptide or peptide molecules, which are characterized by the above-mentioned amino acid sequences. It has to be understood however, that these (poly)peptides may be modified by for example glycosylation, side chain oxidation or phosphorylation as explained above. A very particular type of side chain oxidation is cyclisation by bridge formation between the —SH groups of two cysteine residues in the same (poly)peptide chain. The cyclic (poly)peptides formed in this way by S—S bridging may be particularly suitable to expose epitopes located in the loop structure. Epitopes presented in this manner may be in a better shape to be recognized by the immune system, and more particularly by antibodies possibly present in the serum of HIV-infected persons.

A preferential embodiment of the current invention provides for any of the above-mentioned (poly)peptides in a cyclic form.

Cyclisation may occur between two cysteine residues which are present in the above-cited amino acid sequences. For example, cyclic peptides with a loop structure of about 6 amino acids long may be formed with the amino acid sequences represented by e.g. SEQ ID NO 71 to 82, and 91 to 102, and 137. Another example are the V3-loop peptides of about 35 amino acids long, which may be formed by cyclisation of the cysteine residues of the amino acid sequences represented by e.g. SEQ ID NO 83 to 90, and 135.

On the other hand, cyclisation may also be induced in amino acid sequences which do not contain two cysteine residues naturally, but which have been extended with one or two cysteine residues at their extremities, or at in internal position inside the amino acid chain. The current invention therefore also refers to (poly)peptides characterized by any of the above-mentioned amino acid sequences, modified by addition of one or several cysteine residues, at the C-terminal and/or N-terminal extremity and/or inside the (poly)peptide chain.

Another particular type of modification includes the extension of the N-terminal and/or C-terminal end of the (poly)peptide antigen by linker sequences, said linker sequences comprising for example additional amino acids or other molecules (such as for example biotin). The addition of linker sequences to the polypeptide antigen may have several advantages such as:

a more efficient immobilisation on a solid substrate, a more efficient presentation of the immunoreactive epitope(s) in the (poly)peptide, linkage to other antigenic determinants . . . .

A preferential embodiment therefore includes antigens or antigen fragments comprising any of the above-mentioned amino acid sequences, extended with linker sequences.

It has to be understood that the above-mentioned (poly)peptide antigens of the invention may be prepared by different methods known in the art. They may be prepared by synthetic means as described above, or they may be produced by recombinant DNA technology. In the latter case, they are the result of the expression of the nucleic acids encoding said antigens or antigen fragments in an appropriate host cell.

The invention also relates to a recombinant vector for the expression of any of the above-mentioned polypeptides, recombinant host cells expresssing these polypeptides, and processes for the recombinant expression of these polypeptides; said tools for recombinant expression are well known by anyone skilled in the art, and have been described in more detail for example in WO96/13590.

The invention further provides for a (poly)nucleic acid encoding any of the above-mentioned (poly)peptide antigens.

More particularly, the current invention provides for a polynucleic acid comprising a nucleotide sequence chosen from the group of (I) a nucleotide sequence represented by SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 19, SEQ ID NO 21, SEQ ID NO 23, SEQ ID NO 25, SEQ ID NO 27, SEQ ID NO 29, SEQ ID NO 31, SEQ ID NO 33, SEQ ID NO 35, SEQ ID NO 37, SEQ ID NO 39, SEQ ID NO 41, SEQ ID NO 43, SEQ ID NO 45, SEQ ID NO 47, SEQ ID NO 49, or SEQ ID NO 51, SEQ ID NO 106 or (ii) a nucleotide sequence complementary to a sequence according to (I), or (iii) a nucleotide sequence showing at least 95%, preferably 96%, 97%, 98% and most preferably 99% homology to a sequence according to (I), or (iv) a nucleotide sequence according to (I) whereby T is replaced by U, or (v) a nucleotide sequence according to (I) whereby at least one nucleotide is substituted by a nucleotide analogue.

It is to be noted that, as will be shown further on in the examples section, the above-mentioned polynucleic acids all originate from the env-gene of new HIV-1 group O strains. The nucleic acid sequences represented by SEQ ID NO 1, 3, 5, 7, 9, 11, 13, 15, 17, 19, 21, 23, 25, 27, 29, 31, 33, 35, 37 and 39 correspond to the region encoding the gp41-immunodominant domain in the env-gene, while the nucleic acid sequences represented by SEQ ID NO 41, 43, 45, 47, 49, and 51 correspond to the region encoding the C2V3 region in this same env-gene. The nucleotide sequence represented by SEQ ID NO 106 is illustrated in FIG. 8A, and comprises the full env-gene of a new HIV-1 group O strain, termed MP645, together with additional accompanying genes.

The nucleotide sequences mentioned above under item (iii) represent variant nucleic acid sequences which may be isolated e.g. from strains belonging to the same quasi-species.

More particularly, the invention provides for a polynucleic acid consisting of a nucleotide sequence chosen from the group of (I) a nucleotide sequence represented by SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 19, SEQ ID NO 21, SEQ ID NO 23, SEQ ID NO 25, SEQ ID NO 27, SEQ ID NO 29, SEQ ID NO 31, SEQ ID NO 33, SEQ ID NO 35, SEQ ID NO 37, SEQ ID NO 39, SEQ ID NO 41, SEQ ID NO 43, SEQ ID NO 45, SEQ ID NO 47, SEQ ID NO 49, or SEQ ID NO 51, SEQ ID NO 106 or (ii) a nucleotide sequence complementary to a sequence according to (I), or (iii) a nucleotide sequence showing at least 95%, preferably 96%, 97%, 98% and most preferably 99% homology to a sequence according to (I), or (iv) a nucleotide sequence according to (I) whereby T is replaced by U, or (v) a nucleotide sequence according to (I) whereby at least one nucleotide is substituted by a nucleotide analogue.

The invention further provides for a nucleic acid fragment consisting of a sequence of at least 15, preferably 16, 17, 18, 19, 20, 21, 22, 23, 24, 25 up to 50 contiguous nucleotides of the sequence of a polynucleic acid as specified above, and characterized by the fact that it selectively hybridizes to the polynucleic acid from which it is derived.

The above-described nucleic acid fragment may be used as a specific hybridization probe for the detection of the nucleic acids of the current invention.

The term "selectively hybridizing" means that the hybridization signal obtained after hybridization of the fragment with the nucleic acid from which it is derived, is more intense than the hybridization signal obtained when the fragment is hybridized to the corresponding nucleic acid from another HIV-1 group O strain, under the same stringent hybridization and wash conditions. In practice this means that the nucleic acid fragment will show at least one mismatched nucleotide with the sequence of the corresponding nucleic acid fragment of another HIV-1 group O strain.

The term "stringent hybridization conditions" implies that the hybridization takes place at a temperature which is situated approximately between Tm and (Tm−10° C.), whereby Tm represents the calculated melting temperature of the target nucleic. It is generally known that the stringency depends on the percentage mismatches (=non-matching nucleotides upon alignment) present in the hybridizing duplex. According to a simplified formula, the hybridization temperature may be calculated as follows: Tm−1.2 (% mismatch). A temperature decrease of 10° C. implies a maximum percentage of allowed mismatches of 8.3%.

The invention further provides for a nucleic acid fragment consisting of a sequence of at least 15, preferably 16, 17, 18, 19, 20, 21, 22, 23, 24, 25 up to 50 contiguous nucleotides of the sequence of a polynucleic acid as specified above, and characterized by the fact that it selectively amplifies the polynucleic acid from which it is derived.

The nucleic acid fragment as described above may be used as a specific amplification primer of the nucleic acids of the current invention.

The term "selective amplification" refers to the fact that said nucleic acid fragment may initiate a specific amplification reaction of the nucleic acids of the invention (e.g. a polymerase chain reaction) in the presence of other nucleic acids, under appropriate amplification conditions. It means that, under the appropriate amplification conditions, only the nucleic acids of the invention will be amplified, and not the other nucleic acids possibly present.

Preferred embodiments of the invention comprise polynucleic acids or fragments thereof. as specified below.

A polynucleic acid comprising SEQ ID NO 1, or a fragment consisting of at least 15, preferably 16, 17, 18, 19, 20, 21, 22, 23, 24, 25, up to 50 contiguous nucleotides of said polynucleic acid, said fragment characterized by the fact that it selectively hybridizes to the polynucleic acid comprising SEQ ID NO 1.

A polynucleic acid consisting of SEQ ID NO 1, or a fragment comprising at least 15, preferably 16, 17, 18, 19, 20, 21, 22, 23, 24, 25, 50 up to the maximum number of contiguous nucleotides of SEQ ID NO 1, said fragment characterized by the fact that it selectively hybridizes to the polynucleic acid consisting of SEQ ID NO 1.

A polynucleic acid comprising SEQ ID NO 3, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 3.

A polynucleic acid consisting of SEQ ID NO 3, or a fragment comprising at least 15, preferably 16, 17, 18, 19, 20, 21, 22, 23, 24, 25, 50 up to the maximum number of contiguous nucleotides of SEQ ID NO 3, said fragment characterized by the fact that it selectively hybridizes to the polynucleic acid consisting of SEQ ID NO 3.

A polynucleic acid comprising SEQ ID NO 5, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 5.

A polynucleic acid consisting of SEQ ID NO 5, or a fragment comprising at least 15, preferably 16, 17, 18, 19, 20, 21, 22, 23, 24, 25, 50 up to the maximum number of contiguous nucleotides of SEQ ID NO 5, said fragment characterized by the fact that it selectively hybridizes to the polynucleic acid consisting of SEQ ID NO 5.

A polynucleic acid comprising SEQ ID NO 7, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 7.

A polynucleic acid consisting of SEQ ID NO 7, or a fragment comprising at least 15, preferably 16, 17, 18, 19, 20, 21, 22, 23, 24, 25, 50 up to the maximum number of contiguous nucleotides of SEQ ID NO 7, said fragment characterized by the fact that it selectively hybridizes to the polynucleic acid consisting of SEQ ID NO 7.

A polynucleic acid comprising SEQ ID NO 9, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 9.

A polynucleic acid consisting of SEQ ID NO 9, or a fragment comprising at least 15, preferably 16, 17, 18, 19, 20, 21, 22, 23, 24, 25, 50 up to the maximum number of contiguous nucleotides of SEQ ID NO 9, said fragment characterized by the fact that it selectively hybridizes to the polynucleic acid consisting of SEQ ID NO 9.

A polynucleic acid comprising SEQ ID NO 11, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 11.

A polynucleic acid consisting of SEQ ID NO 11, or a fragment consisting of at least 15, preferably 16, 17, 18, 19, 20, 21, 22, 23, 24, 25, up to 50 contiguous nucleotides of SEQ ID NO 11, said fragment characterized by the fact that it selectively hybridizes to the polynucleic acid consisting of SEQ ID NO 11.

A polynucleic acid comprising SEQ ID NO 13, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 13.

A polynucleic acid consisting of SEQ ID NO 13, or a fragment comprising at least 15, preferably 16, 17, 18, 19, 20, 21, 22, 23, 24, 25, 50, up to the maximum number of contiguous nucleotides of SEQ ID NO 13, said fragment characterized by the fact that it selectively hybridizes to the polynucleic acid consisting of SEQ ID NO 13.

A polynucleic acid comprising SEQ ID NO 15, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 15.

A polynucleic acid consisting of SEQ ID NO 15, or a fragment comprising at least 15, preferably 16, 17, 18, 19, 20, 21, 22, 23, 24, 25, 50 up to the maximum number of contiguous nucleotides of SEQ ID NO 15, said fragment characterized by the fact that it selectively hybridizes to the polynucleic acid consisting of SEQ ID NO 15.

A polynucleic acid comprising SEQ ID NO 17, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 17.

A polynucleic acid consisting of SEQ ID NO 17, or a fragment comprising at least 15, preferably 16, 17, 18, 19, 20, 21, 22, 23, 24, 25, 50 up to the maximum number of contiguous nucleotides of SEQ ID NO 17, said fragment characterized by the fact that it selectively hybridizes to the polynucleic acid consisting of SEQ ID NO 17.

A polynucleic acid comprising SEQ ID NO 19, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 19.

A polynucleic acid consisting of SEQ ID NO 19, or a fragment comprising at least 15, preferably 16, 17, 18, 19, 20, 21, 22, 23, 24, 25,50 up to the maximum number of contiguous nucleotides of SEQ ID NO 19, said fragment characterized by the fact that it selectively hybridizes to the polynucleic acid consisting of SEQ ID NO 19.

A polynucleic acid comprising SEQ ID NO 21, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 21.

A polynucleic acid consisting of SEQ ID NO 21, or a fragment comprising at least 15, preferably 16, 17, 18, 19, 20, 21, 22, 23, 24, 25, 50 up to the maximum number of contiguous nucleotides of SEQ ID NO 21, said fragment characterized by the fact that it selectively hybridizes to the polynucleic acid consisting of SEQ ID NO 21.

A polynucleic acid comprising SEQ ID NO 23, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 23.

A polynucleic acid consisting of SEQ ID NO 23, or a fragment comprising at least 15, preferably 16, 17, 18, 19, 20, 21, 22, 23, 24, 25, 50 up to the maximum number of contiguous nucleotides of SEQ ID NO 23, said fragment characterized by the fact that it selectively hybridizes to the polynucleic acid consisting of SEQ ID NO 23.

A polynucleic acid comprising SEQ ID NO 25, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 25.

A polynucleic acid consisting of SEQ ID NO 25, or a fragment consisting of at least 15, preferably 16, 17, 18, 19, 20, 21, 22, 23, 24, 25, up to 50 contiguous nucleotides of SEQ ID NO 25, said fragment characterized by the fact that it selectively hybridizes to the polynucleic acid consisting of SEQ ID NO 25.

A polynucleic acid comprising SEQ ID NO 27, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 27.

A polynucleic acid consisting of SEQ ID NO 27, or a fragment comprising at least 15, preferably 16, 17, 18, 19, 20, 21, 22, 23, 24, 25, 50 up to the maximum number of contiguous nucleotides of SEQ ID NO 27, said fragment characterized by the fact that it selectively hybridizes to the polynucleic acid consisting of SEQ ID NO 27.

A polynucleic acid comprising SEQ ID NO 29, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 29.

A polynucleic acid consisting of SEQ ID NO 29, or a fragment comprising at least 15, preferably 16, 17, 18, 19, 20, 21, 22, 23, 24, 25, 50 up to the maximum number of contiguous nucleotides of SEQ ID NO 29, said fragment characterized by the fact that it selectively hybridizes to the polynucleic acid consisting of SEQ ID NO 29.

A polynucleic acid comprising SEQ ID NO 31, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 31.

A polynucleic acid consisting of SEQ ID NO 31, or a fragment comprising at least 15, preferably 16, 17, 18, 19, 20, 21, 22, 23, 24, 25, 50 up to the maximum number of contiguous nucleotides of SEQ ID NO 31, said fragment characterized by the fact that it selectively hybridizes to the polynucleic acid consisting of SEQ ID NO 31.

A polynucleic acid comprising SEQ ID NO 33, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 33.

A polynucleic acid consisting of SEQ ID NO 33, or a fragment comprising at least 15, preferably 16, 17, 18, 19, 20, 21, 22, 23, 24, 25, 50 up to the maximum number of contiguous nucleotides of SEQ ID NO 33, said fragment characterized by the fact that it selectively hybridizes to the polynucleic acid consisting of SEQ ID NO 33.

A polynucleic acid comprising SEQ ID NO 35, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 35.

A polynucleic acid consisting of SEQ ID NO 35, or a fragment comprising at least 15, preferably 16, 17, 18, 19, 20, 21, 22, 23, 24, 25, 50 up to the maximum number of contiguous nucleotides of SEQ ID NO 35, said fragment characterized by the fact that it selectively hybridizes to the polynucleic acid consisting of SEQ ID NO 35.

A polynucleic acid comprising SEQ ID NO 37, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 37.

A polynucleic acid consisting of SEQ ID NO 37, or a fragment comprising at least 15, preferably 16, 17, 18, 19, 20, 21, 22, 23, 24, 25, 50 up to the maximum number of contiguous nucleotides of SEQ ID NO 37, said fragment characterized by the fact that it selectively hybridizes to the polynucleic acid consisting of SEQ ID NO 37.

A polynucleic acid comprising SEQ ID NO 39, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 39.

A polynucleic acid consisting of SEQ ID NO 39, or a fragment comprising at least 15, preferably 16, 17, 18, 19, 20, 21, 22, 23, 24, 25,50 up to the maximum number of contiguous nucleotides of SEQ ID NO 39, said fragment characterized by the fact that it selectively hybridizes to the polynucleic acid consisting of SEQ ID NO 39.

A polynucleic acid comprising SEQ ID NO 41, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 41.

A polynucleic acid consisting of SEQ ID NO 41, or a fragment comprising at least 15, preferably 16, 17, 18, 19, 20, 21, 22, 23, 24, 25, 50 up to the maximum number of contiguous nucleotides of SEQ ID NO 41, said fragment characterized by the fact that it selectively hybridizes to the polynucleic acid consisting of SEQ ID NO 41.

A polynucleic acid comprising SEQ ID NO 43, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 43.

A polynucleic acid consisting of SEQ ID NO 43, or a fragment comprising at least 15, preferably 16, 17, 18, 19, 20, 21, 22, 23, 24, 25, 50 up to the maximum number of contiguous nucleotides of SEQ ID NO 43, said fragment characterized by the fact that it selectively hybridizes to the polynucleic acid consisting of SEQ ID NO 43.

A polynucleic acid comprising SEQ ID NO 45, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 45.

A polynucleic acid consisting of SEQ ID NO 45, or a fragment comprising at least 15, preferably 16, 17, 18, 19, 20, 21, 22, 23, 24, 25, 50 up to the maximum number of contiguous nucleotides of SEQ ID NO 45, said fragment characterized by the fact that it selectively hybridizes to the polynucleic acid consisting of SEQ ID NO 45.

A polynucleic acid comprising SEQ ID NO 47, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 47.

A polynucleic acid consisting of SEQ ID NO 47, or a fragment comprising at least 15, preferably 16, 17, 18, 19, 20, 21, 22, 23, 24, 25, 50 up to the maximum number of contiguous nucleotides of SEQ ID NO 47, said fragment characterized by the fact that it selectively hybridizes to the polynucleic acid consisting of SEQ ID NO 47.

A polynucleic acid comprising SEQ ID NO 49, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 49.

A polynucleic acid consisting of SEQ ID NO 49, or a fragment comprising at least 15, preferably 16, 17, 18, 19, 20, 21, 22, 23, 24, 25, 50 up to the maximum number of contiguous nucleotides of SEQ ID NO 49, said fragment characterized by the fact that it selectively hybridizes to the polynucleic acid consisting of SEQ ID NO 49.

A polynucleic acid comprising SEQ ID NO 51, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 51.

A polynucleic acid consisting of SEQ ID NO 51, or a fragment comprising at least 15, preferably 16, 17, 18, 19, 20, 21, 22, 23, 24, 25, 50 up to the maximum number of contiguous nucleotides of SEQ ID NO 51, said fragment characterized by the fact that it selectively hybridizes to the polynucleic acid consisting of SEQ ID NO 51.

A polynucleic acid comprising SEQ ID NO 106, or a fragment consisting of at least 15, preferably 16, 17, 18, 19, 20, 21, 22, 23, 24, 25 up to 50 contiguous nucleotides of said polynucleic acid, said fragment characterized by the fact that it selectively hybridizes to the polynucleic acid comprising SEQ ID NO 106.

A polynucleic acid consisting of SEQ ID NO 106, or a fragment comprising at least 15, preferably 16, 17, 18, 19, 20, 21, 22, 23, 24, 25, 50 up to the maximum number of contiguous nucleotides of SEQ ID NO 106, said fragment characterized by the fact that it selectively hybridizes to the polynucleic acid consisting of SEQ ID NO 106.

The invention further provides for a virus strain belonging to HIV-1 group O, comprising in its genome any of the above-mentioned nucleic acids.

More particularly, the invention provides for a virus strain belonging to HIV-1 group O, comprising in its genome the RNA equivalent of one of the DNA sequences represented by SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 19, SEQ ID NO 21, SEQ ID NO 23, SEQ ID NO 25, SEQ ID NO 27, SEQ ID NO 29, SEQ ID NO 31, SEQ ID NO 33, SEQ ID NO 35, SEQ ID NO 37, SEQ ID NO 39, SEQ ID NO 106 and/or one of the DNA sequences represented by SEQ ID NO 41, SEQ ID NO 43, SEQ ID NO 45, SEQ ID NO 47, SEQ ID NO 49, SEQ ID NO 51, and/or a variant sequence of the above-mentioned DNA sequences, said variant sequence showing at least 95% homology with the entire length of one of the above-mentioned sequences.

More particularly, the invention relates to a strain of HIV-1 group O as defined above, comprising in its genome the RNA equivalent of the DNA sequence represented by SEQ ID NO 5 and/or SEQ ID NO 43 or a variant sequence thereof, said variant sequence showing at least 95% homology with SEQ ID NO 5 and/or SEQ ID NO 43. An HIV-1 group O strain of this type, termed FABA (or synonymously MP331) has been deposited at the ECACC on Jun. 13 1997, under accession No V97061301.

An example of a variant sequence of SEQ ID NO 5 is SEQ ID NO 7. The latter sequence was determined on a serum sample of a patient infected by the strain FABA, while the former sequence was determined on peripheral blood mononuclear cells (PBMC's) taken from the same patient. The nucleic acids represented by SEQ ID NO 5 and SEQ ID NO 7 show 95% homology, and can be said to belong to strains from the same quasi-species.

The invention also relates to a strain of HIV-1 group O as defined above, comprising in its genome the RNA equivalent of the DNA sequence represented by SEQ ID NO 9 and/or SEQ ID NO 45 or a variant sequence, said variant sequence showing at least 95% homology with SEQ ID NO 9 and/or SEQ ID NO 45. An HIV-1 group O strain of this type, termed MP450, has been deposited at the ECACC on Jun. 13, 1997 under accession No. V97061302.

An example of a variant sequence of SEQ ID NO 9 is SEQ ID NO 11. The latter sequence was determined on a serum sample of a patient infected by the strain MP450, while the former sequence was determined on peripheral blood mononuclear cells (PBMC's) taken from the same patient.

Furthermore, the invention also relates to a strain of HIV-1 group O as defined above, comprising in its genome the RNA equivalent of the DNA sequence represented by SEQ ID NO 39 and/or SEQ ID NO 51 or a variant sequence, said variant sequence showing at least 95% homology with SEQ ID NO 39 and/or SEQ ID NO 51. An HIV-1 group O strain of this type, termed MP539, has been deposited at the ECACC on Jun. 13, 1997 under accession No. V97061303.

Furthermore, the invention also relates to a strain of HIV-1 group O as defined above comprising in its genome the RNA equivalent of the DNA sequence represented by SEQ ID NO 1 and/or SEQ ID NO 41 or a variant sequence, said variant sequence showing at least 95% homology with SEQ ID NO 1 and/or SEQ ID NO 41. A strain of this type is termed MP340 throughout this invention.

An example of a variant sequence of SEQ ID NO 1 is SEQ ID NO 3. The latter sequence was determined on a serum sample of a patient infected by the strain MP340, while the former sequence was determined on peripheral blood mononuclear cells (PBMC's) taken from the same patient. The nucleic acids represented by SEQ ID NO 1 and SEQ ID NO 3 show 99% homology, and can be said to belong to strains from the same quasi-species.

Furthermore, the invention also relates to a strain of HIV-1 group O as defined above comprising in its genome the RNA equivalent of the DNA sequence represented by SEQ ID NO 13 and/or SEQ ID NO 47 or a variant sequence, said variant sequence showing at least 95% homology with SEQ ID NO 13 and/or SEQ ID NO 47. A strain of this type is termed MP448 throughout this invention.

Furthermore, the invention also relates to a strain of HIV-1 group O as defined above comprising in its genome the RNA equivalent of the DNA sequence represented by SEQ ID NO 17 and/or SEQ ID NO 49 or a variant sequence, said variant sequence showing at least 95% homology with SEQ ID NO 17 and/or SEQ ID NO 49. A strain of this type is termed 189 throughout this invention.

Furthermore, the invention also relates to a strain of HIV-1 group O as defined above comprising in its genome the RNA equivalent of the DNA sequence represented by SEQ ID NO 19 or a variant sequence showing at least 95% homology with SEQ ID NO 19. A strain of this type is termed 320 throughout this invention.

Furthermore, the invention also relates to a strain of HIV-1 group O as defined above comprising in its genome the RNA equivalent of the DNA sequence represented by SEQ ID NO 21 or a variant sequence showing at least 95% homology with SEQ ID NO 21. A strain of this type is termed BSD422 throughout this invention.

Furthermore, the invention also relates to a strain of HIV-1 group O as defined above comprising in its genome the RNA equivalent of the DNA sequence represented by SEQ ID NO 23 or a variant sequence showing at least 95% homology with SEQ ID NO 23. A strain of this type is termed KGT008 throughout this invention.

Furthermore, the invention also relates to a strain of HIV-1 group O as defined above comprising in its genome the RNA equivalent of the DNA sequence represented by SEQ ID NO 25 or a variant sequence showing at least 95% homology with SEQ ID NO 25. A strain of this type, termed MP575, has been deposited at the ECACC on Jul. 13, 1998, under provisional accession No. V98071301.

Furthermore, the invention also relates to a strain of HIV-1 group O as defined above comprising in its genome the RNA equivalent of the DNA sequence represented by SEQ ID NO 27 or a variant sequence showing at least 95% homology with SEQ ID NO 27. A strain of this type is termed BSD189 throughout this invention.

Furthermore, the invention also relates to a strain of HIV-1 group O as defined above comprising in its genome the RNA equivalent of the DNA sequence represented by SEQ ID NO 29 or a variant sequence showing at least 95% homology with SEQ ID NO 29. A strain of this type is termed BSD649 throughout this invention.

Furthermore, the invention also relates to a strain of HIV-1 group O as defined above comprising in its genome the RNA equivalent of the DNA sequence represented by SEQ ID NO 31 or a variant sequence showing at least 95% homology with SEQ ID NO 31. A strain of this type is termed BSD242 throughout this invention.

Furthermore, the invention also relates to a strain of HIV-1 group-O as defined above comprising in its genome the RNA equivalent of the DNA sequence represented by SEQ ID NO 33 or a variant sequence showing at least 95% homology with SEQ ID NO 33. A strain of this type is termed 533 throughout this invention.

Furthermore, the invention also relates to a strain of HIV-1 group O as defined above comprising in its genome the RNA equivalent of the DNA sequence represented by SEQ ID NO 35 or a variant sequence showing at least 95% homology with SEQ ID NO 35. A strain of this type is termed 772. P94 throughout this invention.

Furthermore, the invention also relates to a strain of HIV-1 group O as defined above comprising in its genome the RNA equivalent of the DNA sequence represented by SEQ ID NO 37 or a variant sequence showing at least 95% homology with SEQ ID NO 37. A strain of this type is termed MP95B throughout this invention.

Furthermore, the invention also relates to a strain of HIV-1 group O as defined above comprising in its genome the RNA equivalent of the DNA sequence represented by SEQ ID NO 106 or a variant sequence showing at least 95% homology with SEQ ID NO 106. A strain of this type, termed MP645, has been deposited at the ECACC on Jul. 13, 1998, under provisional accession No. V98071302.

Another embodiment of the current invention provides for a nucleic acid molecule isolated from any of the HIV-1 group O strains as defined above.

In addition, the current invention provides for an antigen or antigen fragment isolated from any of the HIV-1 group O strains as defined above.

It is to be understood that the current invention also provides for nucleic acid sequences and antigen sequences which are contained in the above-mentioned new HIV-1 group O viral strains, and which extend beyond the explicitly cited sequences represented by SEQ ID NO 1 to 102, 106, 135 to 138. The person skilled in the art will realize that, starting from the partial sequences disclosed above, it is perfectly possible to obtain the complete genomic information of the respective viruses, by standard cloning methods such as the construction of a cDNA library or the construction of a genomic library or by the technique of the polymerase chain reaction. Sometimes a combination of these methods may be necessary to obtain the sequence of the full genome.

The following describes the strategies which may be followed to obtain additional genomic sequence information on HIV-1 group O strains, of which partial sequences have been disclosed above.

1. Construction of a cDNA Library

HIV-1 group O viruses are propagated and isolated using standard methods e.g. by cultivation of peripheral blood lymphocytes (PBMC) from the HIV-infected individual together with stimulated lymphocytes from healthy donors, or alternatively by infecting cell lines with the virus in a permanent way. Once virus is detected in the culture supernatant using standard techniques (e.g. measuring reverse transcriptase activity; measuring p24 antigen . . . ), virus is harvested from the culture supernatant by centrifugation under conditions where the virus is pelleted. RNA is obtained by disrupting the virus in a buffer containing 6M guanidinium chloride and the RNA is pelleted through a 5.5M CsCl cushion. The RNA which is resuspended in a suitable buffer is then phenolized and precipitated with e.g. ethanol and lithium chloride.

cDNA synthesis is performed on the complete RNA or part of the RNA using commercially available kits. OligodT primers, random primers, or HIV-1 specific primers may be used to prime the cDNA synthesis which is done by a reverse transcriptase (RT) enzyme. This leads to a first DNA strand which is complementary to the initial RNA strand and which forms RNA::DNA hybrids. The RNA strand is removed with Rnase H and the second DNA strand is then synthesised with DNA polymerase I. The overhanging single stranded cDNA ends are removed with T4 DNA polymerase. The resulting cDNA is ligated to linkers which contain an appropriate restriction site. After hydrolysis of the cDNA with the appropriate restriction enzyme, the cDNA of suitable size is isolated (e.g. from agarose gel after electrophoresis) and ligated in a suitable vector. The vector containing the cDNA fragments can be propagated in competent $E.$ $coli$ cells using standard methods.

Various techniques to screen for colonies containing HIV-1 specific sequences are known in the art. They involve screening of e.g. a cDNA expression library (e.g. λgt11) with serum (polyclonal or monoclonal serum) or the screening of a cDNA library with $^{32}P$ labelled HIV-1 DNA fragments under non-stringent or stringent hybridization conditions. Background signals are lowered by washing the filters subsequently under more stringent conditions. After identification of the $E.$ $coli$ containing the suitable fragment, the fragment is isolated from the plasmid and is introduced (as a complete entity or a fragment thereof) in expression vectors. Using standard techniques, these vectors produce the protein(s) encoded by the inserted DNA fragment. The resulting proteins is further purified and used for the development of diagnostic assays. Sequence information of the virus is obtained from the plasmid containing viral DNA sequences.

2. Construction of a Genomic Library

Chromosomal DNA is prepared from cells infected with the HIV-1 group O virus (e.g. cells permanently producing the virus) using standard techniques (Maniatis et al. 1982). This DNA may be used to construct a genomic library (Zabarousky and Allikmets 1986). The chromosomal DNA which contains the proviral HIV-1 group O DNA is partially digested with a selected restriction enzyme. Fragments between 9 Kb and 23 Kb, isolated on a 40%–10% sucrose gradient, are manipulated according to standard techniques in order to introduce them in a vector system suitable for the cloning of long DNA fragments e.g. lambda derived vectors or cosmids.

The vector with the DNA fragment is introduced in a suitable *E. coli* strain and is further propagated onto plates. Plaques or colonies from the genomic library are transferred to nylon or nitrocellulose membranes and screened with enzyme or $^{32}$P labelled DNA fragments of the viral genome (plaque or colony screening) under non-stringent or stringent hybridization conditions. Colonies or plaques displaying positive signals are purified from other colonies or plaques. The viral DNA is further subcloned and sequenced. Genes or fragments of genes are further manipulated using standard techniques in order to express important viral proteins or epitopes which may be used for the development of diagnostic assays.

3. Polymerase Chain Reaction (PCR)

HIV-1 group O viral DNA fragments may also be obtained using the polymerase chain reaction (PCR) (Kwok et al. 1987) which is a standard technology used for the cloning of DNA fragments. PCR may be performed on cellular DNA of cells infected with the virus or on cDNA obtained from viral RNA derived from virus culture, lymphocytes, serum, plasma, . . . . The PCR may use primers which contain specific sequences of the virus based on sequences of the virus which are already known, or alternatively, primers which contain sequences derived from related viruses in regions known to be conserved or not conserved among HIV variants. Annealing conditions of the primers should preferentially not be too stringent (e.g. Tm−20° C.), however the best conditions should be experimentally established. The resulting amplification product is subsequently sequenced and new primers are designed based on the newly generated sequence in order to further amplify the viral DNA, again eventually in combination with primers derived from the partially determined sequence of the isolate or from the sequence of related viruses.

Example 4 provides the cloning and sequencing strategy followed in order to obtain the polynucleic acid sequences encoding the antigens Vif, Pol, Vpr, Tat (1st exon), Vpu, Rev (1st exon) and gp160, or fragments thereof, from the HIV-1 group O viruses FABA (MP331), MP448, MP539 and MP 645.

Therefore, in addition to the gp41 and V3 sequences described above, the present invention further provides for a polynucleic acid containing a polynucleic acid sequence encoding at least part of the Vif, Pol, Vpr, Tat (1st exon), Vpu, Rev (1st exon) or gp160 antigens from any of the following HIV-1 group O strains of the invention: MP340, FABA(MP331), MP450, MP448, 189, MP539, 320, BSD422, KGT008, MP575, BSD189, BSD649, BSD242, 533, 772P94, MP95B and MP645.

The terms "Vif, Pol, Vpr, Tat (1st exon), Vpu, Rev (1st exon) and gp160" are terms for HIV-antigens familiar to the person skilled in the art. Vif and Vpu have important roles during virion morphogenesis. Vif is required for the production of fully infectious viruses, while Vpu is necessary for the efficient release of virus particles budding from the cell membrane in cultured cells (Göttlinger et al, 1993). Vpu also mediates the rapid degradation of the CD4 receptor molecule in the endoplasmatic reticulum (Willey et al, 1992, Bour et al, 1995). The Vpr protein is involved in the nuclear migration of the prointegration complex (Heinzinger et al, 1994) and is also found in mature virions and hence a structural component of the virus (Paxton et al, 1993). Tat (transactivator) and Rev (regulator of virion expression) are encoded in overlapping reading frames which generate small regulatory proteins translated from multiple spliced mRNAs (Salfeld et al, 1990; Solomin et al, 1990, Furtado et al, 1991). Both proteins are essential for virus replication and are positive regulators of gene expression (Arya et al, 1985; Feinberg et al, 1986). Pol is encoded by the coding gene pol, which overlaps with the gag information but in a different reading frame. Pol is a precursor protein which is autocleaved to form the following viral enzymes: a protease, a reverse transcriptase with polymerase activity and Rnase H activity, and an integrase (Ross et al, 1991). FIG. 8 illustrates the sequence of a large genomic fragment from a number of HIV-1 group O strains of the current invention (MP645 (SEQ ID NO 106), MP331 (SEQ ID NO 103), MP448 (SEQ ID NO 104) and MP539(SEQ ID NO 105)), and the location of the Vif, Pol, Vpr, Tat (1st exon), Vpu, Rev (1st exon) and gp160 (partially) genes in these sequences.

The present invention thus provides for a polynucleic acid comprising a nucleotide sequence chosen from the group of (I) a nucleotide sequence represented by any of SEQ ID NO 103, SEQ ID NO 104, SEQ ID NO 105, SEQ ID NO 106, or (ii) a nucleotide sequence complementary to a sequence according to (I), or (iii) a nucleotide sequence showing at least 95%, preferably 96%, 97%, 98% and most preferably 99% homology to a sequence according to (I), or (iv) a nucleotide sequence according to (I) whereby T is replaced by U, or (v) a nucleotide sequence according to (I) whereby at least one nucleotide is substituted by a nucleotide analogue, or (vi) a fragment a sequence of at least 15, preferably 16, 17, 18, 19, 20, 21, 22, 23, 24, 25 up to 50 contiguous nucleotides of any of the nucleotide sequences according to (I) to (v), and characterized by the fact that it selectively hybridizes to the polynucleic acid from which it is derived, and/or selectively amplifies the polynucleic acid from which it is derived.

More particularly, the present invention provides for a polynucleic acid consisting of a nucleotide sequence chosen from the group of (I) a nucleotide sequence represented by any of SEQ ID NO 103, SEQ ID NO 104, SEQ ID NO 105, SEQ ID NO 106, or (ii) a nucleotide sequence complementary to a sequence according to (I), or (iii) a nucleotide sequence showing at least 95%, preferably 96%, 97%, 98% and most preferably 99% homology to a sequence according to (I), or (iv) a nucleotide sequence according to (I) whereby T is replaced by U, or (v) a nucleotide sequence according to (I) whereby at least one nucleotide is substituted by a nucleotide analogue (vi) a fragment a sequence of at least 15, preferably 16, 17, 18, 19, 20, 21, 22, 23, 24, 25 up to 50 contiguous nucleotides of any of the nucleotide sequences according to (I) to (v), and characterized by the fact that it selectively hybridizes to the polynucleic acid from which it is derived, and/or selectively amplifies the polynucleic acid from which it is derived.

The above-described nucleic acid fragment may be used as a specific hybridization probe for the detection of the nucleic acids of the current invention.

The term "selectively hybridizing" means that the hybridization signal obtained after hybridization of the fragment with the nucleic acid from which it is derived, is more intense than the hybridization signal obtained when the fragment is hybridized to the corresponding nucleic acid from another HIV-1 group O strain, under the same stringent hybridization and wash conditions. In practice this means that the nucleic acid fragment will show at least one mismatched nucleotide with the sequence of the corresponding nucleic acid fragment of another HIV-1 group O strain.

The term "stringent hybridization conditions" implies that the hybridization takes place at a temperature which is situated approximately between Tm and (Tm−10° C.), whereby Tm represents the calculated melting temperature of the target nucleic. It is generally known that the stringency depends on the percentage mismatches (=non-matching nucleotides upon alignment) present in the hybridizing duplex. According to a simplified formula, the hybridization temperature may be calculated as follows: Tm−1.2 (% mismatch). A temperature decrease of 10° C. implies a maximum percentage of allowed mismatches of 8.3%.

The nucleic acid fragment as described above may also be used as a specific amplification primer of the nucleic acids of the current invention.

The term "selective amplification" refers to the fact that said nucleic acid fragment may initiate a specific amplification reaction of the nucleic acids of the invention (e.g. a polymerase chain reaction) in the presence of other nucleic acids, under appropriate amplification conditions. It means that, under the appropriate amplification conditions, only the nucleic acids of the invention will be amplified, and not the other nucleic acids possibly present.

Preferred embodiments of the invention comprise polynucleic acids or fragments thereof. as specified below.

A polynucleic acid comprising SEQ ID NO 103, or comprising a fragment consisting of at least 15, preferably 16, 17, 18, 19, 20, 21, 22, 23, 24, 25, up to 50 contiguous nucleotides of said polynucleic acid, said fragment characterized by the fact that it selectively hybridizes to the polynucleic acid comprising SEQ ID NO 103.

A polynucleic acid comprising SEQ ID NO 104, or comprising a fragment consisting of at least 15, preferably 16, 17, 18, 19, 20, 21, 22, 23, 24, 25, up to 50 contiguous nucleotides of said polynucleic acid, said fragment characterized by the fact that it selectively hybridizes to the polynucleic acid comprising SEQ ID NO 104.

A polynucleic acid comprising SEQ ID NO 105, or comprising a fragment consisting of at least 15, preferably 16, 17, 18, 19, 20, 21, 22, 23, 24, 25, up to 50 contiguous nucleotides of said polynucleic acid, said fragment characterized by the fact that it selectively hybridizes to the polynucleic acid comprising SEQ ID NO 105.

A polynucleic acid comprising SEQ ID NO 106, or comprising a fragment consisting of at least 15, preferably 16, 17, 18, 19, 20, 21, 22, 23, 24, 25, up to 50 contiguous nucleotides of said polynucleic acid, said fragment characterized by the fact that it selectively hybridizes to the polynucleic acid comprising SEQ ID NO 106.

A polynucleic acid fragment consisting of a sequence of at least 15, preferably 16, 17, 18, 19, 20, 21, 22, 23, 24, 25, up to 50 contiguous nucleotides of SEQ ID NO 103, said fragment characterized by the fact that it selectively amplifies the polynucleic acid from which it is derived.

A polynucleic acid fragment consisting of a sequence of at least 15, preferably 16, 17, 18, 19, 20, 21, 22, 23, 24, 25, up to 50 contiguous nucleotides of SEQ ID NO 104, said fragment characterized by the fact that it selectively amplifies the polynucleic acid from which it is derived.

A polynucleic acid fragment consisting of a sequence of at least 15, preferably 16, 17, 18, 19, 20, 21, 22, 23, 24, 25, up to 50 contiguous nucleotides of SEQ ID NO 105, said fragment characterized by the fact that it selectively amplifies the polynucleic acid from which it is derived.

A polynucleic acid fragment consisting of a sequence of at least 15, preferably 16, 17, 18, 19, 20, 21, 22, 23, 24, 25, up to 50 contiguous nucleotides of SEQ ID NO 106, said fragment characterized by the fact that it selectively amplifies the polynucleic acid from which it is derived.

The invention further provides for an antigen comprising at least part of Vif, Pol, Vpr, Tat (1st exon), Vpu, Rev (1st exon) and/or gp160 encoded by the nucleic acid sequences as described above from any of the following HIV-1 group O strains: MP340, FABA(MP331), MP450, MP448, 189, MP539, 320, BSD422, KGT008, MP575, BSD189, BSD649, BSD242, 533, 772P94, MP95B and MP645.

The current invention more particularly provides for an antigen comprising at least one amino acid sequence chosen from the following groups of sequences Ii) an amino acid sequence represented by any of SEQ ID NO 107, SEQ ID NO 108, SEQ ID NO 109 and SEQ ID NO 110 representing the Vif antigen, (ii) an amino acid sequence represented by any of SEQ ID NO 111, SEQ ID NO 112, SEQ ID NO 113 and SEQ ID NO 114 representing the Vpu antigen, (iii) an amino acid sequence represented by any of SEQ ID NO 115, SEQ ID NO 116, SEQ ID NO 117 and SEQ ID NO 118 representing the Vpr antigen, (iv) an amino acid sequence represented by any of SEQ ID NO 119, SEQ ID NO 120, SEQ ID NO 121 and SEQ ID NO 122 representing the Tat antigen, (v) an amino acid sequence represented by any of SEQ ID NO 123, SEQ ID NO 124, SEQ ID NO 125 and SEQ ID NO 126 representing the Rev antigen, (vi) an amino acid sequence represented by any of SEQ ID NO 127, SEQ ID NO 128, SEQ ID NO 129 and SEQ ID NO 130 representing the Pol antigen, (vii) an amino acid sequence represented by any of SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 2, SEQ ID NO 22, SEQ ID NO 24, SEQ ID NO 26, SEQ ID NO 28, SEQ ID NO 30, SEQ ID NO 32, SEQ ID NO 34, SEQ ID NO 36, SEQ ID NO 38, SEQ ID NO 40, SEQ ID NO 42, SEQ ID NO 44, SEQ ID NO 46, SEQ ID NO 48, SEQ ID NO 50, SEQ ID NO 52, SEQ ID NO 132, and SEQ ID NO 134 representing at least part of the Env antigen, or (viii) a fragment of any of the above-mentioned antigens Ii) to (vii), said fragment consisting of at least 8, preferably 9, 10, 11,12, 13, 14, 15, 16, 17, 18, 19, 20, 21, 22, 23, 24, 25, 50 up to the maximum number of contiguous amino acids of the amino acid sequence of said antigen, and being characterized by the fact that it specifically reacts with antibodies raised against said antigen.

The current invention further provides for an antigen consisting of an amino acid sequence chosen from the following groups of sequences:

Ii) an amino acid sequence SEQ ID NO 107, SEQ ID NO 108, SEQ ID NO 109 and SEQ ID NO 110 representing the Vif antigen, (i) an amino acid sequence SEQ ID NO 111, SEQ ID NO 112, SEQ ID NO 113 and SEQ ID NO 114 representing the Vpu antigen, (iii) an amino acid sequence SEQ ID NO 115, SEQ ID NO 116, SEQ ID NO 117 and SEQ ID NO 118 representing the Vpr antigen,
(iv) an amino acid sequence SEQ ID NO 119, SEQ ID NO 120, SEQ ID NO 121 and SEQ ID NO 122 representing the Tat antigen,
(v) an amino acid sequence SEQ ID NO 123, SEQ ID NO 124, SEQ ID NO 125 and SEQ ID NO 126 representing the Rev antigen,
(vi) an amino acid sequence SEQ ID NO 127, SEQ ID NO 128, SEQ ID NO 129 and SEQ ID NO 130 representing the Pol antigen,
(vii) an amino acid sequence represented by any of SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 20, SEQ ID NO 22, SEQ ID NO 24, SEQ ID NO 26, SEQ ID NO 28, SEQ ID NO 30, SEQ ID NO 32, SEQ ID NO 34, SEQ ID NO 36, SEQ ID NO 38, SEQ ID NO 40, SEQ ID NO 42, SEQ ID NO 44, SEQ ID NO 46, SEQ ID NO 48, SEQ ID NO 50, SEQ ID NO 52, SEQ ID NO 132, and SEQ ID NO 134 representing at least part of the Env antigen, or
(viii) a fragment of any of the above-mentioned antigens (I) to (vii), said fragment consisting of at least 8, preferably 9, 10,11,12, 13, 14, 15, 16, 17, 18, 19, 20, 21,22, 23, 24, 25, 50 up to the maximum number of contiguous amino acids of the amino acid sequence of said antigen, and being characterized by the fact that it specifically reacts with antibodies raised against said antigen.

The current invention thus also relates to:
(I) an antigen derived from the gp160 env precursor protein of the new HIV-1 group O strain MP340 comprising at least one of the sequences according to SEQ ID NO 2, 4, 42, 59, 60, 61, 73, 85, 86, 100, or fragments thereof with said fragments specifically reacting with antibodies raised against the antigen they are derived from;
(ii) a polynucleic acid encoding an antigen according to (I) and comprising at least one of the nucleotide sequences according to SEQ ID NO 1, 3, 41, including homologous sequences, complementary sequences, and fragments hybridizing thereto;
(iii) a virus strain comprising in its genome a polynucleic acid according to (ii), more particularly a virus strain termed MP340, as well as polynucleic acids and antigens isolated therefrom.

The current invention thus also relates to:
(I) an antigen derived from the gp160 env precursor protein of the new HIV-1 group O strain MP331 (or FABA) comprising at least one of the sequences according to SEQ ID NO 6, 8, 44, 56, 57, 58, 82, 83, 84, 138 or fragments thereof with said fragments specifically reacting with antibodies raised against the antigen they are derived from;
(ii) an antigen derived from the Vif, Vpu, Vpr, Tat, Rev, Pol and Env protein of the new HIV-1 group O strain MP331 (or FABA) comprising at least one of the sequences according to SEQ ID NO 107, 111, 115, 119, 123, 127, 131, or fragments thereof with said fragments specifically reacting with antibodies raised against the antigen they are derived from;
(iii) a polynucleic acid encoding an antigen according to (I) or (ii) and comprising at least one of the nucleic acid sequences according to SEQ ID NO 5, 7, 43, 103, including homologous sequences, complementary sequences, and fragments hybridizing thereto;
(iv) a virus strain comprising in its genome said a polynucleic acid according to (iii), more particularly a virus strain termed MP331 (FABA) deposited at the ECACC under accession number V97061301, as well as polynucleic acids and antigens isolated therefrom.

The current invention thus also relates to:
(I) an antigen derived from the gp160 env precursor protein of the new HIV-1 group O strain MP450 comprising at least one of the sequences according to SEQ ID NO 10, 12, 46, 62, 63, 64, 73, 87, 100, or fragments thereof with said fragments specifically reacting with antibodies raised against the antigen they are derived from;
(ii) a polynucleic acid encoding an antigen according to (I) and comprising at least one of the nucleotide sequences according to SEQ ID NO 9, 11, 45, including homologous sequences, complementary sequences, and fragments hybridizing thereto;
(iii) a virus strain comprising in its genome a polynucleic acid according to (ii), more particularly a virus strain termed MP450 deposited at the ECACC under accession number V97061302, as well as polynucleic acids and antigens isolated therefrom.

The current invention thus also relates to:
(I) an antigen derived from the gp160 env precursor protein of the new HIV-1 group O strain MP448 comprising at least one of the sequences according to SEQ ID NO 14, 16, 48, 65, 66, 67, 76, 88, 101, or fragments thereof with said fragments specifically reacting with antibodies raised against the antigen they are derived from;
(ii) an antigen derived from the Vif, Vpu, Vpr, Tat, Rev, Pol and Env protein of the new HIV-1 group O strain MP448 comprising at least one of the sequences according to SEQ ID NO 108, 112, 116, 120, 124, 128, 132 or fragments thereof with said fragments specifically reacting with antibodies raised against the antigen they are derived from;
(iii) a polynucleic acid encoding an antigen according to (I) or (ii) and comprising at least one of the nucleic acid sequences according to SEQ ID NO 13, 15, 47, 104, including homologous sequences, complementary sequences, and fragments hybridizing thereto;
(iv) A virus strain comprising in its genome said polynucleic acid according to (iii), more particularly a virus strain termed MP448, as well as polynucleic acids and antigens isolated therefrom.

The current invention thus also relates to:
(I) an antigen derived from the gp160 env precursor protein of the new HIV-1 group O strain 189 comprising at least one of the sequences according to SEQ ID NO 18, 50, 53, 54, 55, 73, 90, 91, or fragments thereof with said fragments specifically reacting with antibodies raised against the antigen they are derived from;
(ii) a polynucleic acid encoding an antigen according to (I) and comprising at least one of the nucleotide sequences according to SEQ ID NO 17, 49, including homologous sequences, complementary sequences, and fragments hybridizing thereto,
(iii) a virus strain comprising in its genome a polynucleic acid according to (ii), more particularly a virus strain termed 189, as well as polynucleic acids and antigens isolated therefrom.

The current invention thus also relates to:
(I) an antigen derived from the gp160 env precursor protein of the new HIV-1 group O strain MP539 comprising at least one of the sequences according to SEQ ID NO 40, 52, 68, 69, 70, 71, 89, 95 or fragments thereof with said fragments specifically reacting with antibodies raised against the antigen they are derived from;
(ii) an antigen derived from the Vif, Vpu, Vpr, Tat, Rev, Pol and Env protein of the new HIV-1 group O strain MP539 comprising at least one of the sequences according to SEQ ID NO 109, 113, 117, 121, 125, 129, 133, or fragments thereof with said fragments specifically reacting with antibodies raised against the antigen they are derived from.

(iii) a polynucleic acid encoding an antigen according to (I) or (ii) and comprising at least one of the nucleic acid sequences according to SEQ ID NO 39, 51, 105, including homologous sequences, complementary sequences, and fragments hybridizing thereto, (iv) A virus strain comprising in its genome said polynucleic acid according to (iii), more particularly a virus strain deposited at the ECACC under accession number V97061303, as well as polynucleic acids and antigens isolated therefrom.

The current invention thus also relates to:

(I) an antigen derived from the gp160 env precursor protein of the new HIV-1 group O strain 320 comprising at least one of the sequences according to SEQ ID NO 20, 92, or fragments thereof with said fragments specifically reacting with antibodies raised against the antigen they are derived from;

(ii) a polynucleic acid encoding an antigen according to (I) and comprising the nucleotide sequence according to SEQ ID NO 19 including homologous sequences, complementary sequences, and fragments hybridizing thereto;

(iii) a virus strain comprising in its genome a polynucleic acid according to (ii), more particularly a virus strain termed 320, as well as polynucleic acids and antigens isolated therefrom.

The current invention thus also relates to:

(I) an antigen derived from the gp160 env precursor protein of the new HIV-1 group O strain BSD422 comprising at least one of the sequences according to SEQ ID NO 22, 80, 79, or fragments thereof with said fragments specifically reacting with antibodies raised against the antigen they are derived from;

(ii) a polynucleic acid encoding an antigen according to (I) and comprising the nucleotide sequence according to SEQ ID NO 21 including homologous sequences, complementary sequences, and fragments hybridizing thereto;

(iii) a virus strain comprising in its genome a polynucleic acid according to (ii), more particularly a virus strain termed BSD422, as well as polynucleic acids and antigens isolated therefrom.

The current invention thus also relates to:

(I) an antigen derived from the gp160 env precursor protein of the new HIV-1 group O strain KGT008 comprising at least one of the sequences according to SEQ ID NO 24, 79, 99? or fragments thereof with said fragments specifically reacting with antibodies raised against the antigen they are derived from;

(ii) a polynucleic acid encoding an antigen according to (I) and comprising the nucleotide sequence according to SEQ ID NO 23 including homologous sequences, complementary sequences, and fragments hybridizing thereto;

(iii) a virus strain comprising in its genome a polynucleic acid according to (ii), more particularly a virus strain termed KGT008, as well as polynucleic acids and antigens isolated therefrom.

The current invention thus also relates to:

(I) an antigen derived from the gp160 env precursor protein of the new HIV-1 group O strain MP575 comprising the sequence according to SEQ ID NO 26, or fragments thereof with said fragments specifically reacting with antibodies raised against the antigen they are derived from;

(ii) a polynucleic acid encoding an antigen according to Ii) and comprising the nucleotide sequence according to SEQ ID NO 25 including homologous sequences, complementary sequences, and fragments hybridizing thereto;

(iii) A virus strain comprising in its genome said polynucleic acid according to (ii), more particularly a virus strain deposited at the ECACC under provisional accession number V98071301, as well as polynucleic acids and antigens isolated therefrom.

The current invention thus also relates to:

(I) an antigen derived from the gp160 env precursor protein of the new HIV-1 group O strain BSD189 comprising at least one of the sequences according to SEQ ID NO 28, 72, 95, or fragments thereof with said fragments specifically reacting with antibodies raised against the antigen they are derived from;

(ii) a polynucleic acid encoding an antigen according to (I) and comprising the nucleotide sequence according to SEQ ID NO 27 including homologous sequences, complementary sequences, and fragments hybridizing thereto;

(iii) a virus strain comprising in its genome a polynucleic acid according to (ii), more particularly a virus strain termed BSD189, as well as polynucleic acids and antigens isolated therefrom.

The current invention thus also relates to:

(I) an antigen derived from the gp160 env precursor protein of the new HIV-1 group O strain BSD649 comprising at least one of the sequences according to SEQ ID NO 30, 77, 98, or fragments thereof with said fragments specifically reacting with antibodies raised against the antigen they are derived from;

(ii) a polynucleic acid encoding an antigen according to (I) and comprising the nucleotide sequence according to SEQ ID NO 29 including homologous sequences, complementary sequences, and fragments hybridizing thereto;

(iii) a virus strain comprising in its genome a polynucleic acid according to (ii), more particularly a virus strain termed BSD649, as well as polynucleic acids and antigens isolated therefrom.

The current invention thus also relates to:

(I) an antigen derived from the gp160 env precursor protein of the new HIV-1 group O strain BSD242 comprising at least one of the sequences according to SEQ ID NO 32, 81, 96, or fragments thereof with said fragments specifically reacting with antibodies raised against the antigen they are derived from;

(ii) a polynucleic acid encoding an antigen according to (I) and comprising the nucleotide sequence according to SEQ ID NO 31 including homologous sequences, complementary sequences, and fragments hybridizing thereto;

(iii) a virus strain comprising in its genome a polynucleic acid according to (ii), more particularly a virus strain termed BSD242, as well as polynucleic acids and antigens isolated therefrom.

The current invention thus also relates to:

(I) an antigen derived from the gp160 env precursor protein of the new HIV-1 group O strain 533 comprising at least one of the sequences according to SEQ ID NO 34, 81, 93, or fragments thereof with said fragments specifically reacting with antibodies raised against the antigen they are derived from;

(ii) a polynucleic acid encoding an antigen according to (I) and comprising the nucleotide sequence according to SEQ ID NO 33 including homologous sequences, complementary sequences, and fragments hybridizing thereto;

(iii) a virus strain comprising in its genome a polynucleic acid according to (ii), more particularly a virus strain termed 533, as well as polynucleic acids and antigens isolated therefrom.

The current invention thus also relates to:

(I) an antigen derived from the gp160 env precursor protein of the new HIV-1 group O strain 772P94 comprising at least one of the sequences according to SEQ ID NO 36, 75, 94, or fragments thereof with said fragments specifically reacting with antibodies raised against the antigen they are derived from;

(ii) a polynucleic acid encoding an antigen according to (I) and comprising the nucleotide sequence according to SEQ ID NO 35 including homologous sequences, complementary sequences, and fragments hybridizing thereto;

(iii) a virus strain comprising in its genome a polynucleic acid according to (ii), more particularly a virus strain termed 772P94, as well as polynucleic acids and antigens isolated therefrom.

The current invention thus also relates to:

(I) an antigen derived from the gp160 env precursor protein of the new HIV-1 group O strain MP95B comprising at least one of the sequences according to SEQ ID NO 38, 74, 102, or fragments thereof with said fragments specifically reacting with antibodies raised against the antigen they are derived from;

(ii) a polynucleic acid encoding an antigen according to (I) and comprising the nucleotide sequence according to SEQ ID NO 37 including homologous sequences, complementary sequences, and fragments hybridizing thereto;

(iii) a virus strain comprising in its genome a polynucleic acid according to (ii), more particularly a virus strain termed MP95B, as well as polynucleic acids and antigens isolated therefrom.

The current invention thus also relates to:

(I) an antigen derived from the gp160 env precursor protein of the new HIV-1 group O stain MP645 comprising at least one of the sequences according to SEQ ID NO 135, 136, 137, or fragments thereof with said fragments specifically reacting with antibodies raised against the antigen they are derived from;

(ii) an antigen derived from the Vif, Vpu, Vpr, Tat, Rev, Pol and Env protein of the new HIV-1 group O strain MP645 comprising one of the sequences according to SEQ ID NO 110, 114, 118, 122, 126, 130, 134, or fragments thereof with said fragments specifically reacting with antibodies raised against the antigen they are derived from.

(iii) a polynucleic acid encoding an antigen according to (I) or (ii) and comprising the nucleic acid sequence according to SEQ ID NO 106, including homologous sequences, complementary sequences, and fragments hybridizing thereto;

(iv) A virus strain comprising in its genome said polynucleic acid according to (iii), more particularly a virus strain deposited at the ECACC under provisional accession number V98071302, as well as polynucleic acids and antigens isolated therefrom.

In another embodiment, the invention provides for an antibody, preferably a monoclonal antibody, raised against an antigen or antigen fragment as described above. Such an antibody recognizes specifically the antigen or the antigen fragment to which it has been raised.

According to an alternative embodiment, the present invention also relates to an antigen-binding fragment of the antibody, said fragment being of the F(ab')$_2$, Fab or single chain Fv type, or any type of recombinant antibody derived from said specific antibodies or monoclonal antibodies, provided that said antibody fragment or recombinant antibody still recognizes specifically the antigen or antigen fragment to which it has been raised.

The expression "antibody recognizing specifically" means that the binding between the antigen as a ligand and a molecule containing an antibody combining site, such as a Fab portion of a whole antibody, is specific, signifying that no cross-reaction occurs.

The expression "antibody specifically raised against a compound" means that the sole immunogen used to produce said antibody was said compound.

The possible cross-reactivity of polyclonal antisera may be eliminated by preabsorption of the polyclonal antiserum against the cross-reacting antigenic determinants.

In a preferential embodiment, the above-mentioned antibodies are neutralizing antibodies, i.e. antibodies capable of in vitro inhibition of viral growth, determined according to methods known in the art.

Neutralizing antibodies may be used as a reagent in a so-called "passive vaccine" composition, i.e. a composition conferring temporary protection against an infection, upon injection in an individual. The invention also relates to passive vaccine compositions, comprising any of the above-mentioned neutralizing antibodies.

The monoclonal antibodies of the invention can be produced by any hybridoma liable to be formed according to classical methods from splenic cells of an animal, particularly of a mouse or rat, immunized with the antigen of the invention, defined above on the one hand, and of cells of a myeloma cell line on the other hand, and to be selected by the ability of the hybridoma to produce the monoclonal antibodies recognizing the antigen which has been initially used for the immunization of the animals.

The monoclonal antibodies according to a preferred embodiment of the invention may be humanized versions of the mouse monoclonal antibodies made by means of recombinant DNA technology, departing from the mouse and/or human genomic DNA sequences coding for H and L chains or from cDNA clones coding for H and L chains.

Also fragments derived from these monoclonal antibodies such as Fab, F(ab)'$_2$ and ssFv ("single chain variable fragment"), providing they have retained the original binding properties, form part of the present invention. Such fragments are commonly generated by, for instance, enzymatic digestion of the antibodies with papain, pepsin, or other proteases. It is well known to the person skilled in the art that monoclonal antibodies, or fragments thereof, can be modified for various uses.

The antibodies involved in the invention can be labelled by an appropriate label of the enzymatic, fluorescent, or radioactive type.

The invention also relates to the use of the antigens of the invention, or fragments thereof, for the selection of recombinant antibodies by the process of repertoire cloning (Perrson et al., 1991).

The present invention further relates to an anti-idiotype antibody raised against any of the antibodies as defined above.

The term "anti-idiotype antibodies" refers to monoclonal antibodies raised against the antigenic determinants of the variable region of monoclonal antibodies themselves raised against the antigens of the invention. These antigenic determinants of immunoglobulins are known as idiotypes (sets of idiotopes) and can therefore be considered to be the "fingerprint" of an antibody (for review see de Préval, 1978; Fleishmann and Davie,1984). The methods for production of monoclonal anti-idiotypic antibodies have been described by Gheuens and McFarlin (1982). Monoclonal anti-idiotypic antibodies have the property of forming an immunological complex with the idiotype of the monoclonal antibody against which they were raised. In this respect the monoclonal antibody is often referred to as Ab1, and the anti-idiotypic antibody is referred to as Ab2. These anti-idiotype Ab2s may be used as substitutes for the polypeptides of the invention or as competitors for binding of the polypeptides of the invention to their target.

The present invention further relates to antisense peptides derived from the antigens of the invention as described above.

More particularly, the term "antisense peptide" is reviewed by Blalock (1990) and by Roubos (1990). In this respect, the molecular recognition theory (Blalock, 1990) states that not only the complementary nucleic acid sequences interact but that, in addition, interacting sites in proteins are composed of complementary amino acid sequences (sense ligand with receptor or sense ligand with antisense peptides). Thus, two peptides derived from complementary nucleic acid sequences in the same reading frame will show a total interchange of their hydrophobic and hydrophilic amino acids when the amino terminus of one is aligned with the carboxy terminus of the other. This inverted hydropathic pattern might allow two such peptides to assume complementary conformations responsible for specific interaction.

The antisense peptides can be prepared as described in Ghiso et al. (1990). By means of this technology it is possible to logically construct a peptide having a physiologically relevant interaction with a known peptide by simple nucleotide sequence analysis for complementarity, and synthesize the peptide complementary to the binding site.

The present invention further relates to a diagnostic method for detecting the presence of an HIV-1 infection, said method comprising the detection of antibodies against HIV-1, including HIV- group O, using any of the antigens or antigen fragments of the invention as described above, and/or the detection of viral antigen originating from HIV-1, including HIV-1 group O, using any of the antibodies of the invention as described above and/or the detection of viral nucleic acids originating from HIV-1, including HIV-1 group O, using any of the nucleic acids or nucleic acid fragments of the invention as described above, in a biological sample.

Preferably the above-mentioned diagnostic method for detecting the presence of an HIV-1 infection also includes the detection of an HIV-1 group O infection, and more particularly also includes the detection of an infection caused by any of the HIV-1 group O strains of the current invention.

The term "biological sample" refers to any biological sample (tissue or fluid) possibly containing HIV nucleic acids, and/or HIV antigens and/or antibodies against HIV, and refers more particularly to blood, serum, plasma, organs or tissue samples.

In most instances, the [HIV-1 group O]-reagents (=antigens and/or antibodies and/or nucleic acids) of the invention will be used in methods which combine them with other HIV-reagents (=antigens and/or antibodies and/or nucleic acids). The addition of the HIV-1 type O reagents of the current invention to methods and kits for detection of HIV-infection in general, may result in methods and kits showing a higher sensitivity, and/or a higher discriminating power between different types of HIV-infection, for example HIV-1 group M, HIV-1 group O and HIV-2 infection.

The term "sensitivity" refers to the ratio of positively reacting samples/the number of truly infected samples.

More specifically, the present invention relates to a method for in vitro diagnosis of a HIV-1 infection, including a HIV-1 group O infection, comprising at least the step of contacting a biological sample with:

a HIV-1 group O antigen, or antigen fragment, as defined above, under conditions allowing the formation of an immunological complex, and/or, a HIV-1 group O nucleic acid, or nucleic acid fragment, as defined above, under conditions allowing the formation of a hybridization complex, with the nucleic acids of said sample being possibly amplified prior to hybridization, and/or, an antibody specifically directed against an HIV-1 group O antigen as defined above, under conditions allowing the formation of an immunological complex, and/or, an anti-idiotype antibody as defined above, under conditions allowing the formation of an antibody-anti-idiotypic complex, and/or, an antisense peptide as defined above, under conditions allowing the formation of an antigen-antisense peptide complex, and subsequently detecting the complexes formed.

In a more specific embodiment, the invention relates to a method for detecting the presence of antibodies against HIV-1 in a biological sample, in particular antibodies against an HIV-1 group O strain, preferably a serum sample, comprising the following steps:

contacting the biological sample taken from a patient with at least one antigen or antigen fragment as described above, under conditions enabling the formation of an immunological complex, and detecting the immunological complex formed between said antigen or antigen fragment and the antibodies possibly present in the sample.

Conditions allowing the formation of an immunological complex are known to the person skilled in the art.

In a special embodiment, the antigens being used in the above-described method for detection of anti-HIV-1 group O antibodies, can be replaced by anti-idiotype antibodies as described above, acting as their equivalents.

Conditions allowing the formation of an antibody-anti-idiotypic complex are known in the art.

The invention farther relates to a method for detecting the presence of an antigen or an antigen fragment of HIV-1, in particular an antigen or antigen fragment of an HIV-1 group O strain, in a biological sample comprising the following steps:

contacting the biological sample taken from a patient with at least one antibody as described above under conditions enabling the formation of an immunological complex, and detecting the immunological complex formed between said antibody and the antigen or antigen fragment possibly present in the sample.

In a special embodiment, the antibodies being used in the above-described method for detection of HIV-1 group O antigens, may be replaced by anti-sense peptides as described above, acting as their equivalents.

Conditions allowing the formation of an antigen-antisense peptide complex are known in the art.

Design of immunoassays is subject to a great deal of variation, and many formats are known in the art. Protocols may, for example, use solid supports, or immunoprecipitation. Most assays involve the use of labelled antibody or polypeptide; the labels may be, for example, enzymatic, fluorescent, chemoluminescent, radioactive, or dye molecules. Assays which amplify the signals from the immune complex are also known, examples of which are assays which utilize biotin and avidin or streptavidin, and enzyme-labelled and mediated immunoassays, such as ELISA assays.

An advantageous embodiment provides for a method for detection of anti-HIV-1 group O antibodies in a sample, whereby the antigens or antigen fragments of the invention are immobilized on a solid support, for example on a membrane strip. Different antigens or antigen fragments of the invention may be immobilized together or next to each other (e.g. in the form of parallel lines). The antigens of the invention may also be combined with other antigens, e.g. antigens from other HIV-1 group O strains, or from HIV-1 group M or from HIV-2 strains.

The combination of different antigens in one single detection method as described above has certain advantages, such as:

achieving a higher test sensitivity: e.g. by combining several antigenic determinants from different HIV-strains, the total number of positively reacting sera originating from HIV-infected patients will be greater, and/or enabling differentiation between individuals infected by different strains of HIV, more particularly enabling differentiation between HIV-1 group M, HIV-1 group O and HIV-2 infected patients.

The invention thus also relates to a solid support onto which the antigens of the invention, possibly in combination with other antigens, have been immobilized.

Another embodiment of the invention provides for a method for detecting the presence of HIV-1 nucleic acids, including HIV-1 group O nucleic acids, in a biological sample, comprising:

(I) possibly extracting the polynucleic acids contained in the sample, (ii) possibly amplifying the HIV-1 polynucleic acids, including the HIV-1 group O polynucleic acids, with a suitable primer pair, (iii) detecting the amplified nucleic acids, after hybridization with a probe as described above.

The expression "a suitable primer pair" refers to a pair of primers allowing the amplification of the target region to which the probes of the current invention hybridize. Depending on the application, the primer sequences may be chosen such that they amplify specifically the nucleic acids of the current invention, or, on the other hand, it may be preferred to obtain a more general amplification, e.g. of all or nearly all HIV-1 group O sequences, or of all or nearly all HIV-1 sequences, and even HIV-2 sequences.

In case a general amplification of HIV-1 group M and HIV-1 group O sequences is preferred, the following pair of primers may be used to amplify part of the gp41 region:

5'-GGGTTCTTGGGAGCAGCAGGAAGCACTATGGGC-G-3' (SEQ ID NO 139), and

5'-TCTGAAACGACAGAGGTGAGTATCCCTGCCTAA-3' (SEQ ID NO 140)).

In case a more specific amplification of the gp41 region of HIV-1 group O strains is preferred, the following pair of primers may be used:

5'-TGGATCCCACAGTGTACTGAAGGGTATAGTGCA-3' (SEQ ID NO 141), and

5'-CATTTAGTTATGTCAAGCCAATTCCAAA-3' (SEQ ID NO 142)).

The invention also relates to a method for genotyping HIV-1 or HIV-1 type O strains, comprising the following steps:

possibly extracting the nucleic acids from the sample, amplifying the HIV-1 or HIV-1 type O nucleic acids using a suitable primer pair, hybridizing the nucleic acids of the sample with at least one probe as described above, detecting the hybrids formed, inferring the presence of one or more HIV-1 or HIV-1 type O genotypes from the hybridization pattern obtained.

The term "genotyping" refers to the typing of HIV-strains according to the sequence of their nucleic acids. Depending on the application, it may be the intention of a genotyping assay to differentiate between large groups of HIV-strains (e.g. HIV-1 group M; HIV-1 group O or HIV-2) or to subtype smaller entities (such as e.g. the clades withing HIV-1 group M (A to J)). Subtyping within HIV-1 group O may also be accomplished using the nucleic acids of the current invention.

Conditions allowing hybridization are known in the art and e.g. exemplified in Maniatis et al. (1982). However, according to the hybridization solution (SSC, SSPE, etc.), the probes used should be hybridized at their appropriate temperature in order to attain sufficient specificity (in some cases differences at the level of one nucleotide mutation are to be discriminated).

Amplification of nucleic acids present in a sample prior to detection in vitro may be accomplished by first extracting the nucleic acids present in the sample according to any of the techniques known in the art, and second, amplifying the target nucleic acid by any amplification method as specified above. In case of extraction of RNA, generation of cDNA is necessary; otherwise cDNA or genomic DNA is extracted.

The term "labelled" refers to the use of labelled nucleic acids. This may include the use of labelled nucleotides incorporated during the polymerase step of the amplification such as illustrated by Saiki et al. (1988) or Bej et al. (1990) or labelled primers, or by any other method known to the person skilled in the art. Labels may be isotopic ($^{32}P$, $^{35}S$, etc.) or non-isotopic (biotin, digoxigenin, etc.).

Suitable assay methods for purposes of the present invention to detect hybrids formed between oligonucleotide probes according to the invention and the nucleic acid sequences in a sample may comprise any of the assay formats known in the art. For example, the detection can be accomplished using a dot blot format, the unlabelled amplified sample being bound to a membrane, the membrane being incubated with at least one labelled probe under suitable hybridization and wash conditions, and the presence of bound probe being monitored. Probes can be labelled with radioisotopes or with labels allowing chromogenic or chemiluminescent detection such as horse-radish peroxidase coupled probes.

An alternative is a "reverse" dot-blot format, in which the amplified sequence contains a label. In this format, the unlabelled oligonucleotide probes are bound to a solid support and exposed to the labelled sample under appropriate stringent hybridization and subsequent washing conditions. It is to be understood that also any other assay method which relies on the formation of a hybrid between the nucleic acids of the sample and the oligonucleotide probes according to the present invention may be used.

According to an advantageous embodiment, the process of detecting HIV-1 type O nucleic acids contained in a biological sample comprises the steps of contacting amplified copies of the nucleic acids present in the sample, with a solid support on which probes as defined above, have been previously immobilized. Preferably, the amplified nucleic acids are labelled in order to subsequently detect hybridization.

In a very specific embodiment, the probes have been immobilized on a membrane strip in the form of parallel lines. This type of reverse hybridization method is specified further as a Line Probe Assay (LiPA), and has been described more extensively in for example WO 94/12670.

The invention thus also relates to a solid support onto which the nucleic acids of the invention have been immobilized.

The invention also provides for a composition comprising at least one of the antigens or antigen fragments as above described, and/or at least one of the nucleic acids or nucleic acid fragments as above described, and/or an antibody as above described.

Examples of such compositions may be e.g. a diagnostic kit, an immunogenic composition, e.a.

In particular, the invention provides for a kit for the detection of the presence of an HIV-1 infection, comprising at least one of the antigens or antigen fragments as described above and/or at least one of the nucleic acids or nucleic acid fragments as described above and/or an antibody as described above.

More specifically, the current invention provides for a diagnostic kit for determining the presence of HIV-1 nucleic acids, including HIV-1 type O nucleic acids, in a biological sample, said kit comprising at least one nucleic acid fragment as described above. This nucleic acid fragment may be used as a primer or a probe in said kit.

In addition, the current invention provides for a kit for genotyping HIV-1 strains, including HIV-1 type O strains, in a biological sample, said kit comprising at least one nucleic acid fragment as described above. This nucleic acid fragment may be used as a primer or a probe in said kit.

Moreover, the present invention also provides for a kit for determining the presence of anti-HIV-1 type O) antibodies present in a biological sample, comprising at least one antigen or antigen fragment as described above.

In addition, the present invention provides for a kit for determining the presence of HIV-1 type O antigens present in a biological sample, comprising at least one antibody as described above.

The current invention also provides for a vaccine composition which provides protective immunity against HIV-1 infection, in particular against HIV-1 group O infection, comprising as an active principle at least one antigen or antigen fragment as described above, or at least one nucleic acid as described above, or a virus like particle (VLP) comprising at least one antigen or antigen fragment as described above, or an attenuated form of at least one of the HIV-1 type O strains as described above, said active principle being combined with a pharmaceutically acceptable carrier.

In a specific embodiment, polynucleic acid sequences coding for any of the antigens or antigen fragments as defined above, are used as a vaccine, either as naked DNA or as part of recombinant vectors. In this case, it is the aim that said nucleic acids are expressed into immunogenic protein/peptide and thus confer in vivo protection to the vaccinated host (e.g. Ulmer et al., 1993).

The active ingredients of such a vaccine composition may be administered orally, subcutaneously, conjunctivally, intramuscularly, intra nasally, or via any other route known in the art including for instance via the binding to carriers, via incorporation into liposomes, by adding adjuvants known in the art, etc.

BRIEF DESCRIPTION OF THE FIGURES

FIG. 1. Amino acid alignment of gp41 sequences from the HIV-1 group O strains of the current invention, compared to gp41 sequences from some known prototype HIV-1 group O strains (Ant70, MVP5180, VAU: boxed). If the name of a strain is followed by -P or -PBMC, it means that the sequence was performed on strains present in peripheral blood monocytes samples, in stead of serum samples. Asteriks show perfectly conserved amino acids. Dots show well conserved amino acids. Dashes refer to gaps introduced to maximize the alignment. The immunodominant domain is underlined and within this domain the dashed line indicates the immunosuppressive peptide (ISU) and the dotted line indicates the principal immunodominant domain (PID) by analogy to HIV-1 group M viruses. The number of potential N-linked glycosylation sites which are shown by symbol ^ above the amino acid alignment, are indicated at the right of the sequences on FIG. 1 (contd. 1).

FIG. 2. Amino acid alignment of C2V3 sequences originating from some of the HIV-1 group O strains of the current invention (189, FABA, MP340, MP450, MP448, MP539), compared to C2V3 sequences from some known prototype HIV-1 group O strains (Ant70, MVP5180 and VAU: boxed). Asteriks show perfectly conserved amino acids. Dots show well conserved amino acids. Dashes refer to gaps introduced to maximize the alignment. The symbol + indicates the two conserved cysteine residues flanking the V3 loop region.

FIG. 3. Nucleic acid alignment of gp41 sequences originating from the HIV-1 group O strains of the current invention, compared to gp41 sequences from some known prototype HIV-1 group O strains (Ant70, MVP5180, VAU and VI686: in bold). Asteriks show positions of conserved nucleic acids. Dashes refer to gaps introduced to maximize alignment.

FIG. 4. Nucleic acid alignment of C2V3 sequences originating from some of the HIV-1 group O strains of the current invention (189, FABA, MP340, MP448, MP450 and MP539), compared to C2V3 sequences from some known prototype HIV-1 group O strains (MVP5 180, Ant70 and VI686: in bold). Asteriks show positions of conserved nucleic acids. Dashes refer to gaps introduced to maximize alignment.

FIG. 6 Nucleotide and amino acid sequences obtained from the new HIV-1 group O strains of the current invention.

Figure 5:
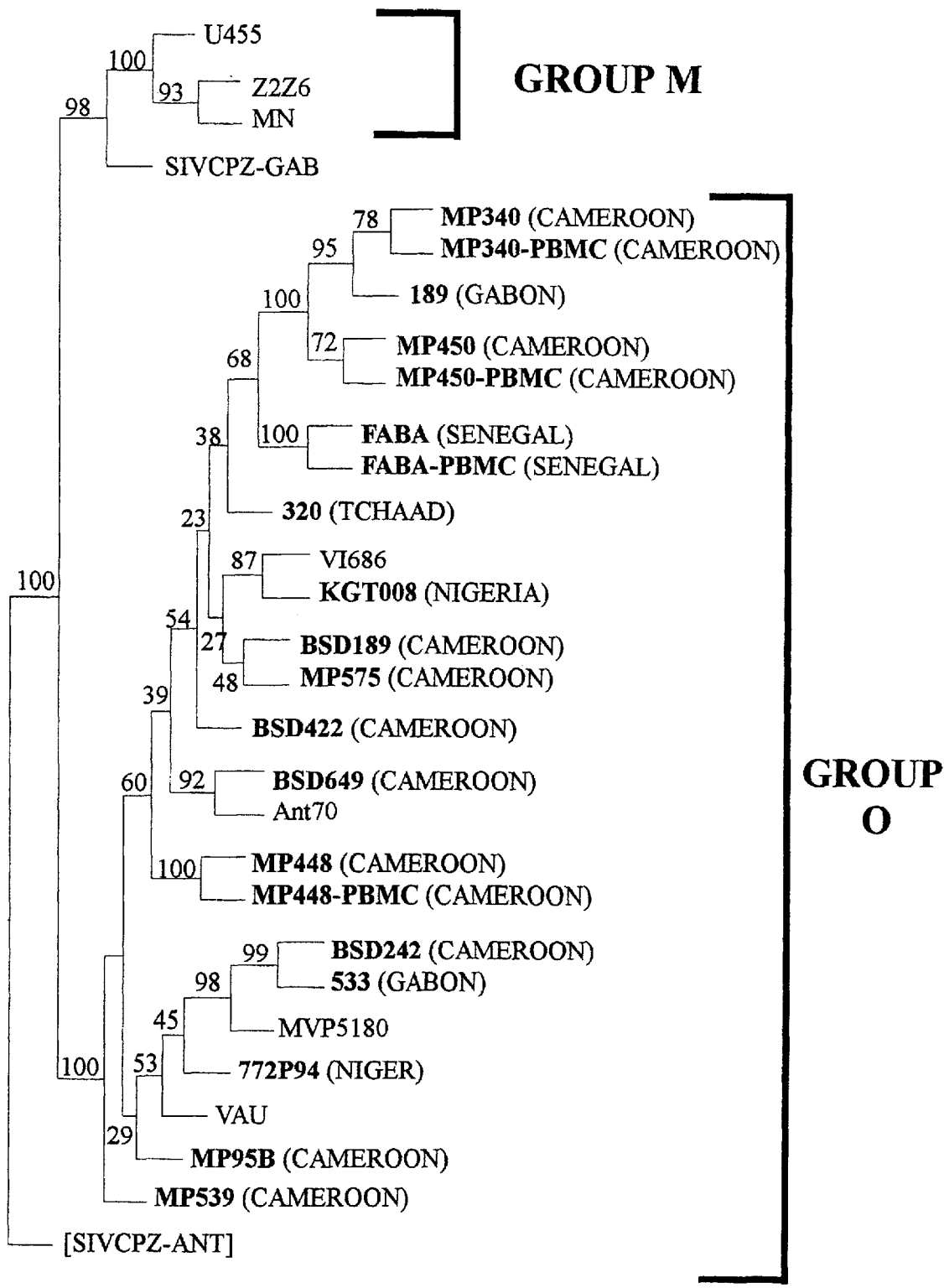
FIG. 5. Phylogenetic tree analysis for the gp41-sequenced region of the new HIV-1 group O strains of the current invention, compared to the prototype HIV-1 group O strains (Ant70, MVP5180, VAU and VI686), HIV-1 group M strains (U455, Z2Z6 and MN), and SIVcpz-strains. SIVcpz-ANT has been used as an "outgroup" for the analysis, and is therefore put between brackets [ ].The viruses of the current invention are indicated in bold. Country of origin is mentioned between parentheses. Phylogenetic relationships were determined using the neighbor joining method, as described in Materials and Methods. The numbers given at the branch points represent bootstrap values out of 100 obtained for the neighbor joining method.

7A. Comparison of the consensus amino acid sequences of the potential gp41-immunosuppressive peptide (ISU) for HIV-1 group M and O strains and ISU-peptide for SIVcpz-GAB and SIVcpzANT.

7B. Antigenicity/hydrophilicity plots of the consensus ISU-peptide (17 amino acids flanked by Leucine (L) residues) for HIV-1 group O and group M viruses. A value of 100% or nearly predicts the considered peptide to be highly immunogenic.

FIG. 8.

8A. Nucleic acid sequence (SEQ ID NO 106) and the corresponding amino acid sequence translation of part of the genome of HIV-1 group O virus MP645. The corresponding polypeptides Pol (partially) (SEQ ID NO130, Vif (SEQ ID NO 110), Vpr (SEQ ID NO 118), Tat (SEQ ID NO 122), Rev (SEQ ID NO 126), Vpu (SEQ ID NO 114) and Env (SEQ ID NO 134) (partially) are underlined and their corresponding name is indicated at the right of each open reading frame.

8B. Nucleic acid sequence (SEQ ID NO 103) and the corresponding amino acid sequence translation of part of the genome of HIV-1 group O virus MP331 (FABA). The corresponding polypeptides Pol (partially) (SEQ ID NO 127), Vif (SEQ ID NO 107), Vpr (SEQ ID NO 115), Tat (SEQ ID NO 119), Rev (SEQ ID NO 123), Vpu (SEQ ID NO 111) and Env (partially) (SEQ ID NO 131) are underlined and their corresponding name is indicated at the right of each open reading frame.

8C. Nucleic acid sequence (SEQ ID NO 104) and the corresponding amino acid sequence translation of part of the genome of HIV-1 group O virus MP448. The corresponding polypeptides Pol (partially) (SEQ ID NO 128), Vif (SEQ ID NO 108), Vpr (SEQ ID NO 116), Tat (SEQ ID NO 120), Rev (SEQ ID NO 124), Vpu (SEQ ID NO 112) and Env (partially) (SEQ ID NO 132) are underlined and their corresponding name is indicated at the right of each open reading frame.

8D. Nucleic acid sequence (SEQ ID NO 105) and the corresponding amino acid sequence translation of part of the genome of HIV-1 group O virus MP539. The corresponding polypeptides Pol (partially) (SEQ ID NO 129), Vif (SEQ ID NO 109), Vpr (SEQ ID NO 117), Tat (SEQ ID NO 121), Rev (SEQ ID NO 125), Vpu (SEQ ID NO 113) and Env (partially) (SEQ ID NO 133) are underlined and their corresponding name is indicated at the right of each open reading frame.

TABLE LEGEND

Table 1:

Divergence between HIV-1 group M and O viruses and the chimpanzee viruses SIVcpzGAB and SIVcpzANT based on gp41 nucleic acid sequences.

$^a$: Divergence from group M viruses was calculated for at least three randomly selected strains for each of the subtypes from A to G.

Table 2:

Percent divergence (=100%-% homology) between the gp41 nucleic acid sequences of the different HIV-1 group O strains of the current invention as specified in FIG. 3.

TABLE 1

| | % genetic divergence | | |
| --- | --- | --- | --- |
| | Group O | Group M | CPZANT |
| CPZGAB | 37.5 (35.2–38.8) | 31.2 (29.3–32.5) | 32.6 |
| CPZANT | 36.5 (32.4–39.1) | 33.7 (32.9–34.3) | |
| Group M | 37.3 (35.0–40.8) | 12.3 (2.2–16.6) | |
| Group O | 14.7 (1.2–21.8) | | |

TABLE 2

| | ANT70 | MVP5180 | VAU | V1686 | MP340 (PBMC) | MP340 | FABA (PBMC) | FABA | MP450 (PBMC) | MP450 | MP448 (PBMC) | MP448 | 189 |
| --- | --- | --- | --- | --- | --- | --- | --- | --- | --- | --- | --- | --- | --- |
| ANT70 | — | 18 | 16 | 9 | 13 | 13 | 12 | 13 | 12 | 12 | 10 | 9 | 14 |
| MVP5180 | | — | 17 | 22 | 24 | 23 | 24 | 25 | 23 | 23 | 16 | 15 | 26 |
| VAU | | | — | 18 | 21 | 21 | 20 | 21 | 20 | 20 | 18 | 17 | 22 |
| V1686 | | | | — | 14 | 14 | 15 | 16 | 14 | 14 | 10 | 10 | 16 |
| MP340 (PBMC) | | | | | — | 1 | 14 | 15 | 2 | 2 | 14 | 14 | 2 |
| MP340 | | | | | | — | 13 | 12 | 2 | 2 | 15 | 15 | 2 |
| FABA (PBMC) | | | | | | | — | 5 | 13 | 13 | 15 | 15 | 13 |
| FABA | | | | | | | | — | 13 | 13 | 15 | 15 | 15 |
| MP450 (PBMC) | | | | | | | | | — | 0 | 13 | 13 | 3 |
| MP450 | | | | | | | | | | — | 13 | 13 | 3 |
| MP448 (PBMC) | | | | | | | | | | | — | 0 | 16 |
| MP448 | | | | | | | | | | | | — | 16 |
| 189 | | | | | | | | | | | | | — |
| 320 | | | | | | | | | | | | | |
| BSD422 | | | | | | | | | | | | | |
| KGT008 | | | | | | | | | | | | | |
| MP575 | | | | | | | | | | | | | |

TABLE 2-continued

BSD189
BSD649
BSD242
533
772P94
MP95B
MP539

|  | 320 | BSD422 | KGT008 | MP575 | BSD189 | BSD649 | BSD242 | 533 | 772P94 | MP95B | MP539 |
|---|---|---|---|---|---|---|---|---|---|---|---|
| ANT70 | 9 | 9 | 11 | 7 | 9 | 6 | 22 | 23 | 19 | 15 | 18 |
| MVP5180 | 21 | 21 | 23 | 21 | 21 | 20 | 7 | 8 | 15 | 13 | 22 |
| VAU | 18 | 18 | 18 | 16 | 17 | 15 | 18 | 18 | 15 | 16 | 15 |
| V1686 | 11 | 12 | 9 | 10 | 10 | 10 | 26 | 25 | 22 | 15 | 18 |
| MP340 (PBMC) | 14 | 15 | 17 | 13 | 11 | 12 | 26 | 24 | 20 | 20 | 20 |
| MP340 | 14 | 14 | 17 | 13 | 11 | 12 | 27 | 24 | 20 | 20 | 19 |
| FABA (PBMC) | 14 | 18 | 17 | 13 | 14 | 13 | 28 | 26 | 20 | 20 | 22 |
| FABA | 15 | 18 | 17 | 14 | 14 | 14 | 29 | 27 | 20 | 20 | 22 |
| MP450 (PBMC) | 12 | 15 | 17 | 12 | 10 | 12 | 26 | 24 | 19 | 19 | 20 |
| MP450 | 12 | 15 | 17 | 12 | 10 | 12 | 26 | 24 | 19 | 19 | 20 |
| MP448 (PBMC) | 10 | 12 | 12 | 10 | 11 | 11 | 19 | 19 | 19 | 15 | 17 |
| MP448 | 11 | 12 | 12 | 9 | 11 | 11 | 18 | 19 | 18 | 14 | 17 |
| 189 | 15 | 17 | 19 | 14 | 13 | 14 | 28 | 26 | 22 | 22 | 22 |
| 320 | — | 12 | 11 | 7 | 11 | 8 | 22 | 22 | 22 | 16 | 18 |
| BSD422 |  | — | 15 | 11 | 13 | 10 | 24 | 26 | 19 | 15 | 18 |
| KGT008 |  |  | — | 10 | 12 | 12 | 26 | 26 | 22 | 19 | 20 |
| MP575 |  |  |  | — | 8 | 7 | 25 | 25 | 20 | 17 | 17 |
| BSD189 |  |  |  |  | — | 9 | 26 | 26 | 19 | 17 | 18 |
| BSD649 |  |  |  |  |  | — | 24 | 23 | 19 | 16 | 18 |
| BSD242 |  |  |  |  |  |  | — | 5 | 16 | 16 | 25 |
| 533 |  |  |  |  |  |  |  | — | 18 | 16 | 23 |
| 772P94 |  |  |  |  |  |  |  |  | — | 17 | 19 |
| MP95B |  |  |  |  |  |  |  |  |  | — | 18 |
| MP539 |  |  |  |  |  |  |  |  |  |  | — |

EXAMPLES

Example 1

Materials and Methods

Patients and Viruses

A total of 16 viruses have been characterized. Patients were identified as being infected with an HIV-1 group O virus using a specific serological testing algorithm, based on V3 peptides from different M and O strains (consensusM, M-Mal, O-ANT-70, O-VI686, O-MVP5180 (INNOLIA HIV-1 type O Research product, Innogenetics, Belgium), as described elsewhere (Peeters et al., in press). Ten patients were from Cameroon (BSD189, BSD242, BSD422, BSD649, MP340, MP95B, MP448, MP575, MP539 and MP450), 2 from Gabon (189, 533) and the others from Tchaad (320), Nigeria (KGT008), Senegal (FABA=331) and Niger (772P94). For 3 patients from Cameroon (MP340, MP448 and MP450) and for the patients from Nigeria and Senegal primary uncultured peripheral blood mononuclear cells (PBMCs) were available, while for the other patients from Cameroon, Gabon, Niger and Tchaad only serum was available. Strain V1686 from Gabon has been described previously (Janssens et al. 1994).

Nucleic Acid Extraction

DNA was extracted from PBMCs using the IsoQuick isolation kit (Microprobe Corp., Garden Cove, Calif., USA), resuspended in the appropriate volume of nuclease free water and 1/10 was used for amplifications. Viral RNA was extracted from 50 μl of plasma by the guanidinium thiocyanate-phenol-chloroform method as described previously by Chomczynsky and Sacchi (1987), resuspended in 5 μl of nuclease free water and further used for reverse transcription reaction.

RT, PCR and Sequencing

The reverse transcription reaction (RT) was performed in a final volume of 20 μl, containing 50 mM TrisHCl pH 8.3, 50 mM KCl, 10 mM MgCl$_2$, 10 mM DTT, 0.5 mM spermidine, 1 mM each deoxynucleoside triphophate, 0.5 μM outer reverse primer (41-4, see further) and 5 U of Avian Myeloblastosis Virus Reverse Transcriptase (Promega), for 30 min at 42° C. Five microliters from the RT reaction were used for PCR amplification.

Nested PCR was used to amplify a fragment of approximately 420 bp from the gp41-region. Outer primers allow amplification of HIV-1 sequences from group O and M (sense 41-1: 5'-GGGTTCTTGGGAGCAGCAGGAAGCA-C TATGGGCG-3' (SEQ ID NO 139), antisense 41-4: 5'-TCTGAAACGACAGAGGTGAGTATCCCTGCCTAA-3' (SEQ ID NO 140)). Inner primers were determined according to the HIV-1-Ant70 sequence (Vanden Haesevelde et al. 1994) (sense 41-6: 5'-TGGATCCCACAGTGTACTGAAGGGTATAGTGCA-3' (SEQ ID NO 141), antisense 41-7: 5'-CATTTAGTTATGTCAAGCCAATTCCAAA-3' (SEQ ID NO 142)). PCRs were performed in a final volume of 100 μl containing 10 mM Tris-HCl (pH 9.0), 50 mM KCl, 1.5 mM MgCl2, 0.2 mM each deoxynucleoside triphosphate, 2.5 U of Taq DNA polymerase (Promega) and 0.4 μM of each primer. After an initial denaturation step of 3 min at 94° C., 30 to 35 cycles were performed at 94° C. for 1 min to 20 s, 50° C. for 1 min to 30 s, 72° C. for 1 min, followed by a final extension of 10 to 7 min. For the second round, 1 to 5 μl of the first amplification were subjected to the same cycling conditions for 35 to 40 PCR cycles.

Amplification of the C2V3-region was obtained by nested PCR using a set of primers selected from the HIV-1-Ant70 sequence. Outer primers were: anti-sense V70-5 (5'-GTTCTCCATATATCTTTCATATCTCCCCCTA-3', SEQ ID NO 143) and sense V70-1 (5'-TTGTACACATGGCATTAGGCCAACAGTAAGT-3', SEQ ID NO 144) and inner primers were: sense V70-2 (5'-TGAATTCCTAATATTGAATGGGACACTCTCT-3', SEQ ID NO 145) and antisense V70-4 (5'-TGGATCCTACAATAAAAGAATTCTCCATGACA-3', SEQ ID NO 146). Amplification conditions were as described above.

Each fragment was sequenced on both strands, as previously described (Bibollet-Ruche 1997), using an Applied Biosystems sequencer (model 373A, Applied Biosystems, Inc) and a dye-deoxy terminator procedure, as specified by the manufacturer.

Sequence Analysis

Overlapping sequences were joined by using SeqEd-1.0 (Applied Biosystems, Inc). Sequences were aligned using CLUSTAL V (Higgins et al 1992; Higgins and Sharp 1988) program. Evolutionary distances were calculated by using the Kimura's two-parameters method with correction for the multiple substitutions and excluding positions with gaps in aligned sequences (Kimura 1983). Phylogenetic relationships were computed from the distance matrix by the neighbor-joining method (Saitou and Nei 1987). Phylogenetic analyses were also performed by a parsimony approach and implemented using DNAPARS. In both cases, reliability of the branching orders was confirmed by the bootstrap approach (Felsenstein 1985). Phylogenetic analyses were also performed for proteic sequences using PROTPARS. These methods were implemented using the PHYLIP 3.56 package (Felsenstein 1993). The results were similar with both methods, for nucleotidic and proteic sequences, in all essential aspects.

Antigenicity Profiles

Antigenicity of the ISU peptides have been calculated according to programs developed by Garnier et al (1978) and Gibrat et al (1987).

Example 2

Nucleic Acid Sequences and Phylogenetic Analysis
Analysis of gp41 Sequences

Figure 7B:
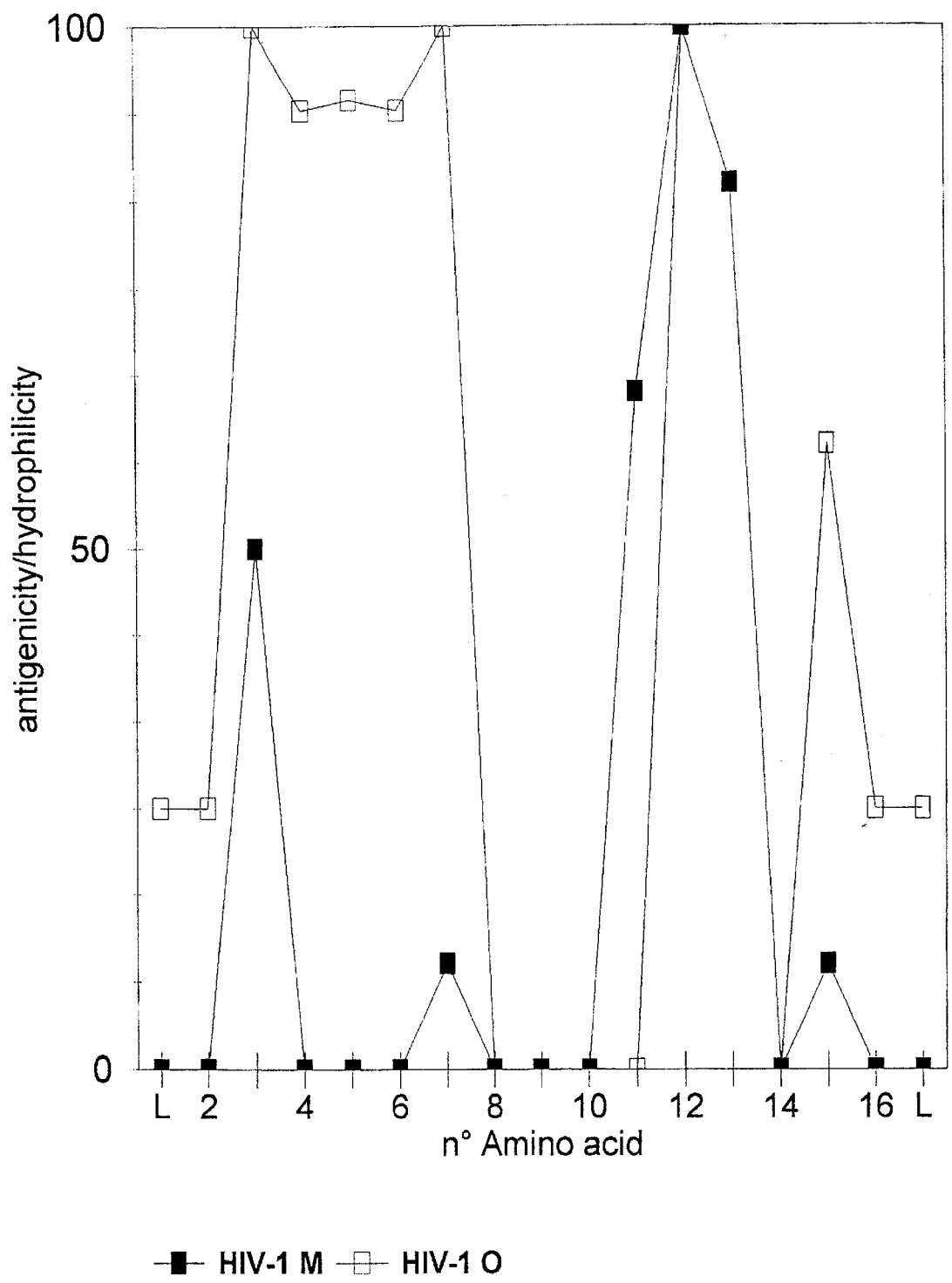
FIG. 7.

For the 16 viruses, 330 to 351 bp of the region spanning the immunodominant domain of the transmembrane gp41 glycoprotein (by analogy to HIV-1 group M viruses) was characterized. The different sequences obtained are represented in FIG. 6. These sequences have been aligned to the corresponding gp41-sequences of known HIV-1 group O strains, as shown in FIG. 3. Moreover, sequence identity was calculated for intra and intergroup similarity by pairwise alignment and comparison (Table 1). For the group M viruses, these values were calculated for randomly selected strains for which sequences were available in the database and which were representative of subtypes A to G (the same sequences were further used for phylogenetic analyses). Divergence between SIVcpz-GAB (Huet et al. 1990) and the group M (mean 31,2%) was lower than divergence between SIVcpz-GAB and the group O (mean 37%). These results were similar when calculated with the second chimpanzee virus, SIVcpz-ANT (Vanden Haesevelde et al. 1996), with mean divergence of 33.7% and 36.5% with group M and O respectively (Table 1). Intragroup divergence for group O viruses ranged from 1.2 to 21.8% (mean 14.7%) while divergence within group M clades (A to G) ranged from 2.2 to 16.6% (mean 12.3%).

Phylogenetic trees were constructed with the 16 new sequences described here, the four group O strains of which the gp41 sequences have already been characterized, nl. Ant70 (Vanden Haesevelde et al. 1994), MVP5180 (Gürtler et al. 1994), VAU (Charneau et al. 1994) and VI686 (Janssens et al. 1994) and group M viruses representative for A (U455), B (MN) and D (Z2Z6) subtypes (see FIG. 5). Trees were constructed from nucleotidic sequences according to the alignment in FIG. 3, by the neighbor-joining and by the maximum-parsimony methods. Consistent results were obtained by the two methods: group M and group O viruses clustered separately (bootstrap values 98 and 100 respectively).

Within the newly characterized HIV-1 type O strains new subclusters may appear, such as for example the subcluster consisting of strains MP340, 189 and MP450, which segregate with a bootstrap value of 100, or the subcluster consisting of strains MVP5180, 533, BSD242 (bootstrap value 98). These subclusters may define different genotypes within group O in analogy to the different group M genotypes (clades). Phylogenetic analyses were also performed for the deduced amino acid sequences for group O and M viruses (data not shown) and the results were consistent with the nucleotidic sequences, although lower bootstrap values were observed (approximately 65%), probably due to the short size of the sequences (109 a.a., gaps excluded, data not shown). The countries from which these viruses were sampled are indicated alongside the strains and no links were found between the manner of clustering and the geographical origins of the strains.

Table 2 shows the percentage divergence between gp41-nucleotide sequences originating from HIV-1 group O strains of the invention and known HIV-1 group O strains (Ant70, MVP5180, VAU and VI686).

Analysis of C2V3 Sequences

For 6 of the 16 new virus strains (189, FABA, MP340, MP448, MP450 and MP539), C2V3 sequences were determined. FIG. 4 shows the alignment of these new C2V3 sequences with the corresponding sequences of known HIV-1 group O strains.

Example 3

Analysis of Deduced Amino Acid Sequences gp41 Amino Acid Sequences

FIG. 1 depicts the alignment of the deduced gp41 amino acid sequences. Although different from group M, this region of the transmembrane glycoprotein is also highly conserved among group O viruses, especially for the region corresponding to the immunodominant region in group M isolates. This region has been divided into two domains, corresponding to an immunosuppressive peptide (ISU-peptide) of 17 amino acids (aa) and to an immunodominant cysteine loop of 7 aa (Oldstone et al. 1991), also called the principal immunodominant domain (PID). The consensus cysteine loop for group O viruses (CKGR/KLV/IC) is quite closely related to the group M consensus (CSGKLIC), suggesting that they could have similar functions in both virus groups. This PID sequence, corresponding to a B-cell epitope recognized by nearly all sera from patients or animals (Bertoni et al. 1994; Chong et al. 1991; Gnann et al. 1987; Norrby et al. 1987; Pancino et al. 1993), seems to be a very conserved structure, in contrast to the variability observed for the neutralizing epitope of the V3 loop of HIV-1 gp120 (Zwart et al. 1991; Zwart et al. 1993). Deletion of this PID peptide or disruption of the cysteine loop severely impairs the gp160 processing, leading to a loss of infectivity in HIV-1 (Dedera et al. 1992, Pancino et al. 1993; Schulz et al. 1992) and also in the far related type D simian retrovirus (Brody and Hunter 1992).

Comparison of ISIU-peptides from the group M, SIVcpz and group O viruses are presented in FIG. 7A. The consensus peptide from group O is quite divergent from the SIVcpz/group M peptide by the presence of an arginine (R, positively charged) in position 2 instead of a phenylalanine (Q, hydrophilic), a leucine (L) in position 5 and 8 instead of a valine (V), and a very different stretch TLIQN instead of RYLKD in position 10–14. Prediction of the secondary structure revealed an alpha helix in each case, and the predicted isoelectric point is 9,7 and 11,3 for group M/SIVcpz and group O strains respectively. FIG. 7B represents the predicted hydrophilicity/antigenicity plot and revealed the presence of a second peak at position 3 to 7 (ARLLA) for group O in addition to the peak at position 12 (L) conserved in group M/SIVcpz and group O viruses.

The divergence of the ISU peptide between group O and M viruses may suggest different functionalities of the ISU peptide in both groups. For several retroviruses this ISU peptide has been shown to suppress a broad range of immune reactions such as the inhibition of IL-2-dependant and concanavaline A-induced proliferation of T lymphocytes (Denner et al. 1994; Ruegg et al. 1989) but also B lymphocyte proliferation for HIV-1 group M (Denner et al. 1996). The principal B-epitope of this ISU peptide has been mapped at the C-terminal end, centered around the leucine residue in position 12 for group M (Denner et al. 1994). The data of FIG. 7 show a similar antigenicity peak for group O viruses but, in contrast to group M and SIVcpz, the presence of a second peak is observed towards the N-terminal part of this peptide. Moreover, antibody response against this region in HIV-1 group M infected individuals has been shown to be vigorous and independent of the stage of the disease (Cumming et al. 1990; Zwart et al. 1994). This result raises the possibility of the design of peptides for the specific detection of antibodies against group O viruses, which could improve the discrimination between the two HIV-1 groups, and could also be useful for the detection of divergent group O viruses given the high conservation of these peptides among the different strains we have characterized.

A third interesting feature concerns the number and the position of the N-linked glycosylation sites in the immunodominant domain (FIG. 1). In group M viruses, 4 sites are conserved in the gp41 extracellular domain and they have been shown to play important roles in the intracellular processing of the gp160 and in the fusogenic properties of gp41 (Dedera et al. 1992; Vanini et al. 1993). Most of the group O viruses described here contain only three potential N-linked glycosylation sites whereas only a few strains contain four. Only the position of the first site is highly conserved (position 60 in the alignment) and the positions of the two or three other sites vary among the strains, in contrast to group M viruses.

In HIV-1 group M viruses, it is known that removal of the thirth glycosylation site abolishes the cleavage of the gp160 precursor and transport to the plasma membrane of infected cells. An immediate consequence of this result, obtained in vitro after transfection of this mutant in HeLa/CD4 cells, is that it fails to induce syncytia (Dash et al. 1994). Roles of the other N-linked glycosylation sites of the gp41 have not been filly explored but their high conservation suggests important functions. In the case of the gp120, the highly conserved sites surrounding the V3 loop have been shown to influence infectivity (Lee et al. 1992), protein folding (Li et al. 1993) and immunogenicity (Benjouad et al 1992) of this domain. For group O viruses, only the first site is conserved in all the strains which were characterized. Even if the importance of N-glycosylation has not been studied for HIV-1 group O viruses, it can be speculated that differences will be observed when compared to group M viruses.

In conclusion, comparison of the gp41 amino acid sequences clearly discriminate the two HIV-1 groups, either by the pattern of N-linked glycosylation sites or by the characteristics of the ISU peptide of the ectodomain of the transmembrane glycoprotein. The differences observed between the two HIV-1 groups in the gp41 region raise the possibility that these viruses use different mechanisms, for example in the intracellular processing of the envelope precursor or in the domains involved in the membrane fusion. Several studies have suggested that the immunodominant region of the gp41 in group M viruses, which is a target for neutralizing but also enhancing antibodies, could be a promising candidate for vaccine development (Cumming et al. 1990; Muster et al. 1993; Zwart et al. 1994). The data disclosed in the current invention suggest that a vaccine developed against HIV-1 group M viruses could be ineffective against group O strains, especially when these viruses could use different pathways to induce immunodeficiency in infected patients.

Analysis of C2V3 Amino Acid Sequences

FIG. 2 depicts the alignment of the deduced C2V3 sequences of 6 of the HIV-1 group O strains of the invention as compared to known HIV-1 group O strains. The delineation of the C2 and V3 region is according to Starcich et al. (1986) and Willey et al. (1986). The C2 region belongs to the rather conserved regions which are important in protein folding and protein function. The V3 region is one of the hypervariable regions, for which amino acid conservation between different HIV-1 isolates is below 50%. Hypervariable regions also contain short deletions or insertions (Myers et al. 1992).

The V3-region of gp120, also known as the principal neutralizing determinant (PND), contains a loop of 35 amino acids, formed by a cysteine-cysteine disulfide bridge. The PND is implicated in several important biological functions, such as:

1. it determines the HIV-1 cell tropism (Hwang et al. 1991, Shioda et al. 1991)
2. it affects fusion (Feed et al. 1991) and viral virulence (Fouchier et al. 1992)
3. it stimulates cytotoxicity (Takahashi et al. 1992)
4. it is the primary target for antibody neutralization (Palker et al. 1989).

The fact that the V3 domain of gp120 may induce a protective immune response, has made this region of particular interest for vaccine research. Although the V3 region as a whole is hypervariable, there is a rather high sequence conservation in its tetrapeptide sequence Gly-Pro-Gly-Arg (GPGR) at the crown of the loop (LaRosa et al. 1990). This motif corresponds to the binding site of the neutralizing antibodies, and single amino acid changes within this epitope highly reduce antibody binding (Meloen et al. 1989).

The alignment in FIG. 2 shows that sequence variability within the V3 loop is high between the different HIV-1 group O strains, including those of the current invention. These new sequences, and more particularly the sequences represented by SEQ ID NO 53 to 70 and SEQ ID NO 83 to 90 are important in the design of new and better (=more sensitive and/or more specific) HIV-diagnostic assays. Moreover, the various sequences in the V3 region will be important with regard to the development of HIV-vaccines providing an as broad as possible protection against HIV-infection.

Example 4

Cloning Strategy to Obtain Vif, Vpu, Vpr, Tat, Rev, Env and Pol

Polymerase Chain Reaction Amplification and Sequencing

The sequences of the nested primer sets were designed on HIV-1 nucleic acid sequences in conserved regions flanking the Vif and Vpu genes. DNA from cultured and uncultured PBMCs was extracted using IsoQuick (Microprobe, Garden Cove, Calif.) according to the manufacturer instructions and quantified spectrophotometrically. Approximately 1 µg of DNA was used for a first round of amplification with an outer primer pair (VIF1, 5' GGGTTTATTACAGGGACAG-CAGAG 3' (SEQ ID NO 147) and VPU1, 5' GGT-TGGGGTCTGTGGGTACACAGG 3') (SEQ ID NO 148) in a final volume of 100 µl of containing 10 mM Tris-HCl (pH 9.0), 50 mM KCl, 1.5 mM MgCl$_2$ a 0.2 mM concentration of each deoxynucleoside triphosphate, 2.5 U of Taq DNA polymerase (Promega, Madison, Wis.), and a 0.4 µM concentration of each primer. Five microliters from this first round was used for a second round with an inner primer pair (VIF2, 5' GCAAAACTACTCTGGAAAGGTG 3' (SEQ ID NO 149) and VPU2, 5' GCWTCTTTCCACACAGGTAC-CCC 3' (SEQ ID NO 150) where W represents an A or a T) under the same reaction conditions. The two rounds of PCR were run for 35 cycles each under the following cycling conditions:94° C. for 30 sec, 50° C. for 30 sec, and 72° C. for 2 mn. The two rounds of PCR were preceded by a denaturation step of 3 min at 94° C. and followed by a final extension step of 7 min at 72° C.

Sequencing of the amplified products was done directly after purification by TAE-low melting point agarose gel electrophoresis (Bibollet-Ruche et al, 1997) using an Applied Biosystems (Foster City, Calif.) 373 Stretch sequencer and a Dye-Deoxy terminator procedure (dye terminator cycle sequencing ready reaction, with AmpliTaq DNA polymerase; Perkin-Elmer. Norwalk, Conn.) as specified by the manufacturer. Inner polymerase chain reaction (PCR) primers (VIF2 and VPU2) and inner sequencing primers (OVIF, 5' CATATTGGGGATTGATGCCAG 3' (SEQ ID NO 151); OVPU, 5' GCATYAGCGTTACT-TACTGC 3': Y=C or T (SEQ ID NO 152)) were used. Overlapping sequences were joined using SeqEd (Applied Biosystems) to obtain the full-length sequence. Direct sequencing was performed on PCR-generated fragments. Ambiguities observed at a limited number of positions in some sequences were resolved when joining the overlapping fragments.

Analyses of Accessory Protein Sequences

Open reading frames for the different accessory proteins (Pol, Vif, Vpr, the first exon of Tat, Vpu and Env) were determined and the deduced protein sequences were obtained using the Translate program option of the PCgene software package. The resulting sequences are indicated in FIG. 8 (B to D). FIG. 8A shows the sequences of HIV-1 group O strain MP645 which was obtained following a similar approach as the one described above for MP448, MP539 and MP331.

REFERENCES

Agarwal et al. 1972. Agnew. Chem. Int. Ed. Engl. 11: 451.

Arya, S., et al 1985. Trans-activator gene of the human T-lymphotropic virus type III (HTLV-III). Science 229: 69–73.

Asseline U, Delarue M, Lancelot G, Toulme F, Thuong N (1984) Nucleic acid-binding molecules with high affinity and base sequence specificity: intercalating agents covalently linked to oligodeoxynucleotides. Proc. Natl. Acad. Sci. USA 81(11):3297–301.

Baeucage et al. 1981. Tetrahedron Letters 22: 1859–1862.

Barany F (1991) Genetic disease detection and DNA amplification using cloned thernostable ligase. Proc. Natl. Acad. Sci USA 88: 189–193.

Barré-Sinoussi et al. 1983. Isolation of a T-lymphotropic retrovirus from a patient at risk for acquired immune deficiency syndrome (AIDS). Science 220:868–871.

Bej A, Mahbubani M, Miller R, Di Cesare J, Haff L, Atlas R (1990) Multiplex PCR amplification and immobilized capture probes for detection of bacterial pathogens and indicators in water. Mol Cell Probes 4:353–365.

Benjouad, A., J.-C. Gluckman, H. Rochat, L. Montagnier, and E. Bahraoui. 1992. Influence of carbohydrate moieties on the immunogenicity of human immunodeficiency virus type 1 recombinant gp160. J. Virol. 66:2473–2483.

Bertoni, G., M.-L. Zahno, R. Zanoni, H.-R. Vogt, E. Peterhans, G. Ruff, W. P. Cheevers, P. Sonigo, and G. Pancino. 1994. Antibody reactivity to the immunodominant epitopes of the caprine arthritis-encephalitis virus gp38 transmembrane glycoprotein associates with the development of arthritis. J. Virol. 68:7139–7147.

Bibollet-Ruche, F., C. Brengues, A. Galat-Luong, G. Galat, X. Pourrut, N. Vidal, F. Veas, J.-P. Durand, and G. Cuny. 1997. Genetic diversity of simian immunodeficiency viruses from west african green monkeys: evidence for multiple genotypes within populations from the same geographical locale. J. Virol. 71:307–313.

Blalock J (1990) Complementarity of peptides specified by 'sense' and 'antisense' strands of DNA. Trends Biotechnol. 8: 140–144.

Bour, S., et al. 1995. The human immunodeficiency virus type 1 Vpu protein specifically binds to the cytoplasmic domein of CD4: implication for the mechanism of degradation. J. Virol. 69: 1510–1520.

Braaten, D., E. K. Franke, and J. Luban. 1996. Cyclophilin A is required for the replication of group M human immunodeficiency virus type 1 (HIV-1) and simian immunodeficiency virus SIVcpzGAB but not group O HIV-1 or other primate immunodeficiency viruses. J. Virol. 70:4220–4227.

Brody, B. A., and E. Hunter. 1992. Mutations within the env gene of Mazon-Pfizer monkey virus: effects on protein transport and SU-TM association. J. Virol. 66:3466–3475.

Centers for Disease Control and Prevention. 1996. Identification of HIV-1 group O infection, Los Angeles County, California. MMWR 45:561–564.

Charneau, P., A. M. Borman, C. Quillent, D. Guetard, S. Chamaret, J. Cohen, G. Remy, L. Montagnier, and F. Clavel. 1994. Isolation and envelope sequence of a highly divergent HIV-1 isolate: definition of a new HIV-1 group. Virology 205:247–253.

Chomczynsky, P., and N. Sacchi. 1987. Single step method of RNA isolation by guanidinium thiocyanate-phenol-chloroform extraction. Anal. Biochem. 162: 156–159.

Chong, Y.-H., J. M. Ball, C. J. Issel, R. C. Montelaro, and K. E. Rushlow. 1991. Analysis of equine humoral responses to the transmembrane envelope glycoprotein (gp45) of equine anemia virus. J. Virol. 65:1013–1018.

Clavel et al. 1986, Molecular cloning and polymorphism of the HIV-type 2. Nature (London) 324: 691–694.

Clavel et al. 1986, Isolation of a new human retrovirus from West African patients with AIDS. Science 233:343–346.

Compton J (1991). Nucleic acid sequence-based amplification. Nature, 350: 91–92.

Cumming, S. A., D. A. McPhee, W. J. Maskill, B. E. Kemp, R. R. Doherty, and I. D. Gust. 1990. Use of conserved immunodorninant epitope of HIV surface glycoprotein gp41 in the detection of early antibodies. AIDS 4:83–86.

Dash, B., A. McIntosh, W. Barrett, and R. Daniels. 1994. Deletion of a single N-linked glycosylation site from the transmembrane envelope protein of human immunodeficiency virus type 1 stops cleavage and transport of gp160 preventing env-mediated fusion. J. Gen. Virol. 75:1389–1397.

de Préval (1978) Immunoglobulins, In: Bach J Immunology, New York, Wiley and Sons: 144–219.

De Leys, R., B. Vanderborght, M. Vanden Haesevelde, L. Heyndrickx, A. van Geel, C. Wauters, R. Bernaerts, E. Saman, P. Nijs, B. Willems, H. Taelman, G. van der Groen, P. Piot, T. Tersmette, J. G. Huisman, and H. Van Heuverswyn. 1990. Isolation and partial characterization of an unusual human immunodeficiency retrovirus from two persons of West-Central African origin. J. Virol. 64:1207–1216.

Dedera, D., R. Gu, and L. Ratner. 1992. Conserved cystein residues in the human immunodeficiency virus type 1 transmembrane envelope protein are essential for precursor envelope cleavage. J. Virol. 66:1207–1209.

Denner, J., S. Norley, and R. Kurth. 1994. The immunosuppressive peptide of HIV-1: functional domains and immune response in AIDS patients. AIDS 8:1063–1072.

Denner, J., C. Persin, T. Vogel, D. Haustein, S. Norley, and R. Kurth. 1996. The immunosuppressive peptide of HIV-1 inhibits T and B lymphocyte stimulation. J. AIDS and Hum. Ret. 12:442–450.

Duck P (1990). Probe amplifier system based on chimeric cycling oligonucleotides. Biotechniques 9, 142–147.

Feinberg, M., et al. 1986. HTLVIII expression and production involve complex regulation at the levels of splicing and translation of viral RNA. Cell 46: 807–817.

Felsenstein, J. 1985. Confidence limits on phylogenies: an approach using the bootstrap. Evolution 39: 783–791.

Felsenstein, J. 1993. PHYLIP (phylogeny interference package) version 3.5c. Department of Genetics, University of Washington, Seattle.

Fleishmann J, Davie J (1984) Immunoglobulins: allotypes and idiotypes. In: Paul W (Ed) Fundamental Immunology. New York, Raven Press: 205–220.

Furtado, M., et al. 1991. Analysis of alternatively spliced human inmunodeficiency virus type 1 mRNA species, one of which encodes a novel tat-env fusion protein. Virology 185: 258–270.

Gallo et al. 1984. Frequent detection and isolation of cytopathic retroviruses (HTLV-III) from patients with AIDS and at risk for AIDS. Science 224, 500–503.

Gao, F., S. G. Morrison, D. L. Robertson, C. L. Thornton, S. Craig, G. Karlsson, J. Sodroski, M. Morgado, B. Galvao-Castro, H. von Briesen, S. Beddows, J. Weber, P. M. Sharp, G. M. Shaw, B. H. Hahn, and the WHO and NIAID networks for HIV isolation and characterization. Molecular cloning and analysis of functional envelope genes from human immunodeficiency virus type 1 sequence subtypes A through G. J. Virol. 70:1651–1667.

Garnier, J., D. J. Osguthorpe, and B Robson. 1978. Analysis of the accuracy and implication of simple methods for predicting the secondary structure of globular proteins. J. Mol. Biol. 120:97–120.

Gheuens J, Mc Farlin D (1982) Use of monoclonal anti-idiotypic antibody to P3-X6Ag8 myeloma protein for analysis and purification of B lymphocyte hybridoma products. Eur J Immunol 12: 701–703.

Ghiso J, Saball E, Leoni J, Rostagno A, Frangion (1990) Binding of cystatin C to C4: the importance of antisense peptides and their interaction. Proc Natl Acad Sci (USA) 87: 1288–1291.

Gibrat, J. F., J. Garnier, and B. Robson. 1987. Further development of protein secondary structure prediction using information theory. New parameters ans consideration of residue pairs. J. Mol. Biol. 198:425–443.

Gnann, J. W., J. A. Nelson, and M. B. A. Oldstone. 1987. Fine mapping of an immunodominant domain in the transmembrane glycoprotein of human immunodeficiency virus. J. Virol. 61:2639–2641.

Göttlinger, H. G., et al. 1993. Vpu protein of human immunodeficiency virus type 1 enhances the release of capsids produced by gag gene constructs of widely divergent retroviruses. Proc. Natl. Acad. Sci. USA 90: 7381–7385.

Guatelli J, Whitfield K, Kwoh D, Barringer K, Richman D, Gengeras T (1990) Isothermal, in vitro amplification of nucleic acids by a multienzyme reaction modeled after retroviral replication. Proc Natl Acad Sci USA 87: 1874–1878.

Gürtler, L. G., P. H. Hauser, J. Eberle, A. von Brunn, S. Knapp, L. Zekeng, J. M. Tsague, and L. Kaptue. 1994. A new subtype of human immunodeficiency virus type 1 (MVP-5180) from Cameroon. J. Virol. 68:1581–1585.

Hampl, H., D. Sawitzky, M. Stöffler-Meilicke, A. Groh, M. Schmitt, J. Eberle, and L. Gürtler. 1995. First case of HIV-1 subtype O infection in Germany. Infection 6:369–370.

Heinzinger, N. K. et al. 1994. The Vpr protein of human immunodeficiency virus type 1 influences nuclear localization of viral nucleic acids in nondividing host cells. Proc. Natl. Acad. Sci. 91: 7311–7315.

Higgins, D. G., A. J. Bleasby, and R. Fuchs. 1992. CLUSTAL V: improved software for multiple sequence alignment. Comp. Appl. Biosci. 8:189–191.

Higgins, D. G., and P. M. Sharp. 1988. CLUSTAL: a package for performing multiple sequence alignment on a microcomputer. Gene 73:237–244.

Hsiung et al. 1979. Nucleic Acid Res. 6:1371.

Huet, T., R. Cheyier, A. Meyerhans, G. Roelants, and S. Wain-Hobson. 1990. Genetic organisation of a chimpanzee lentivirus related to HIV-1. Nature (London) 345:356–358.

Janssens, W., J. N. Nkengasong, L. Heyndrickx, K. Fransen, P. M. Ndumbe, E. Delaporte, M. Peeters, J.-L. Perret, A. Ndoumou, C. Atende, P. Piot, and G. Van der Groen. 1994. Further evidence of the presence of genetically aberrant strains in Cameroon and Gabon. AIDS 8:1012–1013.

Javaherian K, Langlois A, McDanal C et al. 1989. Principal neutralizing domain of human immunodeficiency virus type 1 envelope glycoprotein. Proc Nati Acad Sci USA 86: 5768–5772.

Kimura, M. 1983. The neutral theory of molecular evolution. Cambridge University Press, Cambridge, United Kingdom.

Kostrikis, L. G., E. Bagdades, Y. Cao, L. Zhang, D. Dimitriou, and D. D. Ho. 1995. Genetic analysis of human immunodeficiency type 1 strains from patients in Cyprus: identification of a new subtype designated subtype I. J. Virol. 69:6122–6130.

Kwoh D, Davis G, Whitfield K, Chappelle H, Dimichele L, Gingeras T (1989). Transcription-based amplification system and detection of amplified human immunodeficiency virus type 1 with a bead-based sandwich hybridization format. Proc Natl Acad Sci USA, 86: 1173–1177.

Kwok S, Kellogg D, McKinney N, Spasic D, Goda L, Levenson C, Sinisky J, (1990). Effects of primer-template mismatches on the polymerase chain reaction: Human immunodeficiency views type 1 model studies. Nucl. Acids Res., 18: 999.

Kwok S, Mack D H, Mullis K B et al. (1987) Identification of human immunodeficiency virus sequences by using in vitro enzymatic amplification and oligomer cleavage detection. *J. Virology*, 61: 1690–1694.

Landgren U, Kaiser R, Sanders J, Hood L (1988). A ligase-mediated gene detection technique. Science 241: 1077–1080.

Lee, W. R., W. Syu, B. Du, M. Matsuda, S. Tan, A. Wolf, M. Essex, and T. Lee. 1992. Non-random distribution of gp120 N-linked glycosylation sites important for infectivity of human immunodeficiency virus type 1. Proc. Natl. Acad. Sci. USA 89:2213–2217.

Leonard C, Spellman M, Riddle L et al. 1990. Assignment of intrachain disulfide bonds and characterization of potential glycosylation sites of the type 1 recombinant human immunodeficiency virus envelope glycoprotein (gp120) expressed in chinese hamster ovary cells. J Biol Chem 265: 10373–10382.

Li, Y., L. Luo, N. Rasool, and C. Y. Kang. 1993. Glycosylation is necessary for the correct folding of human immunodeficiency virus gp120 in CD4 binding. J. Virol. 67:584–588.

Lizardi P, Guerra C, Lomeli H, Tussie luna 1, Kramer F. 1988. Exponential amplification of recombiannt RNA hybridization probes. Bio/Technology 6: 1197–1202.

Lomeli H, Tyagi S, Printchard C, Lisardi P, Kramer F (1989) Quantitative assays based on the use of replicatable hybridization probes. Clin Chem 35: 1826–1831.

Loussert-Ajaka, I., T. D. Ly, M.-L. Chaix, D. Ingrand, S. Saragosti, A. M. Couroucé, F. Brun-Vézinet, and F. Simon. 1994. HIV-1/HIV-2 seronegativity in HIV-1 subtype O infected patients. Lancet 343:1393–1394.

Loussert-Ajaka, I., M.-L. Chaix, B. Korber, F. Letourneur, E. Gomas, E. Allen, T.-D. Ly, F. Brun-Vézinet, F. Simon, and S. Saragosti. 1995. Variability of human immunodeficiency virus group O strains isolated from Cameroonian patients living in France. J. Virol. 69:5640–5649.

Louwagie J. , F. McCutchan, M. Peeters, T. P. Brenan, E. Sanders-Buell, G. A. Eddy, G. van der Groen, K. Fransen, G.-M. Gershy-Damet, R. Deleys, and D. S. Burke. 1993. Phylogenetic analysis of gag genes from 70 international HIV-1 isolates provides evidence of multiple genotypes. AIDS 7:769–780.

Maniatis, T., E. F. Fritsch, and J. Sambrook. 1982. Molecular cloning. A laboratory manuel. Cold Spring Harbor Laboratory, Cold Spring Harbor, N.Y.

Matsukura M, Shinozuka K, Zon G, Mitsuya H, Reitz M, Cohen J, Broder S (1987) Phosphorothioate analogs of oligodeoxynucleotides : inhibitors of replication and cytopathic effects of human immunodeficiency virus. Proc. NatI. Acad. Sci. USA 84(21):7706–10.

May, R. M., and R. M. Anderson. 1990. Parasite-host co-evolution. Parasitology 100 (suppl):S89–S101.

Miller P, Yano J, Yano E, Carroll C, Jayaram K, Tso P (1979) Nonionic nucleic acid analogues. Synthesis and characterization of dideoxyribonucleoside methylphosphonates. Biochemistry 18(23):513443.

Monell, C. R., D. R. Hoover, N. Odaka, X. He, A. J. Saah, and M. Strand. 1993. Assessement of the antibody response to the immunosuppressive/immunodominant region of HIV gp41 in a 5-year longitudinal study. J. Med. Virol. 39:125–130.

Muster, T., F. Steindl, M. Purtscher, A. Trkola, A. Klima, G. Himmler, F. Ruker, and H. Katinger. 1993. A conserved neutralizing epitope on gp41 of human immunodeficiency virus type 1. J. Virol. 67:6642–6647.

Myers, G., B. Korber, B. H. Hahn, K.-T. Jeang, J. W. Mellors, F. E. McCutchan; L. E. Henderson, and G. N. Paviakis (Eds.). 1995. Human Retroviruses and AIDS: a compilation and analysis of nucleic acid and amino acid sequences. Theorical Biology and Biophysics Group, Los Alamos National Laboratory, Los Alamos, N. Mex.

Nielsen P, Egholm M, Berg R, Buchardt O (1991) Sequence-selective recognition of DNA by strand displacement with a thymine-substituted polyamide. Science 254(5037): 1497–500.

Nielsen P, Egholm M, Berg R, Buchardt O (1993) Sequence specific inhibition of DNA restriction enzyme cleavage by PNA. Nucleic-Acids-Res. 21(2): 197–200.

Nkengasong, J. N., M. Peeteers, M. Vanden Haesevelde, S. S. Musi, B. Willems, P. M. Ndumbe, E. Delaporte, J. L. Perret, P. Piot, ad G. Van der Groen. 1993. Antigenic evidence of the presence of the aberrant HIV-1 ANT70 virus in Cameroon and Gabon. AIDS 7:1536–1538.

Norrby, E., G. Biberfeld, F. Chiodi, A. von Gegerfeldt, A. Naucler, E. Parks, and R. Lerner. 1987. Discrimination between antibodies to HIV and to related retroviruses using site-directed serology. Nature (London) 329:248–250.

Oldstone, M. B., A. Tishon, H. Lewicki, H. J. Dyson, V. A. Feher, N. Assa-Munt, and P. E. Wright. 1991. Mapping of the anatomy of the immunodominant domain of the human immunodeficiency virus gp41 transmembrane protein: peptide conformation analysis using monoclonal antibodies and proton nuclear magnetic resonance spectroscopy. J. Virol. 65:1727–1734.

Pancino, G., C. Chappey, W. Saurin, and P. Sonigo. 1993. B epitopes and selection pressures in feline immunodeficiency virus envelope glycoproteins. J. Virol. 67:664–672.

Paxton, W., el al. 1993. Incorporation of Vpr into human immunodeficiency virus type 1 virions: requirement for the p6 region of gag and mutational analysis. J. Virol. 67: 7229–7239.

Peeters, M., A. Gueye, S. Mboup, F. Bibollet-Ruche, E. Ekaza, C. Mulanga, R. Ouedrago, R. Gandji, P. Mpele, G. Dibanga, B. Koumare, M. Saidou, E. Esu-Williams, J.-P. Lombart, W. Badombena, N. Luo, M. Vanden Haesevelde, and E. Delaporte. Geographic distribution of HIV-1 group O viruses in Africa. AIDS, in press. Peeters, M., A. Gaye, S. Mboup, W. Badombena, K. Bassabi, M. Prince-David, M. Develoux, F. Liegeois, G. van der Groen, E. Saman, and E. Delaporte. 1996. Presence of HIV-1 group O infection in West Africa. AIDS 10:343–344.

Perrson M, Caothien R, Burton D (1991) Generation of diverse high affinity human monoclonal antibodies by repertoire cloning. Proc. Natl. Acad. Sci. 88:2432–2436.

Robinson, W. E. Jr., M. K. Gorny, J. Y. Xu, W. M. Mitchell, and S. Zolla-Pazner. 1991. Two immunodominant domains of gp41 bind antibodies which enhance human immunodeficiency virus type 1 infection in vitro. J. Virol. 65:41694176.

Ross, E., et al. 1991. Maturation of HIV particles assembled from the gag precursor protein requires in situ processing by gag-pol protease. Aids Res. Hum. Retroviruses 7: 475483.

Roubos E (1990) Sense-antisense complementarity of hormone receptor interaction sites. Trends Biotechnol 8: 279–281.

Ruegg, C. L., C. R. Monell, and M. Strand. 1989. Inhibition of lymphoproliferation by a synthetic peptide with sequence identity to gp41 of human immunodeficiency virus type 1. J. Virol. 63:3257–3260.

Saiki R, Gelfand D, Stoffel S, Scharf S, Higuchi R, Horn G, Mullis K, Erlich H (1988). Primer-directed enzymatic amplification of DNA with a thermostable DNA polymerase. Science 239: 487–491.

Saitou, N., and M. Nei. 1987. The neighbor-joining method: a new method for reconstructing phylogenetic trees. Mol. Biol. Evol. 4:406–425.

Salfeld, J., et al. 1990. Atripartite HIV-1 tat-env-rev fusion protein. EMBO J. 9 965–970.

Schulz, T. F., B. A. Jameson, L. Lopalco, A. G. Siccardi, R. A. Weiss, and J. P. Moore. 1992. Conserved structural features in the interaction between retroviral surface and transmembrane glycoproteins? AIDS Res. Hum. Retroviruses 8:1571–1580.

Sharp, P. M., D. L. Robertson, F. Gao, and B. Hahn. 1994. Origins and diversity of human immunodeficiency viruses. A year in review. AIDS 8:S27–S43.

Simon, F. T. D. Ly, A. Baillou-Beaufils, V. Schneider-Fauveau, J. de Saint-Martin, I. Loussert-Ajaka, M.-L. Chaix, S. Saragosti, A. M. Courroucé, D. Ingrand, C. Janot, and F. Brun-Vézinet. 1994. Sensitivity of screening kits for anti-HIV-1 subtype O antibodies. AIDS 8:1628–1629.

Solornin, L., et al. 1990. Different sites of interaction for rev, tev and rex proteins within the rev-responsive element of the human immunodeficiency virus type 1. J. Virol. 64: 6010–6017.

Soriano, V., M. Guttierez, G. Garcia-Lerma, A. Mas, R. Bravo, 0. Aguilera, M. L. Perez-Labad, and J. Gonzalez-Lahoz. 1996. First case of group O infection in Spain. Vox Sang. 71:66.

Starcich B, Hahn B, Shaw G et al. 1986. Identification and characterization of conserved and variable regions in the envelope gene of HTLVIII/LAV, the retrovirus of AIDS. Cell 45: 637–648.

Vanden Haesevelde, M., J. L. Decourt, R. J. De Leys, B. Vanderbortght, G. van der Groen, H. Van Heuverswijn, and E. Saman. 1994. Genomic cloning and complete sequence analysis of a highly divergent human immunodeficiency virus isolate. J. Virol. 68:1586–1596.

Vanden Haesevelde, M., M. Peeters, G. Jannes, W. Janssens, G. van der Groen, P. M. Sharp, and E. Saman. 1996. Sequence analysis of a highly divergent HIV-1-related lentivirus isolated from a wild captured chimpanzee. Virology 221:346–350.

Vanini, S., R. Longhi, A. Lazzarin, E. Vigo, A. G. Siccardi, and G. Viale. 1993. Discrete regions of HIV-1 gp41 defined by syncitia-inhibiting affinity-purified human antibodies. AIDS 7:167–174.

Walker G, Little M, Nadeau J, Shank D (1992). Isothermal in vitro amplification of DNA by a restriction enzyme/DNA polymerase system. Proc Nati Acad Sci USA 89:392–396.

Willey R, Rutledge R, Dias S et al. (1986). Identification of conserved and divergent domains within the envelope gene of the acquired immune deficiency syndrome retrovirus. Proc Natl Acad Sci USA 83: 5038–5042.

Willey R, el al. 1992. Human immunodeficiency virus type 1 Vpu protein induces rapid degradation of CD4. J. Virol. 66: 7193–7200.

Wu D, Wallace B (1989). The ligation amplification reaction (LAR)—amplification of specific DNA sequences using sequential rounds of template-dependent ligation. Genomics 4:560–569. Barany F (1991). Genetic disease detection and DNA amplification using cloned thermostable ligase. Proc Natl Acad Sci USA 88: 189–193.

Zabarousky E R and Allikmets R L (1986). An improved technique for the efficient construction of gene libraries by partial filling in of cohesive ends. Gene 42: 119–123.

Zhang, L., Y. Huang, T. He, Y. Cao, and D. D. Ho. 1996. HIV-1 subtype and second-receptor use. Nature (London) 383:768.

Zwart, G., H. Langedijk, L. van der Hoek, J. J. de Jong, T. F. W. Wolfs, C. Ramautarsing, M. Bakker, A. de Ronde, and J. Goudsrnit. 1991. Immunodominance and antigenic variation of the principal neutralization domain of HIV-1. Virology 181:481–489.

Zwart, G., L. van der Hoek, M. Valk, M. T. Cornelissen, E. Baan, J. Dekker, M. Koot, C. L. Kuiken, and J. Goudsmit. 1994. Antibody responses to HIV-1 envelope and gag epitopes in HIV-1 seroconverters with rapid versus slow disease progression. Virology 201:285–293.

Zwart, G., T. F. W. Wolfs, R. Bookelman, S. Hartman, M. Baker, C. A. B. Boucher, C. Kuiken, and J. Goudsmit. 1993. Greater diversity of the HIV-1 V3 neutralization domain in Tanzania compared with the Netherlands: serological and genetic analysis. AIDS 7:467–474.

---

SEQUENCE LISTING

<160> NUMBER OF SEQ ID NOS: 152

<210> SEQ ID NO 1
<211> LENGTH: 340
<212> TYPE: DNA
<213> ORGANISM: Human

<400> SEQUENCE: 1

```
aacctgctaa gagcaataca ggcccagcaa gaattgctga ggctatctgt atggggtatc      60
agacaactcc gagctcgcct gctagcctta gaaaccttaa tacagaatca gcagctccta     120
aacctatggg gttgtaaggg aaggatagtc tgctacacat cagtaaaatg gaacgataca     180
tggagacatg tcactaatat gagtgaagtt tgggacaaac taacctggca ggaatgggat     240
cggcagatag acaacataag ctatgttata tatgatgaaa tacaaagagc acaagtacag     300
```
caagaacaaa atgagaagaa gttgctggag ttagatgaat         340

<210> SEQ ID NO 2
<211> LENGTH: 113
<212> TYPE: PRT
<213> ORGANISM: Human

<400> SEQUENCE: 2

```
Asn Leu Leu Arg Ala Ile Gln Ala Gln Gln Glu Leu Leu Arg Leu Ser
 1               5                  10                  15

Val Trp Gly Ile Arg Gln Leu Arg Ala Arg Leu Leu Ala Leu Glu Thr
            20                  25                  30

Leu Ile Gln Asn Gln Gln Leu Leu Asn Leu Trp Gly Cys Lys Gly Arg
        35                  40                  45

Ile Val Cys Tyr Thr Ser Val Lys Trp Asn Asp Thr Trp Arg His Val
    50                  55                  60

Thr Asn Met Ser Glu Val Trp Asp Lys Leu Thr Trp Gln Glu Trp Asp
65                  70                  75                  80

Arg Gln Ile Asp Asn Ile Ser Tyr Val Ile Tyr Asp Glu Ile Gln Arg
                85                  90                  95

Ala Gln Val Gln Gln Glu Gln Asn Glu Lys Lys Leu Leu Glu Leu Asp
                100                 105                 110

Glu
```

<210> SEQ ID NO 3
<211> LENGTH: 340
<212> TYPE: DNA
<213> ORGANISM: Human
<220> FEATURE:
<221> NAME/KEY: misc_feature
<222> LOCATION: (1)..(340)
<223> OTHER INFORMATION: N = any nucleotide

<400> SEQUENCE: 3
aacctgctaa sancaataca ggcccakcaa gaattgctga ggctatctgt atggggtatc    60
agacaamtcc gagstygcct gstagcctta gaaaccttaa tacasaatca gcasctccta   120
aacctatggg gttgtaaagg aaggatastn tgctacacat cagtaaaatg gaacnataca   180
tggaaacatg tcactnatat gagtgaagtt tgggacaaac taacctggca ggaatgggat   240
cggcngatag acaacataag ctatgttata tatgatgnna tacaaagagc acaagtacag   300
caagaacaaa atgagaagaa gttgctggag ttagatgaat                         340

<210> SEQ ID NO 4
<211> LENGTH: 113
<212> TYPE: PRT
<213> ORGANISM: Human
<220> FEATURE:
<221> NAME/KEY: Misc_feature
<222> LOCATION: (1)..(113)
<223> OTHER INFORMATION: Xaa = unknown

<400> SEQUENCE: 4

```
Asn Leu Leu Xaa Xaa Ile Gln Ala Xaa Gln Glu Leu Leu Arg Leu Ser
 1               5                  10                  15

Val Trp Gly Ile Arg Gln Xaa Arg Xaa Xaa Leu Xaa Ala Leu Glu Thr
            20                  25                  30

Leu Ile Xaa Asn Gln Xaa Leu Leu Asn Leu Trp Gly Cys Lys Gly Arg
        35                  40                  45

Ile Xaa Cys Tyr Thr Ser Val Lys Trp Asn Xaa Thr Trp Lys His Val
```

```
        50                  55                  60
Thr Xaa Met Ser Glu Val Trp Asp Lys Leu Thr Trp Gln Glu Trp Asp
 65                  70                  75                  80

Arg Xaa Ile Asp Asn Ile Ser Tyr Val Ile Tyr Asp Xaa Ile Gln Arg
                 85                  90                  95

Ala Gln Val Gln Gln Glu Gln Asn Glu Lys Lys Leu Leu Glu Leu Asp
            100                 105                 110

Glu
```

<210> SEQ ID NO 5
<211> LENGTH: 352
<212> TYPE: DNA
<213> ORGANISM: Human

<400> SEQUENCE: 5

```
aacctgctaa aagcaataca ggcccagcag caattgctga ggttatctgt atggggtatc    60
aaacaactcc gagctcgcct gctagcctta gaaaccttaa tacagaatca gcaactccta   120
aacctatggg gctgtaaagg aaggctagtc tgctacacat cagtaaaatg gaacaataca   180
tggacaaaaa acatcacaaa catcacagac ctagacgaga tttgggacaa atttacatgg   240
caccaatggg atcaacagat aaaccacata agtgatgtca tatatgaaga aataccaaag   300
gcacaagtac agcagggacc aaatgagagg aagttgctgg agttagatga at          352
```

<210> SEQ ID NO 6
<211> LENGTH: 117
<212> TYPE: PRT
<213> ORGANISM: Human

<400> SEQUENCE: 6

```
Asn Leu Leu Lys Ala Ile Gln Ala Gln Gln Gln Leu Leu Arg Leu Ser
 1               5                  10                  15

Val Trp Gly Ile Lys Gln Leu Arg Ala Arg Leu Leu Ala Leu Glu Thr
            20                  25                  30

Leu Ile Gln Asn Gln Gln Leu Leu Asn Leu Trp Gly Cys Lys Gly Arg
        35                  40                  45

Leu Val Cys Tyr Thr Ser Val Lys Trp Asn Asn Thr Trp Thr Lys Asn
 50                  55                  60

Ile Thr Asn Ile Thr Asp Leu Asp Glu Ile Trp Asp Lys Phe Thr Trp
 65                  70                  75                  80

His Gln Trp Asp Gln Gln Ile Asn His Ile Ser Asp Val Ile Tyr Glu
                 85                  90                  95

Glu Ile Pro Lys Ala Gln Val Gln Gln Gly Pro Asn Glu Arg Lys Leu
            100                 105                 110

Leu Glu Leu Asp Glu
        115
```

<210> SEQ ID NO 7
<211> LENGTH: 352
<212> TYPE: DNA
<213> ORGANISM: Human
<220> FEATURE:
<221> NAME/KEY: misc_feature
<222> LOCATION: (1)..(352)
<223> OTHER INFORMATION: N = any nucleotide

<400> SEQUENCE: 7

```
nacctgttaa gagcaataca ggcccagcag caattggtga ggttatctgt atggggtatc    60
```

-continued

```
agacaaatcc gaggtngcct ggtagcctta gaaaccttaa tacagaatca gcaantcctn       120
aacctatggg gctgtaaagg aagggtagtt tgntacacat cagtaaaatg gaacaataca       180
tggacaaaaa acatcacaaa catcacagac ctagacgaga tttgggacaa atttacatgg       240
cagcaatggg atcaacagat aaacaacata agtgatgtcc tatatgaaga aatacaaaag      300
gcacaagtac agcaggaaca aaatgagagg aagttgctgg agttagatga at              352
```

<210> SEQ ID NO 8
<211> LENGTH: 117
<212> TYPE: PRT
<213> ORGANISM: Human
<220> FEATURE:
<221> NAME/KEY: Misc_feature
<222> LOCATION: (1)..(117)
<223> OTHER INFORMATION: Xaa = Unknown

<400> SEQUENCE: 8

```
Xaa Leu Leu Arg Ala Ile Gln Ala Gln Gln Gln Leu Val Arg Leu Ser
 1               5                  10                  15

Val Trp Gly Ile Arg Gln Ile Arg Gly Xaa Leu Val Ala Leu Glu Thr
             20                  25                  30

Leu Ile Gln Asn Gln Xaa Xaa Asn Leu Trp Gly Cys Lys Gly Arg
         35                  40                  45

Val Val Xaa Tyr Thr Ser Val Lys Trp Asn Asn Thr Trp Thr Lys Asn
     50                  55                  60

Ile Thr Asn Ile Thr Asp Leu Asp Glu Ile Trp Asp Lys Phe Thr Trp
 65                  70                  75                  80

Gln Gln Trp Asp Gln Gln Ile Asn Asn Ile Ser Asp Val Leu Tyr Glu
                 85                  90                  95

Glu Ile Gln Lys Ala Gln Val Gln Gln Glu Gln Asn Glu Arg Lys Leu
            100                 105                 110

Leu Glu Leu Asp Glu
            115
```

<210> SEQ ID NO 9
<211> LENGTH: 340
<212> TYPE: DNA
<213> ORGANISM: Human

<400> SEQUENCE: 9

```
aacctgctaa gagcaataca ggcccagcag caattgctga ggctatctgt atgggtatc        60 agacaactcc gagctcgcct gctagcctta gaaaccttaa tacagaatca gcagctccta       120
aacctatggg gttgtaaggg aaggatagtc tgctacacat cagtaaaatg gaacaataca       180
tggagaaatg tcactaatat gagtgaagtt tgggacacac taacctggca ggaatgggat       240
cggcagatag acaacataag ctatgttata tatgatgaaa tacaaagagc acaagtacag       300
caggaacaaa atgagaagaa gttgctggag ttagatgaat                            340
```

<210> SEQ ID NO 10
<211> LENGTH: 113
<212> TYPE: PRT
<213> ORGANISM: Human

<400> SEQUENCE: 10

```
Asn Leu Leu Arg Ala Ile Gln Ala Gln Gln Gln Leu Leu Arg Leu Ser
 1               5                  10                  15

Val Trp Gly Ile Arg Gln Leu Arg Ala Arg Leu Leu Ala Leu Glu Thr
             20                  25                  30
```

```
Leu Ile Gln Asn Gln Gln Leu Leu Asn Leu Trp Gly Cys Lys Gly Arg
        35                  40                  45
Ile Val Cys Tyr Thr Ser Val Lys Trp Asn Asn Thr Trp Arg Asn Val
    50                  55                  60
Thr Asn Met Ser Glu Val Trp Asp Thr Leu Thr Trp Gln Glu Trp Asp
65                  70                  75                  80
Arg Gln Ile Asp Asn Ile Ser Tyr Val Ile Tyr Asp Glu Ile Gln Arg
                85                  90                  95
Ala Gln Val Gln Gln Glu Gln Asn Glu Lys Lys Leu Leu Glu Leu Asp
            100                 105                 110
Glu

<210> SEQ ID NO 11
<211> LENGTH: 340
<212> TYPE: DNA
<213> ORGANISM: Human

<400> SEQUENCE: 11
aacctgctaa gagcaataca ggcccagcag caattgctga ggctatctgt atggggtatc      60
agacaactcc gagctcgcct gctagcctta gaaaccttaa tacagaatca gcagctccta     120
aacctatggg gttgtaaggg aaggatagtc tgctacacat cagtaaaatg gaacaataca     180
tggagaaatg tcactaatat gagtgaagtt tgggacacac taacctggca ggaatgggat     240
cggcagatag acaacataag ctatgttata tatgatgaaa tacaaagagc acaagtacag     300
caggaacaaa atgagaagaa gttgctggag ttagatgaat                           340

<210> SEQ ID NO 12
<211> LENGTH: 113
<212> TYPE: PRT
<213> ORGANISM: Human

<400> SEQUENCE: 12

Asn Leu Leu Arg Ala Ile Gln Ala Gln Gln Leu Leu Arg Leu Ser
1               5                   10                  15

Val Trp Gly Ile Arg Gln Leu Arg Ala Arg Leu Leu Ala Leu Glu Thr
            20                  25                  30

Leu Ile Gln Asn Gln Gln Leu Leu Asn Leu Trp Gly Cys Lys Gly Arg
        35                  40                  45

Ile Val Cys Tyr Thr Ser Val Lys Trp Asn Asn Thr Trp Arg Asn Val
    50                  55                  60

Thr Asn Met Ser Glu Val Trp Asp Thr Leu Thr Trp Gln Glu Trp Asp
65                  70                  75                  80

Arg Gln Ile Asp Asn Ile Ser Tyr Val Ile Tyr Asp Glu Ile Gln Arg
                85                  90                  95

Ala Gln Val Gln Gln Glu Gln Asn Glu Lys Lys Leu Leu Glu Leu Asp
            100                 105                 110

Glu

<210> SEQ ID NO 13
<211> LENGTH: 331
<212> TYPE: DNA
<213> ORGANISM: Human

<400> SEQUENCE: 13
aacctgctaa gagcaataca ggcccagcag cacttgctga ggctatctgt atggggtatc      60
```

```
agacaactcc gagctcgcct gctagcctta gaaaccttaa tacagaatca gcaactccta    120
aactcatggg gctgtaaggg aaagatagtc tgttacacag cagtaaaatg aacaagaca     180 tggacaggaa atgaaagtat ttgggaccac ctcacatggc agcaatggga tcagcagata    240
gacaatgtaa gctccaccat atatgaggaa atactaaaag cacaagtaca gcaggaacag    300
aatgagcaaa agttgctgga gttagatgaa t                                   331
```

<210> SEQ ID NO 14
<211> LENGTH: 110
<212> TYPE: PRT
<213> ORGANISM: Human

<400> SEQUENCE: 14

```
Asn Leu Leu Arg Ala Ile Gln Ala Gln Gln His Leu Leu Arg Leu Ser
1               5                   10                  15

Val Trp Gly Ile Arg Gln Leu Arg Ala Arg Leu Leu Ala Leu Glu Thr
            20                  25                  30

Leu Ile Gln Asn Gln Gln Leu Leu Asn Ser Trp Gly Cys Lys Gly Lys
        35                  40                  45

Ile Val Cys Tyr Thr Ala Val Lys Trp Asn Lys Thr Trp Thr Gly Asn
    50                  55                  60

Glu Ser Ile Trp Asp His Leu Thr Trp Gln Gln Trp Asp Gln Gln Ile
65                  70                  75                  80

Asp Asn Val Ser Ser Thr Ile Tyr Glu Glu Ile Leu Lys Ala Gln Val
                85                  90                  95

Gln Gln Glu Gln Asn Glu Gln Lys Leu Leu Glu Leu Asp Glu
            100                 105                 110
```

<210> SEQ ID NO 15
<211> LENGTH: 331
<212> TYPE: DNA
<213> ORGANISM: Human

<400> SEQUENCE: 15

```
aacctgctaa gagcaataca ggcccagcag cacttgctga ggctatctgt atggggtatc    60
agacaactcc gagctcgcct gctagcctta gaaaccttaa tacagaatca gcaactccta    120
aactcatggg gctgtaaggg aaagatagtc tgttacacag cagtaaaatg aacaggaca     180 tggacaggaa atgaaagtat ttgggaccac ctcacatggc agcaatggga tcagcagata    240
gacaatgtaa gctccaccat atatgaggaa atactaaaag cacaagtaca gcaggaacag    300
aatgagmaaa arttgctgga gttagatgaa t                                   331
```

<210> SEQ ID NO 16
<211> LENGTH: 110
<212> TYPE: PRT
<213> ORGANISM: Human
<220> FEATURE:
<221> NAME/KEY: misc_feature
<222> LOCATION: (1)..(110)
<223> OTHER INFORMATION: Xaa = Unknown

<400> SEQUENCE: 16

```
Asn Leu Leu Arg Ala Ile Gln Ala Gln Gln His Leu Leu Arg Leu Ser
1               5                   10                  15

Val Trp Gly Ile Arg Gln Leu Arg Ala Arg Leu Leu Ala Leu Glu Thr
            20                  25                  30

Leu Ile Gln Asn Gln Gln Leu Leu Asn Ser Trp Gly Cys Lys Gly Lys
        35                  40                  45
```

```
Ile Val Cys Tyr Thr Ala Val Lys Trp Asn Arg Thr Trp Thr Gly Asn
     50                  55                  60
Glu Ser Ile Trp Asp His Leu Thr Trp Gln Gln Trp Asp Gln Ile
 65                  70                  75                  80
Asp Asn Val Ser Ser Thr Ile Tyr Glu Glu Ile Leu Lys Ala Gln Val
                 85                  90                  95
Gln Gln Glu Gln Asn Glu Xaa Xaa Leu Leu Glu Leu Asp Glu
             100                 105                 110
```

<210> SEQ ID NO 17
<211> LENGTH: 340
<212> TYPE: DNA
<213> ORGANISM: Human

<400> SEQUENCE: 17

```
aacctgctaa aagcaataca ggcccagcag gaattgctga ggctatctgt atggggtatc    60
agacaactcc gagctcgcct gctagcctta gaaaccttaa tacaggatca gcagctccta   120
aacctatggg gttgtaaggg aaggatagtc tgctacacat cagtaaaatg gaacgataca   180
tggagacatg tcactaatat gagtgaagtt tgggacaaat taacctggca ggaatgggat   240
cggcagatag acaacataag ctatgttata tatgatgaaa tacaaagagc acaagtacag   300
caaggaccaa atgagaagaa gttgctggag ttagatgaat                         340
```

<210> SEQ ID NO 18
<211> LENGTH: 113
<212> TYPE: PRT
<213> ORGANISM: Human

<400> SEQUENCE: 18

```
Asn Leu Leu Lys Ala Ile Gln Ala Gln Gln Glu Leu Leu Arg Leu Ser
  1               5                  10                  15
Val Trp Gly Ile Arg Gln Leu Arg Ala Arg Leu Leu Ala Leu Glu Thr
                 20                  25                  30
Leu Ile Gln Asp Gln Gln Leu Leu Asn Leu Trp Gly Cys Lys Gly Arg
             35                  40                  45
Ile Val Cys Tyr Thr Ser Val Lys Trp Asn Asp Thr Trp Arg His Val
     50                  55                  60
Thr Asn Met Ser Glu Val Trp Asp Lys Leu Thr Trp Gln Glu Trp Asp
 65                  70                  75                  80
Arg Gln Ile Asp Asn Ile Ser Tyr Val Ile Tyr Asp Glu Ile Gln Arg
                 85                  90                  95
Ala Gln Val Gln Gln Gly Pro Asn Glu Lys Lys Leu Leu Glu Leu Asp
             100                 105                 110
Glu
```

<210> SEQ ID NO 19
<211> LENGTH: 348
<212> TYPE: DNA
<213> ORGANISM: Human

<400> SEQUENCE: 19

```
aacctgctaa gagcaataca ggcccagcag caattgctga ggctatctgt atggggtatc    60
agacaactcc gagctcgcct gctagcctta gaaaccttaa tacagaacca gcaactccta   120
aacctatggg gctgtaaggg aaggctagtc tgctacacat cagtaaaatg gaacaagaca   180
tggataaata aaactgacac tgagatagag aatatttggg aaaatctgac atggcaggaa   240
```

```
tgggatcagc aaataagcaa cataagctcc accatatatg aggaaataca aaaggcacaa      300
atacaacagg aacataatga gaaaaagttg ctggagctag atgaatgg                   348
```

<210> SEQ ID NO 20
<211> LENGTH: 116
<212> TYPE: PRT
<213> ORGANISM: Human

<400> SEQUENCE: 20

```
Asn Leu Leu Arg Ala Ile Gln Ala Gln Gln Leu Leu Arg Leu Ser
1               5                   10                  15

Val Trp Gly Ile Arg Gln Leu Arg Ala Arg Leu Leu Ala Leu Glu Thr
            20                  25                  30

Leu Ile Gln Asn Gln Gln Leu Leu Asn Leu Trp Gly Cys Lys Gly Arg
        35                  40                  45

Leu Val Cys Tyr Thr Ser Val Lys Trp Asn Lys Thr Trp Ile Asn Lys
    50                  55                  60

Thr Asp Thr Glu Ile Glu Asn Ile Trp Glu Asn Leu Thr Trp Gln Glu
65                  70                  75                  80

Trp Asp Gln Gln Ile Ser Asn Ile Ser Ser Thr Ile Tyr Glu Glu Ile
                85                  90                  95

Gln Lys Ala Gln Ile Gln Gln Glu His Asn Glu Lys Lys Leu Leu Glu
                100                 105                 110

Leu Asp Glu Trp
            115
```

<210> SEQ ID NO 21
<211> LENGTH: 349
<212> TYPE: DNA
<213> ORGANISM: Human

<400> SEQUENCE: 21

```
aacctgctaa gagcaataca ggctcagcat caactgctga agctatctgt atggggtatc      60
agacaactcc gagctcgcct gctagcctta gaaacctta tacagaatca gcaactccta     120
aacctatggg gctgtaaagg aaacctaatc tgctacacat cagtaaaatg gaacgaaaca     180 tggaaggag ataggacttt tactgacatg gaaaatattt ggaacaacct aacatggcag     240
gaatgggatc agcagataag caacataagc tccaccatat atgacgaaat acaaaaggca     300
caagtacagc aggaacaaaa tgagaaaaag ttactagagt taagtgaat                349
```

<210> SEQ ID NO 22
<211> LENGTH: 116
<212> TYPE: PRT
<213> ORGANISM: Human

<400> SEQUENCE: 22

```
Asn Leu Leu Arg Ala Ile Gln Ala Gln His Gln Leu Leu Lys Leu Ser
1               5                   10                  15

Val Trp Gly Ile Arg Gln Leu Arg Ala Arg Leu Leu Ala Leu Glu Thr
            20                  25                  30

Phe Ile Gln Asn Gln Gln Leu Leu Asn Leu Trp Gly Cys Lys Gly Asn
        35                  40                  45

Leu Ile Cys Tyr Thr Ser Val Lys Trp Asn Glu Thr Trp Lys Gly Asp
    50                  55                  60

Arg Thr Phe Thr Asp Met Glu Asn Ile Trp Asn Asn Leu Thr Trp Gln
65                  70                  75                  80
```

```
Glu Trp Asp Gln Gln Ile Ser Asn Ile Ser Ser Thr Ile Tyr Asp Glu
                85                  90                  95
Ile Gln Lys Ala Gln Val Gln Gln Gln Asn Glu Lys Lys Leu Leu
            100                 105                 110
Glu Leu Ser Glu
        115
```

<210> SEQ ID NO 23
<211> LENGTH: 346
<212> TYPE: DNA
<213> ORGANISM: Human

<400> SEQUENCE: 23

```
aacctgctaa gagcaataca ggcccagcag caattgctga ggctatctgt atgggtatc      60
agacaactcc gagctcgcct gctagcctta gaaaccttaa tacagagtca gcaactccta   120
aacctgtggg gctgtaaggg aaggctaatc tgctacacct cagtgcattg aataagaca    180
tggacaaata agacagataa ggatttggag gatatgtggg acaacctaac atggcagcaa   240
tgggatcagc agataagtaa cataagcgcc accatatatg aggaaataca aaggcacaa    300
gtacaacaag aatacaatga gagaaagttg ttggagttag atgaat                  346
```

<210> SEQ ID NO 24
<211> LENGTH: 115
<212> TYPE: PRT
<213> ORGANISM: Human

<400> SEQUENCE: 24

```
Asn Leu Leu Arg Ala Ile Gln Ala Gln Gln Leu Leu Arg Leu Ser
1               5                   10                  15
Val Trp Gly Ile Arg Gln Leu Arg Ala Arg Leu Leu Ala Leu Glu Thr
                20                  25                  30
Leu Ile Gln Ser Gln Gln Leu Leu Asn Leu Trp Gly Cys Lys Gly Arg
            35                  40                  45
Leu Ile Cys Tyr Thr Ser Val His Trp Asn Lys Thr Trp Thr Asn Lys
        50                  55                  60
Thr Asp Lys Asp Leu Glu Asp Met Trp Asp Asn Leu Thr Trp Gln Gln
65                  70                  75                  80
Trp Asp Gln Gln Ile Ser Asn Ile Ser Ala Thr Ile Tyr Glu Glu Ile
                85                  90                  95
Gln Lys Ala Gln Val Gln Gln Glu Tyr Asn Glu Arg Lys Leu Leu Glu
            100                 105                 110
Leu Asp Glu
        115
```

<210> SEQ ID NO 25
<211> LENGTH: 340
<212> TYPE: DNA
<213> ORGANISM: Human
<220> FEATURE:
<221> NAME/KEY: misc_feature
<222> LOCATION: (1)..(340)
<223> OTHER INFORMATION: N = any nucleotide

<400> SEQUENCE: 25

```
aacctgctaa gagcaataca ggcccagcag caattgctga ggctatctgt atgggtatc      60
anacaactcc gagctcgcct gctagcatya gaaaccttaa tacagaatcw gcaactcctg   120
aacctatggg gctgtaaggg aakgctagtc tgctacacat cagtamaatg gaacaggaca   180
```

```
tggacaaaca atactaattt agattcaatt tgggaaaatc taacatggca ggaatgggat    240
cagcagataa gcaacataag ctccaccata tatgaagaaa tacaaaaggc acaartacag    300
caggaatacr atgagaaaaa gttgctagag ttagatkaat                          340
```

<210> SEQ ID NO 26
<211> LENGTH: 113
<212> TYPE: PRT
<213> ORGANISM: Human
<220> FEATURE:
<221> NAME/KEY: Misc_feature
<222> LOCATION: (1)..(113)
<223> OTHER INFORMATION: Xaa = unknown

<400> SEQUENCE: 26

```
Asn Leu Leu Arg Ala Ile Gln Ala Gln Gln Gln Leu Leu Arg Leu Ser
1               5                   10                  15

Val Trp Gly Ile Xaa Gln Leu Arg Ala Arg Leu Leu Ala Xaa Glu Thr
            20                  25                  30

Leu Ile Gln Asn Xaa Gln Leu Leu Asn Leu Trp Gly Cys Lys Gly Xaa
        35                  40                  45

Leu Val Cys Tyr Thr Ser Val Xaa Trp Asn Arg Thr Trp Thr Asn Asn
    50                  55                  60

Thr Asn Leu Asp Ser Ile Trp Glu Asn Leu Thr Trp Gln Glu Trp Asp
65                  70                  75                  80

Gln Gln Ile Ser Asn Ile Ser Ser Thr Ile Tyr Glu Glu Ile Gln Lys
                85                  90                  95

Ala Gln Xaa Gln Gln Glu Tyr Xaa Glu Lys Lys Leu Leu Glu Leu Asp
            100                 105                 110

Xaa
```

<210> SEQ ID NO 27
<211> LENGTH: 340
<212> TYPE: DNA
<213> ORGANISM: Human

<400> SEQUENCE: 27

```
aacctgctaa gagcaataca ggcccagcag caattgctga ggctatctgt atggggtatc    60
agacaactcc gagctcgcct gttggcctta gaaaccttaa tacagaatca gcaactccta    120
aacctatggg gatgtaaggg aaggctaatc tgctacacat cagtcaaatg gaacatgaca    180
tggacaaaca attctaatct ggaaacaatt tgggacaacc taacatggca ggaatgggat    240
cagcagataa acagcataag ctctgtcata tatgaggaaa tacaaagggc acaagtacag    300
caggaacaaa acgagaaaaa gttgctggag ttagaggaat                          340
```

<210> SEQ ID NO 28
<211> LENGTH: 113
<212> TYPE: PRT
<213> ORGANISM: Human

<400> SEQUENCE: 28

```
Asn Leu Leu Arg Ala Ile Gln Ala Gln Gln Gln Leu Leu Arg Leu Ser
1               5                   10                  15

Val Trp Gly Ile Arg Gln Leu Arg Ala Arg Leu Leu Ala Leu Glu Thr
            20                  25                  30

Leu Ile Gln Asn Gln Gln Leu Leu Asn Leu Trp Gly Cys Lys Gly Arg
        35                  40                  45
```

```
Leu Ile Cys Tyr Thr Ser Val Gln Trp Asn Met Thr Trp Thr Asn Asn
        50                  55                  60

Ser Asn Leu Glu Thr Ile Trp Asp Asn Leu Thr Trp Gln Glu Trp Asp
 65                  70                  75                  80

Gln Gln Ile Asn Ser Ile Ser Ser Val Ile Tyr Glu Glu Ile Gln Arg
                 85                  90                  95

Ala Gln Val Gln Gln Glu Gln Asn Glu Lys Lys Leu Leu Glu Leu Glu
                100                 105                 110

Glu

<210> SEQ ID NO 29
<211> LENGTH: 331
<212> TYPE: DNA
<213> ORGANISM: Human

<400> SEQUENCE: 29
aacctgctga gagcaataca ggcccagcag caattgctga ggctatctgt atggggtatc    60
agacaactcc gagctcgcct gctagcctta gaaaccttaa tacagaatca gcaactccta   120
aacctatggg gctgtagagg aaggcaagtc tgctacacat cagtaatatg gaatgagaca   180
tggataggaa acgaaaccat ttgggaagaa ctaacatggc aggaatggga tcggcagata   240
agcaacataa gctccaccat atatgatgaa atacaaaagg cacaagtaca gcaggaacaa   300
aatgagaaaa aattgctgga gttagatgaa t                                  331

<210> SEQ ID NO 30
<211> LENGTH: 110
<212> TYPE: PRT
<213> ORGANISM: Human

<400> SEQUENCE: 30

Asn Leu Leu Arg Ala Ile Gln Ala Gln Gln Leu Leu Arg Leu Ser
 1               5                  10                  15

Val Trp Gly Ile Arg Gln Leu Arg Ala Arg Leu Leu Ala Leu Glu Thr
                20                  25                  30

Leu Ile Gln Asn Gln Gln Leu Leu Asn Leu Trp Gly Cys Arg Gly Arg
                 35                  40                  45

Gln Val Cys Tyr Thr Ser Val Ile Trp Asn Glu Thr Trp Ile Gly Asn
         50                  55                  60

Glu Thr Ile Trp Glu Glu Leu Thr Trp Gln Glu Trp Asp Arg Gln Ile
 65                  70                  75                  80

Ser Asn Ile Ser Ser Thr Ile Tyr Asp Glu Ile Gln Lys Ala Gln Val
                 85                  90                  95

Gln Gln Glu Gln Asn Glu Lys Lys Leu Leu Glu Leu Asp Glu
                100                 105                 110

<210> SEQ ID NO 31
<211> LENGTH: 334
<212> TYPE: DNA
<213> ORGANISM: Human
<220> FEATURE:
<221> NAME/KEY: misc_feature
<222> LOCATION: (1)..(334)
<223> OTHER INFORMATION: N = any nucleotide

<400> SEQUENCE: 31
aacctgctga gagcgataca ggcccagcaa cacttgctga ggttatctgt atggggtatt    60
agacaactcc gagctcgcct gcaagcctta gaaacccttta tacagaatca gcaacgccta  120
```

```
aacctatggg gctgtaaggg aaagatgatc tgttacacat cagtaaaatg gaacacatca    180
tggggagact ataatgacag tatttggggc aactanacat ggcaacaatg ggaccaagaa    240
ataagcaatg taagctccat tatatatgac aaaatacaag aagcacagga ccaacaggag    300
aggaatgtaa aagcattgtt ggagctggat gaat                                334
```

<210> SEQ ID NO 32
<211> LENGTH: 111
<212> TYPE: PRT
<213> ORGANISM: Human
<220> FEATURE:
<221> NAME/KEY: Misc_feature
<222> LOCATION: (1)..(111)
<223> OTHER INFORMATION: Xaa = unknown

<400> SEQUENCE: 32

```
Asn Leu Leu Arg Ala Ile Gln Ala Gln Gln His Leu Leu Arg Leu Ser
1               5                   10                  15

Val Trp Gly Ile Arg Gln Leu Arg Ala Arg Leu Gln Ala Leu Glu Thr
            20                  25                  30

Leu Ile Gln Asn Gln Gln Arg Leu Asn Leu Trp Gly Cys Lys Gly Lys
        35                  40                  45

Met Ile Cys Tyr Thr Ser Val Lys Trp Asn Thr Ser Trp Gly Asp Tyr
    50                  55                  60

Asn Asp Ser Ile Trp Gly Asn Xaa Thr Trp Gln Gln Trp Asp Gln Glu
65                  70                  75                  80

Ile Ser Asn Val Ser Ser Ile Ile Tyr Asp Lys Ile Gln Glu Ala Gln
                85                  90                  95

Asp Gln Gln Glu Arg Asn Val Lys Ala Leu Leu Glu Leu Asp Glu
            100                 105                 110
```

<210> SEQ ID NO 33
<211> LENGTH: 334
<212> TYPE: DNA
<213> ORGANISM: Human

<400> SEQUENCE: 33

```
aacctgctga gagcgataca ggcccagcaa cacttgctga ggttatctgt atggggtatc    60
agacaactcc gagctcgcct gcaagcctta gaaaccctta tacagaatca gcaacgccta   120
aacctatggg gctgtaaggg aaagatgatc tgttacacat cagtaccatg gaacacatca   180
tggggaaact ataatgacag tatttgggat aagtatacat ggcaacaatg ggaccgagaa   240
atagacaatg taagctacat tatatatgaa aaaatacaag aagcacaaga ccaacaggag   300
aagaatgtaa aagcattgtt ggagctagat gaat                                334
```

<210> SEQ ID NO 34
<211> LENGTH: 111
<212> TYPE: PRT
<213> ORGANISM: Human

<400> SEQUENCE: 34

```
Asn Leu Leu Arg Ala Ile Gln Ala Gln Gln His Leu Leu Arg Leu Ser
1               5                   10                  15

Val Trp Gly Ile Arg Gln Leu Arg Ala Arg Leu Gln Ala Leu Glu Thr
            20                  25                  30

Leu Ile Gln Asn Gln Gln Arg Leu Asn Leu Trp Gly Cys Lys Gly Lys
        35                  40                  45

Met Ile Cys Tyr Thr Ser Val Pro Trp Asn Thr Ser Trp Gly Asn Tyr
```

```
                  50                  55                  60
Asn Asp Ser Ile Trp Asp Lys Tyr Thr Trp Gln Gln Trp Asp Arg Glu
 65                  70                  75                  80

Ile Asp Asn Val Ser Tyr Ile Ile Tyr Glu Lys Ile Gln Glu Ala Gln
                     85                  90                  95

Asp Gln Gln Glu Lys Asn Val Lys Ala Leu Leu Glu Leu Asp Glu
                100                 105                 110

<210> SEQ ID NO 35
<211> LENGTH: 331
<212> TYPE: DNA
<213> ORGANISM: Human

<400> SEQUENCE: 35
aacctgctga gagcaataca ggcccagcaa catctgctga ggttatctgt atggggtatt      60
agacaactcc gagctcgcct gcaagcctta gaaacccttta tgcaaaatca gcaactccta   120
aacctatggg gctgtaaagg aaaatcaatc tgctacacat cagtaaaatg gaacaacaca   180
tggggaggaa atctctcaat ttgggacagc ttaacatggc agcaatggga tcaacaggta   240
gccaatgtaa gctctttgat atatgacaaa atacaagaag cacaagaaca acaggaggaa   300
aatgaaaggg ccttgctgga gttagatgaa t                                   331

<210> SEQ ID NO 36
<211> LENGTH: 110
<212> TYPE: PRT
<213> ORGANISM: Human

<400> SEQUENCE: 36

Asn Leu Leu Arg Ala Ile Gln Ala Gln Gln His Leu Leu Arg Leu Ser
 1               5                  10                  15

Val Trp Gly Ile Arg Gln Leu Arg Ala Arg Leu Gln Ala Leu Glu Thr
                20                  25                  30

Leu Met Gln Asn Gln Gln Leu Leu Asn Leu Trp Gly Cys Lys Gly Lys
                35                  40                  45

Ser Ile Cys Tyr Thr Ser Val Lys Trp Asn Asn Thr Trp Gly Gly Asn
     50                  55                  60

Leu Ser Ile Trp Asp Ser Leu Thr Trp Gln Gln Trp Asp Gln Gln Val
 65                  70                  75                  80

Ala Asn Val Ser Ser Leu Ile Tyr Asp Lys Ile Gln Glu Ala Gln Glu
                     85                  90                  95

Gln Gln Glu Glu Asn Glu Arg Ala Leu Leu Glu Leu Asp Glu
                100                 105                 110

<210> SEQ ID NO 37
<211> LENGTH: 331
<212> TYPE: DNA
<213> ORGANISM: Human

<400> SEQUENCE: 37
aacctgttga gagcgataca ggcccagcaa cacctgctga ggttatctgt atggggtata      60
agacaactcc gagctcgcct gcaagcctta gaaacccttta tacagaacca gcaactccta   120
agcctatggg gatgtaaggg aaagctaatc tgttacacat ctgtaaaatg gaacacatca   180
tggggaggaa atgagagtat ttggaacaat ctaacatggc agcagtggga tcaacagata   240
gacaacataa gttccatcat atatgatgaa atacaaaagg cacaagagca acaggaacaa   300
aatgagaaaa gcttgctgga gttagatgaa t                                   331
```

<210> SEQ ID NO 38
<211> LENGTH: 110
<212> TYPE: PRT
<213> ORGANISM: Human

<400> SEQUENCE: 38

```
Asn Leu Leu Arg Ala Ile Gln Ala Gln Gln His Leu Leu Arg Leu Ser
1               5                   10                  15

Val Trp Gly Ile Arg Gln Leu Arg Ala Arg Leu Gln Ala Leu Glu Thr
            20                  25                  30

Phe Ile Gln Asn Gln Gln Leu Leu Ser Leu Trp Gly Cys Lys Gly Lys
        35                  40                  45

Leu Ile Cys Tyr Thr Ser Val Lys Trp Asn Thr Ser Trp Gly Gly Asn
    50                  55                  60

Glu Ser Ile Trp Asn Asn Leu Thr Trp Gln Gln Trp Asp Gln Gln Ile
65                  70                  75                  80

Asp Asn Ile Ser Ser Ile Ile Tyr Asp Glu Ile Gln Lys Ala Gln Glu
                85                  90                  95

Gln Gln Glu Gln Asn Glu Lys Ser Leu Leu Glu Leu Asp Glu
            100                 105                 110
```

<210> SEQ ID NO 39
<211> LENGTH: 340
<212> TYPE: DNA
<213> ORGANISM: Human

<400> SEQUENCE: 39

```
aacctgctaa gagcaataca ggcccagcaa gagctgctga ggctatctgt atggggtatc    60
agacaactcc gagctcgcct gctagcctta gaaacctttta tacggaatca gcaactccta   120
aacctctggg gctgtaaggg aaggctaatt tgctatacat cagtacaatg gaacaaaaca   180
tggggtaatt tgamwgataa tgagtcaatt tgggatgaca tracatggca ggagtgggat   240
aagcgggtag akaatgtaag ygccaccata tttgaagaaa tacgaagggc acaagaacaa   300
caggaacaaa atgagaaggc tttgctagaa ttagatgaat                         340
```

<210> SEQ ID NO 40
<211> LENGTH: 113
<212> TYPE: PRT
<213> ORGANISM: Human
<220> FEATURE:
<221> NAME/KEY: Misc_feature
<222> LOCATION: (1)..(113)
<223> OTHER INFORMATION: Xaa = unknown

<400> SEQUENCE: 40

```
Asn Leu Leu Arg Ala Ile Gln Ala Gln Gln Glu Leu Leu Arg Leu Ser
1               5                   10                  15

Val Trp Gly Ile Arg Gln Leu Arg Ala Arg Leu Leu Ala Leu Glu Thr
            20                  25                  30

Phe Ile Arg Asn Gln Gln Leu Leu Asn Leu Trp Gly Cys Lys Gly Arg
        35                  40                  45

Leu Ile Cys Tyr Thr Ser Val Gln Trp Asn Lys Thr Trp Gly Asn Leu
    50                  55                  60

Xaa Asp Asn Glu Ser Ile Trp Asp Asp Xaa Thr Trp Gln Glu Trp Asp
65                  70                  75                  80

Lys Arg Val Xaa Asn Val Xaa Ala Thr Ile Phe Glu Glu Ile Arg Arg
                85                  90                  95
```

Ala Gln Glu Gln Gln Glu Gln Asn Glu Lys Ala Leu Leu Glu Leu Asp
            100                 105                 110

Glu

<210> SEQ ID NO 41
<211> LENGTH: 315
<212> TYPE: DNA
<213> ORGANISM: Human

<400> SEQUENCE: 41
taagattatg ggaaaaaata tctcggacag tgcagaaaat atcatagtga ccctaaattc    60
tactgtaaac ataacctgtg agagaccagg gaatcagtca gtacaagaga taaaaatagg   120
tccaatggcc tggtacagca ttggcatagg gacaacaccc gcaaactggt caaggatagc   180
ttattgccag tataatatca ctgattggga aaaagcctta aaacaaacag ctgaaaggta   240
cttagaactt gtaaaccata caagaaatga tactgttagc ataacattca atagcagcac   300
tggtggagat ctaga                                                    315

<210> SEQ ID NO 42
<211> LENGTH: 103
<212> TYPE: PRT
<213> ORGANISM: Human

<400> SEQUENCE: 42

Ile Met Gly Lys Asn Ile Ser Asp Ser Ala Glu Asn Ile Ile Val Thr
1               5                   10                  15

Leu Asn Ser Thr Val Asn Ile Thr Cys Glu Arg Pro Gly Asn Gln Ser
            20                  25                  30

Val Gln Glu Ile Lys Ile Gly Pro Met Ala Trp Tyr Ser Ile Gly Ile
        35                  40                  45

Gly Thr Thr Pro Ala Asn Trp Ser Arg Ile Ala Tyr Cys Gln Tyr Asn
    50                  55                  60

Ile Thr Asp Trp Glu Lys Ala Leu Lys Gln Thr Ala Glu Arg Tyr Leu
65                  70                  75                  80

Glu Leu Val Asn His Thr Arg Asn Asp Thr Val Ser Ile Thr Phe Asn
                85                  90                  95

Ser Ser Thr Gly Gly Asp Leu
            100

<210> SEQ ID NO 43
<211> LENGTH: 327
<212> TYPE: DNA
<213> ORGANISM: Human

<400> SEQUENCE: 43
attataggaa aaaacatttc ggacagtggg aaaaatatca tagtgaccct aaatcctact    60
gtaaacctga cttgtgagag accaggaaat aattcaatac aacagatgaa ataggtcca   120 ctggcctggt acagcatggg cctagagaga acaaaagct caatctctag attagcttat   180
tgcaggtata ataccactac gtgggaacaa gccttacaac aaacagctga aggtatcta   240 gaacttgtga caacacgga caatattaca ataatgttca atcgcagcac tgatggagat   300
tcagaggtaa cccatatgca tttaac                                        327

<210> SEQ ID NO 44
<211> LENGTH: 109
<212> TYPE: PRT

<213> ORGANISM: Human

<400> SEQUENCE: 44

| Ile | Ile | Gly | Lys | Asn | Ile | Ser | Asp | Ser | Gly | Lys | Asn | Ile | Ile | Val | Thr |
| 1 | | | | 5 | | | | | 10 | | | | | 15 | |
| Leu | Asn | Pro | Thr | Val | Asn | Leu | Thr | Cys | Glu | Arg | Pro | Gly | Asn | Asn | Ser |
| | | | 20 | | | | | 25 | | | | | 30 | | |
| Ile | Gln | Gln | Met | Lys | Ile | Gly | Pro | Leu | Ala | Trp | Tyr | Ser | Met | Gly | Leu |
| | | | 35 | | | | 40 | | | | | 45 | | | |
| Glu | Arg | Asn | Lys | Ser | Ser | Ile | Ser | Arg | Leu | Ala | Tyr | Cys | Arg | Tyr | Asn |
| | | 50 | | | | | 55 | | | | | 60 | | | |
| Thr | Thr | Thr | Trp | Glu | Gln | Ala | Leu | Gln | Gln | Thr | Ala | Glu | Arg | Tyr | Leu |
| 65 | | | | | 70 | | | | | 75 | | | | | 80 |
| Glu | Leu | Val | Asn | Asn | Thr | Asp | Asn | Ile | Thr | Ile | Met | Phe | Asn | Arg | Ser |
| | | | | 85 | | | | | 90 | | | | | 95 | |
| Thr | Asp | Gly | Asp | Ser | Glu | Val | Thr | His | Met | His | Phe | Asn | | | |
| | | | 100 | | | | | 105 | | | | | | | |

<210> SEQ ID NO 45
<211> LENGTH: 356
<212> TYPE: DNA
<213> ORGANISM: Human

<400> SEQUENCE: 45

```
ataagaatta tgggaaaaaa tatctcgaac agtgcagtaa atatcatagt gaccctgaat      60
tctactgtaa acataacctg tgtgagacca tggaatcaga cagtacaaga gatacaaaca    120
ggtccaatgg cctggtatag cattcacttg aggacaccac tcgcaaactt gtcaaggata    180
gcttattgca agtataatgc cgctgattgg gaaaaagcct aaaacaaac agctgaaagg     240
tacttagaac ttgtaaataa tacaagtaat aataatgtta ccataatatt caataacagc    300
actggtggag atccagagac aacccagtta cattttaact gtcatggagt tcttta       356
```

<210> SEQ ID NO 46
<211> LENGTH: 116
<212> TYPE: PRT
<213> ORGANISM: Human

<400> SEQUENCE: 46

| Ile | Met | Gly | Lys | Asn | Ile | Ser | Asn | Ser | Ala | Val | Asn | Ile | Ile | Val | Thr |
| 1 | | | | 5 | | | | | 10 | | | | | 15 | |
| Leu | Asn | Ser | Thr | Val | Asn | Ile | Thr | Cys | Val | Arg | Pro | Trp | Asn | Gln | Thr |
| | | | 20 | | | | | 25 | | | | | 30 | | |
| Val | Gln | Glu | Ile | Gln | Thr | Gly | Pro | Met | Ala | Trp | Tyr | Ser | Ile | His | Leu |
| | | | 35 | | | | 40 | | | | | 45 | | | |
| Arg | Thr | Pro | Leu | Ala | Asn | Leu | Ser | Arg | Ile | Ala | Tyr | Cys | Lys | Tyr | Asn |
| | | 50 | | | | | 55 | | | | | 60 | | | |
| Ala | Ala | Asp | Trp | Glu | Lys | Ala | Leu | Lys | Gln | Thr | Ala | Glu | Arg | Tyr | Leu |
| 65 | | | | | 70 | | | | | 75 | | | | | 80 |
| Glu | Leu | Val | Asn | Asn | Thr | Ser | Asn | Asn | Val | Thr | Ile | Ile | Phe | Asn | |
| | | | | 85 | | | | | 90 | | | | | 95 | |
| Asn | Ser | Thr | Gly | Gly | Asp | Pro | Glu | Thr | Thr | Gln | Leu | His | Phe | Asn | Cys |
| | | | 100 | | | | | 105 | | | | | 110 | | |
| His | Gly | Val | Leu | | | | | | | | | | | | |
| | | | 115 | | | | | | | | | | | | |

<210> SEQ ID NO 47

```
<211> LENGTH: 317
<212> TYPE: DNA
<213> ORGANISM: Human

<400> SEQUENCE: 47
ataagactga tggcaaaaaa tatttcggct actggccaaa atatcatagt gaccctaaat    60
actactataa acatgacctg ccagagacca ggaaatctaa caatacagga ataaagata   120
ggtccaatgt cctggtacag catgggcata ggcaggaag accactctaa gtcaagaaac   180
gcttattgtg agtataatat cactgattgg gtacaggcct taaaacagac agctgaaagg   240
tatttagaat tagtaaacaa tacaaatact aatataaaca tgacattcga aacagtact   300
ggaggagatc cagaggt                                                  317

<210> SEQ ID NO 48
<211> LENGTH: 103
<212> TYPE: PRT
<213> ORGANISM: Human

<400> SEQUENCE: 48

Leu Met Ala Lys Asn Ile Ser Ala Thr Gly Gln Asn Ile Ile Val Thr
 1               5                  10                  15

Leu Asn Thr Thr Ile Asn Met Thr Cys Gln Arg Pro Gly Asn Leu Thr
                20                  25                  30

Ile Gln Glu Ile Lys Ile Gly Pro Met Ser Trp Tyr Ser Met Gly Ile
            35                  40                  45

Gly Gln Glu Asp His Ser Lys Ser Arg Asn Ala Tyr Cys Glu Tyr Asn
        50                  55                  60

Ile Thr Asp Trp Val Gln Ala Leu Lys Gln Thr Ala Glu Arg Tyr Leu
65                  70                  75                  80

Glu Leu Val Asn Asn Thr Asn Thr Asn Ile Asn Met Thr Phe Glu Asn
                85                  90                  95

Ser Thr Gly Gly Asp Pro Glu
            100

<210> SEQ ID NO 49
<211> LENGTH: 319
<212> TYPE: DNA
<213> ORGANISM: Human

<400> SEQUENCE: 49
taagaataat gggaaaaaat atttcagaca atgggaaaaa tatcatagta accctaaatt    60
ctactctaaa aatgacctgt gagagaccag gaatcatac agtacaacag atgaagatag   120
gtccaatgtc ctggtatagc atgggcttag agaaaaacaa taccagctca agaagagctt   180
tttgcaagta taatgccact aattgggaaa aaaccttaaa acaaatggct gaaaggtatt   240
tagaactcgt aaacaataca agtaataaca cagtgacaat gatattcaat acaagcagtg   300
atggagatcc agaggtacc                                                319

<210> SEQ ID NO 50
<211> LENGTH: 104
<212> TYPE: PRT
<213> ORGANISM: Human

<400> SEQUENCE: 50

Ile Met Gly Lys Asn Ile Ser Asp Asn Gly Lys Asn Ile Ile Val Thr
 1               5                  10                  15

Leu Asn Ser Thr Leu Lys Met Thr Cys Glu Arg Pro Gly Asn His Thr
```

```
                   20                  25                  30
Val Gln Gln Met Lys Ile Gly Pro Met Ser Trp Tyr Ser Met Gly Leu
                35                  40                  45
Glu Lys Asn Asn Thr Ser Ser Arg Arg Ala Phe Cys Lys Tyr Asn Ala
     50                  55                  60
Thr Asn Trp Glu Lys Thr Leu Lys Gln Met Ala Glu Arg Tyr Leu Glu
 65                  70                  75                  80
Leu Val Asn Asn Thr Ser Asn Asn Thr Val Thr Met Ile Phe Asn Thr
                 85                  90                  95
Ser Ser Asp Gly Asp Pro Glu Val
                100
```

```
<210> SEQ ID NO 51
<211> LENGTH: 331
<212> TYPE: DNA
<213> ORGANISM: Human

<400> SEQUENCE: 51
aagaaggatg ggggaaaaca atccttcaga tcggaagaag atcctagtga ccctaaattc    60
ccctataaac ataacctgcg agagaccata ctatcagtca gtacaagagt taaggatagg   120
tccaatggct tggtacagca tgacattaga acgagacagg gcaggcagtg acataagggc   180
agcttattgc aagtataatg cctctgactg gagaaataca ttaaaggag tagctgagag    240 atatttagaa cttagaaatg aggaaggccc ggtgaacgtg accttcaatg gaagtgcggg   300
tggagatcca gagatacgct ttctgcattt t                                  331
```

```
<210> SEQ ID NO 52
<211> LENGTH: 109
<212> TYPE: PRT
<213> ORGANISM: Human

<400> SEQUENCE: 52

Arg Met Gly Glu Asn Asn Pro Ser Asp Arg Lys Lys Ile Leu Val Thr
 1               5                  10                  15
Leu Asn Ser Pro Ile Asn Ile Thr Cys Glu Arg Pro Tyr Tyr Gln Ser
                20                  25                  30
Val Gln Glu Leu Arg Ile Gly Pro Met Ala Trp Tyr Ser Met Thr Leu
                35                  40                  45
Glu Arg Asp Arg Ala Gly Ser Asp Ile Arg Ala Ala Tyr Cys Lys Tyr
     50                  55                  60
Asn Ala Ser Asp Trp Arg Asn Thr Leu Lys Gly Val Ala Glu Arg Tyr
 65                  70                  75                  80
Leu Glu Leu Arg Asn Glu Glu Gly Pro Val Asn Val Thr Phe Asn Gly
                 85                  90                  95
Ser Ala Gly Gly Asp Pro Glu Ile Arg Phe Leu His Phe
                100                 105
```

```
<210> SEQ ID NO 53
<211> LENGTH: 6
<212> TYPE: PRT
<213> ORGANISM: Human
<220> FEATURE:
<221> NAME/KEY: PEPTIDE
<222> LOCATION: (1)..(6)

<400> SEQUENCE: 53

Val Gln Gln Met Lys Ile
 1               5
```

```
<210> SEQ ID NO 54
<211> LENGTH: 11
<212> TYPE: PRT
<213> ORGANISM: Human
<220> FEATURE:
<221> NAME/KEY: PEPTIDE
<222> LOCATION: (1)..(11)

<400> SEQUENCE: 54

Lys Ile Gly Pro Met Ser Trp Tyr Ser Met Gly
1               5                   10

<210> SEQ ID NO 55
<211> LENGTH: 6
<212> TYPE: PRT
<213> ORGANISM: Human
<220> FEATURE:
<221> NAME/KEY: PEPTIDE
<222> LOCATION: (1)..(6)

<400> SEQUENCE: 55

Met Gly Leu Glu Lys Asn
1               5

<210> SEQ ID NO 56
<211> LENGTH: 6
<212> TYPE: PRT
<213> ORGANISM: Human
<220> FEATURE:
<221> NAME/KEY: PEPTIDE
<222> LOCATION: (1)..(6)

<400> SEQUENCE: 56

Ile Gln Gln Met Lys Ile
1               5

<210> SEQ ID NO 57
<211> LENGTH: 11
<212> TYPE: PRT
<213> ORGANISM: Human
<220> FEATURE:
<221> NAME/KEY: PEPTIDE
<222> LOCATION: (1)..(11)

<400> SEQUENCE: 57

Lys Ile Gly Pro Leu Ala Trp Tyr Ser Met Gly
1               5                   10

<210> SEQ ID NO 58
<211> LENGTH: 6
<212> TYPE: PRT
<213> ORGANISM: Human
<220> FEATURE:
<221> NAME/KEY: PEPTIDE
<222> LOCATION: (1)..(6)

<400> SEQUENCE: 58

Met Gly Leu Glu Arg Asn
1               5

<210> SEQ ID NO 59
<211> LENGTH: 8
<212> TYPE: PRT
<213> ORGANISM: Human
<220> FEATURE:
<221> NAME/KEY: PEPTIDE
<222> LOCATION: (1)..(8)
```

<400> SEQUENCE: 59

Gln Ser Val Gln Glu Ile Lys Ile
1               5

<210> SEQ ID NO 60
<211> LENGTH: 11
<212> TYPE: PRT
<213> ORGANISM: Human
<220> FEATURE:
<221> NAME/KEY: PEPTIDE
<222> LOCATION: (1)..(11)

<400> SEQUENCE: 60

Lys Ile Gly Pro Met Ala Trp Tyr Ser Ile Gly
1               5                   10

<210> SEQ ID NO 61
<211> LENGTH: 6
<212> TYPE: PRT
<213> ORGANISM: Human
<220> FEATURE:
<221> NAME/KEY: PEPTIDE
<222> LOCATION: (1)..(6)

<400> SEQUENCE: 61

Ile Gly Ile Gly Thr Thr
1               5

<210> SEQ ID NO 62
<211> LENGTH: 6
<212> TYPE: PRT
<213> ORGANISM: Human
<220> FEATURE:
<221> NAME/KEY: PEPTIDE
<222> LOCATION: (1)..(6)

<400> SEQUENCE: 62

Val Gln Glu Ile Gln Thr
1               5

<210> SEQ ID NO 63
<211> LENGTH: 11
<212> TYPE: PRT
<213> ORGANISM: Human
<220> FEATURE:
<221> NAME/KEY: PEPTIDE
<222> LOCATION: (1)..(11)

<400> SEQUENCE: 63

Gln Thr Gly Pro Met Ala Trp Tyr Ser Ile His
1               5                   10

<210> SEQ ID NO 64
<211> LENGTH: 6
<212> TYPE: PRT
<213> ORGANISM: Human
<220> FEATURE:
<221> NAME/KEY: PEPTIDE
<222> LOCATION: (1)..(6)

<400> SEQUENCE: 64

Ile His Leu Arg Thr Pro
1               5

<210> SEQ ID NO 65
<211> LENGTH: 6

```
<212> TYPE: PRT
<213> ORGANISM: Human
<220> FEATURE:
<221> NAME/KEY: PEPTIDE
<222> LOCATION: (1)..(6)

<400> SEQUENCE: 65

Ile Gln Glu Ile Lys Ile
1               5

<210> SEQ ID NO 66
<211> LENGTH: 11
<212> TYPE: PRT
<213> ORGANISM: Human
<220> FEATURE:
<221> NAME/KEY: PEPTIDE
<222> LOCATION: (1)..(11)

<400> SEQUENCE: 66

Lys Ile Gly Pro Met Ser Trp Tyr Ser Met Gly
1               5                   10

<210> SEQ ID NO 67
<211> LENGTH: 6
<212> TYPE: PRT
<213> ORGANISM: Human
<220> FEATURE:
<221> NAME/KEY: PEPTIDE
<222> LOCATION: (1)..(6)

<400> SEQUENCE: 67

Met Gly Ile Gly Gln Glu
1               5

<210> SEQ ID NO 68
<211> LENGTH: 7
<212> TYPE: PRT
<213> ORGANISM: Human
<220> FEATURE:
<221> NAME/KEY: PEPTIDE
<222> LOCATION: (1)..(7)

<400> SEQUENCE: 68

Ser Val Gln Glu Leu Arg Ile
1               5

<210> SEQ ID NO 69
<211> LENGTH: 11
<212> TYPE: PRT
<213> ORGANISM: Human
<220> FEATURE:
<221> NAME/KEY: PEPTIDE
<222> LOCATION: (1)..(11)

<400> SEQUENCE: 69

Arg Ile Gly Pro Met Ala Trp Tyr Ser Met Thr
1               5                   10

<210> SEQ ID NO 70
<211> LENGTH: 6
<212> TYPE: PRT
<213> ORGANISM: Human
<220> FEATURE:
<221> NAME/KEY: PEPTIDE
<222> LOCATION: (1)..(6)

<400> SEQUENCE: 70

Met Thr Leu Glu Arg Asp
```

<210> SEQ ID NO 71
<211> LENGTH: 17
<212> TYPE: PRT
<213> ORGANISM: Human
<220> FEATURE:
<221> NAME/KEY: PEPTIDE
<222> LOCATION: (1)..(17)

<400> SEQUENCE: 71

Arg Asn Gln Gln Leu Leu Asn Leu Trp Gly Cys Lys Gly Arg Leu Ile
1               5                   10                  15
Cys

<210> SEQ ID NO 72
<211> LENGTH: 15
<212> TYPE: PRT
<213> ORGANISM: Human
<220> FEATURE:
<221> NAME/KEY: PEPTIDE
<222> LOCATION: (1)..(15)

<400> SEQUENCE: 72

Cys Lys Gly Arg Leu Ile Cys Tyr Thr Ser Val Gln Trp Asn Met
1               5                   10                  15

<210> SEQ ID NO 73
<211> LENGTH: 10
<212> TYPE: PRT
<213> ORGANISM: Human
<220> FEATURE:
<221> NAME/KEY: PEPTIDE
<222> LOCATION: (1)..(10)

<400> SEQUENCE: 73

Leu Trp Gly Cys Lys Gly Arg Ile Val Cys
1               5                   10

<210> SEQ ID NO 74
<211> LENGTH: 11
<212> TYPE: PRT
<213> ORGANISM: Human
<220> FEATURE:
<221> NAME/KEY: PEPTIDE
<222> LOCATION: (1)..(11)

<400> SEQUENCE: 74

Ser Leu Trp Gly Cys Lys Gly Lys Leu Ile Cys
1               5                   10

<210> SEQ ID NO 75
<211> LENGTH: 7
<212> TYPE: PRT
<213> ORGANISM: Human
<220> FEATURE:
<221> NAME/KEY: PEPTIDE
<222> LOCATION: (1)..(7)

<400> SEQUENCE: 75

Cys Lys Gly Lys Ser Ile Cys
1               5

<210> SEQ ID NO 76
<211> LENGTH: 7
<212> TYPE: PRT
<213> ORGANISM: Human

```
<220> FEATURE:
<221> NAME/KEY: PEPTIDE
<222> LOCATION: (1)..(7)

<400> SEQUENCE: 76

Cys Lys Gly Lys Ile Val Cys
1               5

<210> SEQ ID NO 77
<211> LENGTH: 7
<212> TYPE: PRT
<213> ORGANISM: Human
<220> FEATURE:
<221> NAME/KEY: PEPTIDE
<222> LOCATION: (1)..(7)

<400> SEQUENCE: 77

Cys Arg Gly Arg Gln Val Cys
1               5

<210> SEQ ID NO 78

<400> SEQUENCE: 78

000

<210> SEQ ID NO 79
<211> LENGTH: 12
<212> TYPE: PRT
<213> ORGANISM: Human
<220> FEATURE:
<221> NAME/KEY: PEPTIDE
<222> LOCATION: (1)..(12)

<400> SEQUENCE: 79

Cys Lys Gly Arg Leu Ile Cys Tyr Thr Ser Val His
1               5                   10

<210> SEQ ID NO 80
<211> LENGTH: 7
<212> TYPE: PRT
<213> ORGANISM: Human
<220> FEATURE:
<221> NAME/KEY: PEPTIDE
<222> LOCATION: (1)..(7)

<400> SEQUENCE: 80

Cys Lys Gly Asn Leu Ile Cys
1               5

<210> SEQ ID NO 81
<211> LENGTH: 7
<212> TYPE: PRT
<213> ORGANISM: Human
<220> FEATURE:
<221> NAME/KEY: PEPTIDE
<222> LOCATION: (1)..(7)

<400> SEQUENCE: 81

Cys Lys Gly Lys Met Ile Cys
1               5

<210> SEQ ID NO 82
<211> LENGTH: 7
<212> TYPE: PRT
<213> ORGANISM: Human
<220> FEATURE:
<221> NAME/KEY: PEPTIDE
```

<222> LOCATION: (1)..(7)

<400> SEQUENCE: 82

Cys Lys Gly Arg Val Val Cys
1               5

<210> SEQ ID NO 83
<211> LENGTH: 37
<212> TYPE: PRT
<213> ORGANISM: Human
<220> FEATURE:
<221> NAME/KEY: PEPTIDE
<222> LOCATION: (1)..(37)

<400> SEQUENCE: 83

Cys Glu Arg Pro Gly Asn Asn Ser Ile Gln Gln Met Lys Ile Gly Pro
1               5                   10                  15

Leu Ala Trp Tyr Ser Met Gly Leu Glu Arg Asn Lys Ser Ser Ile Ser
            20                  25                  30

Arg Leu Ala Tyr Cys
        35

<210> SEQ ID NO 84
<211> LENGTH: 37
<212> TYPE: PRT
<213> ORGANISM: Human
<220> FEATURE:
<221> NAME/KEY: PEPTIDE
<222> LOCATION: (1)..(37)

<400> SEQUENCE: 84

Cys Glu Arg Pro Gly Asn Asn Ser Ile Gln Gln Met Lys Ile Gly Pro
1               5                   10                  15

Met Ala Trp Tyr Ser Met Gly Leu Glu Arg Asn Lys Ser Ser Ile Ser
            20                  25                  30

Arg Leu Ala Tyr Cys
        35

<210> SEQ ID NO 85
<211> LENGTH: 37
<212> TYPE: PRT
<213> ORGANISM: Human
<220> FEATURE:
<221> NAME/KEY: PEPTIDE
<222> LOCATION: (1)..(37)

<400> SEQUENCE: 85

Cys Glu Arg Pro Gly Asn Gln Ser Val Gln Glu Ile Lys Ile Gly Pro
1               5                   10                  15

Met Ala Trp Tyr Ser Ile Gly Ile Gly Thr Thr Pro Ala Asn Trp Ser
            20                  25                  30

Arg Ile Ala Tyr Cys
        35

<210> SEQ ID NO 86
<211> LENGTH: 38
<212> TYPE: PRT
<213> ORGANISM: Human
<220> FEATURE:
<221> NAME/KEY: PEPTIDE
<222> LOCATION: (1)..(38)

<400> SEQUENCE: 86

Cys Glu Arg Pro Gly Asn Gln Ser Val Gln Glu Ile Lys Ile Gly Pro

-continued

```
              1               5              10              15
Met Ala Trp Tyr Ser Ile Gly Ile Gly Thr Thr Pro Thr Tyr Asn Trp
                      20              25              30

Ser Arg Ile Ala Tyr Cys
            35
```

<210> SEQ ID NO 87
<211> LENGTH: 37
<212> TYPE: PRT
<213> ORGANISM: Human
<220> FEATURE:
<221> NAME/KEY: PEPTIDE
<222> LOCATION: (1)..(37)

<400> SEQUENCE: 87

```
Cys Val Arg Pro Trp Asn Gln Thr Val Gln Glu Ile Gln Thr Gly Pro
 1               5                  10                  15

Met Ala Trp Tyr Ser Ile His Leu Arg Thr Pro Leu Ala Asn Leu Ser
                20                  25                  30

Arg Ile Ala Tyr Cys
            35
```

<210> SEQ ID NO 88
<211> LENGTH: 37
<212> TYPE: PRT
<213> ORGANISM: Human
<220> FEATURE:
<221> NAME/KEY: PEPTIDE
<222> LOCATION: (1)..(37)

<400> SEQUENCE: 88

```
Cys Gln Arg Pro Gly Asn Leu Thr Ile Gln Glu Ile Lys Ile Gly Pro
 1               5                  10                  15

Met Ser Trp Tyr Ser Met Gly Ile Gly Gln Glu Asp His Ser Lys Ser
                20                  25                  30

Arg Asn Ala Tyr Cys
            35
```

<210> SEQ ID NO 89
<211> LENGTH: 38
<212> TYPE: PRT
<213> ORGANISM: Human
<220> FEATURE:
<221> NAME/KEY: PEPTIDE
<222> LOCATION: (1)..(38)

<400> SEQUENCE: 89

```
Cys Glu Arg Pro Tyr Tyr Gln Ser Val Gln Glu Leu Arg Ile Gly Pro
 1               5                  10                  15

Met Ala Trp Tyr Ser Met Thr Leu Glu Arg Asp Arg Ala Gly Ser Asp
                20                  25                  30

Ile Arg Ala Ala Tyr Cys
                35
```

<210> SEQ ID NO 90
<211> LENGTH: 36
<212> TYPE: PRT
<213> ORGANISM: Human
<220> FEATURE:
<221> NAME/KEY: PEPTIDE
<222> LOCATION: (1)..(36)

<400> SEQUENCE: 90

Cys Glu Arg Pro Gly Asn His Thr Val Gln Gln Met Lys Ile Gly Pro
1               5                   10                  15

Met Ser Trp Tyr Ser Met Gly Leu Glu Lys Asn Asn Thr Ser Ser Arg
                20                  25                  30

Arg Ala Phe Cys
            35

<210> SEQ ID NO 91
<211> LENGTH: 23
<212> TYPE: PRT
<213> ORGANISM: Human
<220> FEATURE:
<221> NAME/KEY: PEPTIDE
<222> LOCATION: (1)..(23)

<400> SEQUENCE: 91

Asp Gln Gln Leu Leu Asn Leu Trp Gly Cys Lys Gly Arg Ile Val Cys
1               5                   10                  15

Tyr Thr Ser Val Lys Trp Asn
                20

<210> SEQ ID NO 92
<211> LENGTH: 24
<212> TYPE: PRT
<213> ORGANISM: Human
<220> FEATURE:
<221> NAME/KEY: PEPTIDE
<222> LOCATION: (1)..(24)

<400> SEQUENCE: 92

Asn Gln Gln Leu Leu Asn Leu Trp Gly Cys Lys Gly Arg Leu Val Cys
1               5                   10                  15

Tyr Thr Ser Val Lys Trp Asn Lys
                20

<210> SEQ ID NO 93
<211> LENGTH: 23
<212> TYPE: PRT
<213> ORGANISM: Human
<220> FEATURE:
<221> NAME/KEY: PEPTIDE
<222> LOCATION: (1)..(23)

<400> SEQUENCE: 93

Asn Gln Gln Arg Leu Asn Leu Trp Gly Cys Lys Gly Lys Met Ile Cys
1               5                   10                  15

Tyr Thr Ser Val Pro Trp Asn
                20

<210> SEQ ID NO 94
<211> LENGTH: 23
<212> TYPE: PRT
<213> ORGANISM: Human
<220> FEATURE:
<221> NAME/KEY: PEPTIDE
<222> LOCATION: (1)..(23)

<400> SEQUENCE: 94

Asn Gln Gln Leu Leu Asn Leu Trp Gly Cys Lys Gly Lys Ser Ile Cys
1               5                   10                  15

Tyr Thr Ser Val Lys Trp Asn
                20

<210> SEQ ID NO 95

```
<211> LENGTH: 23
<212> TYPE: PRT
<213> ORGANISM: Human
<220> FEATURE:
<221> NAME/KEY: PEPTIDE
<222> LOCATION: (1)..(23)

<400> SEQUENCE: 95

Asn Gln Gln Leu Leu Asn Leu Trp Gly Cys Lys Gly Arg Leu Ile Cys
1               5                   10                  15

Tyr Thr Ser Val Gln Trp Asn
            20

<210> SEQ ID NO 96
<211> LENGTH: 23
<212> TYPE: PRT
<213> ORGANISM: Human
<220> FEATURE:
<221> NAME/KEY: PEPTIDE
<222> LOCATION: (1)..(23)

<400> SEQUENCE: 96

Asn Gln Gln Arg Leu Asn Leu Trp Gly Cys Lys Gly Lys Met Ile Cys
1               5                   10                  15

Tyr Thr Ser Val Lys Trp Asn
            20

<210> SEQ ID NO 97
<211> LENGTH: 23
<212> TYPE: PRT
<213> ORGANISM: Human
<220> FEATURE:
<221> NAME/KEY: PEPTIDE
<222> LOCATION: (1)..(23)

<400> SEQUENCE: 97

Asn Gln Gln Leu Leu Asn Leu Trp Gly Cys Lys Gly Asn Leu Ile Cys
1               5                   10                  15

Tyr Thr Ser Val Lys Trp Asn
            20

<210> SEQ ID NO 98
<211> LENGTH: 23
<212> TYPE: PRT
<213> ORGANISM: Human
<220> FEATURE:
<221> NAME/KEY: PEPTIDE
<222> LOCATION: (1)..(23)

<400> SEQUENCE: 98

Asn Gln Gln Leu Leu Asn Leu Trp Gly Cys Arg Gly Arg Gln Val Cys
1               5                   10                  15

Tyr Thr Ser Val Ile Trp Asn
            20

<210> SEQ ID NO 99
<211> LENGTH: 23
<212> TYPE: PRT
<213> ORGANISM: Human
<220> FEATURE:
<221> NAME/KEY: PEPTIDE
<222> LOCATION: (1)..(23)

<400> SEQUENCE: 99

Ser Gln Gln Leu Leu Asn Leu Trp Gly Cys Lys Gly Arg Leu Ile Cys
1               5                   10                  15
```

Tyr Thr Ser Val His Trp Asn
            20

<210> SEQ ID NO 100
<211> LENGTH: 23
<212> TYPE: PRT
<213> ORGANISM: Human
<220> FEATURE:
<221> NAME/KEY: PEPTIDE
<222> LOCATION: (1)..(23)

<400> SEQUENCE: 100

Asn Gln Gln Leu Leu Asn Leu Trp Gly Cys Lys Gly Arg Ile Val Cys
1               5                   10                  15
Tyr Thr Ser Val Lys Trp Asn
            20

<210> SEQ ID NO 101
<211> LENGTH: 23
<212> TYPE: PRT
<213> ORGANISM: Human
<220> FEATURE:
<221> NAME/KEY: PEPTIDE
<222> LOCATION: (1)..(23)

<400> SEQUENCE: 101

Asn Gln Gln Leu Leu Asn Ser Trp Gly Cys Lys Gly Lys Ile Val Cys
1               5                   10                  15
Tyr Thr Ala Val Lys Trp Asn
            20

<210> SEQ ID NO 102
<211> LENGTH: 23
<212> TYPE: PRT
<213> ORGANISM: Human
<220> FEATURE:
<221> NAME/KEY: PEPTIDE
<222> LOCATION: (1)..(23)

<400> SEQUENCE: 102

Asn Gln Gln Leu Leu Ser Leu Trp Gly Cys Lys Gly Lys Leu Ile Cys
1               5                   10                  15
Tyr Thr Ser Val Lys Trp Asn
            20

<210> SEQ ID NO 103
<211> LENGTH: 1339
<212> TYPE: DNA
<213> ORGANISM: Human

<400> SEQUENCE: 103
attaaagtag taccaagaag aaaggcaaaa ataatcagac attatggaaa acagatggca      60
ggtgctgata gtatggcaag tggacagaca gaaagtgaaa gcgtggaaca gcctggtgaa     120
ataccataag tacaggtcta ggaaggccaa ggactggtgt tacagacacc attttgaatc     180
tagaaatcca agagtcagtt caagtgtaca tattccagta gggatggctt gggtaatagt     240
gaccacatat tgggattga tgccagggga gagagaggaa cagttgggac atggggttag     300
tatagaatgg cagtacaaaa agtatacaac acagattgac cctgaaacag cagacaggat     360
gatacatctg tattatttta cctgttttac agattcagca gtcaggaaag ccatcttagg     420
gcagagaata ctgaccaagt gtgaataccc tgcaggacat agtcaggtag ggacattgca     480

```
actactagct ctaagagtag tagtaaaagc aaaaagaaat aagcctcccc tacccagtgt    540
ccagaaatta acagaagata gatggagcga gcacctgagg atcaggggcc agctagagag    600
cctttcaatg aatgggcact agagatccta gaagagctaa aagcagaggc agtaagacat    660
ttccctaggc agtggctaca ggccttggga cagtacattt atgagactta tggggacact    720
tgggtaggag ttatggcaat tacaagaatc ttacaacaaa tactatttgc ccattttaga    780
attggatgtc aacatagtag aataggaatt aacccaacta atacaagagg aagaggaaga    840
agaaatggat ccagtagatc ctgagatgcc cccttggcat caccctggga gtcagcccca    900
gatcccttgt aacaattgct attgcaaaag atgctgctat cattgccttg tttgtttcac    960
aagaaagggt ttgggatct cctatggcag gaagaagcgg cgacaacgaa gagctgctgc   1020
gagccatccg gataataaag atcttgtacc agagcagtaa gtaacgctaa tgcatcatag   1080
ggacctgcta gtattaataa ttattagtgc tttgctgctt ataaatgtaa ttatatggat   1140
gtttattctt agacaatatt tagaacagaa gaaacaggac agaagggaaa gagacatact   1200
tgaaaggtta agaagaatag cagaaattaa agatgatagt gactatgaaa gcaatgaaga   1260
ggaggaacag gaagttagag atcttataca tagtcatggc tttgataatc ccatgtttga   1320
gctctgatca gaagtatgc                                                1339

<210> SEQ ID NO 104
<211> LENGTH: 1282
<212> TYPE: DNA
<213> ORGANISM: Human

<400> SEQUENCE: 104
attaaagtag taccaagaag aaaggcaaaa ataatcagag attatggaaa acaaatggca     60
ggtactgata gtatggcaag tagacagaca gaaagtgaaa acgtggaaca gcttggtgaa    120
ataccataag tacaggtcta ggaaggccaa ggactggtac tacagacatc attatgaatc    180
tagaaatcca agaatcagtt caggtgtata tattccagta gggccggctt gtatagtagt    240
gaacacatat tggggattga tgccaggaga aagagatgaa catctgggac atggggttag    300
tatagaatgg cagtacaaga agtatacaac acagattgac cctgaaacag cagacaggat    360
gatacatcta tactatttta cctgttttac agaatcagca atcaggaaag ccatcctagg    420
gcagagagta ctgaccaagt gtgaatacccc tgcaggacat agccaggtag ggacactaca    480
actactagct ctaagagttg tagtaaaaga gagaaaacat aggcctcccc tacccagtgt    540
ccagaaatta acagaagata gatggaacaa gcacctgagg atcagggacc agctagagag    600
ccattcaatg aatgggacact agagctccta gaagagctaa aagcagaagc agtaagacat    660
tttcctaggc cttggctaca ggccttggga caatacattt atgatactta tggggacact    720
tgggtaggag ttatggcaat tataagactc ttacaattaa tgatatttgc ccattttaga    780
agaaatggat ccagtagacc ctgagatgcc cccttggcat caccctggaa gtcagcccca    840
gaatccttgt aataaatgct attgcaaaaa atgctgctat cattgctatg tttgtttcac    900
aagcaagggt ttggaatct cctatggcag gaagaagcga cgacgaccag cagctgctgc    960
aagccgcccg gataataaag atcttgtacc agagcagtaa gtaacgctaa tgcagcaaaa   1020
ggacctgcta ttattagtaa ttattagtgc tttgctgctt ataaatataa ttctatggat   1080
gtttaatctt agaaaatatt tagaacaaaa gaaacaagac agaagggaaa gagaaatact   1140
tgaaggata agaagaataa gagaaattag agatgatagt gactatgaaa gcaatgaaga   1200
ggaagaacaa gaagttaggg gtcatcttgt gcatatgttt ggctttgcta atcccgtgtt   1260
```
tgagatctaa tgacctatat gc            1282

<210> SEQ ID NO 105
<211> LENGTH: 1339
<212> TYPE: DNA
<213> ORGANISM: Human

<400> SEQUENCE: 105

| | | | | | |
|---|---|---|---|---|---|
| atcaaggtag | taccaagaag | aaaagcaaaa | atactcaggg | attatggaaa | acagatggca | 60 |
| ggtgctgata | gtatggcaag | tggacagaca | gaaagtgaaa | gcatggaata | gcctggtaaa | 120 |
| ataccataag | tacaggtcta | gaaagaccca | gaactgggat | tatagacatc | attatgaaat | 180 |
| cagaaatcca | agaatcagct | caggtgtata | tattccagta | ggtgaagcta | agatagtagt | 240 |
| gactacatat | tggggattaa | tgccagggga | aagagatgag | catttgggac | atggagtcag | 300 |
| tatagaatgg | caatacaaaa | attatagtac | acagattgac | cctgaaacag | cagataaaat | 360 |
| aatacatctg | cattatttca | cctgttttac | agagtcagca | atcaggagag | ccattttagg | 420 |
| gcagagagtg | ctgaccaggt | gtgaataccc | tgcaggacta | gtcaggtag | ggacactgca | 480 |
| actcctagca | ttaagagcag | tagtaaaaga | caaagaagt | aaacctcccc | tacccagtgt | 540 |
| ccagaagtta | acaggagaca | gatggaacag | gcacctgaga | atcagggacc | agcaagagag | 600 |
| ccattcaatg | aatgggcatt | agagaccctg | gaagaaataa | aagcagaagc | agtaagacac | 660 |
| tttcctaggc | cttggctaca | aagcttagga | caatacatct | atgagactta | tggagacacc | 720 |
| tgggaaggag | ttatggcaat | cataagaatc | ttacaacagt | tgatatttgc | ccattttaga | 780 |
| attggatgcc | aacatagtag | aataggaatt | accccatcta | acgcaagagg | aagaggaaga | 840 |
| agaaatggat | ccagtagatc | ctgaggtgcc | ccctggcat | caccctggaa | gtcagccccc | 900 |
| aaccccttgc | aacgcttgct | attgcaaaag | atgctgttat | cattgctatc | tttgtttcac | 960 |
| aaagaagggt | ttgggaatct | cccatggcag | gaagaagcga | cgacgaccag | cagctgctgc | 1020 |
| aagctcttcg | aataataaag | atcttgtacc | agagcagtaa | gtaaagctaa | tgcatcataa | 1080 |
| ggacttgcta | atcttaatag | ttgctagtat | tttgcttttt | acaaatatag | tgatatggac | 1140 |
| atttattctt | aagaaatatt | tagagcagaa | ggaacaagat | agaagggaaa | gagaactact | 1200 |
| gaaaagaata | aaaagaataa | gagaagtcag | ggatgatagt | gattatgaaa | gcaatggaga | 1260 |
| tggaggacaa | gaagttatac | atcttgtgca | tactcatggt | tttgttaacc | ccatgtttga | 1320 |
| gctctgacaa | gctatatcg | | | | | 1339 |

<210> SEQ ID NO 106
<211> LENGTH: 3600
<212> TYPE: DNA
<213> ORGANISM: Human

<400> SEQUENCE: 106

| | | | | | |
|---|---|---|---|---|---|
| ttcacaattt | taaagaaaa | gggggattg | ggggtacag | tgcagggaa | agaataatag | 60 |
| acataatagc | atcagatata | caaactaaag | aactacaaaa | acaaattaca | aaattcaaa | 120 |
| attttcgggt | ttattacagg | gacagcagag | atccaatttg | gaaggacca | gcaaaactac | 180 |
| tctggaaagg | tgaaggggca | gtagtaatac | aggacaatag | tgatataaag | gtagtaccaa | 240 |
| gaagaaaagc | aaaaatcatt | aaggattatg | gaaaacagat | ggcaggtgat | gattgtgtgg | 300 |
| caagtagaca | gaatgaggat | tagaacatgg | aacagtctag | taaagcatca | tatgtatatt | 360 |
| tctaagaaag | ctacagattg | ggtttataaa | catcactatg | atagtagaca | tccaaaagta | 420 |

-continued

```
agctcagaag tacacattcc actaggggat gctaaattgg taataagaac atattggggt    480
ctacatacag gagaaagaga ctggcatttg ggtcatgggg tctccataga atggaaacag    540
agaagatata gcacacaaat agatcctgac ctagcagacc aactgattca cctgcattat    600
tttaactgtt tttcagaatc tgccataaga aaagccatac taggacaagt agttagacct    660
aggtgtgatt atccagcagg acatagtaag gtaggatctc tacaatattt ggcactgaaa    720
gcattagtaa caccaacaag gacaaagcca cctttgccta gtgttaagaa attaacagaa    780
gacagatgga acaagcccca gaagaccagg ggcacagag ggagcggtcc aatgtatgga     840
cattagatct attagaggag cttaaacatg aagctgttag acattttcct aggccttggc    900
tccagggatt aggacaatat atctatgaaa catatgggga tacctgggaa ggagttgaag    960
ctataataag aattttgcaa caactactgt ttgcccattt tagaattgga tgccaacata   1020
gtaggatagg aattaaccca tctaacccaa gaggaaaagg aagaagaaat ggatccagta   1080
gatcctgaga tacccccttg gcatcaccct ggaagtcagc cccagacccc ttgtaataac   1140
tgctcttgca aaaaatgctg ctaccattgc tatgtgtgtt tcacaagaaa gggtttggaa   1200
atctcctatg gcaggaagaa gcgacgaaga tcagccgctg aaacgcgtca tccagataat   1260
caagatattg taccagagca gtaagtaacg ctaatgcagc ttagggacca gctaacatta   1320
ataattatta gtgctttgtt gcttgtaaat gtagttctat ggacatttat tcttagacaa   1380
tatttaaagc aaaagaaaca agatagaagg ggaagagaaa tacttgaaag gttaagaaga   1440
ataagacaaa ttgaagatga cagtgactat gaaagcgatg gaaaagagga acaggaagtt   1500
agggatcttg tgcatagtta tggctttgat aaccccatgt ttgagccatg accaacgcta   1560
tgcaacagtg tatgctgggg tacctgtatg ggaagaggca aacccagtat tattttgtgc   1620
ttcagatgct aacctaacaa gcactgagaa gcataatatc tgggcatcac aagcctgtgt   1680
tcccacagac cccactccac atgaatatcc tttacacaat gtgacagata actttaatat   1740
atggaaaaat tacatggtag aacaaatgca ggatgacatt attagcttat gggaacagag   1800
tttaaaacct tgtgttcaaa tgactttcct gtgtgtacaa atgaattgta caagtgtaag   1860
taatagtagt gtaagtaata gtagtgtaag taatagtagt gtaagtaata gtagtgtaag   1920
tgatagtact atacccaaga agaaaaataa cagcagctca gaggaccttc tgaaacagtg   1980
tgattttaat gcaaccacag ttctcaaaga caaaaggag aaaaaacaga ctctatttta    2040
tgtatcagat ttgatgaaac tgacaaatgt cacaaatgac acaatgtata cattaattaa   2100
ttgtaactcc acaaccatta agcaagcctg tccaaaggta acttttgagc caattccaat   2160
acactattgt gctccagcgg ggtatgccat ctttaagtgt aacaacacag agtttaatgg   2220
aacgggccca tgcaacaaca ttacagtagt tacttgtaca catggtatca ggccaacagt   2280
gagtacgcaa ctaatattaa acgggacact ctctgaagga aaataagaa ttatgggaag    2340 aaatatcacg gacagtggaa aaaatattat agttacccta aattatacta taaacataac   2400
ttgtgagaga acatggaatc agtcagtaca agagatacct ataggtccaa tggcctggta   2460
cagcatgagc gtagagaaag acaaaaacac aactggctcg aggtcagcag attgccagta   2520
taacacctct gaatggacaa gagccttaga acaaacagct gaaaggtatt tagaactgat   2580
gaacaataca ggtaatactg ataatactac agtgatattc aatcatagca ctggtggaga   2640
tccagaggta tccttcctac atttaattg tcatggagag ttcttctatt gtaacacatc    2700
tgggatgttt aattatacct tttcatgtaa aggaactaac tgtacccaag ttggttccca   2760
aaatgaatat aataatcata caaccaagat accttgcagg ataaaacagg tggtaaggtc   2820
```

-continued

```
atggataagg ggagggtcgg gactctatgc acctcccagg caaggtcccc taaaatgtag      2880
ctcaaacata actggaatga ttctacaatt ggataagcca tggaacagaa gtgggcacaa      2940
caatgacacc acatttagac caataggagg agaaatgaaa gatatatgga gaactgaatt      3000
gttcaaatac aaagtagtaa aagtaaaacc ttttagtgtg gcacctacaa aaattgcaag      3060
gccagtcata ggcacgggca ctcaaagaga aagagagca gtaggattgg gaatgctatt      3120
cttaggggtt ctaagtgcag caggtagcac tatgggcgca gcggcaacaa cgctggcggt      3180
acagacccac actttgatga agggtatagt gcaacagcag acaacctgc taagagcaat      3240 acaggcccag cagcaattgc tgaggctatc tgtatggggt atcagacaac tccgagctcg      3300
cctgctagca ttagaaacct aatacagaa tcagcaactc ctgaacctat ggggctgtaa      3360
gggaaggcta gtctgctaca catcagtaca atggaacagg acatggacaa acaatactaa      3420
tttagattca atttgggaaa atctaacatg gcaggaatgg gatcagcaga taagcaacat      3480
aagctccacc atatatgagg aaatacaaaa ggcacaaata cagcaggaat acaatgagaa      3540
aaagttgcta gagttagatg aatgggcttc tatttggaat tggcttgaca taactaaatg      3600
```

<210> SEQ ID NO 107
<211> LENGTH: 192
<212> TYPE: PRT
<213> ORGANISM: Human

<400> SEQUENCE: 107

```
Met Glu Asn Arg Trp Gln Val Leu Ile Val Trp Gln Val Asp Arg Gln
 1               5                  10                  15

Lys Val Lys Ala Trp Asn Ser Leu Val Lys Tyr His Lys Tyr Arg Ser
            20                  25                  30

Arg Lys Ala Lys Asp Trp Cys Tyr Arg His His Phe Glu Ser Arg Asn
        35                  40                  45

Pro Arg Val Ser Ser Val His Ile Pro Val Gly Met Ala Trp Val
    50                  55                  60

Ile Val Thr Thr Tyr Trp Gly Leu Met Pro Gly Glu Arg Glu Glu Gln
65                  70                  75                  80

Leu Gly His Gly Val Ser Ile Glu Trp Gln Tyr Lys Lys Tyr Thr Thr
                85                  90                  95

Gln Ile Asp Pro Glu Thr Ala Asp Arg Met Ile His Leu Tyr Tyr Phe
            100                 105                 110

Thr Cys Phe Thr Asp Ser Ala Val Arg Lys Ala Ile Leu Gly Gln Arg
        115                 120                 125

Ile Leu Thr Lys Cys Glu Tyr Pro Ala Gly His Ser Gln Val Gly Thr
    130                 135                 140

Leu Gln Leu Leu Ala Leu Arg Val Val Lys Ala Lys Arg Asn Lys
145                 150                 155                 160

Pro Pro Leu Pro Ser Val Gln Lys Leu Thr Glu Asp Arg Trp Ser Glu
                165                 170                 175

His Leu Arg Ile Arg Gly Gln Leu Glu Ser Leu Ser Met Asn Gly His
            180                 185                 190
```

<210> SEQ ID NO 108
<211> LENGTH: 192
<212> TYPE: PRT
<213> ORGANISM: Human

<400> SEQUENCE: 108

```
Met Glu Asn Lys Trp Gln Val Leu Ile Val Trp Gln Val Asp Arg Gln
1               5                   10                  15

Lys Val Lys Thr Trp Asn Ser Leu Val Lys Tyr His Lys Tyr Arg Ser
            20                  25                  30

Arg Lys Ala Lys Asp Trp Tyr Tyr Arg His His Tyr Glu Ser Arg Asn
            35                  40                  45

Pro Arg Ile Ser Ser Gly Val Tyr Ile Pro Val Gly Pro Ala Cys Ile
        50                  55                  60

Val Val Asn Thr Tyr Trp Gly Leu Met Pro Gly Arg Asp Glu His
65                  70                  75                  80

Leu Gly His Gly Val Ser Ile Glu Trp Gln Tyr Lys Lys Tyr Thr Thr
                85                  90                  95

Gln Ile Asp Pro Glu Thr Ala Asp Arg Met Ile His Leu Tyr Tyr Phe
                100                 105                 110

Thr Cys Phe Thr Glu Ser Ala Ile Arg Lys Ala Ile Leu Gly Gln Arg
            115                 120                 125

Val Leu Thr Lys Cys Glu Tyr Pro Ala Gly His Ser Gln Val Gly Thr
    130                 135                 140

Leu Gln Leu Leu Ala Leu Arg Val Val Lys Glu Arg Lys His Arg
145                 150                 155                 160

Pro Pro Leu Pro Ser Val Gln Lys Leu Thr Glu Asp Arg Trp Asn Lys
                165                 170                 175

His Leu Arg Ile Arg Asp Gln Leu Glu Ser His Ser Met Asn Gly His
                180                 185                 190
```

<210> SEQ ID NO 109
<211> LENGTH: 192
<212> TYPE: PRT
<213> ORGANISM: Human

<400> SEQUENCE: 109

```
Met Glu Asn Arg Trp Gln Val Leu Ile Val Trp Gln Val Asp Arg Gln
1               5                   10                  15

Lys Val Lys Ala Trp Asn Ser Leu Val Lys Tyr His Lys Tyr Arg Ser
            20                  25                  30

Arg Lys Thr Gln Asn Trp Asp Tyr Arg His His Tyr Glu Ile Arg Asn
            35                  40                  45

Pro Arg Ile Ser Ser Gly Val Tyr Ile Pro Val Gly Glu Ala Lys Ile
        50                  55                  60

Val Val Thr Thr Tyr Trp Gly Leu Met Pro Gly Arg Asp Glu His
65                  70                  75                  80

Leu Gly His Gly Val Ser Ile Glu Trp Gln Tyr Lys Asn Tyr Ser Thr
                85                  90                  95

Gln Ile Asp Pro Glu Thr Ala Asp Lys Ile Ile His Leu His Tyr Phe
                100                 105                 110

Thr Cys Phe Thr Glu Ser Ala Ile Arg Arg Ala Ile Leu Gly Gln Arg
            115                 120                 125

Val Leu Thr Arg Cys Glu Tyr Pro Ala Gly His Ser Gln Val Gly Thr
    130                 135                 140

Leu Gln Leu Leu Ala Leu Arg Ala Val Val Lys Asp Lys Arg Ser Lys
145                 150                 155                 160

Pro Pro Leu Pro Ser Val Gln Lys Leu Thr Gly Asp Arg Trp Asn Arg
                165                 170                 175

His Leu Arg Ile Arg Asp Gln Gln Glu Ser His Ser Met Asn Gly His
                180                 185                 190
```

<210> SEQ ID NO 110
<211> LENGTH: 192
<212> TYPE: PRT
<213> ORGANISM: Human

<400> SEQUENCE: 110

Met Glu Asn Arg Trp Gln Val Met Ile Val Trp Gln Val Asp Arg Met
1               5                   10                  15

Arg Ile Arg Thr Trp Asn Ser Leu Val Lys His His Met Tyr Ile Ser
            20                  25                  30

Lys Lys Ala Thr Asp Trp Val Tyr Lys His His Tyr Asp Ser Arg His
        35                  40                  45

Pro Lys Val Ser Ser Glu Val His Ile Pro Leu Gly Asp Ala Lys Leu
    50                  55                  60

Val Ile Arg Thr Tyr Trp Gly Leu His Thr Gly Glu Arg Asp Trp His
65                  70                  75                  80

Leu Gly His Gly Val Ser Ile Glu Trp Lys Gln Arg Arg Tyr Ser Thr
                85                  90                  95

Gln Ile Asp Pro Asp Leu Ala Asp Gln Leu Ile His Leu His Tyr Phe
            100                 105                 110

Asn Cys Phe Ser Glu Ser Ala Ile Arg Lys Ala Ile Leu Gly Gln Val
        115                 120                 125

Val Arg Pro Arg Cys Asp Tyr Pro Ala Gly His Ser Lys Val Gly Ser
    130                 135                 140

Leu Gln Tyr Leu Ala Leu Lys Ala Leu Val Thr Pro Thr Arg Thr Lys
145                 150                 155                 160

Pro Pro Leu Pro Ser Val Lys Lys Leu Thr Glu Asp Arg Trp Asn Lys
                165                 170                 175

Pro Gln Lys Thr Arg Gly His Arg Gly Ser Gly Pro Met Tyr Gly His
            180                 185                 190

<210> SEQ ID NO 111
<211> LENGTH: 85
<212> TYPE: PRT
<213> ORGANISM: Human

<400> SEQUENCE: 111

Met His His Arg Asp Leu Leu Val Leu Ile Ile Ser Ala Leu Leu
1               5                   10                  15

Leu Ile Asn Val Ile Ile Trp Met Phe Ile Leu Arg Gln Tyr Leu Glu
            20                  25                  30

Gln Lys Lys Gln Asp Arg Arg Glu Arg Asp Ile Leu Glu Arg Leu Arg
        35                  40                  45

Arg Ile Ala Glu Ile Lys Asp Asp Ser Asp Tyr Glu Ser Asn Glu Glu
    50                  55                  60

Glu Glu Gln Glu Val Arg Asp Leu Ile His Ser His Gly Phe Asp Asn
65                  70                  75                  80

Pro Met Phe Glu Leu
                85

<210> SEQ ID NO 112
<211> LENGTH: 86
<212> TYPE: PRT
<213> ORGANISM: Human

<400> SEQUENCE: 112

-continued

Met Gln Gln Lys Asp Leu Leu Leu Val Ile Ile Ser Ala Leu Leu
1               5                   10                  15

Leu Ile Asn Ile Ile Leu Trp Met Phe Asn Leu Arg Lys Tyr Leu Glu
            20                  25                  30

Gln Lys Lys Gln Asp Arg Arg Glu Arg Glu Ile Leu Glu Arg Ile Arg
        35                  40                  45

Arg Ile Arg Glu Ile Arg Asp Asp Ser Asp Tyr Glu Ser Asn Glu Glu
    50                  55                  60

Glu Glu Gln Glu Val Arg Gly His Leu Val His Met Phe Gly Phe Ala
65                  70                  75                  80

Asn Pro Val Phe Glu Ile
                85

<210> SEQ ID NO 113
<211> LENGTH: 85
<212> TYPE: PRT
<213> ORGANISM: Human

<400> SEQUENCE: 113

Met His His Lys Asp Leu Leu Ile Leu Ile Val Ala Ser Ile Leu Leu
1               5                   10                  15

Phe Thr Asn Ile Val Ile Trp Thr Phe Ile Leu Lys Lys Tyr Leu Glu
            20                  25                  30

Gln Lys Glu Gln Asp Arg Arg Glu Arg Glu Leu Leu Lys Arg Ile Lys
        35                  40                  45

Arg Ile Arg Glu Val Arg Asp Asp Ser Asp Tyr Glu Ser Asn Gly Asp
    50                  55                  60

Gly Gly Gln Glu Val Ile His Leu Val His Thr His Gly Phe Val Asn
65                  70                  75                  80

Pro Met Phe Glu Leu
                85

<210> SEQ ID NO 114
<211> LENGTH: 85
<212> TYPE: PRT
<213> ORGANISM: Human

<400> SEQUENCE: 114

Met Gln Leu Arg Asp Gln Leu Thr Leu Ile Ile Ser Ala Leu Leu
1               5                   10                  15

Leu Val Asn Val Val Leu Trp Thr Phe Ile Leu Arg Gln Tyr Leu Lys
            20                  25                  30

Gln Lys Lys Gln Asp Arg Arg Gly Arg Glu Ile Leu Glu Arg Leu Arg
        35                  40                  45

Arg Ile Arg Gln Ile Glu Asp Asp Ser Asp Tyr Glu Ser Asp Gly Lys
    50                  55                  60

Glu Glu Gln Glu Val Arg Asp Leu Val His Ser Tyr Gly Phe Asp Asn
65                  70                  75                  80

Pro Met Phe Glu Pro
                85

<210> SEQ ID NO 115
<211> LENGTH: 100
<212> TYPE: PRT
<213> ORGANISM: Human

<400> SEQUENCE: 115

Met Glu Arg Ala Pro Glu Asp Gln Gly Pro Ala Arg Glu Pro Phe Asn

```
  1               5                   10                  15
Glu Trp Ala Leu Glu Ile Leu Glu Glu Leu Lys Ala Glu Ala Val Arg
                20                  25                  30

His Phe Pro Arg Gln Trp Leu Gln Ala Leu Gly Gln Tyr Ile Tyr Glu
                35                  40                  45

Thr Tyr Gly Asp Thr Trp Val Gly Val Met Ala Ile Thr Arg Ile Leu
            50                  55                  60

Gln Gln Ile Leu Phe Ala His Phe Arg Ile Gly Cys Gln His Ser Arg
 65                  70                  75                  80

Ile Gly Ile Asn Pro Thr Asn Thr Arg Gly Arg Gly Arg Asn Gly
                    85                  90                  95

Ser Ser Arg Ser
            100

<210> SEQ ID NO 116
<211> LENGTH: 100
<212> TYPE: PRT
<213> ORGANISM: Human

<400> SEQUENCE: 116

Met Glu Gln Ala Pro Glu Asp Gln Gly Pro Ala Arg Glu Pro Phe Asn
 1               5                  10                  15

Glu Trp Thr Leu Glu Leu Leu Glu Glu Leu Lys Ala Glu Ala Val Arg
                20                  25                  30

His Phe Pro Arg Pro Trp Leu Gln Ala Leu Gly Gln Tyr Ile Tyr Asp
                35                  40                  45

Thr Tyr Gly Asp Thr Trp Val Gly Val Met Ala Ile Ile Arg Leu Leu
            50                  55                  60

Gln Leu Met Ile Phe Ala His Phe Arg Ile Gly Cys Gln His Ser Arg
 65                  70                  75                  80

Ile Gly Ile Asn Pro Ser Asn Thr Arg Gly Arg Gly Arg Arg Asn Gly
                    85                  90                  95

Ser Ser Arg Pro
            100

<210> SEQ ID NO 117
<211> LENGTH: 93
<212> TYPE: PRT
<213> ORGANISM: Human

<400> SEQUENCE: 117

Met Glu Gln Ala Pro Glu Asn Gln Gly Pro Ala Arg Glu Pro Phe Asn
 1               5                  10                  15

Glu Trp Ala Leu Glu Thr Leu Glu Glu Ile Lys Ala Glu Ala Val Arg
                20                  25                  30

His Phe Pro Arg Pro Trp Leu Gln Ser Leu Gly Gln Tyr Ile Tyr Glu
                35                  40                  45

Thr Tyr Gly Asp Thr Trp Glu Gly Val Met Ala Ile Ile Arg Ile Leu
            50                  55                  60

Gln Gln Leu Ile Phe Ala His Phe Arg Ile Gly Cys Gln His Ser Arg
 65                  70                  75                  80

Ile Gly Ile Thr Pro Ser Asn Ala Arg Gly Arg Gly Arg
                    85                  90

<210> SEQ ID NO 118
<211> LENGTH: 100
<212> TYPE: PRT
```

```
<213> ORGANISM: Human

<400> SEQUENCE: 118

Met Gln Ala Pro Glu Asp Gln Gly Ala Gln Arg Glu Arg Ser Asn
1               5                   10                  15

Val Trp Thr Leu Asp Leu Leu Glu Glu Leu Lys His Glu Ala Val Arg
            20                  25                  30

His Phe Pro Arg Pro Trp Leu Gln Gly Leu Gly Gln Tyr Ile Tyr Glu
            35                  40                  45

Thr Tyr Gly Asp Thr Trp Glu Gly Val Glu Ala Ile Ile Arg Ile Leu
        50                  55                  60

Gln Gln Leu Leu Phe Ala His Phe Arg Ile Gly Cys Gln His Ser Arg
65                  70                  75                  80

Ile Gly Ile Asn Pro Ser Asn Pro Arg Gly Lys Gly Arg Arg Asn Gly
                85                  90                  95

Ser Ser Arg Ser
            100

<210> SEQ ID NO 119
<211> LENGTH: 71
<212> TYPE: PRT
<213> ORGANISM: Human

<400> SEQUENCE: 119

Met Asp Pro Val Asp Pro Glu Met Pro Pro Trp His His Pro Gly Ser
1               5                   10                  15

Gln Pro Gln Ile Pro Cys Asn Asn Cys Tyr Cys Lys Arg Cys Cys Tyr
            20                  25                  30

His Cys Leu Val Cys Phe Thr Arg Lys Gly Leu Gly Ile Ser Tyr Gly
            35                  40                  45

Arg Lys Lys Arg Arg Gln Arg Arg Ala Ala Ala Ser His Pro Asp Asn
        50                  55                  60

Lys Asp Leu Val Pro Glu Gln
65                  70

<210> SEQ ID NO 120
<211> LENGTH: 71
<212> TYPE: PRT
<213> ORGANISM: Human

<400> SEQUENCE: 120

Met Asp Pro Val Asp Pro Glu Met Pro Pro Trp His His Pro Gly Ser
1               5                   10                  15

Gln Pro Gln Asn Pro Cys Asn Lys Cys Tyr Cys Lys Lys Cys Cys Tyr
            20                  25                  30

His Cys Tyr Val Cys Phe Thr Ser Lys Gly Leu Gly Ile Ser Tyr Gly
            35                  40                  45

Arg Lys Lys Arg Arg Arg Pro Ala Ala Ala Ala Ser Arg Pro Asp Asn
        50                  55                  60

Lys Asp Leu Val Pro Glu Gln
65                  70

<210> SEQ ID NO 121
<211> LENGTH: 71
<212> TYPE: PRT
<213> ORGANISM: Human

<400> SEQUENCE: 121
```

```
Met Asp Pro Val Asp Pro Glu Val Pro Pro Trp His His Pro Gly Ser
1               5                   10                  15

Gln Pro Pro Thr Pro Cys Asn Ala Cys Tyr Cys Lys Arg Cys Cys Tyr
                20                  25                  30

His Cys Tyr Leu Cys Phe Thr Lys Lys Gly Leu Gly Ile Ser His Gly
            35                  40                  45

Arg Lys Lys Arg Arg Pro Ala Ala Ala Ser Ser Ser Asn Asn
    50                  55                  60

Lys Asp Leu Val Pro Glu Gln
65              70

<210> SEQ ID NO 122
<211> LENGTH: 71
<212> TYPE: PRT
<213> ORGANISM: Human

<400> SEQUENCE: 122

Met Asp Pro Val Asp Pro Glu Ile Pro Pro Trp His His Pro Gly Ser
1               5                   10                  15

Gln Pro Gln Thr Pro Cys Asn Asn Cys Ser Cys Lys Lys Cys Cys Tyr
                20                  25                  30

His Cys Tyr Val Cys Phe Thr Arg Lys Gly Leu Glu Ile Ser Tyr Gly
            35                  40                  45

Arg Lys Lys Arg Arg Ser Ala Ala Glu Thr Arg His Pro Asp Asn
    50                  55                  60

Gln Asp Ile Val Pro Glu Gln
65              70

<210> SEQ ID NO 123
<211> LENGTH: 13
<212> TYPE: PRT
<213> ORGANISM: Human

<400> SEQUENCE: 123

Ala Ile Arg Ile Ile Lys Ile Leu Tyr Gln Ser Ser Lys
1               5                   10

<210> SEQ ID NO 124
<211> LENGTH: 26
<212> TYPE: PRT
<213> ORGANISM: Human

<400> SEQUENCE: 124

Met Ala Gly Arg Ser Asp Asp Gln Gln Leu Leu Gln Ala Ala Arg
1               5                   10                  15

Ile Ile Lys Ile Leu Tyr Gln Ser Ser Lys
                20                  25

<210> SEQ ID NO 125
<211> LENGTH: 26
<212> TYPE: PRT
<213> ORGANISM: Human

<400> SEQUENCE: 125

Met Ala Gly Arg Ser Asp Asp Gln Gln Leu Leu Gln Ala Leu Arg
1               5                   10                  15

Ile Ile Lys Ile Leu Tyr Gln Ser Ser Lys
                20                  25

<210> SEQ ID NO 126
```

```
<211> LENGTH: 26
<212> TYPE: PRT
<213> ORGANISM: Human

<400> SEQUENCE: 126

Met Ala Gly Arg Ser Asp Glu Asp Gln Pro Leu Lys Arg Val Ile Gln
1               5                   10                  15

Ile Ile Lys Ile Leu Tyr Gln Ser Ser Lys
            20                  25

<210> SEQ ID NO 127
<211> LENGTH: 42
<212> TYPE: PRT
<213> ORGANISM: Human

<400> SEQUENCE: 127

Ile Lys Val Val Pro Arg Arg Lys Ala Lys Ile Ile Arg His Tyr Gly
1               5                   10                  15

Lys Gln Met Ala Gly Ala Asp Ser Met Ala Ser Gly Gln Thr Glu Ser
            20                  25                  30

Glu Ser Val Glu Gln Pro Gly Glu Ile Pro
        35                  40

<210> SEQ ID NO 128
<211> LENGTH: 42
<212> TYPE: PRT
<213> ORGANISM: Human

<400> SEQUENCE: 128

Ile Lys Val Val Pro Arg Arg Lys Ala Lys Ile Ile Arg Asp Tyr Gly
1               5                   10                  15

Lys Gln Met Ala Gly Thr Asp Ser Met Ala Ser Arg Gln Thr Glu Ser
            20                  25                  30

Glu Asn Val Glu Gln Leu Gly Glu Ile Pro
        35                  40

<210> SEQ ID NO 129
<211> LENGTH: 36
<212> TYPE: PRT
<213> ORGANISM: Human

<400> SEQUENCE: 129

Ile Lys Val Val Pro Arg Arg Lys Ala Lys Ile Leu Arg Asp Tyr Gly
1               5                   10                  15

Lys Gln Met Ala Gly Ala Asp Ser Met Ala Ser Gly Gln Thr Glu Ser
            20                  25                  30

Glu Ser Met Glu
        35

<210> SEQ ID NO 130
<211> LENGTH: 106
<212> TYPE: PRT
<213> ORGANISM: Human

<400> SEQUENCE: 130

His Asn Phe Lys Arg Lys Gly Gly Ile Gly Gly Tyr Ser Ala Gly Glu
1               5                   10                  15

Arg Ile Ile Asp Ile Ile Ala Ser Asp Ile Gln Thr Lys Glu Leu Gln
            20                  25                  30

Lys Gln Ile Thr Lys Ile Gln Asn Phe Arg Val Tyr Tyr Arg Asp Ser
            35                  40                  45
```

-continued

Arg Asp Pro Ile Trp Lys Gly Pro Ala Lys Leu Leu Trp Lys Gly Glu
     50                  55                  60

Gly Ala Val Val Ile Gln Asp Asn Ser Asp Ile Lys Val Val Pro Arg
65                  70                  75                  80

Arg Lys Ala Lys Ile Ile Lys Asp Tyr Gly Lys Gln Met Ala Gly Asp
                85                  90                  95

Asp Cys Val Ala Ser Arg Gln Asn Glu Asp
            100                 105

<210> SEQ ID NO 131
<211> LENGTH: 35
<212> TYPE: PRT
<213> ORGANISM: Human

<400> SEQUENCE: 131

Met Ile Val Thr Met Lys Ala Met Lys Arg Arg Asn Arg Lys Leu Glu
1               5                   10                  15

Ile Leu Tyr Ile Val Met Ala Leu Ile Ile Pro Cys Leu Ser Ser Asp
                20                  25                  30

Gln Lys Tyr
        35

<210> SEQ ID NO 132
<211> LENGTH: 36
<212> TYPE: PRT
<213> ORGANISM: Human

<400> SEQUENCE: 132

Met Ile Val Thr Met Lys Ala Met Lys Arg Lys Asn Lys Lys Leu Gly
1               5                   10                  15

Val Ile Leu Cys Ile Cys Leu Ala Leu Leu Ile Pro Cys Leu Arg Ser
                20                  25                  30

Asn Asp Leu Tyr
        35

<210> SEQ ID NO 133
<211> LENGTH: 35
<212> TYPE: PRT
<213> ORGANISM: Human

<400> SEQUENCE: 133

Met Ile Val Ile Met Lys Ala Met Glu Met Glu Asp Lys Lys Leu Tyr
1               5                   10                  15

Ile Leu Cys Ile Leu Met Val Leu Leu Thr Pro Cys Leu Ser Ser Asp
                20                  25                  30

Lys Leu Tyr
        35

<210> SEQ ID NO 134
<211> LENGTH: 715
<212> TYPE: PRT
<213> ORGANISM: Human

<400> SEQUENCE: 134

Met Thr Val Thr Met Lys Ala Met Glu Lys Arg Asn Arg Lys Leu Gly
1               5                   10                  15

Ile Leu Cys Ile Val Met Ala Leu Ile Thr Pro Cys Leu Ser His Asp
                20                  25                  30

Gln Arg Tyr Ala Thr Val Tyr Ala Gly Val Pro Val Trp Glu Glu Ala

-continued

```
           35                  40                  45
Asn Pro Val Leu Phe Cys Ala Ser Asp Ala Asn Leu Thr Ser Thr Glu
 50                  55                  60
Lys His Asn Ile Trp Ala Ser Gln Ala Cys Val Pro Thr Asp Pro Thr
65                   70                  75                  80
Pro His Glu Tyr Pro Leu His Asn Val Thr Asp Asn Phe Asn Ile Trp
                 85                  90                  95
Lys Asn Tyr Met Val Glu Gln Met Gln Asp Asp Ile Ile Ser Leu Trp
                100                 105                 110
Glu Gln Ser Leu Lys Pro Cys Val Gln Met Thr Phe Leu Cys Val Gln
            115                 120                 125
Met Asn Cys Thr Ser Val Ser Asn Ser Ser Val Ser Asn Ser Ser Val
            130                 135                 140
Ser Asn Ser Ser Val Ser Asn Ser Ser Val Ser Asp Ser Thr Ile Pro
145                 150                 155                 160
Lys Lys Lys Asn Asn Ser Ser Glu Asp Leu Leu Lys Gln Cys Asp
                165                 170                 175
Phe Asn Ala Thr Thr Val Leu Lys Asp Lys Glu Lys Lys Gln Thr
            180                 185                 190
Leu Phe Tyr Val Ser Asp Leu Met Lys Leu Thr Asn Val Thr Asn Asp
            195                 200                 205
Thr Met Tyr Thr Leu Ile Asn Cys Asn Ser Thr Thr Ile Lys Gln Ala
            210                 215                 220
Cys Pro Lys Val Thr Phe Glu Pro Ile Pro Ile His Tyr Cys Ala Pro
225                 230                 235                 240
Ala Gly Tyr Ala Ile Phe Lys Cys Asn Asn Thr Glu Phe Asn Gly Thr
                245                 250                 255
Gly Pro Cys Asn Asn Ile Thr Val Val Thr Cys Thr His Gly Ile Arg
                260                 265                 270
Pro Thr Val Ser Thr Gln Leu Ile Leu Asn Gly Thr Leu Ser Glu Gly
            275                 280                 285
Lys Ile Arg Ile Met Gly Arg Asn Ile Thr Asp Ser Gly Lys Asn Ile
            290                 295                 300
Ile Val Thr Leu Asn Tyr Thr Ile Asn Ile Thr Cys Glu Arg Thr Trp
305                 310                 315                 320
Asn Gln Ser Val Gln Glu Ile Pro Ile Gly Pro Met Ala Trp Tyr Ser
                325                 330                 335
Met Ser Val Glu Lys Asp Lys Asn Thr Thr Gly Ser Arg Ser Ala Asp
                340                 345                 350
Cys Gln Tyr Asn Thr Ser Glu Trp Thr Arg Ala Leu Glu Gln Thr Ala
            355                 360                 365
Glu Arg Tyr Leu Glu Leu Met Asn Asn Thr Gly Asn Thr Asp Asn Thr
370                 375                 380
Thr Val Ile Phe Asn His Ser Thr Gly Gly Asp Pro Glu Val Ser Phe
385                 390                 395                 400
Leu His Phe Asn Cys His Gly Glu Phe Phe Tyr Cys Asn Thr Ser Gly
                405                 410                 415
Met Phe Asn Tyr Thr Phe Ser Cys Lys Gly Thr Asn Cys Thr Gln Val
                420                 425                 430
Gly Ser Gln Asn Glu Tyr Asn Asn His Thr Thr Lys Ile Pro Cys Arg
            435                 440                 445
Ile Lys Gln Val Val Arg Ser Trp Ile Arg Gly Gly Ser Gly Leu Tyr
450                 455                 460
```

-continued

```
Ala Pro Pro Arg Gln Gly Pro Leu Lys Cys Ser Ser Asn Ile Thr Gly
465                 470                 475                 480

Met Ile Leu Gln Leu Asp Lys Pro Trp Asn Arg Ser Gly His Asn Asn
                485                 490                 495

Asp Thr Thr Phe Arg Pro Ile Gly Gly Glu Met Lys Asp Ile Trp Arg
            500                 505                 510

Thr Glu Leu Phe Lys Tyr Lys Val Val Lys Val Lys Pro Phe Ser Val
        515                 520                 525

Ala Pro Thr Lys Ile Ala Arg Pro Val Ile Gly Thr Gly Thr Gln Arg
    530                 535                 540

Glu Lys Arg Ala Val Gly Leu Gly Met Leu Phe Leu Gly Val Leu Ser
545                 550                 555                 560

Ala Ala Gly Ser Thr Met Gly Ala Ala Thr Thr Leu Ala Val Gln
                565                 570                 575

Thr His Thr Leu Met Lys Gly Ile Val Gln Gln Asp Asn Leu Leu
            580                 585                 590

Arg Ala Ile Gln Ala Gln Gln Leu Leu Arg Leu Ser Val Trp Gly
            595                 600                 605

Ile Arg Gln Leu Arg Ala Arg Leu Leu Ala Leu Glu Thr Leu Ile Gln
    610                 615                 620

Asn Gln Gln Leu Leu Asn Leu Trp Gly Cys Lys Gly Arg Leu Val Cys
625                 630                 635                 640

Tyr Thr Ser Val Gln Trp Asn Arg Thr Trp Thr Asn Asn Thr Asn Leu
                645                 650                 655

Asp Ser Ile Trp Glu Asn Leu Thr Trp Gln Glu Trp Asp Gln Gln Ile
            660                 665                 670

Ser Asn Ile Ser Ser Thr Ile Tyr Glu Glu Ile Gln Lys Ala Gln Ile
        675                 680                 685

Gln Gln Glu Tyr Asn Glu Lys Lys Leu Leu Glu Leu Asp Glu Trp Ala
    690                 695                 700

Ser Ile Trp Asn Trp Leu Asp Ile Thr Lys Cys
705                 710                 715
```

<210> SEQ ID NO 135
<211> LENGTH: 38
<212> TYPE: PRT
<213> ORGANISM: Human
<220> FEATURE:
<221> NAME/KEY: PEPTIDE
<222> LOCATION: (1)..(38)

<400> SEQUENCE: 135

```
Cys Glu Arg Thr Trp Asn Gln Ser Val Gln Glu Ile Pro Ile Gly Pro
1               5                   10                  15

Met Ala Trp Tyr Ser Met Ser Val Glu Leu Asp Leu Asn Thr Thr Gly
                20                  25                  30

Ser Arg Ser Ala Asp Cys
            35
```

<210> SEQ ID NO 136
<211> LENGTH: 7
<212> TYPE: PRT
<213> ORGANISM: Human
<220> FEATURE:
<221> NAME/KEY: PEPTIDE
<222> LOCATION: (1)..(7)

<400> SEQUENCE: 136

Ser Val Gln Glu Ile Pro Ile
1               5

<210> SEQ ID NO 137
<211> LENGTH: 23
<212> TYPE: PRT
<213> ORGANISM: Human
<220> FEATURE:
<221> NAME/KEY: PEPTIDE
<222> LOCATION: (1)..(23)

<400> SEQUENCE: 137

Asn Gln Gln Leu Leu Asn Leu Trp Gly Cys Lys Gly Arg Leu Val Cys
1               5                   10                  15

Tyr Thr Ser Val Gln Trp Asn
            20

<210> SEQ ID NO 138
<211> LENGTH: 24
<212> TYPE: PRT
<213> ORGANISM: Human
<220> FEATURE:
<221> NAME/KEY: PEPTIDE
<222> LOCATION: (1)..(24)

<400> SEQUENCE: 138

Asn Gln Gln Leu Leu Asn Leu Trp Gly Cys Lys Gly Arg Leu Val Cys
1               5                   10                  15

Tyr Thr Ser Val Lys Trp Asn Asn
            20

<210> SEQ ID NO 139
<211> LENGTH: 34
<212> TYPE: DNA
<213> ORGANISM: Human

<400> SEQUENCE: 139
gggttcttgg gagcagcagg aagcactatg ggcg                              34

<210> SEQ ID NO 140
<211> LENGTH: 33
<212> TYPE: DNA
<213> ORGANISM: Human

<400> SEQUENCE: 140
tctgaaacga cagaggtgag tatccctgcc taa                               33

<210> SEQ ID NO 141
<211> LENGTH: 33
<212> TYPE: DNA
<213> ORGANISM: Human

<400> SEQUENCE: 141
tggatcccac agtgtactga agggtatagt gca                               33

<210> SEQ ID NO 142
<211> LENGTH: 28
<212> TYPE: DNA
<213> ORGANISM: Human

<400> SEQUENCE: 142
catttagtta tgtcaagcca attccaaa                                     28

```
<210> SEQ ID NO 143
<211> LENGTH: 31
<212> TYPE: DNA
<213> ORGANISM: Human

<400> SEQUENCE: 143
gttctccata tatctttcat atctcccct a                                31

<210> SEQ ID NO 144
<211> LENGTH: 31
<212> TYPE: DNA
<213> ORGANISM: Human

<400> SEQUENCE: 144
ttgtacacat ggcattaggc caacagtaag t                               31

<210> SEQ ID NO 145
<211> LENGTH: 31
<212> TYPE: DNA
<213> ORGANISM: Human

<400> SEQUENCE: 145
tgaattccta atattgaatg ggacactctc t                               31

<210> SEQ ID NO 146
<211> LENGTH: 32
<212> TYPE: DNA
<213> ORGANISM: Human

<400> SEQUENCE: 146
tggatcctac aataaaagaa ttctccatga ca                              32

<210> SEQ ID NO 147
<211> LENGTH: 24
<212> TYPE: DNA
<213> ORGANISM: Human

<400> SEQUENCE: 147
gggtttatta cagggacagc agag                                       24

<210> SEQ ID NO 148
<211> LENGTH: 24
<212> TYPE: DNA
<213> ORGANISM: Human

<400> SEQUENCE: 148
ggttggggtc tgtgggtaca cagg                                       24

<210> SEQ ID NO 149
<211> LENGTH: 22
<212> TYPE: DNA
<213> ORGANISM: Human

<400> SEQUENCE: 149
gcaaaactac tctggaaagg tg                                         22

<210> SEQ ID NO 150
<211> LENGTH: 23
<212> TYPE: DNA
<213> ORGANISM: Human

<400> SEQUENCE: 150
gcwtctttcc acacaggtac ccc                                        23
```

```
<210> SEQ ID NO 151
<211> LENGTH: 21
<212> TYPE: DNA
<213> ORGANISM: Human

<400> SEQUENCE: 151
catattgggg attgatgcca g                                         21

<210> SEQ ID NO 152
<211> LENGTH: 20
<212> TYPE: DNA
<213> ORGANISM: Human

<400> SEQUENCE: 152
gcatyagcgt tacttactgc                                           20
```

What is claimed is:

1. An isolated antigen from the HIV-1 group O strain gp160 env precursor protein comprising the amino acid sequence of SEQ ID NO:100.

2. A method for detecting anti-HIV-1 antibodies in a sample comprising:
   a) contacting the sample with an isolated antigen from the HIV-1 group O strain gp160 env precursor protein comprising the amino acid sequence of SEQ ID NO:100,
   b) allowing the isolated antigen and anti-HIV antibodies to interact, and
   c) detecting the interaction between the antigen and the anti-HIV antibodies.

3. A kit for detecting HIV-1 antibodies comprising an isolated antigen from the HIV-1 group O strain gp160 env precursor protein comprising the amino acid sequence of SEQ ID NO:100.

4. An immunogenic composition comprising:
   a) an isolated antigen from the HIV-1 group O strain gp160 env precursor protein which comprises the amino acid sequence of SEQ ID NO:100; and
   b) a pharmaceutically acceptable carrier.

* * * * *